US012049505B2

(12) United States Patent
Vasiljeva et al.

(10) Patent No.: US 12,049,505 B2
(45) Date of Patent: Jul. 30, 2024

(54) MATRIX METALLOPROTEASE-CLEAVABLE AND SERINE OR CYSTEINE PROTEASE-CLEAVABLE SUBSTRATES AND METHODS OF USE THEREOF

(71) Applicant: CytomX Therapeutics, Inc., South San Francisco, CA (US)

(72) Inventors: Olga Vasiljeva, Freemont, CA (US); Michael B. Winter, San Francisco, CA (US)

(73) Assignee: CytomX Therapeutics, Inc., South San Francisco, CA (US)

( * ) Notice: Subject to any disclaimer, the term of this patent is extended or adjusted under 35 U.S.C. 154(b) by 449 days.

(21) Appl. No.: 16/705,124

(22) Filed: Dec. 5, 2019

(65) Prior Publication Data

US 2020/0377602 A1 Dec. 3, 2020

Related U.S. Application Data

(60) Provisional application No. 62/778,062, filed on Dec. 11, 2018, provisional application No. 62/776,409, filed on Dec. 6, 2018.

(51) Int. Cl.

| | |
|---|---|
| ***C07K 16/28*** | (2006.01) |
| ***A61K 39/00*** | (2006.01) |
| ***A61P 35/00*** | (2006.01) |
| ***C07K 7/06*** | (2006.01) |
| ***C12N 15/11*** | (2006.01) |
| ***C12N 15/62*** | (2006.01) |
| ***C12N 15/63*** | (2006.01) |

(52) U.S. Cl.

CPC .......... *C07K 16/2863* (2013.01); *A61P 35/00* (2018.01); *C07K 7/06* (2013.01); *C12N 15/11* (2013.01); *C12N 15/62* (2013.01); *C12N 15/63* (2013.01); *A61K 2039/505* (2013.01); *C07K 2317/51* (2013.01); *C07K 2317/515* (2013.01); *C07K 2317/92* (2013.01); *C07K 2317/94* (2013.01); *C07K 2319/50* (2013.01)

(58) Field of Classification Search

None

See application file for complete search history.

(56) References Cited

U.S. PATENT DOCUMENTS

| | | | |
|---|---|---|---|
| 3,773,919 | A | 11/1973 | Boswell |
| 4,485,045 | A | 11/1984 | Regen |
| 4,522,811 | A | 6/1985 | Eppstein et al. |
| 4,544,545 | A | 10/1985 | Ryan et al. |
| 5,013,556 | A | 5/1991 | Woodle et al. |
| 5,030,719 | A | 7/1991 | Umemeto et al. |
| 5,151,510 | A | 9/1992 | Stec et al. |
| 6,551,795 | B1 | 4/2003 | Rubenfield et al. |
| 6,558,728 | B1 | 5/2003 | Poulsen et al. |
| 7,276,497 | B2 | 10/2007 | Chari et al. |
| 7,439,319 | B2 | 10/2008 | Smith et al. |
| 7,442,159 | B1 | 10/2008 | Riechmann et al. |
| 7,465,790 | B2 | 12/2008 | Waldmann et al. |
| 7,666,817 | B2 | 2/2010 | Daugherty et al. |
| 7,935,785 | B2 | 5/2011 | Smith et al. |
| 8,513,390 | B2 | 8/2013 | Stagliano et al. |
| 8,518,404 | B2 | 8/2013 | Daugherty et al. |
| 8,524,220 | B1 | 9/2013 | Bermudes |
| 8,529,898 | B2 | 9/2013 | Daugherty et al. |
| 8,541,203 | B2 | 9/2013 | Daugherty et al. |
| 8,563,269 | B2 | 10/2013 | Stagliano et al. |
| 8,809,504 | B2 | 8/2014 | Lauermann |
| 9,120,853 | B2 | 9/2015 | Lowman et al. |
| 9,127,053 | B2 | 9/2015 | West et al. |
| 9,169,321 | B2 | 10/2015 | Daugherty et al. |

(Continued)

FOREIGN PATENT DOCUMENTS

| | | |
|---|---|---|
| EP | 1 523 503 | 4/2009 |
| EP | 1 324 771 | 6/2011 |

(Continued)

OTHER PUBLICATIONS

Juliano et al. "Differences in substrate specificities between cysteine protease CPB isoforms of Leishmania mexicana are mediated by a few amino acid changes" Eur. J. Biochem. 271:3704-3714. (Year: 2004).*

Neitzel J "Enzyme Catalysis: The Serine Proteases" Nature Education 3:21 (Year: 2010).*

Prudova et al., "Multiplex N-terminome analysis of MMP-2 and MMP-9 substrate degradomes by iTRAQ-TAILS quantitative proteomics", Mol. Cell Proteomics (2010) 9(5):894-911.

Ramakrishnan et al., "Comparison of the Selective Cytotoxic Effects of Immunotoxins Containing Ricin A Chain or Pokeweed Antiviral Protein and Anti-Thy 1.1 Monoclonal Antibodies", Cancer Res. (1984) 44:201-208.

(Continued)

*Primary Examiner* — Sudhakar Katakam
*Assistant Examiner* — Zachary J Miknis
(74) *Attorney, Agent, or Firm* — Rothwell, Figg, Ernst & Manbeck

(57) ABSTRACT

The invention relates generally to polypeptides that include at least a first cleavable moiety (CM1) that is a substrate for at least one matrix metalloprotease (MMP) and at least a second cleavable moiety (CM2) that is a substrate for at least one serine protease (SP) or at least one cysteine protease (CP), to activatable antibodies and other larger molecules that include these polypeptides that include at least a CM1 that is a substrate for at least one MMP protease and at least a CM2 that is a substrate for at least one SP protease or at least one cysteine protease (CP), and to methods of making and using these polypeptides that include at least a CM1 that is a substrate for at least one MMP protease and at least a CM2 that is a substrate for at least one SP protease or at least one cysteine protease (CP) in a variety of therapeutic, diagnostic and prophylactic indications.

23 Claims, 9 Drawing Sheets

Specification includes a Sequence Listing.

(56) References Cited

U.S. PATENT DOCUMENTS

| | | | |
|---|---|---|---|
| 9,309,510 | B2 | 4/2016 | La Porte et al. |
| 9,453,078 | B2 | 9/2016 | Stagliano et al. |
| 9,562,073 | B2 | 2/2017 | Moore et al. |
| 10,059,762 | B2 | 8/2018 | Stagliano et al. |
| 10,077,300 | B2 | 9/2018 | Daugherty et al. |
| 10,118,961 | B2 | 11/2018 | Stagliano et al. |
| 10,138,272 | B2 | 11/2018 | Moore et al. |
| 10,179,817 | B2 | 1/2019 | Sagert et al. |
| 10,233,244 | B2 | 3/2019 | Sagert et al. |
| 10,336,824 | B2 | 7/2019 | West et al. |
| 10,513,558 | B2 | 12/2019 | Tipton et al. |
| 10,669,337 | B2 | 6/2020 | Irving et al. |
| 10,669,339 | B2 | 6/2020 | West et al. |
| 10,745,481 | B2 | 8/2020 | West et al. |
| 10,875,913 | B2 | 12/2020 | Stagliano et al. |
| 11,028,126 | B2 | 6/2021 | Moore et al. |
| 11,267,896 | B2 | 3/2022 | Sagert et al. |
| 2003/0219402 | A1 | 11/2003 | Rutter |
| 2004/0109855 | A1 | 6/2004 | Waldmann et al. |
| 2004/0123343 | A1 | 6/2004 | La Rosa et al. |
| 2005/0208602 | A1 | 9/2005 | Rosen et al. |
| 2007/0218074 | A1 | 9/2007 | Man |
| 2008/0166375 | A1 | 7/2008 | Leppla et al. |
| 2009/0304719 | A1 | 12/2009 | Daugherty et al. |
| 2010/0041588 | A1 | 2/2010 | Keay et al. |
| 2010/0189651 | A1 | 7/2010 | Stagliano et al. |
| 2010/0221212 | A1 | 9/2010 | Stagliano et al. |
| 2011/0214205 | A1 | 9/2011 | Dietrich et al. |
| 2011/0280908 | A1 | 11/2011 | Leppla et al. |
| 2011/0287517 | A1 | 11/2011 | Steward et al. |
| 2012/0149061 | A1 | 6/2012 | Stagliano et al. |
| 2012/0207756 | A1 | 8/2012 | Stagliano et al. |
| 2012/0237512 | A1 | 9/2012 | Daugherty et al. |
| 2012/0237977 | A1 | 9/2012 | Daugherty et al. |
| 2012/0244154 | A1 | 9/2012 | Daugherty et al. |
| 2012/0321626 | A1 | 12/2012 | Zhou et al. |
| 2013/0078203 | A1 | 3/2013 | Goksoyr |
| 2013/0150558 | A1 | 6/2013 | Williams et al. |
| 2013/0266568 | A1 | 10/2013 | Brinkmann et al. |
| 2013/0309230 | A1 | 11/2013 | Stagliano et al. |
| 2014/0010810 | A1 | 1/2014 | West et al. |
| 2014/0023664 | A1 | 1/2014 | Lowman et al. |
| 2014/0024810 | A1 | 1/2014 | Stagliano et al. |
| 2014/0045195 | A1 | 2/2014 | Daugherty et al. |
| 2014/0255313 | A1 | 9/2014 | Vasiljeva et al. |
| 2014/0363430 | A1 | 12/2014 | West et al. |
| 2015/0005477 | A1 | 1/2015 | Lowman et al. |
| 2015/0087810 | A1 | 3/2015 | Moore et al. |
| 2016/0122425 | A1 | 5/2016 | Daugherty et al. |
| 2016/0194399 | A1 | 7/2016 | Irving et al. |
| 2016/0228546 | A1 | 8/2016 | Stagliano et al. |
| 2016/0311903 | A1 | 10/2016 | West et al. |
| 2016/0355587 | A1 | 12/2016 | West et al. |
| 2016/0355592 | A1 | 12/2016 | Sagert et al. |
| 2016/0355599 | A1 | 12/2016 | Sagert et al. |
| 2017/0044259 | A1 | 2/2017 | Tipton et al. |
| 2017/0081397 | A1 | 3/2017 | Stagliano et al. |
| 2017/0204139 | A1 | 7/2017 | Moore et al. |
| 2019/0119370 | A1 | 4/2019 | Stagliano et al. |
| 2019/0135864 | A1 | 5/2019 | Moore et al. |
| 2019/0211089 | A1 | 7/2019 | Daugherty et al. |
| 2020/0377602 | A1 | 12/2020 | Vasiljeva et al. |
| 2021/0284721 | A1 | 9/2021 | Stagliano et al. |

FOREIGN PATENT DOCUMENTS

| | | | | |
|---|---|---|---|---|
| EP | 3890764 | A2 | 10/2021 | |
| WO | 1994011026 | A2 | 5/1994 | |
| WO | 9915563 | A1 | 4/1999 | |
| WO | 2001057182 | A2 | 8/2001 | |
| WO | 2001091798 | A2 | 12/2001 | |
| WO | 2002012475 | A2 | 2/2002 | |
| WO | 2002030460 | A2 | 4/2002 | |
| WO | 2002038796 | A1 | 5/2002 | |
| WO | WO 2003/004681 | | 1/2003 | |
| WO | 2003038083 | A1 | 5/2003 | |
| WO | WO 2003/068934 | | 8/2003 | |
| WO | 2004009638 | A1 | 1/2004 | |
| WO | WO 2006/068975 | | 6/2006 | |
| WO | 2006110599 | A2 | 10/2006 | |
| WO | WO 2007/047995 | | 4/2007 | |
| WO | 2007105027 | A1 | 9/2007 | |
| WO | 2008052187 | A2 | 5/2008 | |
| WO | WO 2008/083312 | | 7/2008 | |
| WO | WO 2008/149143 | | 12/2008 | |
| WO | WO 2008/149147 | | 12/2008 | |
| WO | WO 2008/149148 | | 12/2008 | |
| WO | WO 2008/149149 | | 12/2008 | |
| WO | WO 2008/149150 | | 12/2008 | |
| WO | 2009025846 | A2 | 2/2009 | |
| WO | 2010046628 | A1 | 4/2010 | |
| WO | 2010081173 | A2 | 7/2010 | |
| WO | 2010088691 | A2 | 8/2010 | |
| WO | 2010096838 | A2 | 8/2010 | |
| WO | WO 2010/091122 | | 8/2010 | |
| WO | 2010129609 | A2 | 11/2010 | |
| WO | 2011028698 | A2 | 3/2011 | |
| WO | WO 2011/151426 | | 12/2011 | |
| WO | WO 2011/161260 | | 12/2011 | |
| WO | 2012156919 | A1 | 11/2012 | |
| WO | WO 2012/158818 | | 11/2012 | |
| WO | WO 2013/003649 | | 1/2013 | |
| WO | 2013163631 | A2 | 10/2013 | |
| WO | 2013192546 | A1 | 12/2013 | |
| WO | 2013192550 | A2 | 12/2013 | |
| WO | 2014026136 | A2 | 2/2014 | |
| WO | 2014052462 | A2 | 4/2014 | |
| WO | WO-2014052462 | A2 * | 4/2014 | ............ A61K 47/65 |
| WO | 2014107599 | A2 | 7/2014 | |
| WO | 2014176284 | A1 | 10/2014 | |
| WO | 2014193973 | A2 | 12/2014 | |
| WO | WO 2014/197612 | | 12/2014 | |
| WO | 2015048329 | A2 | 4/2015 | |
| WO | 2015116933 | A2 | 8/2015 | |
| WO | 2016014974 | A2 | 1/2016 | |
| WO | 2016118629 | A1 | 7/2016 | |
| WO | WO-2016118629 | A1 * | 7/2016 | ............ A61K 38/05 |
| WO | 2016179257 | A2 | 10/2016 | |
| WO | WO 2016/210447 | | 12/2016 | |
| WO | WO 2020/077267 | | 4/2020 | |
| WO | 2020118109 | A2 | 6/2020 | |

OTHER PUBLICATIONS

Ratnikov et al., "Basis for substrate recognition and distinction by matrix metalloproteinases", Proc. Natl. Acad. Sci. USA (2014) 111(4):E4148-55.

Rothberg et al., "An integrated semiconductor device enabling non-optical genome sequencing", Nature (2011) 475(7356):348-52.

Scheraga, H.A., "Predicting Three-Dimensional Structures of Oligopeptides" Rev. Computational Chem., (vol. 3, K.B. Lipkowitz and D.B. Boyd (Eds.), John Wiley & Sons, Inc., Hoboken, NJ, (1992).

Stec et al., "Automated solid-phase synthesis, separation, and stereochemistry of phosphorothioate analogs of oligodeoxyribonucleotides", J. Am. Chem. Soc. (1984) 106(20):6077-6079.

Stein et al., "Physicochemical properties of phosphorothioate oligodeoxynucleotides", Nucl. Acids Res. (1988) 16(8):3209-3221.

Takeuchi T et al. "Cellular Location of Membrane-type Serine Protease 1 and Identification of Protease-activated Receptor-2 and Single-chain Urokinase-type Plasminogen Activator as Substrates", J. Biol. Chem. (2000) 275(34):26333-26342.

Tateno et al. (Jul. 24, 1998) "Isolation and Characterization of Rhamnose-binding Lectins from Eggs of Steelhead Trout (Oncorhynchus mykiss) Homologous to Low Density Lipoprotein Receptor Superfamily", J. Biol. Chem. (1998) 273(30):19190-19197.

Thornton et al., "Prediction of progress at last", Nature (1991) 354:105.

Toshihiko et al., "Cellular Location of Membrane-type Serine Protease 1 and Identification of Protease-activated Receptor-2 and

(56) References Cited

OTHER PUBLICATIONS

Single-chain Urokinase-type Plasminogen Activator as Substrates", J. Biol. Chem. (2000) 274(34):26333-26342.
Turk et al., "Determination of protease cleavage site motifs using mixture-based oriented peptide libraries", Nat. Biotechnol. (2001) 19(7):661-7.
Uhlmann and Peyman, "Antisense Oligonucleotides: A New Therapeutic Principle", Chemical Reviews (1990) 90(4):543-584.
UniProtKB B1FZS3; Retrieved from internet on Jul. 25, 2018: https://www.uniprot.org/uniprot/B1FZS3.
Uniprot Assession No. B8J087 (uncharacterized protein), Mar. 3, 2009.
Uniprot Assession No. Q9ZZR8 (Cytochrome b), May 1, 1999.
Venkatesh et al., "Elephant shark genome provides unique insights into gnathostome evolution", Nature (2014) 505(7482):174-179.
Villacres et al., "Cloning, Chromosomal Mapping, and Expression of Human Fetal Brain Type I Adenylyl Cyclase", Genomics (1993) 16(2):473-478.
Vitetta et al., "Redesigning nature's poisons to create anti-tumor reagents", Science (1987) 238(4830): 1098-1104.
Wang W., "Lyophilization and development of solid protein pharmaceuticals", Int. J. Pharm. (2000) 203(1-2):1-60.
Waterhouse et al., "Jalview Version 2—a multiple sequence alignment editor and analysis workbench", Bioinform. (2009) 9:1189-1191.
Zhao et al., "A novel strategy to tag matrix metalloproteinases-positive cells for in vivo imaging of invasive and metastatic activity of tumor cells", J. Control Release (2010) 144(1):109-114.
Zon et al., "Phosphorothioate oligonucleotides: chemistry, purification, analysis, scale-up and future directions", Anticancer Drug Des. (1991) 6(6):539-568.
De Groot N.: "AsnC family protein from Sedimentitalea nanhaiensis", Apr. 12, 2017 (Apr. 12, 2017), XP093016536, Retrieved from the Internet: URL:https://rest.uniprot.org/unisave/AOA117CZR5?format=txt&versions=3, 1 page.
Communication pursuant to Rule 164(2)(b) and Article 94(3) EPC issued in EP19 828 467.1 dated Feb. 24, 2023, 18 pgs.
Oshone, R., "Uncharacterized protein from Frankia Torreyi", Retrieved from the Internet, XP055665772, Nov. 7, 2018, URL: http://www.uniproto.org/uniprot/A0A0D8, 1 page.
Durrens, "Clavispora lusitaniae hypothetical protein", Retrieved from the Internet, XP055665684, Jun. 15, 2017, URL: https://www.ebi.ac.uk/ena/browser/api/embl/0VF07168.1?linelimit=1000, 2 pages.
Chen et al., "Selective antibody activation through protease-activated pro-antibodies that mask binding sites with inhibitory domains", Scientific Reports, vol. 7, No. 1, Sep. 14, 2017, 12 pages.
Kukreja, "The hight throughput multiplexed peptide-centric profiling illustrates both the substrate cleavage redundancy and specificity in the MMP family", Chem Biol, vol. 22, No. 8, Aug. 20, 2015, pp. 1122-1133.
Anonymous, "Uncharacterized protein form Saprolegnia diclina", Retrieved from the Internet, Jun. 7, 2017, XP055674716, URL:https://www.uniprot.org/uniprot/TORF53.txt?version=5, 1 page.
International Search Report issued in PCT/2019/064779, dated Jun. 23, 2020, 9 pages.
Bendig, Mary M., "Humanization of Rodent Monoclonal Antibodies by CDR Grafting", Methods: A Companion to Methods in Enzymology (1995); 8:83-93.
Colman, Peter M. "Effects of amino acid sequence changes on antibody-antigen interactions", Res. Immunol. (1994) 145(1): 33-36.
Murphy et al., "Enhancing recombinant antibody performance by optimally engineering its format", J. Immunol. Methods (2018) 463:127-133.
Rudikoff et al., "Single Amino Acid Substitution altering antigen-binding specificity", Proc. Natl. Acad. Sci. USA (1982) 79(6):1979-1983.
ADC review, Retrieved on Mar. 17, 2016 from http://adcreview.com/adc-university/adcs-101/cytotoxic-agents/maytansine/ (4 pages).
Baldrick P. "Pharmaceutical excipient development: the need for preclinical guidance." Regul. Toxicol Pharmacol. (2000) 32(2):210-218.
BLAST search of SEQ ID No. 362; Received on Mar. 17, 2016 from http://blast.ncbi.nlm.nih.gov/Blast.cgi (8 pages).
BLAST search of SEQ ID No. 363; Received on Mar. 17, 2016 from http://blast.ncbi.nlm.nih.gov/Blast.cgi (7 pages).
BLAST search of SEQ ID No. 364; Received on Mar. 17, 2016 from http://blast.ncbi.nlm.nih.gov/Blast.cgi (8 pages).
Bowie et al., "A method to identify protein sequences that fold into a known three-dimensional structure", Science (1991) 253(5016):164-170.
Casadaban et al., "Analysis of gene control signals by DNA fusion and cloning in *Escherichia coli*", JMB (1980) 138(2):179-207.
Charman WN, "Lipids, lipophilic drugs, and oral drug delivery-some emerging concepts." J. Pharm. Sci. (2000) 89(8):967-978.
Chothia & Lesk, "Canonical Structures for the Hypervariable Regions of Immunoglobulins", J. Mol. Biol. (1987) 196:901-917.
Chothia et al., "Conformations of immunoglobulin hypervariable regions", Nature (1989) 342:878-883.
Database EMBL, Accession No. AF099373 (Jan. 2, 2014) "Callorhinchus milii (elephant shark) protein ITFG3", Venkatesh et al. [online]; Retrieved from Internet on Jan. 9, 2017 (2 pages): https://www.ebi.ac.uk/ena/browser/api/embl/AF099373.
Davies et al., "Antibody-antigen complexes", Annual Rev. Biochem. (1990) 59:439-473.
"Derivative (chemistry)", Wikipedia, Accessed Sep. 11, 2017 (1 page); Retrieved from: https://en.wikipedia.org/w/ index.php?title=Derivative_(chemistry)&oldid=779855519.
Donaldson et al., "Design and development of masked therapeutic antibodies to limit off-target effects: application to anti-EGFR antibodies", Cancer Bio. & Therapy (2009) 8(22):2147-2152.
Eppstein et al., "Biological activity of liposome-encapsulated murine interferon gamma is mediated by a cell membrane receptor", Proc. Natl. Acad. Sci. USA, (1985) 82(11):3688-3692.
GenBank Accession No. ADA97619, "Sequence 28102 from U.S. Pat. No. 6,551,795" (Rubenfield et al.), Retrieved from internet on Mar. 17, 2016 (3 pages): http://seqdata.uspto.gov /?pageRequest=viewSequence&DocID=06551795B1&seqID =28102.
Genbank Accession No. AKP45152.1, Retrieved from internet on Jul. 25, 2018: https://www.ncbi.nlm.nih.gov/protein/Akp45152.
Genbank Accession No. AEL07912.1 [online], Retrieved from internet on Dec. 18, 2017: https://www.ncbi.nlm.nih.gov/protein/AEL07912.
Genbank Accession No. YP_005352726.1 [online], Retrieved from internet on Dec. 18, 2017: https://www.ncbi.nlm.nihgov/ protein/YP_005352726.1.
Geneseq Assession No. AAB46481, B. brevis tyrocidn sythetases activating domain 9 (Apr. 9, 2001).
GENPEPT Assession No. P0C9K2.1, RecName: Full=Protein MGF 110-14L; Flags: Precursor (Sep. 28, 2018); https://www.ncbi.nlm.nih.gov/ protein/229544532?sat=12&satkev =1040226.
Gerspach et al., "Target-selective activation of a TNF prodrug by urokinase-type plasminogen activator (uPA) mediated proteolytic processing at the cell surface", Cancer Immunol. (2006) 55(12):1590-1600.
Gerspach et al., "Restoration of membrane TNF-like activity by cell surface targeting and matrix metalloproteinase-mediated processing of a TNF prodrug", Cell Death and Differentiation (2006) 13(2):273-284.
Harris et al., "Rapid and general profiling of protease specificity by using combinatorial fluorogenic substrate libraries", PNAS (2000) 97(14): 7754-7759.
Henikoff et al., "Amino acid substitution matrices from protein blocks", Proc Natl Acad Sci USA (1992) 89(22):10915-10919.
Hwang et al., "Hepatic uptake and degradation of unilamellar sphingomyelin/cholesterol liposomes: a kinetic study", Proc. Natl Acad. Sci. USA (1980) 77(7):4030-4034.
Irving, "Probodies Empower a New Generation of Antibody Immunotherapies," presented at Keystone Symposia on Molecular and Cellular Biology, Feb. 2015.

(56) References Cited

OTHER PUBLICATIONS

Jabaiah et al., "Directed evolution of protease beacons that enable sensitive detection of endogenous MT1-MMP activity in tumor cell lines", Chem. Biol. (2011) 18(3):392-401.
Jansen et al., "Immunotoxins: hybrid molecules combining high specificity and potent cytotoxicity", Immunological Reviews (1982) 62:185-216.
Jeong et al., "Recombinant antibodies: Engineering and production in yeast and bacterial hosts", Biotechnol. J. (2011) 6(1):16-27.
Kawato et al., "Hypothetical protein [Pseudomonas phage PPpW-3]" Accession No. VP_008873205, Dec. 9, 2013.
Ke et al., "Optimal Subsite Occupancy and Design of a Selective Inhibitor of Urokinase", J. Biol. Chem., (1997) 272(33):20456-20462.
Ke et al., "Distinguishing the specificities of closely related proteases role of p3 in substrate and inhibitor discrimination between tissue-type plasminogen activator and urokinase", J. Bio. Chem. (1997) 272(26):16603-16609.
Killen and Lindstrom, "Specific killing of lymphocytes that cause experimental autoimmune myasthenia gravis by ricin toxin-acetylcholine receptor conjugates", J. Immunol. (1984) 133(5):2549-2553.
Kopylov et al., "Methods of quantitative proteomics", Biomed Khim. (2007) 53(6):613-643. (English Abstract only).
Kridel et al., "Substrate hydrolysis by matrix metalloproteinase-9", J. Biol. Chem. (2001) 276(23):20572-20578 (Epub Mar. 14, 2001).
Kridel et al., "A Unique Substrate Binding Mode Discriminates Membrane Type-I Matrix Metalloproteinase from Other Matrix Metalloproteinases", J. Biol. Chem. (2002) 277(26): 23788-23793.
LaPlanche et al., "Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric O-ethyl phosphorothioates", Nucl. Acids Res. (1986) 14(22):9081-9093.
Liu et al., "Intermolecular complementation achieves high-specificity tumor targeting by anthrax toxin", Nature Biotech. (2005) 23(6):725-730.
Lopez-Otin et al., "Protease Degradomics: A New Challenge for Proteomics", Nature Rev. Mol. Cell Biol. (2002) 3:509-519.
Malmqvist M., "Biospecific interaction analysis using biosensor technology", Nature (1993) 361(6408):186-187.
Marasco et al., "Design, intracellular expression, and activity of a human anti-human immunodeficiency virus type 1 gp120 single-chain antibody", Proc. Natl. Acad. Sci. USA (1993) 90(16):7889-7893.
Martin et al., "Irreversible coupling of immunoglobulin fragments to preformed vesicles. An improved method for liposome targeting", J. Biol. Chem. (1982) 257(1):286-288.
Maytansinoid DM4, Retrieved from internet on Mar. 17, 2016, (9 pages): https://pubchem.ncbi.nlm.nih.gov/compound/46926355#section=Top.
Mitra and Lawton, "Reagents for the crosslinking of proteins by equilibrium transfer alkylation", J. Amer. Chem. Soc. (1979) 101(11):3097-3110.
Nangia-Makker et al., "Galectin-3 cleavage: a novel surrogate marker for matrix metalloproteinase activity in growing breast cancers", Cancer Res. (2007) 67(24): 11760-11768.
Paul, W., Fundamental Immunology, (3rd Edition, Lippincott Williams & Wilkins, (1993) p. 292-295).
Portolano et al., "Lack of promiscuity in autoantigen-specific H and L chain combinations as revealed by human H and L chain roulette", J. Immunol. (1993) 150(3):880-887.
Powell et al. "Compendium of excipients for parenteral formulations" PDA J Pharm Sci Technol. (1998) 52(5):238-311.
UniProt A0A0D8BN56, Oshone, R. et al., "Permanent Draft Genome Sequences for Two Variants of *Frankia* sp. Strain Cpl1, the First Frankia Strain Isolated from Root Nodules of Comptonia peregrina", 2016, [online] [retrieved Jun. 13, 2023] Found at https://rest.uniprot.org/uniprotkb/A0A0D8BN56.txt?version=12.
Office Action issued in Eurasian Patent Application No. 202191582 on Jun. 13, 2023, 16 pages.
"Uncharacterized protein from Saprolegnia parasitica", ID : A0A067BQW3_SAPPC, Uniprot,: https://rest.uniprot.org/unisave/A0A067BQW3?format=txt&versions=1; Sep. 3, 2014.
"AsnC family protein from Sedimentitalea nanhaiensis", ID: A0A1I7CZR5_9RHOB, Uniprot,: https://rest.uniprot.org/unisave/A0A1I7CZR5?format=txt&versions=3; Jun. 7, 2017.
Russian Office Action issued on Dec. 21, 2022 in RU Application No. 2020106752, 20 pages.
Japanese Office Action issued on Sep. 20, 2022 in JP Application No. 2021-016630, 7 pages.
Khantasup et al., "Design and Generation of Humanized Single-chain Fv Derived from Mouse Hybridoma for Potential Targeting Application", Monoclon. Antib. Immunodiagn. Immunother. (2015) 34(6):404-417.
Liu et al., "Targeting of Tumor Cells by Cell Surface Urokinase Plasminogen Activator dependent Anthrax Toxin", J. Biol. Chem. (2001) 276(21):17976-17984.
Canadian Office Action for corresponding Canadian Application No. 3,120,327 dated Jan. 23, 2024. (3 pages).

* cited by examiner

MATRIX METALLOPROTEASE-CLEAVABLE AND SERINE OR CYSTEINE PROTEASE-CLEAVABLE SUBSTRATES AND METHODS OF USE THEREOF

CROSS-REFERENCE TO RELATED APPLICATIONS

This application claims the benefit of U.S. Provisional Application Nos. 62/776,409, filed Dec. 6, 2018, and 62/778,062, filed Dec. 11, 2018, the contents of which are incorporated herein by reference in their entireties.

The "Sequence Listing" submitted electronically concurrently herewith pursuant to 37 C.F.R. § 1.821 in computer readable form (CFR) via EFS-Web as file name "CYTX_058_US_ORD_081720_ST25.txt" is incorporated herein by reference. The electronic copy of the Sequence Listing was created on Aug. 17, 2020, and the disk size is 173,481 bytes.

FIELD OF THE INVENTION

The invention relates generally to polypeptides that include at least a first cleavable moiety (CM1) that is a substrate for at least one matrix metalloprotease (MMP) and at least a second cleavable moiety (CM2) that is a substrate for at least one serine protease (SP) and/or at least one cysteine protease (CP), to activatable antibodies and other larger molecules that include these polypeptides that include at least a CM1 that is a substrate for at least one MMP protease and a CM2 that is a substrate for at least one SP protease and/or at least one CP protease, and to methods of making and using these polypeptides that include at least a CM1 that is a substrate for at least one MMP protease and a CM2 that is a substrate for at least one SP protease and/or at least one CP protease in a variety of therapeutic, diagnostic and prophylactic indications.

BACKGROUND OF THE INVENTION

Proteases are enzymes that degrade proteins by cleaving the peptide bonds between amino acid residues. Proteases occur naturally in all organisms and are involved in a variety of physiological reactions from simple degradation to highly regulated pathways. Some proteases are known to break specific peptide bonds based on the presence of a particular amino acid sequence within a protein.

Accordingly, there exists a need to identify new substrates for proteases and to use these substrates in a variety of therapeutic, diagnostic and prophylactic indications.

SUMMARY OF THE INVENTION

In an aspect of the present invention, provided herein is an isolated polypeptide comprising a tandem substrate, wherein the tandem substrate comprises at least a first cleavable moiety (CM1) that is a substrate for at least one matrix metalloprotease (MMP) and at least a second cleavable moiety (CM2) that is a substrate for at least one serine protease (SP) or cysteine protease (CP), wherein CM1 comprises the amino acid sequence AHGL or PRQV, and wherein the N-terminal to C-terminal arrangement of the tandem substrate is CM1-CM2 or CM2-CM1. In some embodiments, the CM1 of the isolated polypeptide comprises an amino acid sequence that is selected from the group consisting of ALAHGLF (SEQ ID NO: 1), ALAHGL (SEQ ID NO: 52), LAHGLF (SEQ ID NO: 50), LAHGL (SEQ ID NO: 53), and AHGLF (SEQ ID NO: 51). In some embodiments, the CM1 of the isolated polypeptide comprises an amino acid sequence that is selected from the group consisting of HVPRQV (SEQ ID NO: 8) and VPRQV (SEQ ID NO: 60). In some embodiments, the isolated polypeptide of the present disclosure comprises a CM1 and CM2 that are linked via a linking peptide. In some embodiments, the CM1 and CM2 of the isolated polypeptide are directly linked to each other. In some embodiments, the isolated polypeptide of the present disclosure comprises a CM2 that comprises a substrate for a CP enzyme, and wherein the CP enzyme is a legumain. In some embodiments, the isolated polypeptide of the present disclosure comprises a CM2 that comprises a substrate for a SP enzyme selected from the group consisting of a urokinase, a matriptase, and a neutrophil elastase. In some embodiments, the isolated polypeptide of present disclosure includes a CM2 that comprises a substrate for a SP enzyme selected from the group consisting of a urokinase, a matriptase, and a neutrophil elastase and a substrate for a CP enzyme, and wherein the CP enzyme is a legumain. In some embodiments, the isolated polypeptide of the present disclosure comprises a CM1 that comprises a substrate for a MMP enzyme selected from the group consisting of MMP2, MMP9, or MMP14.

In some embodiments, the isolated polypeptide of the present disclosure includes a CM2 that comprises an amino acid sequence selected from the group consisting of SGR, LSGR (SEQ ID NO: 73), ARG, PRS, TFVH (SEQ ID NO: 141), AAN, SAN, and GPTN (SEQ ID NO: 152). In some embodiments, the isolated polypeptide of the present disclosure includes a CM2 that comprises an amino acid sequence selected from the group consisting of SGR, LSGR (SEQ ID NO: 73), LSGRS (SEQ ID NO: 72), LSGRSD (SEQ ID NO: 71), LSGRSA(SEQ ID NO: 110), LSGRSDN (SEQ ID NO: 70), LSGRSAN (SEQ ID NO: 109), LSGRSDNH (SEQ ID NO: 20), LSGRSGNH (SEQ ID NO: 78), LSGRSDNP (SEQ ID NO: 90), LSGRSDNI (SEQ ID NO: 84), LSGRSANI (SEQ ID NO: 108), LSGRSANP (SEQ ID NO: 114), LSGRSDYH (SEQ ID NO: 86), LSGRSDTH (SEQ ID NO: 92), LSGRSDQH (SEQ ID NO: 96), LSGRSDIH (SEQ ID NO: 100), and LSGRSDDH (SEQ ID NO: 104). In some embodiments, the isolated polypeptide of the present disclosure includes a CM2 that comprises an amino acid sequence selected from the group consisting of ARGP (SEQ ID NO: 128), TARG (SEQ ID NO: 125), and TARGP (SEQ ID NO: 124). In some embodiments, the isolated polypeptide of the present disclosure includes a CM2 that comprises an amino acid sequence selected from the group consisting of APRS (SEQ ID NO: 131), APRSF (SEQ ID NO: 130), and PRSF (SEQ ID NO: 132). In some embodiments, the isolated polypeptide of the present disclosure includes a CM2 that comprises an amino acid sequence selected from the group consisting of GLPTFVHL (SEQ ID NO: 135), GLPTFVH (SEQ ID NO: 136), GLPTFV (SEQ ID NO: 137), LPTFVHL (SEQ ID NO: 138), LPTFVH (SEQ ID NO: 139), and LPTFV (SEQ ID NO: 140). In some embodiments, the isolated polypeptide of the present disclosure includes a CM2 that comprises an amino acid sequence selected from the group consisting of AAN, SAN, and GPTN (SEQ ID NO: 152). In some embodiments, the isolated polypeptide of the present disclosure includes a CM2 that comprises an amino acid sequence selected from the group consisting of AAN, SAN, and GPTN (SEQ ID NO: 152); and an amino acid sequence selected from the group consisting of SGR, LSGR (SEQ ID NO: 73), LSGRS (SEQ ID NO: 72), LSGRSD (SEQ ID NO: 71), LSGRSA(SEQ ID NO: 110), LSGRSDN (SEQ ID NO:

70), LSGRSAN (SEQ ID NO: 109), LSGRSDNH (SEQ ID NO: 20), LSGRSGNH (SEQ ID NO: 78), LSGRSDNP (SEQ ID NO: 90), LSGRSDNI (SEQ ID NO: 84), LSGRSANI (SEQ ID NO: 108), LSGRSANP (SEQ ID NO: 114), LSGRSDYH (SEQ ID NO: 86), LSGRSDTH (SEQ ID NO: 92), LSGRSDQH (SEQ ID NO: 96), LSGRSDIH (SEQ ID NO: 100), and LSGRSDDH (SEQ ID NO: 104).

In some embodiments, the isolated polypeptide of the present disclosure has the N-terminal to C-terminal arrangement of the tandem substrate is CM1-CM2. In some embodiments, the isolated polypeptide of the present disclosure has the N-terminal to C-terminal arrangement of the tandem substrate is CM2-CM1.

In some embodiments, the isolated polypeptide of the present disclosure has the cleavability of the CM1 first cleavable moiety by MMP9 and MMP14 that are each at least 80%. In some embodiments, the isolated polypeptide of the present disclosure has the cleavability of the CM1 first cleavable moiety by MMP9 and MMP14 that are each at least 85%. In some embodiments, the isolated polypeptide of the present disclosure has the cleavability of the CM1 first cleavable moiety by MMP9 and MMP14 that are each at least 90%.

In some embodiments, the isolated polypeptide of the present disclosure has the in vivo stability of the CM1 first cleavable moiety is less than 30% activation. In some embodiments, the isolated polypeptide of the present disclosure has the in vivo stability of the CM1 first cleavable moiety is less than 25% activation.

In some embodiments, the isolated polypeptide of the present disclosure has the cleavability of the tandem substrate by MMP9 and MMP14 that are each at least 30%. In some embodiments, the isolated polypeptide of the present disclosure has the cleavability of the tandem substrate by MMP9 and MMP14 that are each at least 50%. In some embodiments, the isolated polypeptide of the present disclosure has the cleavability of the tandem substrate by MMP9 and MMP14 that are each at least 70%.

In some embodiments, the isolated polypeptide of the present disclosure has the cleavability of the tandem substrate by MMP9 and MMP14 that are each at least 15% and the cleavability of the tandem substrate by matriptase is at least 30%. In some embodiments, the isolated polypeptide of the present disclosure has the cleavability of the tandem substrate by MMP9 and MMP14 that are each at least 30% and the cleavability of the tandem substrate by matriptase is at least 30%. In some embodiments, the isolated polypeptide of the present disclosure has the cleavability of the tandem substrate by MMP9 and MMP14 that are each at least 50% and the cleavability of the tandem substrate by matriptase is at least 50%. In some embodiments, the isolated polypeptide of the present disclosure has the cleavability of the tandem substrate by MMP9 and MMP14 that are each at least 70% and the cleavability of the tandem substrate by matriptase is at least 70%.

In some embodiments, the isolated polypeptide of the present disclosure has a tandem substrate with the in vivo stability of less than 40% activation. In some embodiments, the isolated polypeptide of the present disclosure has a tandem substrate with the in vivo stability of less than 30% activation. In some embodiments, the isolated polypeptide of the present disclosure has a tandem substrate with the in vivo stability of less than 25% activation. In some embodiments, the isolated polypeptide of the present disclosure has a tandem substrate with the in vivo stability of less than 20% activation.

In some embodiments, the isolated polypeptide of the present disclosure comprises the tandem substrate comprising an amino acid sequence selected from the group consisting of SEQ ID NOs: 25-43. In some embodiments, the isolated polypeptide of the present disclosure comprises the tandem substrate comprising an amino acid sequence selected from the group consisting of SEQ ID NOs: 25, 26, 29, 31, 32, 34, 36, and 37. In some embodiments, the isolated polypeptide of the present disclosure comprises the tandem substrate comprising an amino acid sequence selected from the group consisting of SEQ ID NOs: 27, 28, 30, 33, and 35. In some embodiments, the isolated polypeptide of the present disclosure comprises the tandem substrate comprising an amino acid sequence selected from the group consisting of SEQ ID NOs: 25, 29, 31, 36, and 37. In some embodiments, the isolated polypeptide of the present disclosure comprises the tandem substrate comprising an amino acid sequence selected from the group consisting of SEQ ID NOs: 26, 32, and 34. In some embodiments, the isolated polypeptide of the present disclosure comprises the tandem substrate comprising an amino acid sequence selected from the group consisting of SEQ ID NOs: 27, 28, and 33. In some embodiments, the isolated polypeptide of the present disclosure comprises the tandem substrate comprising an amino acid sequence selected from the group consisting of SEQ ID NOs: 30 and 35.

In some embodiments, provided herein is an isolated polypeptide of the present disclosure that comprises an antibody or antigen binding fragment thereof (AB) that specifically binds a target; at least a first cleavable moiety (CM1) that is a substrate for at least one matrix metalloprotease (MMP); and at least a second cleavable moiety (CM2) that is a substrate for at least one serine protease (SP) or cysteine protease (CP), wherein CM1 comprises the amino acid sequence AHGL or PRQV, and wherein the N-terminal to C-terminal arrangement of the tandem substrate is CM1-CM2 or CM2-CM1. In some embodiments, at least one of the MMP, the CP, and SP are co-localized in a tissue with the target. In some embodiments, the isolated polypeptide of the present disclosure comprises an antigen binding fragment thereof selected from the group consisting of a Fab fragment, a $F(ab')_2$ fragment, a scFv, a scAb, a dAb, a single domain heavy chain antibody, and a single domain light chain antibody. In some embodiments, the isolated polypeptide of the present disclosure comprises an AB that is linked to the CM1. In some embodiments, the isolated polypeptide of the present disclosure comprises an AB that is linked directly to the CM1. In some embodiments, the isolated polypeptide of the present disclosure comprises an AB that is linked to the CM1 via a linking peptide. In some embodiments, the isolated polypeptide of the present disclosure comprises an AB that is linked to the CM2. In some embodiments, the isolated polypeptide of the present disclosure comprises an AB that is linked directly to the CM2. In some embodiments, the isolated polypeptide of the present disclosure comprises an AB that is linked to the CM2 via a linking peptide. In some embodiments, the isolated polypeptide of the present disclosure comprises an AB that comprises a light chain variable region of an antibody or antigen binding fragment thereof, and wherein the CM1 or the CM2 is linked to the N-terminus of the light chain variable region of the AB. In some embodiments, the isolated polypeptide of the present disclosure comprises an AB that comprises a heavy chain variable region of an antibody or antigen binding fragment thereof, and wherein the CM1 or the CM2 is linked to the N-terminus of the heavy chain variable region of the AB.

In some embodiments, the isolated polypeptide of the present disclosure comprises a masking moiety (MM). In some embodiments, the isolated polypeptide of the present disclosure comprises a MM that has a dissociation constant for binding to the AB that is greater than the dissociation constant of the AB for binding to the target. In some embodiments, the isolated polypeptide of the present disclosure comprises a MM that is a polypeptide of no more than 40 amino acids in length. In some embodiments, the isolated polypeptide of the present disclosure comprises a MM that is linked to the CM1 such that the isolated polypeptide in an uncleaved state comprises the structural arrangement from N-terminus to C-terminus as follows: MM-CM1-CM2-AB or AB-CM2-CM1-MM. In some embodiments, the isolated polypeptide of the present disclosure comprises a linking peptide between the MM and the CM1. In some embodiments, the isolated polypeptide of the present disclosure comprises a linking peptide between the CM2 and the AB. In some embodiments, the isolated polypeptide of the present disclosure comprises a linking peptide between the MM and the CM1 and a linking peptide between the CM2 and the AB. In some embodiments, the isolated polypeptide of the present disclosure comprises a MM that is linked to the CM1 such that the isolated polypeptide in an uncleaved state comprises the structural arrangement from N-terminus to C-terminus as follows: MM-CM2-CM1-AB or AB-CM1-CM2-MM. In some embodiments, the isolated polypeptide of the present disclosure comprises a linking peptide between the MM and the CM2. In some embodiments, the isolated polypeptide of the present disclosure comprises a linking peptide between the CM1 and the AB. In some embodiments, the isolated polypeptide of the present disclosure comprises a linking peptide between the MM and the CM2 and a linking peptide between the CM1 and the AB.

In some embodiments, the isolated polypeptide of the present disclosure comprises a first linking peptide (LP1) and a second linking peptide (LP2), and wherein the isolated polypeptide has the structural arrangement from N-terminus to C-terminus as follows in the uncleaved state: MM-LP1-CM1-CM2-LP2-AB, AB-LP2-CM2-CM1-LP1-MM, MM-LP1-CM2-CM1-LP2-AB, or AB-LP2-CM1-CM2-LP1-MM. In some embodiments, the two linking peptides are not identical to each other. In some embodiments, each of LP1 and LP2 is a peptide of about 1 to 20 amino acids in length. In some embodiments, the isolated polypeptide comprises a third linking peptide (LP') between CM1 and CM2. In some embodiments, the isolated polypeptide of the present disclosure comprises an AB that comprises a light chain variable region of an antibody or antigen binding fragment thereof, and wherein the LP2 is linked to the N-terminus of the light chain variable region of the AB. In some embodiments, the isolated polypeptide of the present disclosure comprises an AB that comprises a heavy chain variable region of an antibody or antigen binding fragment thereof, and wherein the LP2 is linked to the N-terminus of the heavy chain variable region of the AB.

In some embodiments, the isolated polypeptide of the present disclosure comprises a MM wherein the amino acid sequence of the MM is different from that of the target and is no more than 10% identical to the amino acid sequence of a natural binding partner of the AB. In some embodiments, the isolated polypeptide of the present disclosure comprises a MM that does not interfere or compete with the AB for binding to the target in a cleaved state.

In some embodiments, the isolated polypeptide comprises a light chain amino acid sequence that is selected from the group consisting of SEQ ID NOs: 450-462. In some embodiments, the isolated polypeptide comprises a light chain amino acid sequence that is selected from the group consisting of SEQ ID NOs: 450-462, and a heavy chain amino acid sequence comprising SEQ ID NO: 400.

In another aspect of the present invention, provided herein is an activatable antibody that, in an activated state, specifically binds to a target, comprising an antibody or an antigen binding fragment thereof (AB) that specifically binds to the target, a masking moiety (MM) coupled to the AB, wherein the MM inhibits the binding of the AB to the target when the activatable antibody is in an uncleaved state; and a cleavable moiety (CM) comprising a tandem substrate according to any one of the tandem substrates provided herein. In some embodiments, the activatable antibody includes an MM that has a dissociation constant for binding to the AB that is greater than the dissociation constant of the AB for binding to the target. In some embodiments, the activatable antibody includes an MM that is a polypeptide of no more than 40 amino acids in length. In some embodiments, the activatable antibody includes an antigen binding fragment thereof that is selected from the group consisting of a Fab fragment, a $F(ab')_2$ fragment, a scFv, a scAb, a dAb, a single domain heavy chain antibody, and a single domain light chain antibody. In some embodiments, the activatable antibody includes an MM that has a dissociation constant for binding to the AB that is greater than the dissociation constant of the AB for binding to the target.

In some embodiments, the activatable antibody includes a MM that is linked to the CM1 such that the activatable antibody in an uncleaved state comprises the structural arrangement from N-terminus to C-terminus as follows: MM-CM1-CM2-AB or AB-CM2-CM1-MM. In some embodiments, the activatable antibody comprises a linking peptide between the MM and the CM1. In some embodiments, the activatable antibody comprises a linking peptide between the CM2 and the AB. In some embodiments, the activatable antibody comprises a linking peptide between the MM and the CM1 and a linking peptide between the CM2 and the AB.

In some embodiments, the activatable antibody includes a MM that is linked to the CM1 such that the activatable antibody in an uncleaved state comprises the structural arrangement from N-terminus to C-terminus as follows: MM-CM2-CM1-AB or AB-CM1-CM2-MM. In some embodiments, the activatable antibody comprises a linking peptide between the MM and the CM2. In some embodiments, the activatable antibody comprises a linking peptide between the CM1 and the AB. In some embodiments, the activatable antibody comprises a linking peptide between the MM and the CM2 and a linking peptide between the CM1 and the AB.

In some embodiments, the activatable antibody comprises an AB that comprises a light chain variable region of an antibody or antigen binding fragment thereof, and wherein the CM1 or the CM2 is linked to the N-terminus of the light chain variable region of the AB. In some embodiments, the activatable antibody comprises an AB that comprises a heavy chain variable region of an antibody or antigen binding fragment thereof, and wherein the CM1 or the CM2 is linked to the N-terminus of heavy light chain variable region of the AB.

In some embodiments, the activatable antibody comprises a first linking peptide (LP1) and a second linking peptide (LP2), and wherein the activatable antibody has the structural arrangement from N-terminus to C-terminus as follows in the uncleaved state: MM-LP1-CM1-CM2-LP2-AB, AB-LP2-CM2-CM1-LP1-MM, MM-LP1-CM2-CM1-LP2-AB, or AB-LP2-CM1-CM2-LP1-MM. In some embodiments, the two linking peptides are not identical to each other. In some embodiments, each of LP1 and LP2 is a peptide of about 1 to 20 amino acids in length. In some embodiments, the activatable antibody comprises a third linking peptide (LP') between CM1 and CM2. In some embodiments, the activatable antibody comprises an AB that comprises a light chain variable region of an antibody or antigen binding fragment thereof, and wherein the LP2 is linked to the N-terminus of the light chain variable region of the AB. In some embodiments, the activatable antibody comprises an AB that comprises a heavy chain variable region of an antibody or antigen binding fragment thereof, and wherein the LP2 is linked to the N-terminus of the heavy chain variable region of the AB.

In some embodiments, the activatable antibody comprises a light chain amino acid sequence that is selected from the group consisting of SEQ ID NOs: 450-462. In some embodiments, the activatable antibody comprises a light chain amino acid sequence that is selected from the group consisting of SEQ ID NOs: 450-462, and a heavy chain amino acid sequence comprising SEQ ID NO: 400.

In some embodiments, the activatable antibody comprises a MM that is different from that of the target and is no more than 10% identical to the amino acid sequence of a natural binding partner of the AB. In some embodiments, the activatable antibody comprises a MM that does not interfere or compete with the AB for binding to the target in a cleaved state.

In another aspect of the present invention, provided herein is a conjugated activatable antibody comprising the activatable antibody conjugated to an agent. In some embodiments, the agent is conjugated to the AB via a linker. In some embodiments, the agent is conjugated to the AB via a cleavable linker. In some embodiments, the agent is conjugated to the AB via a non-cleavable linker.

In some embodiments, the conjugated activatable antibody comprises an agent that is a toxin or fragment thereof. In some embodiments, the conjugated activatable antibody comprises an agent that is a microtubule inhibitor. In some embodiments, the conjugated activatable antibody comprises an agent that is a nucleic acid damaging agent. In some embodiments, the conjugated activatable antibody comprises an agent that is a dolastatin or a derivative thereof, an auristatin or a derivative thereof, a maytansinoid or a derivative thereof, a duocarmycin or a derivative thereof, a calicheamicin or a derivative thereof, auristatin E or a derivative thereof, monomethyl auristatin E (MMAE), monomethyl auristatin D (MMAD), or a maytansinoid selected from the group consisting of DM1 and DM4. In some embodiments, the conjugated activatable antibody comprises an agent that is a detectable moiety or a diagnostic agent.

In another aspect of the present invention, provided herein is a pharmaceutical composition comprising an isolated polypeptide of the present disclosure or an activatable antibody of the present disclosure or a conjugated activatable antibody of the present disclosure; and a carrier. In some embodiments, the pharmaceutical composition comprises an additional agent. In some embodiments, the pharmaceutical composition comprises an additional agent, which is a therapeutic agent.

In another aspect of the present invention, provided herein is an isolated nucleic acid molecule encoding the isolated polypeptide of the present disclosure or the activatable antibody of the present disclosure. In some embodiments, a vector comprises the isolated nucleic acid molecule of present disclosure.

In another aspect of the present invention, provided herein is a method of producing an antibody or an activatable antibody by culturing a cell under conditions that lead to expression of the isolated polypeptide of the present disclosure or the activatable antibody of the present disclosure. In another aspect of the present invention, provided herein is a method of manufacturing an activatable antibody that, in an activated state, binds a target, the method comprising: culturing a cell comprising a nucleic acid construct that encodes the activatable antibody of the present disclosure and recovering the activatable antibody.

In another aspect of the present invention, provided herein is a method of treating, alleviating a symptom of, or delaying the progression of a disorder or disease comprising administering to a subject in need thereof a therapeutically effective amount of the isolated polypeptide of the present disclosure or the activatable antibody of the present disclosure or the conjugated activatable antibody of the present disclosure or the pharmaceutical composition of the present disclosure. In some embodiments, the disorder or disease is cancer. In some embodiments, the method comprises administering to the subject an additional agent. In some embodiments, the method comprises administering to the subject an additional therapeutic agent.

BRIEF DESCRIPTION OF THE DRAWINGS

FIGS. 2A and 2B are graphs showing exemplary results of the in vitro binding to EGFR of the indicated anti-EGFR activatable antibodies of the present disclosure. These exemplary results showed that the MMP substrate effected the masking efficiency of the prodomain of the activatable antibody.

These exemplary results showed that activatable antibodies with certain MMP substrates of the present disclosure showed efficacy in this xenograft model that was comparable to unmasked anti-EGFR cetuximab antibody.

Figure 7:
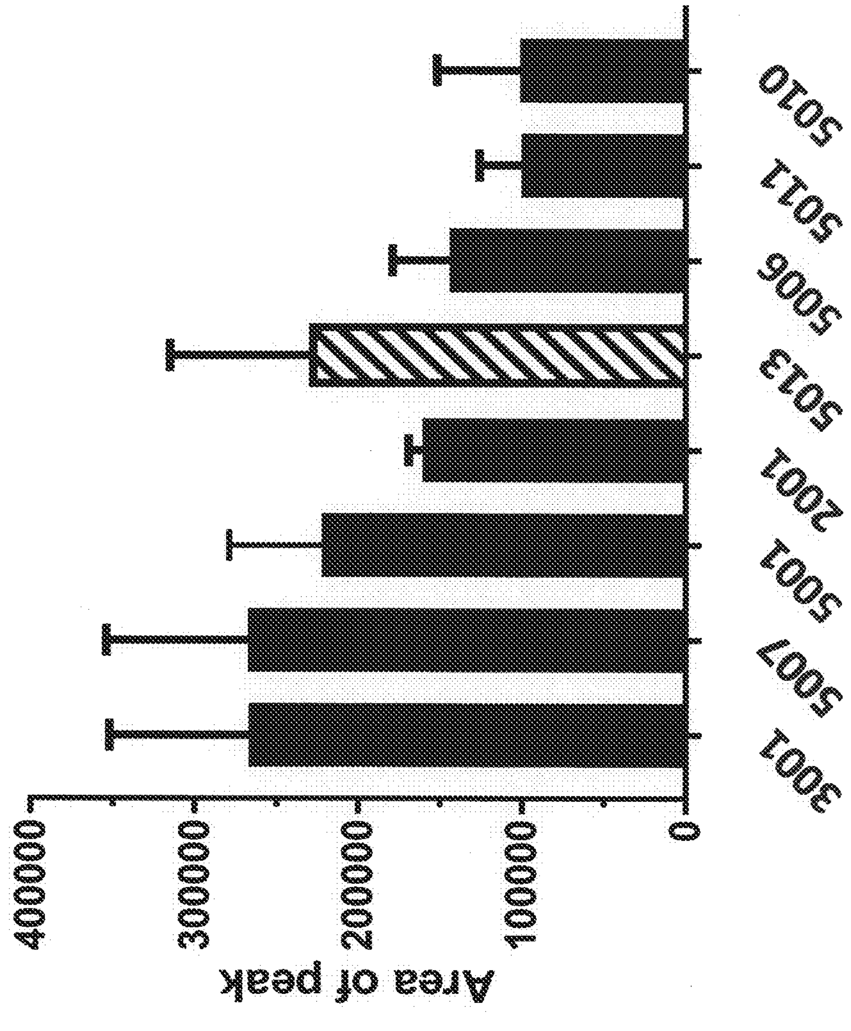

FIG. 7 is a graph showing exemplary results of the percent of the indicated activatable anti-EGFR antibodies of the present disclosure that were activated within intra-tumoral tissue following administration to a mouse H292 xenograft model.

Figure 8:
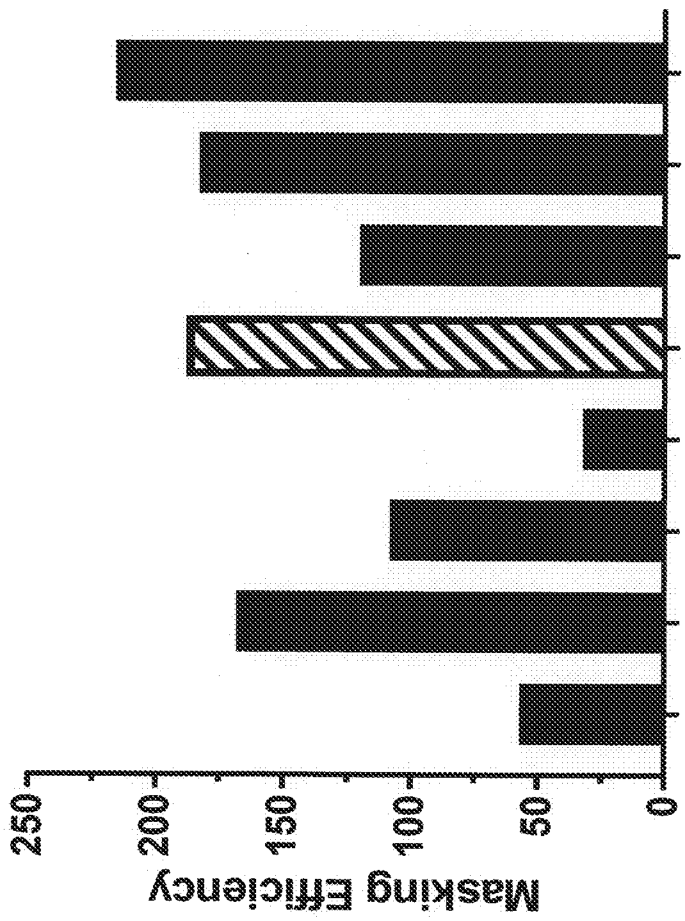

FIG. 8 is a graph showing exemplary results of the calculated masking efficiency calculated from the in vitro binding to EGFR of the indicated anti-EGFR activatable antibodies of the present disclosure. These exemplary results showed that the tandem substrates effected the masking efficiency of the prodomain of the activatable antibody.

Figure 9:
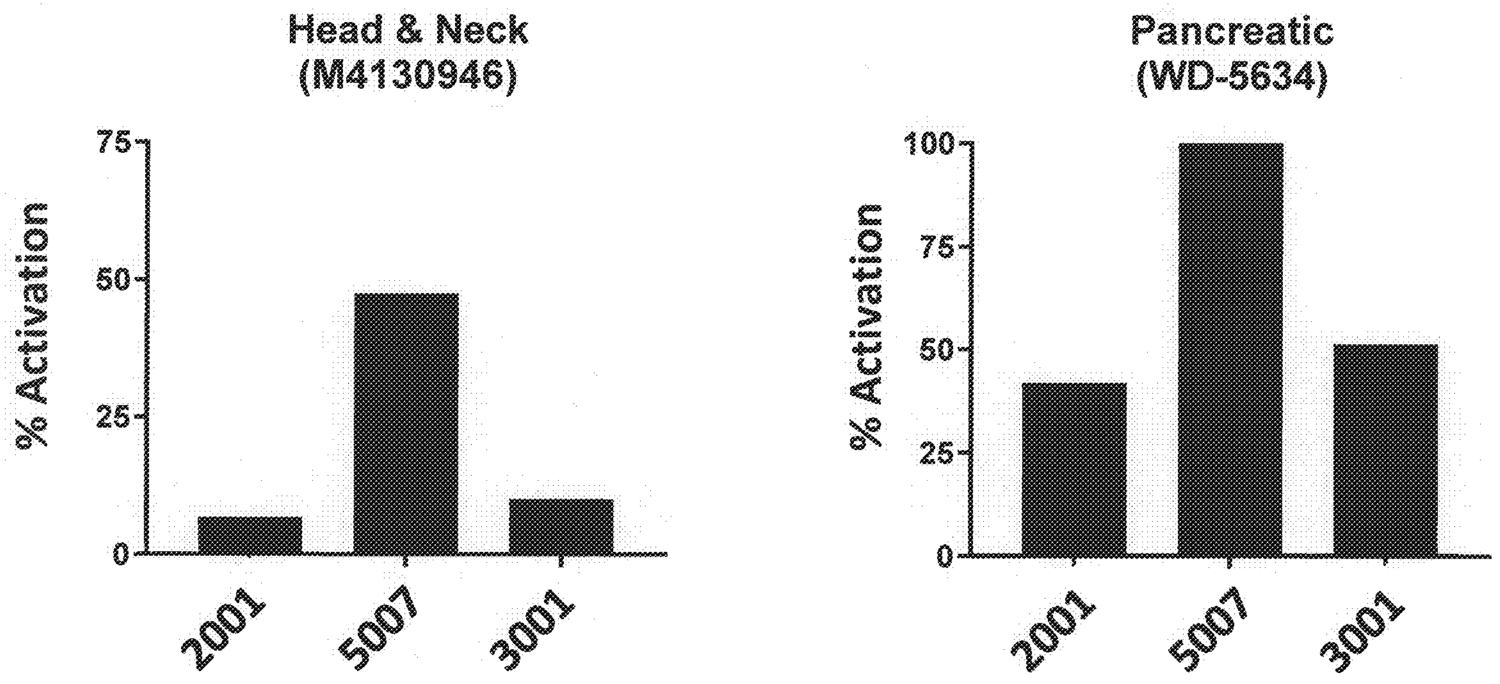

FIG. 9 is a graph showing exemplary results of the percent of the indicated activatable anti-EGFR antibodies of the present disclosure that were activated following incubation with human tumor tissue.

DETAILED DESCRIPTION OF THE INVENTION

The present disclosure provides amino acid sequences that include at least a first cleavable moiety (CM1) that is a substrate for at least one matrix metalloprotease (MMP) and at least a second cleavable moiety (CM2) that is a substrate for at least one serine protease (SP) and/or at least one cysteine protease (CP). These amino acid sequences are collectively referred to herein as “tandem substrates.” This term is not intended to convey any requirement regarding the orientation or other structural arrangement of the first cleavable moiety (CM1) that is a substrate for at least one matrix metalloprotease (MMP) and at least a second cleavable moiety (CM2) that is a substrate for at least one serine protease (SP) and/or at least one cysteine protease (CP). Thus, the term “tandem substrates” encompasses CM1-CM2 substrates having the structural arrangement from N-terminus to C-terminus as follows: CM1-CM2 or CM2-CM1. The term “tandem substrates” also encompasses substrates where at least a portion of the CM1 sequence overlaps with at least a portion of the CM2 sequence.

In some embodiments, CM2 includes at least two substrates. In some embodiments, CM2 includes a substrate for a first serine protease and a substrate for a second serine protease. In some embodiments, CM2 includes a substrate for a serine protease and a substrate for a cysteine protease.

The CM1-CM2 substrates described herein are useful in a variety of therapeutic, diagnostic and prophylactic indications. For example, these CM1-CM2 substrates are useful in activatable antibodies that include antibodies or antigen-binding fragments thereof (AB) that includes a prodomain. The prodomain includes at least one masking moiety (MM) linked to at least one antigen- or epitope-binding domain of the AB such that coupling of the MM reduces the ability of the AB to bind its target.

In some embodiments, the activatable antibody includes at least a first CM (CM1) and a second CM (CM2). In some embodiments, at least a portion of the CM1 substrate sequence overlaps with at least a portion of the CM2 sequence. In some embodiments, the CM1 substrate sequence and the CM2 substrate sequence share at least one amino acid residue in common. In some embodiments, the CM1 substrate sequence and the CM2 substrate sequence share at least two amino acid residues in common. In some embodiments, the CM1 substrate sequence and the CM2 substrate sequence share at least three amino acid residues in common. In some embodiments, the CM1 substrate sequence and the CM2 substrate sequence share three or more amino acid residues in common.

In some embodiments, CM1 and CM2 are separate polypeptides that are operably linked together.

In some embodiments, CM1 and CM2 are separate polypeptides that are directly linked together, i.e., the N-terminus of one substrate is linked directly to the C-terminus of the other substrate polypeptide. In some embodiments, the N-terminus of the CM1 is linked directly to the C-terminus of the CM2. In some embodiments, the N-terminus of the CM2 is linked directly to the C-terminus of the CM1.

In some embodiments, CM1 and CM2 are separate polypeptides that are operably linked together via at least one linking moiety.

In some embodiments, the first cleavable moiety CM1 and the second cleavable moiety CM2 in the activatable antibody in the uncleaved state have the structural arrangement from N-terminus to C-terminus as follows: MM-CM1-CM2-AB, AB-CM2-CM1-MM, MM-CM2-CM1-AB, or AB-CM1-CM2-MM.

In some embodiments, the activatable antibody includes a linking peptide (LP') between CM1 and CM2. In some embodiments, the activatable antibody includes a linking peptide (LP'') between the masking moiety (MM) and CM1. In some embodiments, the activatable antibody includes a linking peptide (LP''') between CM2 and AB. In some embodiments, the activatable antibody includes a linking peptide (LP'') between the MM and CM1 and a linking peptide (LP''') between CM2 and AB. In some embodiments, the activatable antibody includes a linking peptide between the MM and CM1 (LP'') and a linking peptide between CM1 and CM2 (LP'). In some embodiments, the activatable antibody includes a linking peptide (LP') between CM1 and CM2 and a linking peptide (LP''') between CM2 and AB. In some embodiments, the activatable antibody includes a linking peptide (LP'') between the MM and CM1, a linking peptide (LP') between CM1 and CM2, and a linking peptide (LP''') between CM2 and AB.

In some embodiments, the activatable antibody includes a linking peptide (LP') between CM1 and CM2. In some embodiments, the activatable antibody includes a linking peptide (LP'') between the AB and CM1. In some embodiments, the activatable antibody includes a linking peptide (LP''') between CM2 and the masking moiety (MM). In some embodiments, the activatable antibody includes a linking peptide (LP'') between the AB and CM1 and a linking peptide (LP''') between CM2 and MM. In some embodiments, the activatable antibody includes a linking peptide between the AB and CM1 (LP'') and a linking peptide between CM1 and CM2 (LP'). In some embodiments, the activatable antibody includes a linking peptide (LP') between CM1 and CM2 and a linking peptide (LP''') between CM2 and MM. In some embodiments, the activatable antibody includes a linking peptide (LP'') between the AB and CM1, a linking peptide (LP') between CM1 and CM2, and a linking peptide (LP''') between CM2 and MM.

In some embodiments, LP' is GG. In some embodiments, LP' is GGSGGS (SEQ ID NO: 218).

In some embodiments, CM1 is a substrate for at least one matrix metalloprotease (MMP). Examples of MMPs include MMP1; MMP2; MMP3; MMP7; MMP8; MMP9; MMP10; MMP11; MMP12; MMP13; MMP14; MMP15; MMP16; MMP17; MMP19; MMP20; MMP23; MMP24; MMP26; and MMP27.

In some embodiments, CM1 is a substrate for MMP2, MMP9, MMP14, MMP1, MMP3, MMP13, MMP17, MMP11, and/or MMP19. In some embodiments, CM1 is a substrate for MMP2. In some embodiments, CM1 is a substrate for MMP9. In some embodiments, CM1 is a substrate for MMP14. In some embodiments, CM1 is a substrate for two or more MMPs. In some embodiments, CM1 is a substrate for at least MMP9 and MMP14. In some embodiments, CM1 is a substrate for at least MMP2 and MMP9. In some embodiments, CM1 is a substrate for at least MMP2 and MMP14. In some embodiments, CM1 is a substrate for three or more MMPs. In some embodiments, CM1 is a substrate for at least MMP2, MMP9, and MMP14. In some embodiments, the CM1 comprises two or more substrates for the same MMP. In some embodiments, the CM1 comprises at least two or more MMP2 substrates. In some embodiments, the CM1 comprises at least two or more MMP9 substrates. In some embodiments, the CM1 comprises at least two or more MMP14 substrates.

In some embodiments, CM1 is a substrate for an MMP and includes at least the sequence ALAHGLF (SEQ ID NO: 1); DLAHPLL (SEQ ID NO: 2); AFRHLR (SEQ ID NO: 3); PHGFFQ (SEQ ID NO: 4); SVHHLI (SEQ ID NO: 5); RGPKLYW (SEQ ID NO: 6); RFPYGVW (SEQ ID NO: 7); HVPRQV (SEQ ID NO: 8); SNPFKY (SEQ ID NO: 9); RFPLKV (SEQ ID NO: 10); PFHLSR (SEQ ID NO: 11); STVFHM (SEQ ID NO: 12); MGPWFM (SEQ ID NO: 13); RHLAKL (SEQ ID NO: 14); PLGVRGK (SEQ ID NO: 15); and QNQALRIA (SEQ ID NO: 16).

In some embodiments, the CM1 comprises the amino acid sequence ALAHGLF (SEQ ID NO: 1). In some embodiments, the CM1 comprises the amino acid sequence DLAHPLL (SEQ ID NO: 2). In some embodiments, the CM1 comprises the amino acid sequence AFRHLR (SEQ ID NO: 3). In some embodiments, the CM1 comprises the amino acid sequence PHGFFQ (SEQ ID NO: 4). In some embodiments, the CM1 comprises the amino acid sequence SVHHLI (SEQ ID NO: 5). In some embodiments, the CM1 comprises the amino acid sequence RGPKLYW (SEQ ID NO: 6). In some embodiments, the CM1 comprises the amino acid sequence RFPYGVW (SEQ ID NO: 7). In some embodiments, the CM1 comprises the amino acid sequence HVPRQV (SEQ ID NO: 8). In some embodiments, the CM1 comprises the amino acid sequence SNPFKY (SEQ ID NO: 9). In some embodiments, the CM1 comprises the amino acid sequence RFPLKV (SEQ ID NO: 10). In some embodiments, the CM1 comprises the amino acid sequence PFHLSR (SEQ ID NO: 11). In some embodiments, the CM1 comprises the amino acid sequence STVFHM (SEQ ID NO: 12). In some embodiments, the CM1 comprises the amino acid sequence MGPWFM (SEQ ID NO: 13). In some embodiments, the CM1 comprises the amino acid sequence RHLAKL (SEQ ID NO: 14). In some embodiments, the CM1 comprises the amino acid sequence PLGVRGK (SEQ ID NO: 15). In some embodiments, the CM1 comprises the amino acid sequence QNQALRIA (SEQ ID NO: 16).

In some embodiments, CM1 comprises the amino acid sequence LAHGLF (SEQ ID NO: 50). In some embodiments, CM1 comprises the amino acid sequence AHGLF (SEQ ID NO: 51). In some embodiments, CM1 comprises the amino acid sequence ALAHGL (SEQ ID NO: 52). In some embodiments, CM1 comprises the amino acid sequence LAHGL (SEQ ID NO: 53). In some embodiments, CM1 comprises the amino acid sequence AHGL (SEQ ID NO: 54). In some embodiments, CM1 comprises the amino acid sequence ALAHG (SEQ ID NO: 55). In some embodiments, CM1 comprises the amino acid sequence LAHG (SEQ ID NO: 56). In some embodiments, CM1 comprises the amino acid sequence AHG.

In some embodiments, CM1 comprises the amino acid sequence VPRQV (SEQ ID NO: 60). In some embodiments, CM1 comprises the amino acid sequence PRQV (SEQ ID NO: 61). In some embodiments, CM1 comprises the amino acid sequence HVPRQ (SEQ ID NO: 62). In some embodiments, CM1 comprises the amino acid sequence VPRQ (SEQ ID NO: 63). In some embodiments, CM1 comprises the amino acid sequence PRQ.

In some embodiments, CM2 is a substrate for at least one serine protease (SP). In some embodiments, the SP is selected from u-type plasminogen activator (uPA, also referred to as urokinase), matriptase (also referred to herein as MT-SP1 or MTSP1), neutrophil elastase (e.g., human neutrophil elastase), and combinations thereof. Examples of other SP that cleave a CM2 described herein include, by way of non-limiting example, activated protein C; Cathepsin A; Cathepsin G; Chymase; a coagulation factor protease such as, e.g., FVIIa, FIXa, FXa, FXIa, FXIIa; Elastase; Granzyme B; Guanidinobenzoatase; HtrAl; Lactoferrin; Marapsin; NS3/4A; PACE4; Plasmin; PSA; tPA; Thrombin; Tryptase; a Type II Transmembrane Serine Protease (TTSP) such as, e.g., DESC1, DPP-4, FAP, Hepsin, Matriptase-2, TMPRSS2, TMPRSS3, and/or TMPRSS4.

For example, suitable CM2 are cleaved by at least one serine protease and may include at least one sequence selected from the following amino acid sequences: LSGRSDNH (SEQ ID NO: 20), LSGRSDN (SEQ ID NO: 70), LSGRSD (SEQ ID NO: 71), LSGRS (SEQ ID NO: 72), LSGR (SEQ ID NO: 73), SGRSDN (SEQ ID NO: 74), SGRSD (SEQ ID NO: 75), SGRS (SEQ ID NO: 76), SGR, LSGRSGNH (SEQ ID NO: 78), LSGRSGN (SEQ ID NO: 79), LSGRSG (SEQ ID NO: 80), SGRSGNH (SEQ ID NO: 81), SGRSGN (SEQ ID NO: 82), SGRSG (SEQ ID NO: 83), LSGRSDNI (SEQ ID NO: 84), SGRSDNI (SEQ ID NO: 85), LSGRSDYH (SEQ ID NO: 86), LSGRSDY (SEQ ID NO: 87), SGRSDYH (SEQ ID NO: 88), SGRSDY (SEQ ID NO: 89), LSGRSDNP (SEQ ID NO: 90), SGRSDNP (SEQ ID NO: 91), LSGRSDTH (SEQ ID NO: 92), LSGRSDT (SEQ ID NO: 93), SGRSDTH (SEQ ID NO: 94), SGRSDT (SEQ ID NO: 95), LSGRSDQH (SEQ ID NO: 96), LSGRSDQ (SEQ ID NO: 97), SGRSDQH (SEQ ID NO: 98), SGRSDQ (SEQ ID NO: 99), LSGRSDIH (SEQ ID NO: 100), LSGRSDI (SEQ ID NO: 101), SGRSDIH (SEQ ID NO: 102), SGRSDI (SEQ ID NO: 103), LSGRSDDH (SEQ ID NO: 104), LSGRSDD (SEQ ID NO: 105), SGRSDDH (SEQ ID NO: 106), SGRSDD (SEQ ID NO: 107), LSGRSANI (SEQ ID NO: 108), LSGRSAN (SEQ ID NO: 109), LSGRSA (SEQ ID NO: 110), SGRSANI (SEQ ID NO: 111), SGRSAN (SEQ ID NO: 112), SGRSA (SEQ ID NO: 113), LSGRSANP (SEQ ID NO: 114), and SGRSANP (SEQ ID NO: 115).

In some embodiments, suitable CM2 are cleaved by at least one serine protease and may include at least one sequence selected from the following amino acid sequences: TARGPSFK (SEQ ID NO: 120), ARGPSFK (SEQ ID NO: 121), TARGPSF (SEQ ID NO: 122), TARGPS (SEQ ID NO: 123), TARGP (SEQ ID NO: 124), TARG (SEQ ID NO: 125), ARGPSF (SEQ ID NO: 126), ARGPS (SEQ ID NO: 127), ARGP (SEQ ID NO: 128), and ARG.

In some embodiments, suitable CM2 are cleaved by at least one serine protease and may include at least one sequence selected from the following amino acid sequences: APRSF (SEQ ID NO: 130), APRS (SEQ ID NO: 131), and PRSF (SEQ ID NO: 132).

In some embodiments, suitable CM2 are cleaved by at least one serine protease and may include at least one sequence selected from the following amino acid sequences:

GLPTFVHL (SEQ ID NO: 135), GLPTFVH (SEQ ID NO: 136), GLPTFV (SEQ ID NO: 137), LPTFVHL (SEQ ID NO: 138), LPTFVH (SEQ ID NO: 139), and LPTFV (SEQ ID NO: 140).

In some embodiments, CM2 is a substrate for at least one cysteine protease (CP). In some embodiments, the CP is a legumain. In some embodiments, suitable CM2 are cleaved by at least one cysteine protease and may include at least one sequence selected from the following amino acid sequences: AAN, SAN, and GPTN (SEQ ID NO: 152).

In some embodiments, the CM1-CM2 substrate comprises an amino acid sequence selected from the group consisting of: LSGRSALAHGLF (SEQ ID NO: 25), ALAHGLFSGRSAN (SEQ ID NO: 26), HVPRQVLSGRS (SEQ ID NO: 27), HVPRQVLSGRSAN (SEQ ID NO: 28), TARGPALAHGLF (SEQ ID NO: 29), TARGPVPRQV (SEQ ID NO: 30), APRSALAHGLF (SEQ ID NO: 31), ALAHGLFAPRSF (SEQ ID NO: 32), HVPRQVAPRSF (SEQ ID NO: 33), ALAHGLPTFVHL (SEQ ID NO: 34), GLPTFVHLPRQV (SEQ ID NO: 35), AANALAHGLF (SEQ ID NO: 36), GPTNALAHGLF (SEQ ID NO: 37), ISSGLLSGRSNI (SEQ ID NO: 38), AVGLLAPPGGLS-GRSNI (SEQ ID NO: 39), ISSGLLSGRSNIGS (SEQ ID NO: 40), AVGLLAPPGGLSGRSNIGS (SEQ ID NO: 41), ISSGLLSGRSNIG (SEQ ID NO: 42), and AVGLLAPPG-GLSGRSNIG (SEQ ID NO: 43).

In some embodiments, the activatable antibody in the uncleaved state has the structural arrangement from N-terminus to C-terminus as follows: MM-CM1-CM2-AB, AB-CM2-CM1-MM, MM-CM2-CM1-AB, or AB-CM1-CM2-MM.

In some embodiments, the activatable antibody comprises a first linking peptide (LP1) and a second linking peptide (LP2), and the antibody in the uncleaved state has the structural arrangement from N-terminus to C-terminus as follows: MM1-LP1-CM1-CM2-LP2-AB, AB-LP2-CM2-CM1-LP1-MM, MM1-LP1-CM2-CM1-LP2-AB, or AB-LP2-CM1-CM2-LP1-MM. In some embodiments, each of LP1 and LP2 is a peptide of about 1 to 20 amino acids in length. In some embodiments, the two linking peptides need not be identical to each other.

In some embodiments, the activatable antibody includes a linking peptide (LP') between CM1 and CM2. In some embodiments, the activatable antibody includes a linking peptide (LP1) between the masking moiety (MM) and CM1. In some embodiments, the activatable antibody includes a linking peptide (LP2) between CM2 and AB. In some embodiments, the activatable antibody includes a linking peptide (LP1) between the MM and CM1 and a linking peptide (LP2) between CM2 and AB. In some embodiments, the activatable antibody includes a linking peptide between the MM and CM1 (LP1) and a linking peptide between CM1 and CM2 (LP'). In some embodiments, the activatable antibody includes a linking peptide (LP') between CM1 and CM2 and a linking peptide (LP2) between CM2 and AB. In some embodiments, the activatable antibody includes a linking peptide (LP1) between the MM and CM1, a linking peptide (LP') between CM1 and CM2, and a linking peptide (LP2) between CM2 and AB.

In some embodiments, the activatable antibody includes a linking peptide (LP') between CM1 and CM2. In some embodiments, the activatable antibody includes a linking peptide (LP1) between the AB and CM1. In some embodiments, the activatable antibody includes a linking peptide (LP2) between CM2 and the masking moiety (MM). In some embodiments, the activatable antibody includes a linking peptide (LP1) between the AB and CM1 and a linking peptide (LP2) between CM2 and MM. In some embodiments, the activatable antibody includes a linking peptide between the AB and CM1 (LP1) and a linking peptide between CM1 and CM2 (LP'). In some embodiments, the activatable antibody includes a linking peptide (LP') between CM1 and CM2 and a linking peptide (LP2) between CM2 and MM. In some embodiments, the activatable antibody includes a linking peptide (LP1) between the AB and CM1, a linking peptide (LP') between CM1 and CM2, and a linking peptide (LP2) between CM2 and MM.

In some embodiments, LP' is GG. In some embodiments, LP' is GGSGGS (SEQ ID NO: 218).

In some embodiments, at least one of LP1 or LP2 comprises an amino acid sequence selected from the group consisting of $(GS)_n$, $(GGS)_n$, $(GSGGS)_n$ (SEQ ID NO: 200) and $(GGGS)_n$ (SEQ ID NO: 201), where n is an integer of at least one.

In some embodiments, at least one of LP1 or LP2 comprises an amino acid sequence selected from the group consisting of GGSG (SEQ ID NO: 202), GGSGG (SEQ ID NO: 203), GSGSG (SEQ ID NO: 204), GSGGG (SEQ ID NO: 205), GGGSG (SEQ ID NO: 206), and GSSSG (SEQ ID NO: 207).

In some embodiments, LP1 comprises the amino acid sequence GSSGGSGGSGGSG (SEQ ID NO: 208), GSSGGSGGSGG (SEQ ID NO: 209), GSSGGSGGSGGS (SEQ ID NO: 210), GSSGGSGGSGGSGGGS (SEQ ID NO: 211), GSSGGSGGSG (SEQ ID NO: 212), or GSSGGSGGSGS (SEQ ID NO: 213), GGGSSGGS (SEQ ID NO: 214), and GSSGGSGGSGGSG (SEQ ID NO: 215).

In some embodiments, LP2 comprises the amino acid sequence GSS, GGS, GGGS (SEQ ID NO: 216), GSSGT (SEQ ID NO: 217) or GSSG (SEQ ID NO: 218). In some embodiments, LP2 comprises the amino acid sequence GGS. In some embodiments, LP2 comprises the amino acid sequence GGGS (SEQ ID NO: 216).

In some embodiments, CM1 is a substrate for an MMP and includes at least the sequence ALAHGLF (SEQ ID NO: 1); DLAHPLL (SEQ ID NO: 2); AFRHLR (SEQ ID NO: 3); PHGFFQ (SEQ ID NO: 4); SVHHLI (SEQ ID NO: 5); RGPKLYW (SEQ ID NO: 6); RFPYGVW (SEQ ID NO: 7); HVPRQV (SEQ ID NO: 8); SNPFKY (SEQ ID NO: 9); RFPLKV (SEQ ID NO: 10); PFHLSR (SEQ ID NO: 11); STVFHM (SEQ ID NO: 12); MGPWFM (SEQ ID NO: 13); RHLAKL (SEQ ID NO: 14); PLGVRGK (SEQ ID NO: 15); and QNQALRIA (SEQ ID NO: 16).

In some embodiments, an isolated polypeptide of the present disclosure or an activatable antibody of the present disclosure comprises an CM1-CM2 substrate and an LP2 linker, wherein the CM1-CM2 comprises an amino acid sequence selected from the group consisting of: LSGR-SALAHGLF (SEQ ID NO: 25), ALAHGLFSGRSAN (SEQ ID NO: 26), HVPRQVLSGRS (SEQ ID NO: 27), HVPRQVLSGRSAN (SEQ ID NO: 28), TARGPALAHGLF (SEQ ID NO: 29), TARGPVPRQV (SEQ ID NO: 30), APRSALAHGLF (SEQ ID NO: 31), ALAHGLFAPRSF (SEQ ID NO: 32), HVPRQVAPRSF (SEQ ID NO: 33), ALAHGLPTFVHL (SEQ ID NO: 34), GLPTFVHLPRQV (SEQ ID NO: 35), AANALAHGLF (SEQ ID NO: 36), GPTNALAHGLF (SEQ ID NO: 37), ISSGLLSGRSNI (SEQ ID NO: 38), and AVGLLAPPGGLSGRSNI (SEQ ID NO: 39), and the LP2 linker comprises GGGS (SEQ ID NO: 216).

In some embodiments, an isolated polypeptide of the present disclosure or an activatable antibody of the present disclosure comprises an CM1-CM2 substrate and an LP2 linker, wherein the CM1-CM2 comprises an amino acid sequence selected from the group consisting of: LSGRSALAHGLF (SEQ ID NO: 25), ALAHGLFSGRSAN (SEQ ID NO: 26), HVPRQVLSGRS (SEQ ID NO: 27), HVPRQVLSGRSAN (SEQ ID NO: 28), TARGPALAHGLF (SEQ ID NO: 29), TARGPVPRQV (SEQ ID NO: 30), APRSALAHGLF (SEQ ID NO: 31), ALAHGLFAPRSF (SEQ ID NO: 32), HVPRQVAPRSF (SEQ ID NO: 33), ALAHGLPTFVHL (SEQ ID NO: 34), GLPTFVHLPRQV (SEQ ID NO: 35), AANALAHGLF (SEQ ID NO: 36), GPTNALAHGLF (SEQ ID NO: 37), ISSGLLSGRSNI (SEQ ID NO: 38), and AVGLLAPPGGLSGRSNI (SEQ ID NO: 39), and the LP2 linker comprises GGS.

In some embodiments, an isolated polypeptide of the present disclosure or an activatable antibody of the present disclosure comprises an CM1-CM2 substrate and an LP2 linker, wherein the CM1-CM2 and LP2 comprises an amino acid sequence selected from the group consisting of: LSGRSALAHGLFGGGS (SEQ ID NO: 226), ALAHGLFSGRSANGGGS (SEQ ID NO: 227), HVPRQVLSGRSGGGS (SEQ ID NO: 228), HVPRQVLSGRSANGGGS (SEQ ID NO: 229), TARGPALAHGLFGGGS (SEQ ID NO: 230), TARGPVPRQVGGGS (SEQ ID NO: 231), APRSALAHGLFGGGS (SEQ ID NO: 232), ALAHGLFAPRSFGGGS (SEQ ID NO: 233), HVPRQVAPRSFGGGS (SEQ ID NO: 234), ALAHGLPTFVHLGGGS (SEQ ID NO: 235), GLPTFVHLPRQVGGGS (SEQ ID NO: 236), AANALAHGLFGGGS (SEQ ID NO: 237), GPTNALAHGLFGGGS (SEQ ID NO: 238), ISSGLLSGRSNIGGGS (SEQ ID NO: 239), and AVGLLAPPGGLSGRSNIGGGS (SEQ ID NO: 240).

In some embodiments, an isolated polypeptide of the present disclosure or an activatable antibody of the present disclosure comprises an CM1-CM2 substrate and an LP2 linker, wherein the CM1-CM2 and LP2 comprises an amino acid sequence selected from the group consisting of: LSGRSALAHGLFGGS (SEQ ID NO: 241), ALAHGLFSGRSANGGS (SEQ ID NO: 242), HVPRQVLSGRSGGS (SEQ ID NO: 243), HVPRQVLSGRSANGGS (SEQ ID NO: 244), TARGPALAHGLFGGS (SEQ ID NO: 245), TARGPVPRQVGGS (SEQ ID NO: 246), APRSALAHGLFGGS (SEQ ID NO: 247), ALAHGLFAPRSFGGS (SEQ ID NO: 248), HVPRQVAPRSFGGS (SEQ ID NO: 249), ALAHGLPTFVHLGGS (SEQ ID NO: 250), GLPTFVHLPRQVGGS (SEQ ID NO: 251), AANALAHGLFGGS (SEQ ID NO: 252), GPTNALAHGLFGGS (SEQ ID NO: 253), ISSGLLSGRSNIGGS (SEQ ID NO: 254), and AVGLLAPPGGLSGRSNIGGS (SEQ ID NO: 255).

In some embodiments, the AB has a dissociation constant of about 100 nM or less for binding to the target.

In some embodiments, the activatable antibody includes an antibody or antigen-binding fragment (AB) thereof that specifically binds a target. In some embodiments, the AB is a full-length antibody. In some embodiments, the AB is an immunologically active fragment. In some embodiments, the AB is an antigen-binding fragment. In some embodiments, the AB is a monoclonal antibody, domain antibody, single chain, Fab fragment, a $F(ab')_2$ fragment, a scFv, a scab, a dAb, a single domain heavy chain antibody, or a single domain light chain antibody. In some embodiments, such an AB is a mouse, other rodent, chimeric, humanized or fully human monoclonal antibody.

In some embodiments, the MMP protease is co-localized with the target in a tissue, and the MMP protease cleaves the CM1 in the antibody when the antibody is exposed to the protease. In some embodiments, the SP protease is co-localized with the target in a tissue, and the SP protease cleaves the CM2 substrate in the antibody when the antibody is exposed to the protease. In some embodiments, the CP protease is co-localized with the target in a tissue, and the CP protease cleaves the CM2 substrate in the antibody when the antibody is exposed to the protease. In some embodiments, the MMP protease and/or the SP protease are co-localized with the target in a tissue, and the MMP protease and/or the SP protease cleave the CM1-CM2 substrate in the antibody when the antibody is exposed to the protease. In some embodiments, the MMP protease and the SP protease are co-localized with the target in a tissue, and at least one of the MMP protease and the SP protease cleave the CM1-CM2 substrate in the antibody when the antibody is exposed to the protease. In some embodiments, the MMP protease and/or the CP protease are co-localized with the target in a tissue, and the MMP protease and/or the CP protease cleave the CM1-CM2 substrate in the antibody when the antibody is exposed to the protease. In some embodiments, the MMP protease and the CP protease are co-localized with the target in a tissue, and at least one of the MMP protease and the CP protease cleave the CM1-CM2 substrate in the antibody when the antibody is exposed to the protease. In some embodiments, the MMP protease and/or the CP protease and/or the SP protease are co-localized with the target in a tissue, and the MMP protease and/or the CP protease and/or the SP protease cleave the CM1-CM2 substrate in the antibody when the antibody is exposed to the protease. In some embodiments, the MMP protease and the CP protease and the SP protease are co-localized with the target in a tissue, and at least one of the MMP protease, the SP protease, and the CP protease cleave the CM1-CM2 substrate in the antibody when the antibody is exposed to the protease.

In some embodiments, each of the CM1 substrate sequence and the CM2 substrate sequence of the CM1-CM2 substrate is independently a polypeptide of up to 15 amino acids in length.

In some embodiments, the CM1 substrate sequence of the CM1-CM2 substrate is a substrate for at least one MMP and comprises a polypeptide sequence that is not substantially identical to any polypeptide sequence, e.g., any animal polypeptide sequence, that is naturally cleaved by the same MMP protease. In some embodiments, the CM1 substrate sequence of the CM1-CM2 substrate is a substrate for at least one MMP and comprises a polypeptide sequence that is not substantially identical to any mammalian polypeptide sequence that is naturally cleaved by the same MMP protease. In some embodiments, the CM1 substrate sequence of the CM1-CM2 substrate is a substrate for at least one MMP and comprises a polypeptide sequence that is not substantially identical to any human polypeptide sequence that is naturally cleaved by the same MMP protease. In some embodiments, the CM1 substrate sequence of the CM1-CM2 substrate is a substrate for at least one MMP and comprises a polypeptide sequence that is no more than 90% or more identical to any polypeptide sequence, e.g., any animal polypeptide sequence, that is naturally cleaved by the same MMP protease. In some embodiments, the CM1 substrate sequence of the CM1-CM2 substrate is a substrate for at least one MMP and comprises a polypeptide sequence that is no more than 90% or more identical to any mammalian polypeptide sequence that is naturally cleaved by the same MMP protease. In some embodiments, the CM1 substrate sequence of the CM1-CM2 substrate is a substrate for at least one MMP and comprises a polypeptide sequence that is no more than 90% or more identical to any human polypeptide sequence that is naturally cleaved by the same MMP protease.

In some embodiments, the CM2 substrate sequence of the CM1-CM2 substrate is a substrate for at least one SP and/or one CP and comprises a polypeptide sequence that is not substantially identical to any polypeptide sequence, e.g., any animal polypeptide sequence, that is naturally cleaved by the same SP protease. In some embodiments, the CM2 substrate sequence of the CM1-CM2 substrate is a substrate for at least one SP and/or one CP and comprises a polypeptide sequence that is not substantially identical to any mammalian polypeptide sequence that is naturally cleaved by the same SP and/or CP protease. In some embodiments, the CM2 substrate sequence of the CM1-CM2 substrate is a substrate for at least one SP and/or one CP and comprises a polypeptide sequence that is not substantially identical to any human polypeptide sequence that is naturally cleaved by the same SP and/or CP protease. In some embodiments, the CM2 substrate sequence of the CM1-CM2 substrate is a substrate for at least one SP and/or one CP and comprises a polypeptide sequence that is no more than 90% or more identical to any polypeptide sequence, e.g., any animal polypeptide sequence, that is naturally cleaved by the same SP and/or CP protease. In some embodiments, the CM2 substrate sequence of the CM1-CM2 substrate is a substrate for at least one SP and/or one CP and comprises a polypeptide sequence that is no more than 90% or more identical to any mammalian polypeptide sequence that is naturally cleaved by the same SP and/or CP protease. In some embodiments, the CM2 substrate sequence of the CM1-CM2 substrate is a substrate for at least one SP and/or one CP and comprises a polypeptide sequence that is no more than 90% or more identical to any human polypeptide sequence that is naturally cleaved by the same SP and/or CP protease.

In some embodiments, the CM1-CM2 substrate of the present disclosure comprises an amino acid sequence selected from the group consisting of SEQ ID NOs: 25-43. In some embodiments, the CM1-CM2 substrate of the present disclosure comprises an amino acid sequence selected from the group consisting of SEQ ID NOs: 25, 26, 29, 31, 32, 34, 36, and 37. In some embodiments, the CM1-CM2 substrate of the present disclosure comprises an amino acid sequence selected from the group consisting of SEQ ID NOs: 27, 28, 30, 33, and 35. In some embodiments, the CM1-CM2 substrate of the present disclosure comprises an amino acid sequence selected from the group consisting of SEQ ID NOs: 25, 29, 31, 36, and 37. In some embodiments, the CM1-CM2 substrate of the present disclosure comprises an amino acid sequence selected from the group consisting of SEQ ID NOs: 26, 32, and 34. In some embodiments, the CM1-CM2 substrate of the present disclosure comprises an amino acid sequence selected from the group consisting of SEQ ID NOs: 27, 28, and 33. In some embodiments, the CM1-CM2 substrate of the present disclosure comprises an amino acid sequence selected from the group consisting of SEQ ID NOs: 30 and 35.

In some embodiments, an activatable antibody of the present disclosure comprises a CM1-CM2 substrate comprising an amino acid sequence selected from the group consisting of SEQ ID NOs: 25-43, as well as an antibody or antigen binding fragment thereof (AB) that binds a target and a masking moiety (MM) that reduces the ability of the antigen- or epitope-binding domain of the AB to bind its target. In some embodiments, an activatable antibody of the present disclosure comprises a CM1-CM2 substrate comprising an amino acid sequence selected from the group consisting of SEQ ID NOs: 25, 26, 29, 31, 32, 34, 36, and 37, as well as an antibody or antigen binding fragment thereof (AB) that binds a target and a masking moiety (MM) that reduces the ability of the antigen- or epitope-binding domain of the AB to bind its target. In some embodiments, an activatable antibody of the present disclosure comprises a CM1-CM2 substrate comprising an amino acid sequence selected from the group consisting of SEQ ID NOs: 27, 28, 30, 33, and 35, as well as an antibody or antigen binding fragment thereof (AB) that binds a target and a masking moiety (MM) that reduces the ability of the antigen- or epitope-binding domain of the AB to bind its target. In some embodiments, an activatable antibody of the present disclosure comprises a CM1-CM2 substrate comprising an amino acid sequence selected from the group consisting of SEQ ID NOs: 25, 29, 31, 36, and 37, as well as an antibody or antigen binding fragment thereof (AB) that binds a target and a masking moiety (MM) that reduces the ability of the antigen- or epitope-binding domain of the AB to bind its target. In some embodiments, an activatable antibody of the present disclosure comprises a CM1-CM2 substrate comprising an amino acid sequence selected from the group consisting of SEQ ID NOs: 26, 32, and 34, as well as an antibody or antigen binding fragment thereof (AB) that binds a target and a masking moiety (MM) that reduces the ability of the antigen- or epitope-binding domain of the AB to bind its target. In some embodiments, an activatable antibody of the present disclosure comprises a CM1-CM2 substrate comprising an amino acid sequence selected from the group consisting of SEQ ID NOs: 27, 28, and 33, as well as an antibody or antigen binding fragment thereof (AB) that binds a target and a masking moiety (MM) that reduces the ability of the antigen- or epitope-binding domain of the AB to bind its target. In some embodiments, an activatable antibody of the present disclosure comprises a CM1-CM2 substrate comprising an amino acid sequence selected from the group consisting of SEQ ID NOs: 30 and 35, as well as an antibody or antigen binding fragment thereof (AB) that binds a target and a masking moiety (MM) that reduces the ability of the antigen- or epitope-binding domain of the AB to bind its target.

In some embodiments, an activatable antibody comprises a CM1-CM2 substrate comprising an amino acid sequence selected from the group consisting of SEQ ID NOs: 25-43, and an anti-EGFR antibody comprising an amino acid sequence of an anti-EGFR antibody disclosed herein. In some embodiments, an activatable antibody comprises a CM1-CM2 substrate comprising an amino acid sequence selected from the group consisting of SEQ ID NOs: 25-43, and an antibody having a light chain comprising amino acid sequence SEQ ID NO: 401 and a heavy chain comprising amino acid sequence SEQ ID NO: 400.

In some embodiments, the CM1-CM2 is included in an activatable antibody having a light chain amino acid sequence selected from the group consisting of SEQ ID NOs: 450-462, and a heavy chain amino acid sequence of SEQ ID NO: 400.

In some embodiments, an isolated polypeptide of the present disclosure comprises a CM1 substrate that is a substrate for at least one MMP and comprises a polypeptide sequence that is not substantially identical to any polypeptide sequence, e.g., any animal polypeptide sequence, that is naturally cleaved by the same MMP protease. In some embodiments, the CM1 substrate sequence is a substrate for at least one MMP and comprises a polypeptide sequence that is not substantially identical to any mammalian polypeptide sequence that is naturally cleaved by the same MMP protease. In some embodiments, the CM1 substrate sequence is a substrate for at least one MMP and comprises a polypeptide sequence that is not substantially identical to any human polypeptide sequence that is naturally cleaved by the same MMP protease. In some embodiments, the CM1 substrate sequence is a substrate for at least one MMP and comprises a polypeptide sequence that is no more than 90% or more identical to any polypeptide sequence, e.g., any animal polypeptide sequence, that is naturally cleaved by the same MMP protease. In some embodiments, the CM1 substrate sequence is a substrate for at least one MMP and comprises a polypeptide sequence that is no more than 90% or more identical to any mammalian polypeptide sequence that is naturally cleaved by the same MMP protease. In some embodiments, the CM1 substrate sequence is a substrate for at least one MMP and comprises a polypeptide sequence that is no more than 90% or more identical to any human polypeptide sequence that is naturally cleaved by the same MMP protease. In some embodiments, the CM1 substrate sequence that is a substrate for at least one MMP and comprises a polypeptide sequence that is selected from the group consisting of: ALAHGLF (SEQ ID NO: 1), DLAHPLL (SEQ ID NO: 2), RGPKLYW (SEQ ID NO: 6), RFPYGVW (SEQ ID NO: 7), and QNQALRIA (SEQ ID NO: 16).

In some embodiments, an activatable antibody of the present disclosure comprises a CM1 substrate comprising an amino acid sequence selected from the group consisting of ALAHGLF (SEQ ID NO: 1), DLAHPLL (SEQ ID NO: 2), RGPKLYW (SEQ ID NO: 6), RFPYGVW (SEQ ID NO: 7), and QNQALRIA (SEQ ID NO: 16), as well as an antibody or antigen binding fragment thereof (AB) that binds a target and a masking moiety (MM) that reduces the ability of the antigen- or epitope-binding domain of the AB to bind its target.

In some embodiments, an isolated polypeptide of the present disclosure comprises a CM2 substrate that is a substrate for at least one SP protease and comprises a polypeptide sequence that is not substantially identical to any polypeptide sequence, e.g., any animal polypeptide sequence, that is naturally cleaved by the same SP protease. In some embodiments, the CM2 substrate sequence is a substrate for at least one SP and comprises a polypeptide sequence that is not substantially identical to any mammalian polypeptide sequence that is naturally cleaved by the same SP protease. In some embodiments, the CM2 substrate sequence is a substrate for at least one SP and comprises a polypeptide sequence that is not substantially identical to any human polypeptide sequence that is naturally cleaved by the same SP protease. In some embodiments, the CM2 substrate sequence is a substrate for at least one SP and comprises a polypeptide sequence that is no more than 90% or more identical to any polypeptide sequence, e.g., any animal polypeptide sequence, that is naturally cleaved by the same SP protease. In some embodiments, the CM2 substrate sequence is a substrate for at least one SP and comprises a polypeptide sequence that is no more than 90% or more identical to any mammalian polypeptide sequence that is naturally cleaved by the same SP protease. In some embodiments, the CM2 substrate sequence is a substrate for at least one SP and comprises a polypeptide sequence that is no more than 90% or more identical to any human polypeptide sequence that is naturally cleaved by the same SP protease. In some embodiments, the CM2 substrate sequence that is a substrate for at least one SP and comprises a polypeptide sequence that is selected from the group consisting of: APRSF (SEQ ID NO: 130) and GLPTFVHL (SEQ ID NO: 135).

In some embodiments, an activatable antibody of the present disclosure comprises a CM2 substrate comprising an amino acid sequence selected from the group consisting of APRSF (SEQ ID NO: 130) and GLPTFVHL (SEQ ID NO: 135), as well as an antibody or antigen binding fragment thereof (AB) that binds a target and a masking moiety (MM) that reduces the ability of the antigen- or epitope-binding domain of the AB to bind its target.

In some embodiments, an activatable antibody of the present disclosure comprises a substrate comprising an amino acid sequence selected from the group consisting of SEQ ID NO: 1-16, as well as an antibody or antigen binding fragment thereof (AB) that binds a target and a masking moiety (MM) that reduces the ability of the antigen- or epitope-binding domain of the AB to bind its target.

In some embodiments, the CM1-CM2, CM1, or CM2 substrate is also a substrate for at least one additional protease.

In some embodiments, the at least one additional protease is a different MMP protease than the MMP protease that cleaves the CM1. In some embodiments, the at least one additional protease is an MMP protease selected from the group consisting of MMP1; MMP2; MMP3; MMP7; MMP8; MMP9; MMP10; MMP11; MMP12; MMP13; MMP14; MMP15; MMP16; MMP17; MMP19; MMP20; MMP23; MMP24; MMP26; and MMP27.

In some embodiments, the at least one additional protease is a different SP protease than the SP protease that cleaves CM2. In some embodiments, the at least one additional SP protease is selected from the group consisting of uPA; matriptase; activated protein C; Cathepsin A; Cathepsin G; Chymase; a coagulation factor protease such as, e.g., FVIIa, FIXa, FXa, FXIa, FXIIa; Elastase; Granzyme B; Guanidinobenzoatase; HtrAl; Human Neutrophil Elastase; Lactoferrin; Marapsin; NS3/4A; PACE4; Plasmin; PSA; tPA; Thrombin; Tryptase; a Type II Transmembrane Serine Protease (TTSP) such as, e.g., DESC1, DPP-4, FAP, Hepsin, Matriptase-2, TMPRSS2, TMPRSS3, and TMPRSS4.

In some embodiments, the at least one additional protease is selected from the group consisting of those shown in Table 6.

TABLE 6

| Exemplary Proteases and/or Enzymes |
|---|
| ADAMS, ADAMTS, e.g. |
| ADAM8 |
| ADAM9 |
| ADAM10 |
| ADAM12 |
| ADAM15 |
| ADAM17/TACE |
| ADAMDEC1 |
| ADAMTS1 |
| ADAMTS4 |
| ADAMTS5 |
| Aspartate proteases, e.g., |
| BACE |
| Renin |
| Aspartic cathepsins, e.g., |
| Cathepsin D |
| Cathepsin E |
| Caspases, e.g., |
| Caspase 1 |
| Caspase 2 |
| Caspase 3 |
| Caspase 4 |

TABLE 6-continued

| Exemplary Proteases and/or Enzymes |
|---|
| Caspase 5 |
| Caspase 6 |
| Caspase 7 |
| Caspase 8 |
| Caspase 9 |
| Caspase 10 |
| Caspase 14 |
| Cysteine cathepsins, e.g., |
| Cathepsin B |
| Cathepsin C |
| Cathepsin K |
| Cathepsin L |
| Cathepsin S |
| Cathepsin V/L2 |
| Cathepsin X/Z/P |
| Cysteine proteinases, e.g., |
| Cruzipain |
| Legumain |
| Otubain-2 |
| KLKs, e.g., |
| KLK4 |
| KLK5 |
| KLK6 |
| KLK7 |
| KLK8 |
| KLK10 |
| KLK11 |
| KLK13 |
| KLK14 |
| Metallo proteinases, e.g., |
| Meprin |
| Neprilysin |
| PSMA |
| BMP-1 |

The disclosure also provides an antibody includes at least a first CM1 and a second CM2 and is conjugated to an agent. In some embodiments, the first CM1 and the second CM2 are each polypeptides of no more than 15 amino acids long. In some embodiments, the activatable antibody is a conjugated activatable antibody that, in the uncleaved state has the structural arrangement from N-terminus to C-terminus as follows: MM-CM1-CM2-AB-Agent, Agent-AB-CM2-CM1-MM, MM-CM2-CM1-AB-Agent, or Agent-AB-CM1-CM2-MM. In some embodiments, the activatable antibody is a conjugated activatable antibody that, in the uncleaved state has the structural arrangement from N-terminus to C-terminus as follows: Agent-MM-CM1-CM2-AB, AB-CM2-CM1-MM-Agent, Agent-MM-CM2-CM1-AB, or AB-CM1-CM2-MM-Agent. In some embodiments, the activatable antibody is a conjugated activatable antibody that, in the uncleaved state has the structural arrangement from N-terminus to C-terminus as follows: Agent-MM-CM1-CM2-AB-Agent, Agent-AB-CM2-CM1-MM-Agent, Agent-MM-CM2-CM1-AB-Agent, or Agent-AB-CM1-CM2-MM-Agent.

In some embodiments, the activatable antibody is a conjugated activatable antibody that comprises a masking moiety (MM), a first linking peptide (LP1) and a second linking peptide (LP2), and the antibody in the uncleaved state has the structural arrangement from N-terminus to C-terminus as follows: MM1-LP1-CM1-CM2-LP2-AB-Agent, Agent-AB-LP2-CM2-CM1-LP1-MM, MM1-LP1-CM2-CM1-LP2-AB-Agent, or Agent-AB-LP2-CM1-CM2-LP1-MM. In some embodiments, each of LP1 and LP2 is a peptide of about 1 to 20 amino acids in length. In some embodiments, the two linking peptides need not be identical to each other.

In some embodiments, the activatable antibody is a conjugated activatable antibody that comprises a masking moiety (MM), a first linking peptide (LP1) and a second linking peptide (LP2), and the antibody in the uncleaved state has the structural arrangement from N-terminus to C-terminus as follows: Agent-MM1-LP1-CM1-CM2-LP2-AB, AB-LP2-CM2-CM1-LP1-MM-Agent, Agent-MM1-LP1-CM2-CM1-LP2-AB, or AB-LP2-CM1-CM2-LP1-MM-Agent. In some embodiments, each of LP1 and LP2 is a peptide of about 1 to 20 amino acids in length. In some embodiments, the two linking peptides need not be identical to each other.

In some embodiments, the activatable antibody is a conjugated activatable antibody that comprises a masking moiety (MM), a first linking peptide (LP1) and a second linking peptide (LP2), and the antibody in the uncleaved state has the structural arrangement from N-terminus to C-terminus as follows: Agent-MM1-LP1-CM1-CM2-LP2-AB-Agent, Agent-AB-LP2-CM2-CM1-LP1-MM-Agent, Agent-MM1-LP1-CM2-CM1-LP2-AB-Agent, or Agent-AB-LP2-CM1-CM2-LP1-MM-Agent. In some embodiments, each of LP1 and LP2 is a peptide of about 1 to 20 amino acids in length. In some embodiments, the two linking peptides need not be identical to each other.

In some embodiments, the conjugated activatable antibody includes a linking peptide (LP') between CM1 and CM2. In some embodiments, the conjugated activatable antibody includes a linking peptide (LP1) between the masking moiety (MM) and CM1. In some embodiments, the conjugated activatable antibody includes a linking peptide (LP2) between CM2 and AB. In some embodiments, the conjugated activatable antibody includes a linking peptide (LP1) between the MM and CM1 and a linking peptide (LP2) between CM2 and AB. In some embodiments, the conjugated activatable antibody includes a linking peptide between the MM and CM1 (LP1) and a linking peptide between CM1 and CM2 (LP'). In some embodiments, the conjugated activatable antibody includes a linking peptide (LP') between CM1 and CM2 and a linking peptide (LP2) between CM2 and AB. In some embodiments, the conjugated activatable antibody includes a linking peptide (LP1) between the MM and CM1, a linking peptide (LP') between CM1 and CM2, and a linking peptide (LP2) between CM2 and AB.

In some embodiments, the conjugated activatable antibody includes a linking peptide (LP') between CM1 and CM2. In some embodiments, the conjugated activatable antibody includes a linking peptide (LP1) between the AB and CM1. In some embodiments, the conjugated activatable antibody includes a linking peptide (LP2) between CM2 and the masking moiety (MM). In some embodiments, the conjugated activatable antibody includes a linking peptide (LP1) between the AB and CM1 and a linking peptide (LP2) between CM2 and MM. In some embodiments, the conjugated activatable antibody includes a linking peptide between the AB and CM1 (LP1) and a linking peptide between CM1 and CM2 (LP'). In some embodiments, the conjugated activatable antibody includes a linking peptide (LP') between CM1 and CM2 and a linking peptide (LP2) between CM2 and MM. In some embodiments, the conjugated activatable antibody includes a linking peptide (LP1) between the AB and CM1, a linking peptide (LP') between CM1 and CM2, and a linking peptide (LP2) between CM2 and MM.

In some embodiments, LP' is GG. In some embodiments, LP' is GGSGGS (SEQ ID NO: 218).

In some embodiments, at least one of LP1 or LP2 comprises an amino acid sequence selected from the group consisting of $(GS)_n$, $(GGS)_n$, $(GSGGS)_n$ (SEQ ID NO: 381) and $(GGGS)_n$ (SEQ ID NO: 382), where n is an integer of at least one.

In some embodiments, at least one of LP1 or LP2 comprises an amino acid sequence selected from the group consisting of GGSG (SEQ ID NO: 202), GGSGG (SEQ ID NO: 203), GSGSG (SEQ ID NO: 204), GSGGG (SEQ ID NO: 205), GGGSG (SEQ ID NO: 206), and GSSSG (SEQ ID NO: 207).

In some embodiments, LP1 comprises the amino acid sequence GSSGGSGGSGGSG (SEQ ID NO: 208), GSSGGSGGSGG (SEQ ID NO: 209), GSSGGSGGSGGS (SEQ ID NO: 210), GSSGGSGGSGGSGGGS (SEQ ID NO: 211), GSSGGSGGSG (SEQ ID NO: 212), or GSSGGSGGSGS (SEQ ID NO: 213), and GGGSSGGS (SEQ ID NO: 214).

In some embodiments, LP2 comprises the amino acid sequence GSS, GGS, GGGS (SEQ ID NO: 215), GSSGT (SEQ ID NO: 216) or GSSG (SEQ ID NO: 217).

In some embodiments, the CM1-CM2 substrate is linked or otherwise attached to an antibody. For example, the CM1-CM2 is used to link one or more agents to the antibody or antigen binding fragment thereof (AB) that binds a given target, such that the CM1-CM2 is cleaved when exposed to the MMP and/or the SP and/or the CP, and the agent is released from the AB. Exemplary targets include, but are not limited to the targets shown in Table 1. Exemplary ABs include, but are not limited to, the antibodies shown in Table 2.

In some embodiments, the AB has a dissociation constant of about 100 nM or less for binding to the target.

In some embodiments, the antibody includes an antibody or antigen-binding fragment thereof that specifically binds a target. In some embodiments, the antibody or immunologically active fragment thereof that binds the target is a monoclonal antibody, domain antibody, single chain, Fab fragment, a $F(ab')_2$ fragment, a scFv, a scab, a dAb, a single domain heavy chain antibody, or a single domain light chain antibody. In some embodiments, such an antibody or immunologically active fragment thereof that binds the target is a mouse, other rodent, chimeric, humanized or fully human monoclonal antibody.

In some embodiments, the MM has a dissociation constant for binding to the AB that is no more than the dissociation constant of the AB to the target.

In some embodiments, the MM does not interfere or compete with the AB for binding to the target in a cleaved state.

In some embodiments, the MM is a polypeptide of about 2 to 40 amino acids in length. For example, the MM is a polypeptide of up to about 40 amino acids in length.

In some embodiments, the MM polypeptide sequence is different from that of any natural binding partner of the AB. In some embodiments, the MM polypeptide sequence is no more than 50% identical to any natural binding partner of the AB. In some embodiments, the MM polypeptide sequence is no more than 40%, 30%, 25%, 20%, 15%, or 10% identical to any natural binding partner of the AB.

In some embodiments, the agent conjugated to the AB or the AB of an activatable antibody is a therapeutic agent. In some embodiments, the agent is an antineoplastic agent. In some embodiments, the agent is a toxin or fragment thereof. As used herein, a fragment of a toxin is a fragment that retains toxic activity. In some embodiments, the agent is conjugated to the AB via a cleavable linker. In some embodiments, the agent is conjugated to the AB via a linker that includes at least one CM1-CM2 substrate sequence. In some embodiments, the agent is conjugated to the AB via a noncleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is an anti-inflammatory agent.

In some embodiments, the antibody and/or activatable antibody also includes a detectable moiety. In some embodiments, the detectable moiety is a diagnostic agent.

In some embodiments, the conjugated antibody and/or conjugated activatable antibody includes a detectable label. In some embodiments, the detectable label includes an imaging agent, a contrasting agent, an enzyme, a fluorescent label, a chromophore, a dye, one or more metal ions, or a ligand-based label. In some embodiments, the imaging agent comprises a radioisotope. In some embodiments, the radioisotope is indium or technetium. In some embodiments, the contrasting agent comprises iodine, gadolinium or iron oxide. In some embodiments, the enzyme comprises horseradish peroxidase, alkaline phosphatase, or β-galactosidase. In some embodiments, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the luminescent label comprises an N-methylacrydium derivative. In some embodiments, the label comprises an Alexa Fluor® label, such as Alex Fluor® 680 or Alexa Fluor® 750. In some embodiments, the ligand-based label comprises biotin, avidin, streptavidin or one or more haptens.

In some embodiments, the antibody and/or the AB of the activatable antibody naturally contains one or more disulfide bonds. In some embodiments, the AB can be engineered to include one or more disulfide bonds.

In some embodiments, the antibody and/or conjugated antibody is monospecific. In some embodiments, the antibody and/or conjugated antibody is multispecific, referred to herein as multispecific antibodies and/or conjugated multispecific antibodies. In some embodiments, the multispecific antibody and/or conjugated multispecific antibody is bispecific or trifunctional. In some embodiments, the antibody and/or conjugated antibody is formulated as part of a pro-Bispecific T Cell Engager (pro-BITE) molecule. In some embodiments, the antibody and/or conjugated antibody is formulated as part of a pro-Chimeric Antigen Receptor (pro-CAR) modified T cell or other engineered receptor or other immune effector cell, such as a CAR modified NK cell. In some embodiments, the activatable antibody and/or conjugated activatable antibody is formulated as part of a pro-Chimeric Antigen Receptor (CAR) modified T cell. In some embodiments, the activatable antibody and/or conjugated activatable antibody is formulated as part of a pro-Chimeric Antigen Receptor (CAR) modified NK cell.

In some embodiments, the activatable antibody and/or conjugated activatable antibody is monospecific. In some embodiments, the activatable antibody and/or conjugated activatable antibody is multispecific, referred to herein as multispecific activatable antibodies and/or conjugated multispecific activatable antibodies. As used herein, terms such as "activatable antibody" and all grammatical variations thereof, unless otherwise noted, are intended to encompass, but are not limited to embodiments where the activatable antibody is a multispecific activatable antibody of the disclosure. As used herein, terms such as "conjugated activatable antibody" and all grammatical variations thereof, unless otherwise noted, are intended to encompass, but are not limited to embodiments where the conjugated activatable antibody is a conjugated multispecific activatable antibody of the disclosure. In some embodiments, the multispecific activatable antibody and/or conjugated multispecific activatable antibody is bispecific or trifunctional. In some embodiments, the activatable antibody and/or conjugated activatable antibody is formulated as part of a pro-Bispecific T Cell Engager (pro-BITE) molecule. In some embodiments, the activatable antibody and/or conjugated activatable antibody is formulated as part of a pro-Chimeric Antigen Receptor (pro-CAR) modified T cell or other engineered receptor.

In some embodiments, the antibodies, antibody conjugates, activatable antibodies, conjugated activatable antibodies, multispecific activatable antibodies, and/or conjugated multispecific activatable antibodies described herein are used in conjunction with one or more additional agents or a combination of additional agents. Suitable additional agents include current pharmaceutical and/or surgical therapies for an intended application, such as, for example, cancer. For example, the activatable antibodies, conjugated activatable antibodies, multispecific activatable antibodies, and/or conjugated multispecific activatable antibodies can be used in conjunction with an additional chemotherapeutic or anti-neoplastic agent.

In some embodiments, the activatable antibody is a multispecific activatable antibody. The multispecific activatable antibodies provided herein are multispecific antibodies that recognize two or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a CM1-CM2 substrate that functions as a substrate for at least one MMP protease and at least one SP protease. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds Epidermal Growth Factor Receptor (EGFR) and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes at least the amino acid sequence NYGVH (SEQ ID NO: 220); a VH CDR2 sequence that includes at least the amino acid sequence VIWSGGNTDYNTPFTS (SEQ ID NO: 221); a VH CDR3 sequence that includes at least the amino acid sequence ALTYYDYEFAY (SEQ ID NO: 222); and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes at least the amino acid sequence RASQSIGTNIH (SEQ ID NO: 223); a VL CDR2 sequence that includes at least the amino acid sequence KYASESIS (SEQ ID NO: 224); and a VL CDR3 sequence that includes at least the amino acid sequence QQNNNWPTT (SEQ ID NO: 225), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes a sequence that is at least 90%, 91%, 92%, 93%, 94%, 95%, 96%, 97%, 98%, 99% or more identical to the amino acid sequence NYGVH (SEQ ID NO: 220); a VH CDR2 sequence that includes a sequence that is at least 90%, 91%, 92%, 93%, 94%, 95%, 96%, 97%, 98%, 99% or more identical to the amino acid sequence VIWSGGNTDYNTPFTS (SEQ ID NO: 221); a VH CDR3 sequence that includes a sequence that is at least 90%, 91%, 92%, 93%, 94%, 95%, 96%, 97%, 98%, 99% or more identical to the amino acid sequence ALTYYDYEFAY (SEQ ID NO: 222); and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes a sequence that is at least 90%, 91%, 92%, 93%, 94%, 95%, 96%, 97%, 98%, 99% or more identical to the amino acid sequence RASQSIGTNIH (SEQ ID NO: 223); a VL CDR2 sequence that includes a sequence that is at least 90%, 91%, 92%, 93%, 94%, 95%, 96%, 97%, 98%, 99% or more identical to the amino acid sequence KYASESIS (SEQ ID NO: 224); and a VL CDR3 sequence that includes a sequence that is at least 90%, 91%, 92%, 93%, 94%, 95%, 96%, 97%, 98%, 99% or more identical to the amino acid sequence QQNNNWPTT (SEQ ID NO: 225), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes at least the amino acid sequence NYGVH (SEQ ID NO: 220); the VH CDR2 sequence includes at least the amino acid sequence VIWSGGNTDYNTPFTS (SEQ ID NO: 221); the VH CDR3 sequence includes at least the amino acid sequence ALTYYDYEFAY (SEQ ID NO: 222); the VL CDR1 sequence includes at least the amino acid sequence RASQSIGTNIH (SEQ ID NO: 223); the VL CDR2 sequence includes at least the amino acid sequence KYASESIS (SEQ ID NO: 224); and the VL CDR3 sequence includes at least the amino acid sequence QQNNNWPTT (SEQ ID NO: 225).

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes a sequence that is at least 90%, 91%, 92%, 93%, 94%, 95%, 96%, 97%, 98%, 99% or more identical to the amino acid sequence NYGVH (SEQ ID NO: 220); the VH CDR2 sequence includes a sequence that is at least 90%, 91%, 92%, 93%, 94%, 95%, 96%, 97%, 98%, 99% or more identical to the amino acid sequence VIWSGGNTDYNTPFTS (SEQ ID NO: 221); the VH CDR3 sequence includes a sequence that is at least 90%, 91%, 92%, 93%, 94%, 95%, 96%, 97%, 98%, 99% or more identical to the amino acid sequence ALTYYDYEFAY (SEQ ID NO: 222); the VL CDR1 sequence includes a sequence that is at least 90%, 91%, 92%, 93%, 94%, 95%, 96%, 97%, 98%, 99% or more identical to the amino acid sequence RASQSIGTNIH (SEQ ID NO: 223); the VL CDR2 sequence includes a sequence that is at least 90%, 91%, 92%, 93%, 94%, 95%, 96%, 97%, 98%, 99% or more identical to the amino acid sequence KYASESIS (SEQ ID NO: 224); and the VL CDR3 sequence includes a sequence that is at least 90%, 91%, 92%, 93%, 94%, 95%, 96%, 97%, 98%, 99% or more identical to the amino acid sequence QQNNNWPTT (SEQ ID NO: 225).

In some embodiments, the activatable antibody and/or conjugated activatable antibody provided herein, including but not limited to a multispecific activatable antibody and/or conjugated multispecific activatable antibody of the disclosure, comprises a CM1-CM2 substrate comprising an amino acid sequence selected from the group consisting of SEQ ID NOs: 25-43, and an anti-Jagged antibody comprising an amino acid sequence of an anti-Jagged antibody disclosed herein. In some embodiments, the activatable antibody and/or conjugated activatable antibody provided herein, including but not limited to a multispecific activatable antibody and/or conjugated multispecific activatable antibody of the disclosure, comprises a CM1-CM2 substrate comprising an amino acid sequence selected from the group consisting of SEQ ID NOs: 25-43, and an antibody having a light chain comprising amino acid sequence SEQ ID NO: 401 and a heavy chain comprising amino acid sequence SEQ ID NO: 400.

In some embodiments, the activatable antibody and/or conjugated activatable antibody provided herein, including but not limited to a multispecific activatable antibody and/or conjugated multispecific activatable antibody of the disclosure, includes at least a heavy chain amino acid sequence of SEQ ID NO: 400 and a light chain amino acid sequence selected from the group consisting of SEQ ID NOs: 403-423 and 450-462.

In some embodiments, the activatable antibody also includes an agent conjugated to the AB. In some embodiments, the agent is a therapeutic agent. In some embodiments, the agent is an antineoplastic agent. In some embodiments, the agent is a toxin or a fragment thereof. In some embodiments, the agent is conjugated to the AB via a linker. In some embodiments, the linker is a cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is conjugated to the AB via a linker that includes at least one CM1-CM2 substrate sequence. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is an anti-inflammatory agent.

In some embodiments, the activatable antibody also includes a detectable moiety. In some embodiments, the detectable moiety is a diagnostic agent.

In some embodiments, the conjugated antibody includes a detectable label. In some embodiments, the detectable label includes an imaging agent, a contrasting agent, an enzyme, a fluorescent label, a chromophore, a dye, one or more metal ions, or a ligand-based label. In some embodiments, the imaging agent comprises a radioisotope. In some embodiments, the radioisotope is indium or technetium. In some embodiments, the contrasting agent comprises iodine, gadolinium or iron oxide. In some embodiments, the enzyme comprises horseradish peroxidase, alkaline phosphatase, or β-galactosidase. In some embodiments, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the luminescent label comprises an N-methylacrydium derivative. In some embodiments, the label comprises an Alexa Fluor® label, such as Alex Fluor® 680 or Alexa Fluor® 750. In some embodiments, the ligand-based label comprises biotin, avidin, streptavidin or one or more haptens.

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer is joined directly to the MM of the activatable antibody in the structural arrangement from N-terminus to C-terminus of spacer-MM-CM1-CM2 substrate-AB. An example of a spacer joined directly to the N-terminus of MM of the activatable antibody is an amino acid sequence selected from the group consisting of QGQSGQ (SEQ ID NO: 153), GQSGQ (SEQ ID NO: 154), QSGQ (SEQ ID NO: 155), SGQ, GQ, and Q. In some embodiments, the spacer includes at least the amino acid sequence QGQSGQ (SEQ ID NO: 153). In some embodiments, the spacer includes at least the amino acid sequence GQSGQ (SEQ ID NO: 154). In some embodiments, the spacer includes at least the amino acid sequence QSGQ (SEQ ID NO: 155). In some embodiments, the spacer includes at least the amino acid sequence SGQ. In some embodiments, the spacer includes at least the amino acid sequence GQ. In some embodiments, the spacer includes at least the amino acid sequence Q.

In some embodiments, the AB of the activatable antibody naturally contains one or more disulfide bonds. In some embodiments, the AB can be engineered to include one or more disulfide bonds.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is similar to that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism. In some embodiments, the serum half-life of the activatable antibody is at least 9 days when administered to an organism. In some embodiments, the serum half-life of the activatable antibody is at least 8 days when administered to an organism. In some embodiments, the serum half-life of the activatable antibody is at least 7 days when administered to an organism. In some embodiments, the serum half-life of the activatable antibody is at least 6 days when administered to an organism. In some embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

The disclosure also provides compositions and methods that include an activatable antibody that includes an antibody or antibody fragment (AB) that specifically binds a given target, where the AB is coupled to a masking moiety (MM) that decreases the ability of the AB to bind its target. In some embodiments, the activatable antibody further includes a CM1-CM2 substrate that is a substrate for at least one MMP and at least one SP. The compositions and methods provided herein enable the attachment of one or more agents to one or more cysteine residues in the AB without compromising the activity (e.g., the masking, activating or binding activity) of the activatable antibody. In some embodiments, the compositions and methods provided herein enable the attachment of one or more agents to one or more cysteine residues in the AB without reducing or otherwise disturbing one or more disulfide bonds within the MM. The compositions and methods provided herein produce an activatable antibody that is conjugated to one or more agents, e.g., any of a variety of therapeutic, diagnostic and/or prophylactic agents, for example, in some embodiments, without any of the agent(s) being conjugated to the MM of the activatable antibody. The compositions and methods provided herein produce conjugated activatable antibodies in which the MM retains the ability to effectively and efficiently mask the AB of the activatable antibody in an uncleaved state. The compositions and methods provided herein produce conjugated activatable antibodies in which the activatable antibody is still activated, i.e., cleaved, in the presence of a MMP that can cleave the CM1-CM2 substrate.

The activatable antibodies have at least one point of conjugation for an agent, but in the methods and compositions provided herein less than all possible points of conjugation are available for conjugation to an agent. In some embodiments, the one or more points of conjugation are sulfur atoms involved in disulfide bonds. In some embodiments, the one or more points of conjugation are sulfur atoms involved in interchain disulfide bonds. In some embodiments, the one or more points of conjugation are sulfur atoms involved in interchain sulfide bonds, but not sulfur atoms involved in intrachain disulfide bonds. In some embodiments, the one or more points of conjugation are sulfur atoms of cysteine or other amino acid residues containing a sulfur atom. Such residues may occur naturally in the antibody structure or may be incorporated into the antibody by site-directed mutagenesis, chemical conversion, or mis-incorporation of non-natural amino acids.

Also provided are methods of preparing a conjugate of an activatable antibody having one or more interchain disulfide bonds in the AB and one or more intrachain disulfide bonds in the MM, and a drug reactive with free thiols is provided. The method generally includes partially reducing interchain disulfide bonds in the activatable antibody with a reducing agent, such as, for example, TCEP; and conjugating the drug reactive with free thiols to the partially reduced activatable antibody. As used herein, the term partial reduction refers to situations where an activatable antibody is contacted with a reducing agent and less than all disulfide bonds, e.g., less than all possible sites of conjugation are reduced. In some embodiments, less than 99%, 98%, 97%, 96%, 95%, 90%, 85%, 80%, 75%, 70%, 65%, 60%, 55%, 50%, 45%, 40%, 35%, 30%, 25%, 20%, 15%, 10% or less than 5% of all possible sites of conjugation are reduced.

In some embodiments, a method of reducing and conjugating an agent, e.g., a drug, to an activatable antibody resulting in selectivity in the placement of the agent is provided. The method generally includes partially reducing the activatable antibody with a reducing agent such that any conjugation sites in the masking moiety or other non-AB portion of the activatable antibody are not reduced, and conjugating the agent to interchain thiols in the AB. The conjugation site(s) are selected to allow desired placement of an agent to allow conjugation to occur at a desired site. The reducing agent is, for example, TCEP. The reduction reaction conditions such as, for example, the ratio of reducing agent to activatable antibody, the length of incubation, the temperature during the incubation, the pH of the reducing reaction solution, etc., are determined by identifying the conditions that produce a conjugated activatable antibody in which the MM retains the ability to effectively and efficiently mask the AB of the activatable antibody in an uncleaved state. The ratio of reduction agent to activatable antibody will vary depending on the activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

In some embodiments, a method of reducing interchain disulfide bonds in the AB of an activatable antibody and conjugating an agent, e.g., a thiol-containing agent such as a drug, to the resulting interchain thiols to selectively locate agent(s) on the AB is provided. The method generally includes partially reducing the AB with a reducing agent to form at least two interchain thiols without forming all possible interchain thiols in the activatable antibody; and conjugating the agent to the interchain thiols of the partially reduced AB. For example, the AB of the activatable antibody is partially reduced for about 1 hour at about 37° C. at a desired ratio of reducing agent:activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

The thiol-containing reagent can be, for example, cysteine or N-acetyl cysteine. The reducing agent can be, for example, TCEP. In some embodiments, the reduced activatable antibody can be purified prior to conjugation, using for example, column chromatography, dialysis, or diafiltration. In some embodiments, the reduced antibody is not purified after partial reduction and prior to conjugation.

The disclosure also provides partially reduced activatable antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to the target, a masking moiety (MM) that inhibits the binding of the AB of the activatable antibody in an uncleaved state to the target, and a CM1-CM2 substrate coupled to the AB, wherein the CM1-CM2 substrate is a polypeptide that functions as a substrate for at least one MMP and one SP. In some embodiments, the MM is coupled to the AB via the CM1-CM2 substrate. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM1-CM2 substrate-AB or AB-CM1-CM2 substrate-MM. In some embodiments, the reducing agent is TCEP.

The disclosure also provides partially reduced activatable antibodies, including but not limited to multispecific activatable antibodies of the disclosure, in which at least one interchain disulfide bond in the activatable antibody has been reduced with a reducing agent without disturbing or otherwise compromising the activity and/or efficacy of the activatable antibody, wherein the activatable antibody includes an antibody or an antigen binding fragment thereof (AB) that specifically binds to a target, a masking moiety (MM) that inhibits the binding of the AB of the activatable antibody in an uncleaved state to the target, and a CM1-CM2 substrate coupled to the AB, and the CM1-CM2 substrate is a polypeptide that functions as a substrate for a protease. The activity and/or efficacy of the activatable antibody is, by way of nonlimiting example, masking activity, activation of the activatable antibody, and/or binding activity of the activated activatable antibody. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM1-CM2 substrate-AB or AB-CM1-CM2 substrate-MM. In some embodiments, the reducing agent is TCEP.

The disclosure also provides conjugated activatable antibodies that include an activatable antibody linked to monomethyl auristatin D (MMAD) payload, wherein the activatable antibody includes an antibody or an antigen binding fragment thereof (AB) that specifically binds to a target, a masking moiety (MM) that inhibits the binding of the AB of the activatable antibody in an uncleaved state to the target, and CM1-CM2 substrate coupled to the AB, and the CM1-CM2 substrate is a polypeptide that functions as a substrate for at least one MMP protease and at least one SP protease.

In some embodiments, the MMAD-conjugated activatable antibody can be conjugated using any of several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB.

In some embodiments, the MMAD payload is conjugated to the AB via a linker. In some embodiments, the MMAD payload is conjugated to a cysteine in the AB via a linker. In some embodiments, the MMAD payload is conjugated to a lysine in the AB via a linker. In some embodiments, the MMAD payload is conjugated to another residue of the AB via a linker, such as those residues disclosed herein. In some embodiments, the linker is a thiol-containing linker. In some embodiments, the linker is a cleavable linker. In some embodiments, the linker is a non-cleavable linker. In some embodiments, the linker is selected from the group consisting of the linkers shown in Tables 5 and 6. In some embodiments, the activatable antibody and the MMAD payload are linked via a maleimide caproyl-valine-citrulline linker. In some embodiments, the activatable antibody and the MMAD payload are linked via a maleimide PEG-valine-citrulline linker. In some embodiments, the activatable antibody and the MMAD payload are linked via a maleimide caproyl-valine-citrulline-para-aminobenzyloxycarbonyl linker. In some embodiments, the activatable antibody and the MMAD payload are linked via a maleimide PEG-valine-citrulline-para-aminobenzyloxycarbonyl linker. In some embodiments, the MMAD payload is conjugated to the AB using the partial reduction and conjugation technology disclosed herein.

The disclosure also provides polypeptides and other larger molecules that include one or more of the CM1-CM2 substrate sequences presented herein. By way of non-limiting example, the CM1-CM2 substrate sequences presented herein are useful in prodrug compositions and methods of use thereof. These CM1-CM2 substrate sequences presented herein are also useful in probes and other detection agents and methods of use thereof. For example, the CM1-CM2 substrate sequences presented herein can be used in conjunction with fluors and other quenchers to produce detection agents, such as imaging agents and/or other diagnostic agents. Those of ordinary skill in the art will appreciate that the CM1-CM2 substrate sequences presented herein are useful in any composition and/or method in the art that would use a substrate that is cleavable by at least one MMP and at least one SP.

The disclosure also provides an isolated nucleic acid molecule encoding an antibody and/or an activatable antibody described herein, as well as vectors that include these isolated nucleic acid sequences. The disclosure provides methods of producing an antibody and/or activatable antibody by culturing a cell under conditions that lead to expression of the antibody and/or activatable antibody, wherein the cell comprises such a vector.

The disclosure provides a method of manufacturing a conjugated antibody of the disclosure that bind a given target by (a) culturing a cell comprising a nucleic acid construct that encodes the antibody under conditions that lead to expression of the antibody, (i) wherein the antibody includes a CM1-CM2 substrate, and (ii) wherein the CM1-CM2 substrate is a polypeptide that functions as a substrate for a matrix metalloprotease and a serine protease; (b) recovering the antibody; and (c) conjugating the recovered antibody to one or more additional agents.

The disclosure also provides a method of manufacturing the activatable antibodies of the disclosure that bind in an activated state a given target by (a) culturing a cell comprising a nucleic acid construct that encodes the activatable antibody under conditions that lead to expression of the activatable antibody, wherein the activatable antibody comprises a masking moiety (MM), a CM1-CM2 substrate, and an antibody or an antigen binding fragment thereof (AB) that specifically binds the target, (i) wherein the CM1-CM2 substrate is a polypeptide that functions as a substrate for a MMP and a SP; and (ii) wherein the CM1-CM2 substrate is positioned in the activatable antibody such that, in an uncleaved state, the MM interferes with specific binding of the AB to the target and in a cleaved state the MM does not interfere or compete with specific binding of the AB to the target; and (b) recovering the activatable antibody.

The disclosure also provides a method of manufacturing the conjugated activatable antibodies of the disclosure that bind in an activated state a given target by (a) culturing a cell comprising a nucleic acid construct that encodes the activatable antibody under conditions that lead to expression of the activatable antibody, wherein the activatable antibody comprises a masking moiety (MM), a CM1-CM2 substrate, and an antibody or an antigen binding fragment thereof (AB) that specifically binds the target, (i) wherein the CM1-CM2 substrate is a polypeptide that functions as a substrate for a MMP and a SP and/or CP; and (ii) wherein the CM1-CM2 substrate is positioned in the activatable antibody such that, in an uncleaved state, the MM interferes with specific binding of the AB to the target and in a cleaved state the MM does not interfere or compete with specific binding of the AB to the target; (b) recovering the activatable antibody; and (c) conjugating the recovered antibody to one or more additional agents.

The disclosure provides methods of preventing, delaying the progression of, treating, alleviating a symptom of, or otherwise ameliorating a target-related disease in a subject by administering a therapeutically effective amount of a conjugated antibody, an activatable antibody and/or a conjugated activatable antibody described herein to a subject in need thereof.

The disclosure provides methods of preventing, delaying the progression of, treating, alleviating a symptom of, or otherwise ameliorating inflammation and/or an inflammatory disorder in a subject by administering a therapeutically effective amount of a conjugated antibody, an activatable antibody and/or a conjugated activatable antibody described herein to a subject in need thereof. The disclosure also provides methods of preventing, delaying the progression of, treating, alleviating a symptom of, or otherwise ameliorating cancer in a subject by administering a therapeutically effective amount of a conjugated antibody, an activatable antibody and/or a conjugated activatable antibody described herein to a subject in need thereof. The disclosure also provides methods of preventing, delaying the progression of, treating, alleviating a symptom of, or otherwise ameliorating an autoimmune disease in a subject by administering a therapeutically effective amount a conjugated antibody, an activatable antibody and/or a conjugated activatable antibody described herein to a subject in need thereof.

A conjugated antibody, an activatable antibody and/or a conjugated activatable antibody used in any of the embodiments of these methods and uses can be administered at any stage of the disease. For example, such a conjugated antibody, activatable antibody and/or conjugated activatable antibody can be administered to a patient suffering cancer of any stage, from early to metastatic. The terms subject and patient are used interchangeably herein.

In some embodiments, the subject is a mammal, such as a human, non-human primate, companion animal (e.g., cat, dog, horse), farm animal, work animal, or zoo animal. In some embodiments, the subject is a rodent. In some embodiments, the subject is a human. In some embodiments, the subject is a companion animal. In some embodiments, the subject is an animal in the care of a veterinarian.

The conjugated antibody, activatable antibody and/or conjugated activatable antibody and therapeutic formulations thereof are administered to a subject suffering from or susceptible to a disease or disorder associated with aberrant target expression and/or activity. A subject suffering from or susceptible to a disease or disorder associated with aberrant target expression and/or activity is identified using any of a variety of methods known in the art. For example, subjects suffering from cancer or other neoplastic condition are identified using any of a variety of clinical and/or laboratory tests such as, physical examination and blood, urine and/or stool analysis to evaluate health status. For example, subjects suffering from inflammation and/or an inflammatory disorder are identified using any of a variety of clinical and/or laboratory tests such as physical examination and/or bodily fluid analysis, e.g., blood, urine and/or stool analysis, to evaluate health status.

Administration of a conjugated antibody, an activatable antibody and/or a conjugated activatable antibody to a patient suffering from a disease or disorder associated with aberrant target expression and/or activity is considered successful if any of a variety of laboratory or clinical objectives is achieved. For example, administration of a conjugated antibody, an activatable antibody and/or a conjugated activatable antibody to a patient suffering from a disease or disorder associated with aberrant target expression and/or activity is considered successful if one or more of the symptoms associated with the disease or disorder is alleviated, reduced, inhibited or does not progress to a further, i.e., worse, state. Administration of a conjugated antibody, an activatable antibody and/or a conjugated activatable antibody to a patient suffering from a disease or disorder associated with aberrant target expression and/or activity is considered successful if the disease or disorder enters remission or does not progress to a further, i.e., worse, state.

In some embodiments, the antibodies, conjugated antibodies, activatable antibodies, and/or conjugated activatable antibodies described herein are used in conjunction with one or more additional agents or a combination of additional agents. Suitable additional agents include current pharmaceutical and/or surgical therapies for an intended application, such as, for example, cancer. For example, the antibodies, conjugated antibodies, activatable antibodies, and/or conjugated activatable antibodies can be used in conjunction with an additional chemotherapeutic or anti-neoplastic agent.

In some embodiments, the additional agent(s) is a chemotherapeutic agent, such as a chemotherapeutic agent selected from the group consisting of docetaxel, paclitaxel, abraxane (i.e., albumin-conjugated paclitaxel), doxorubicin, oxaliplatin, carboplatin, cisplatin, irinotecan, and gemcitabine.

In some embodiments, the additional agent(s) is a checkpoint inhibitor, a kinase inhibitor, an agent targeting inhibitors in the tumor microenvironment, and/or a T cell or NK agonist. In some embodiments, the additional agent(s) is radiation therapy, alone or in combination with another additional agent(s) such as a chemotherapeutic or anti-neoplastic agent. In some embodiments, the additional agent(s) is a vaccine, an oncovirus, and/or a DC-activating agent such as, by way of non-limiting example, a toll-like receptor (TLR) agonist and/or α-CD40. In some embodiments, the additional agent(s) is a tumor-targeted antibody designed to kill the tumor via ADCC or via direct conjugation to a toxin (e.g., an antibody drug conjugate (ADC).

In some embodiments, the checkpoint inhibitor is an inhibitor of a target selected from the group consisting of CTLA-4, LAG-3, PD-1, PD-1, TIGIT, TIM-3, B7H4, BTLA, and Vista. In some embodiments, the kinase inhibitor is selected from the group consisting of B-RAFi, MEKi, and Btk inhibitors, such as ibrutinib. In some embodiments, the kinase inhibitor is crizotinib. In some embodiments, the tumor microenvironment inhibitor is selected from the group consisting of an IDO inhibitor, an α-CSF1R inhibitor, an α-CCR4 inhibitor, a TGF-beta, a myeloid-derived suppressor cell, or a T-regulatory cell. In some embodiments, the agonist is selected from the group consisting of Ox40, GITR, CD137, ICOS, CD27, and HVEM.

In some embodiments, the inhibitor is a CTLA-4 inhibitor. In some embodiments, the inhibitor is a LAG-3 inhibitor. In some embodiments, the inhibitor is a PD-1 inhibitor. In some embodiments, the inhibitor is a PD-1 inhibitor. In some embodiments, the inhibitor is a TIGIT inhibitor. In some embodiments, the inhibitor is a TIM-3 inhibitor. In some embodiments, the inhibitor is a B7H4 inhibitor. In some embodiments, the inhibitor is a Vista inhibitor. In some embodiments, the inhibitor is a B-RAFi inhibitor. In some embodiments, the inhibitor is a MEKi inhibitor. In some embodiments, the inhibitor is a Btk inhibitor. In some embodiments, the inhibitor is ibrutinib. In some embodiments, the inhibitor is crizotinib. In some embodiments, the inhibitor is an IDO inhibitor. In some embodiments, the inhibitor is an α-CSF1R inhibitor. In some embodiments, the inhibitor is an α-CCR4 inhibitor. In some embodiments, the inhibitor is a TGF-beta. In some embodiments, the inhibitor is a myeloid-derived suppressor cell. In some embodiments, the inhibitor is a T-regulatory cell.

In some embodiments, the agonist is Ox40. In some embodiments, the agonist is GITR. In some embodiments, the agonist is CD137. In some embodiments, the agonist is ICOS. In some embodiments, the agonist is CD27. In some embodiments, the agonist is HVEM.

In some embodiments, the antibody, conjugated antibody, activatable antibody, and/or conjugated activatable antibody is administered during and/or after treatment in combination with one or more additional agents such as, for example, a chemotherapeutic agent, an anti-inflammatory agent, and/or an immunosuppressive agent. In some embodiments, the antibody, conjugated antibody, activatable antibody, and/or conjugated activatable antibody and the additional agent are formulated into a single therapeutic composition, and the antibody, conjugated antibody, activatable antibody, and/or conjugated activatable antibody and additional agent are administered simultaneously. Alternatively, the antibody, conjugated antibody, activatable antibody, and/or conjugated activatable antibody and additional agent are separate from each other, e.g., each is formulated into a separate therapeutic composition, and the antibody, conjugated antibody, activatable antibody, and/or conjugated activatable antibody and the additional agent are administered simultaneously, or the antibody, conjugated antibody, activatable antibody, and/or conjugated activatable antibody and the additional agent are administered at different times during a treatment regimen. For example, the antibody, conjugated antibody, activatable antibody, and/or conjugated activatable antibody is administered prior to the administration of the additional agent, the antibody, conjugated antibody, activatable antibody, and/or conjugated activatable antibody is administered subsequent to the administration of the additional agent, or the antibody, conjugated antibody, activatable antibody, and/or conjugated activatable antibody and the additional agent are administered in an alternating fashion. As described herein, the antibody, conjugated antibody, activatable antibody, and/or conjugated activatable antibody and additional agent are administered in single doses or in multiple doses.

In some embodiments, the antibody, conjugated antibody, activatable antibody, and/or conjugated activatable antibody and the additional agent(s) are administered simultaneously. For example, the antibody, conjugated antibody, activatable antibody, and/or conjugated activatable antibody and the additional agent(s) can be formulated in a single composition or administered as two or more separate compositions. In some embodiments, the antibody, conjugated antibody, activatable antibody, and/or conjugated activatable antibody and the additional agent(s) are administered sequentially, or the antibody, conjugated antibody, activatable antibody, and/or conjugated activatable antibody and the additional agent are administered at different times during a treatment regimen.

In some embodiments, the conjugated antibody, activatable antibody and/or conjugated activatable antibody is administered during and/or after treatment in combination with one or more additional agents such as, by way of non-limiting example, an anti-inflammatory agent, an immunosuppressive agent, a chemotherapeutic agent, such as an alkylating agent, an anti-metabolite, an anti-microtubule agent, a topoisomerase inhibitor, a cytotoxic antibiotic, and/or any other nucleic acid damaging agent. In some embodiments, the additional agent is a taxane, such as paclitaxel (e.g., Abraxane®). In some embodiments, the additional agent is an anti-metabolite, such as gemcitabine. In some embodiments, the additional agent is an alkylating agent, such as platinum-based chemotherapy, such as carboplatin or cisplatin. In some embodiments, the additional agent is a targeted agent, such as a kinase inhibitor, e.g., sorafenib or erlotinib. In some embodiments, the additional agent is a targeted agent, such as another antibody, e.g., a monoclonal antibody (e.g., bevacizumab), a bispecific antibody, or a multispecific antibody. In some embodiments, the additional agent is a proteosome inhibitor, such as bortezomib or carfilzomib. In some embodiments, the additional agent is an immune modulating agent, such as lenolidominde or IL-2. In some embodiments, the additional agent is radiation. In some embodiments, the additional agent is an agent considered standard of care by those skilled in the art. In some embodiments, the additional agent is a chemotherapeutic agent well known to those skilled in the art.

In some embodiments, the additional agent is an antibody, another conjugated antibody, another activatable antibody and/or another conjugated activatable antibody. In some embodiments the additional agent is an antibody, another conjugated antibody, another activatable antibody and/or another conjugated activatable antibody against the same target as the first conjugated antibody, activatable antibody and/or a conjugated activatable antibody. In some embodiments the additional agent is an antibody, another conjugated antibody, another activatable antibody and/or another conjugated activatable antibody against a target different than the target of the first conjugated antibody, activatable antibody and/or a conjugated activatable antibody.

In some embodiments, the conjugated antibody, activatable antibody and/or conjugated activatable antibody and the additional agent(s) are administered simultaneously. For example, the conjugated antibody, activatable antibody and/or conjugated activatable antibody and the additional agent(s) can be formulated in a single composition or administered as two or more separate compositions. In some embodiments, the conjugated antibody, activatable antibody and/or conjugated activatable antibody and the additional agent(s) are administered sequentially, or the antibody and/or conjugated antibodies and the additional agent are administered at different times during a treatment regimen. For example, the antibody and/or conjugated antibodies is administered prior to the administration of the additional agent, the antibody and/or conjugated antibodies is administered subsequent to the administration of the additional agent, or the antibody and/or conjugated antibodies and the additional agent are administered in an alternating fashion. As described herein, the antibody and/or conjugated antibodies and additional agent are in single doses or in multiple doses.

The disclosure also provides methods and kits for using the conjugated antibodies, activatable antibodies and/or conjugated activatable antibodies in a variety of diagnostic and/or prophylactic indications.

Pharmaceutical compositions according to the disclosure can include an antibody, conjugated antibody, activatable antibody and/or a conjugated activatable antibody of the disclosure and a carrier. These pharmaceutical compositions can be included in kits, such as, for example, diagnostic kits.

The conjugated antibodies, activatable antibodies, and/or conjugated activatable antibodies include an antibody or antigen-binding fragment thereof (AB) that specifically binds a target. Exemplary classes of targets of an AB include, but are not necessarily limited to, cell surface receptors and secreted binding proteins (e.g., growth factors), soluble enzymes, structural proteins (e.g. collagen, fibronectin) and the like. In some embodiments, conjugated antibodies and/or activatable antibodies have an AB that binds an extracellular target, usually an extracellular protein target. In some embodiments, conjugated antibodies and/or activatable antibodies are designed for cellular uptake and are switchable inside a cell.

As a non-limiting example, the AB is a binding partner for any target listed in Table 1.

TABLE 1

| Exemplary Targets | | | | | |
|---|---|---|---|---|---|
| 1-92-LFA-3 | CD52 | DL44 | HVEM | LIF-R | STEAP1 |
| Alpha-4 integrin | CD56 | DLK1 | Hyaluronidase | Lewis X | STEAP2 |
| Alpha-V integrin | CD64 | DLL4 | ICOS | LIGHT | TAG-72 |

TABLE 1-continued

| Exemplary Targets | | | | | |
|---|---|---|---|---|---|
| alpha4beta1 integrin | CD70 | DPP-4 | IFNalpha | LRP4 | TAPA1 |
| alpha4beta7 integrin | CD71 | DSG1 | IFNbeta | LRRC26 | TGFbeta |
| AGR2 | CD74 | EGFR | IFNgamma | MCSP | TIGIT |
| Anti-Lewis-Y | | EGFRviii | IgE | Mesothelin | TIM-3 |
| Apelin J receptor | CD80 | Endothelin B receptor (ETBR) | IgE Receptor (FceRI) | MRP4 | TLR2 |
| APRIL | CD81 | ENPP3 | IGF | MUC1 | TLR4 |
| B7-H4 | CD86 | EpCAM | IGF1R | Mucin-16 (MUC16, CA-125) | TLR6 |
| BAFF | CD95 | EPHA2 | IL1B | Na/K ATPase | TLR7 |
| BTLA | CD117 | EPHB2 | IL1R | Neutrophil elastase | TLR8 |
| C5 complement | CD125 | ERBB3 | IL2 | NGF | TLR9 |
| C-242 | CD132 (IL-2RG) | F protein of RSV | IL11 | Nicastrin | TMEM31 |
| CA9 | CD133 | FAP | IL12 | Notch Receptors | TNFalpha |
| CA19-9 (Lewis a) | CD137 | FGF-2 | IL12p40 | Notch 1 | TNFR |
| Carbonic anhydrase 9 | CD138 | FGF8 | IL-12R, IL-12Rbeta 1 | Notch 2 | TNFRS12A |
| CD2 | CD166 | FGFR1 | IL13 | Notch 3 | TRAIL-R1 |
| CD3 | CD172A | FGFR2 | IL13R | Notch 4 | TRAIL-R2 |
| CD6 | CD248 | FGFR3 | IL15 | NOV | Transferrin |
| CD9 | CDH6 | FGFR4 | IL17 | OSM-R | Transferrin receptor |
| CD11a | CEACAM5 (CEA) | Folate receptor | IL18 | OX-40 | TRK-A |
| CD19 | CEACAM6 (NCA-90) | GAL3ST1 | IL21 | PAR2 | TRK-B |
| CD20 | CLAUDIN-3 | G-CSF | IL23 | PDGF-AA | uPAR |
| CD22 | CLAUDIN-4 | G-CSFR | IL23R | PDGF-BB | VAP1 |
| CD24 | cMet | GD2 | IL27/IL27R (wsx1) | PDGFRalpha | VCAM-1 |
| CD25 | Collagen | GITR | IL29 | PDGFRbeta | VEGF |
| CD27 | Cripto | GLUT1 | IL-31R | PD-1 | VEGF-A |
| CD28 | CSFR | GLUT4 | IL31/IL31R | PD-L1 | VEGF-B |
| CD30 | CSFR-1 | GM-CSF | IL2R | PD-L2 | VEGF-C |
| CD33 | CTLA-4 | GM-CSFR | IL4 | Phosphatidyl-serine | VEGF-D |
| CD38 | CTGF | GP IIb/IIIa receptors | IL4R | P1GF | VEGFR1 |
| CD40 | CXCL10 | Gp130 | IL6, IL6R | PSCA | VEGFR2 |
| CD40L | CXCL13 | GPIIB/IIIA | Insulin Receptor | PSMA | VEGFR3 |
| CD41 | CXCR1 | GPNMB | Jagged Ligands | RAAG12 | VISTA |
| CD44 | CXCR2 | GRP78 | Jagged 1 | RAGE | WISP-1 |
| CD44v6 | | HER2/neu | Jagged 2 | SLC44A4 | WISP-2 |
| CD47 | CXCR4 | HGF | LAG-3 | Sphingosine 1 Phosphate | WISP-3 |
| CD51 | CYR61 | hGH | | | |

As a non-limiting example, the AB is or is derived from an antibody listed in Table 2.

TABLE 2

| Exemplary sources for Abs | |
|---|---|
| Antibody Trade Name (antibody name) | Target |
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |
| Tysabri ™ (natalizumab) | Integrinα4 |
| Simulect ™ (basiliximab) | IL2R |

TABLE 2-continued

| Exemplary sources for Abs | |
|---|---|
| Antibody Trade Name (antibody name) | Target |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Ocrelizumab | CD20 |
| Arzerra ™ (ofatumumab) | CD20 |
| Gazyva ™ (Obinutuzumab) | CD20 |
| Zenapax ™ (daclizumab) | CD25 |
| Adcetris ™ (brentuximab vedotin) | CD30 |
| Myelotarg ™ (gemtuzumab) | CD33 |

TABLE 2-continued

Exemplary sources for Abs

| Antibody Trade Name (antibody name) | Target |
|---|---|
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |
| Xolair ™ (omalizumab) | IgE |
| Herceptin ™ (trastuzumab) | Her2 |
| Kadcyla ™ (trastuzumab emtansine) | Her2 |
| Synagis ™ (palivizumab) | F protein of RSV |
| (ipilimumab) | CTLA-4 |
| (tremelimumab) | CTLA-4 |
| Hu5c8 | CD40L |
| (pertuzumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |
| (mapatumumab) | EGFR |
| (matuzumab) | EGFR |
| (nimotuzumab) | EGFR |
| ICR62 | EGFR |
| mAb 528 | EGFR |
| CH806 | EGFR |
| MDX-447 | EGFR/CD64 |
| (edrecolomab) | EpCAM |
| RAV12 | RAAG12 |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta |
| | Notch, e.g., Notch 1 |
| | Jagged 1 or Jagged 2 |
| (adecatumumab) | EpCAM |
| (figitumumab) | IGF1R |
| (tocilizumab) | IL-6 receptor |
| Stelara ™ (ustekinumab) | IL-12/IL-23 |
| Prolia ™ (denosumab) | RANKL |

The activatable antibodies and activatable antibody compositions provided herein contain at least an antibody or antibody fragment thereof (collectively referred to as AB throughout the disclosure) that specifically binds a target, e.g., a human target, wherein the AB is modified by a masking moiety (MM).

In some embodiments, the masking moiety is selected for use with a specific antibody or antibody fragment. For example, suitable masking moieties for use with antibodies that bind EGFR include MMs that include the sequence CISPRG (SEQ ID NO: 165). By way of non-limiting examples, the MM can include a sequence such as CISPRGC (SEQ ID NO: 166); CISPRGCG (SEQ ID NO: 167); CISPRGCPDGPYVMY (SEQ ID NO: 168); CISPRGCPDGPYVM (SEQ ID NO: 169), CISPRGCEPGTYVPT (SEQ ID NO: 170) and CISPRGCPGQIWHPP (SEQ ID NO: 171). Other suitable masking moieties include any of the EGFR-specific masks disclosed in PCT Publication No. WO 2010/081173, such as, by way of non-limiting example, GSHCLIPINMGAPSC (SEQ ID NO: 172); CISPRGCGGSSASQSGQGSHCLIPINMGAPSC (SEQ ID NO: 173); CNHHYFYTCGCISPRGCPG (SEQ ID NO: 174); ADHVFWGSYGCISPRGCPG (SEQ ID NO: 175); CHHVYWGHCGCISPRGCPG (SEQ ID NO: 176); CPHFTTTSCGCISPRGCPG (SEQ ID NO: 177); CNHHYHYYCGCISPRGCPG (SEQ ID NO: 178); CPHVSFGSCGCISPRGCPG (SEQ ID NO: 179); CPYYTLSYCGCISPRGCPG (SEQ ID NO: 180); CNHVYFGTCGCISPRGCPG (SEQ ID NO: 181);

CNHFTLTTCGCISPRGCPG (SEQ ID NO: 182); CHHFTLTTCGCISPRGCPG (SEQ ID NO: 183); YNPCATPMCCISPRGCPG (SEQ ID NO: 184); CNHHYFYTCGCISPRGCG (SEQ ID NO: 185); CNHHYHYYCGCISPRGCG (SEQ ID NO: 186); CNHVYFGTCGCISPRGCG (SEQ ID NO: 187); CHHVYWGHCGCISPRGCG (SEQ ID NO: 188); CPHFTTTSCGCISPRGCG (SEQ ID NO: 189); CNHFTLTTCGCISPRGCG (SEQ ID NO: 190); CHHFTLTTCGCISPRGCG (SEQ ID NO: 191); CPYYTLSYCGCISPRGCG (SEQ ID NO: 192); CPHVSFGSCGCISPRGCG (SEQ ID NO: 193); ADHVFWGSYGCISPRGCG (SEQ ID NO: 194); YNPCATPMCCISPRGCG (SEQ ID NO: 195); CHHVYWGHCGCISPRGCG (SEQ ID NO: 196); C(N/P)H(H/V/F)(Y/T)(F/W/T/L)(Y/G/T/S)(T/S/Y/H)CGCISPRGCG (SEQ ID NO: 197); CISPRGCGQPIPSVK (SEQ ID NO: 198); CISPRGCTQPYHVSR (SEQ ID NO: 199); and/or CISPRGCNAVSGLGS (SEQ ID NO: 164).

When the AB is modified with a MM and is in the presence of the target, specific binding of the AB to its target is reduced or inhibited, as compared to the specific binding of the AB not modified with an MM or the specific binding of the parental AB to the target.

The $K_d$ of the AB modified with a MM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM or of the parental AB towards the target. Conversely, the binding affinity of the AB modified with a MM towards the target is at least 2, 3, 4, 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM or of the parental AB towards the target.

The dissociation constant ($K_d$) of the MM towards the AB is generally greater than the $K_d$ of the AB towards the target. The $K_d$ of the MM towards the AB can be at least 5, 10, 25, 50, 100, 250, 500, 1,000, 2,500, 5,000, 10,000, 100,000, 1,000,000 or even 10,000,000 times greater than the $K_d$ of the AB towards the target. Conversely, the binding affinity of the MM towards the AB is generally lower than the binding affinity of the AB towards the target. The binding affinity of MM towards the AB can be at least 5, 10, 25, 50, 100, 250, 500, 1,000, 2,500, 5,000, 10,000, 100,000, 1,000,000 or even 10,000,000 times lower than the binding affinity of the AB towards the target.

When the AB is modified with a MM and is in the presence of the target specific binding of the AB to its target is reduced or inhibited, as compared to the specific binding of the AB not modified with an MM or the specific binding of the parental AB to the target. When compared to the binding of the AB not modified with an MM or the binding of the parental AB to the target the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or more when measured in vivo or in an in vitro assay.

The MM inhibits the binding of the AB to the target. The MM binds the antigen binding domain of the AB and inhibits binding of the AB to the target. The MM can sterically inhibit the binding of the AB to the target. The MM can allosterically inhibit the binding of the AB to its target. In these embodiments when the AB is modified or coupled to a MM and in the presence of target there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

When an AB is coupled to or modified by a MM, the MM 'masks' or reduces or otherwise inhibits the specific binding of the AB to the target. When an AB is coupled to or modified by a MM, such coupling or modification can effect a structural change that reduces or inhibits the ability of the AB to specifically bind its target.

An AB coupled to or modified with an MM can be represented by the following formulae (in order from an amino (N) terminal region to carboxyl (C) terminal region:

(MM)-(AB)

(AB)-(MM)

(MM)-L-(AB)

(AB)-L-(MM)

where MM is a masking moiety, the AB is an antibody or antibody fragment thereof, and the L is a linker. In many embodiments, it may be desirable to insert one or more linkers, e.g., flexible linkers, into the composition to provide for flexibility.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 25% identical to any natural binding partner of the AB. In some embodiments, the MM is no more than 50% identical to any natural binding partner of the AB. In some embodiments, the MM is no more than 20% identical to any natural binding partner of the AB. In some embodiments, the MM is no more than 10% identical to any natural binding partner of the AB.

In some embodiments, the activatable antibodies include an AB that is modified by an MM and also includes at least one cleavable moiety (CM1) that is a substrate for at least one matrix metalloprotease (MMP) and at least a second cleavable moiety (CM2) that is a subject for at least one serine protease (SP). Such activatable antibodies exhibit activatable/switchable binding, to the AB's target. Activatable antibodies generally include an antibody or antibody fragment (AB), modified by or coupled to a masking moiety (MM) and a CM1-CM2 substrate.

The elements of the activatable antibodies are arranged so that the MM and CM1-CM2 substrate are positioned such that in a cleaved (or relatively active) state and in the presence of a target, the AB binds a target while in an uncleaved (or relatively inactive) state in the presence of the target, specific binding of the AB to its target is reduced or inhibited. The specific binding of the AB to its target can be reduced due to the inhibition or masking of the AB's ability to specifically bind its target by the MM.

The $K_d$ of the AB modified with a MM and a CM1-CM2 substrate towards the target is at least 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM and a CM1-CM2 substrate or of the parental AB towards the target. Conversely, the binding affinity of the AB modified with a MM and a CM1-CM2 substrate towards the target is at least 2, 3, 4, 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM and a CM1-CM2 substrate or of the parental AB towards the target.

When the AB is modified with a MM and a CM1-CM2 substrate and is in the presence of the target but not in the presence of a modifying agent (for example a MMP and a SP), specific binding of the AB to its target is reduced or inhibited, as compared to the specific binding of the AB not modified with an MM and a CM1-CM2 substrate or of the parental AB to the target. When compared to the binding of the parental AB or the binding of an AB not modified with an MM and a CM1-CM2 substrate to its target, the AB's ability to bind the target when modified with an MM and a CM1-CM2 substrate can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

As used herein, the term cleaved state refers to the condition of the activatable antibodies following modification, i.e., cleavage, of the CM1-CM2 substrate by at least one matrix metalloprotease and/or at least one serine protease. The term uncleaved state or fully uncleaved, as used herein, refers to the condition of the activatable antibodies in the absence of cleavage of the CM1-CM2 substrate by a MMP and/or a SP. As discussed above, the term "activatable antibodies" is used herein to refer to an activatable antibody in both its uncleaved (native) state, as well as in its cleaved state. An activatable antibody in its cleaved state is also referred to herein as an activated antibody and/or activated activatable antibody. It will be apparent to the ordinarily skilled artisan that in some embodiments, a cleaved activatable antibody may lack an MM due to cleavage of the CM1-CM2 substrate by protease, resulting in release of at least the MM.

By activatable or switchable is meant that the activatable antibody exhibits a first level of binding to a target when in a inhibited, masked or uncleaved state (i.e., a first conformation), and a second level of binding to the target in the uninhibited, unmasked and/or cleaved state (i.e., a second conformation), where the second level of target binding is greater than the first level of binding. In general, the access of target to the AB of the activatable antibody is greater in the presence of a cleaving agent capable of cleaving the CM1-CM2 substrate than in the absence of such a cleaving agent. Thus, when the activatable antibody is in the uncleaved state, the AB is inhibited from target binding and can be masked from target binding (i.e., the first conformation is such the AB cannot bind the target), and in the cleaved state the AB is not inhibited or is unmasked to target binding.

The CM1-CM2 substrate and AB of the activatable antibodies are selected so that the AB represents a binding moiety for a given target, and the CM1-CM2 substrate represents a substrate for a MMP and a SP, where the MMP and/or the SP are co-localized with the target at a treatment site or diagnostic site in a subject. The activatable antibodies disclosed herein find particular use where, for example, a MMP and a SP, each capable of cleaving a site in the CM1-CM2 substrate, are present at relatively higher levels in target-containing tissue of a treatment site or diagnostic site than in tissue of non-treatment sites (for example in healthy tissue).

In some embodiments, activatable antibodies provide for reduced toxicity and/or adverse side effects that could otherwise result from binding of the AB at non-treatment sites if the AB were not masked or otherwise inhibited from binding to the target.

In general, an activatable antibody can be designed by selecting an AB of interest and constructing the remainder of the activatable antibody so that, when conformationally constrained, the MM provides for masking of the AB or reduction of binding of the AB to its target. Structural design criteria can be to be taken into account to provide for this functional feature.

Activatable antibodies exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of an activatable antibody, the dynamic range refers to the ratio of (a) a maximum detected level of target protein binding to an activatable antibody in the presence of a MMP and a SP that are capable of cleaving the CM1-CM2 substrate of the activatable antibodies to (b) a minimum detected level of target protein binding to an activatable antibody in the absence of the protease. The dynamic range of an activatable antibody can be calculated as the ratio of the dissociation constant of an activatable antibody cleaving agent (e.g., enzyme) treatment to the dissociation constant of the activatable antibodies cleaving agent treatment. The greater the dynamic range of an activatable antibody, the better the switchable phenotype of the activatable antibody. Activatable antibodies having relatively higher dynamic range values (e.g., greater than 1) exhibit more desirable switching phenotypes such that target protein binding by the activatable antibodies occurs to a greater extent (e.g., predominantly occurs) in the presence of a cleaving agent (e.g., enzyme) capable of cleaving the CM1-CM2 substrate of the activatable antibodies than in the absence of a cleaving agent.

Activatable antibodies can be provided in a variety of structural configurations. Exemplary formulae for activatable antibodies are provided below. It is specifically contemplated that the N- to C-terminal order of the AB, MM and CM1-CM2 substrate may be reversed within an activatable antibody. It is also specifically contemplated that the CM and MM may overlap in amino acid sequence, e.g., such that the CM1-CM2 substrate is at least partially contained within the MM.

For example, activatable antibodies can be represented by the following formula (in order from an amino (N) terminal region to carboxyl (C) terminal region:

(MM)-(CM1-CM2 substrate)-(AB)

(AB)-(CM1-CM2 substrate)-(MM)

where MM is a masking moiety, the CM1-CM2 substrate is a cleavable moiety, and AB is an antibody or fragment thereof. As noted above, the term "CM1-CM2 substrate" is not intended to convey any requirement regarding the orientation or other structural arrangement of the first cleavable moiety (CM1) that is a substrate for at least one matrix metalloprotease (MMP) and at least a second cleavable moiety (CM2) that is a substrate for at least one serine protease (SP). Thus, the term "CM1-CM2 substrates" encompasses CM1-CM2 substrates having the structural arrangement from N-terminus to C-terminus as follows: CM1-CM2 or CM2-CM1. The term "CM1-CM2 substrates" also encompasses substrates where at least a portion of the CM1 sequence overlaps with at least a portion of the CM2 sequence. It should also be noted that although MM and CM1-CM2 substrate are indicated as distinct components in the formulae above, in all exemplary embodiments (including formulae) disclosed herein it is contemplated that the amino acid sequences of the MM and the CM1-CM2 substrate could overlap, e.g., such that the CM1-CM2 substrate is completely or partially contained within the MM. In addition, the formulae above provide for additional amino acid sequences that may be positioned N-terminal or C-terminal to the activatable antibodies elements.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 50% identical to any natural binding partner of the AB. In some embodiments, the MM is no more than 25% identical to any natural binding partner of the AB. In some embodiments, the MM is no more than 20% identical to any natural binding partner of the AB. In some embodiments, the MM is no more than 10% identical to any natural binding partner of the AB.

In many embodiments, it may be desirable to insert one or more linkers, e.g., flexible linkers, into the activatable antibody construct to provide for flexibility at one or more of the MM-CM1-CM2 substrate junction, the CM1-CM2 substrate-AB junction, or both. For example, the AB, MM, and/or CM1-CM2 substrate may not contain a sufficient number of residues (e.g., Gly, Ser, Asp, Asn, especially Gly and Ser, particularly Gly) to provide the desired flexibility. As such, the switchable phenotype of such activatable antibody constructs may benefit from introduction of one or more amino acids to provide for a flexible linker. In addition, as described below, where the activatable antibody is provided as a conformationally constrained construct, a flexible linker can be operably inserted to facilitate formation and maintenance of a cyclic structure in the uncleaved activatable antibody.

For example, in certain embodiments, an activatable antibody comprises one of the following formulae (where the formula below represents an amino acid sequence in either N- to C-terminal direction or C- to N-terminal direction):

(MM)-LP1-(CM1-CM2 substrate)-(AB)

(MM)-(CM1-CM2 substrate)-LP2-(AB)

(MM)-LP1-(CM1-CM2 substrate)-LP2-(AB)

wherein MM, CM1-CM2 substrate, and AB are as defined above; wherein LP1 and LP2 are each independently and optionally present or absent, are the same or different flexible linkers that include at least 1 flexible amino acid (e.g., Gly). In addition, the formulae above provide for additional amino acid sequences that may be positioned N-terminal or C-terminal to the activatable antibodies elements. Examples include, but are not limited to, targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HAS)).

The CM1-CM2 substrate is specifically cleaved by at least one MMP at a rate of about $0.001\text{-}1500\times10^4\ M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500\times10^4\ M^{-1}S^{-1}$ and is specifically cleaved by at least one SP at a rate of about $0.001\text{-}1500\times10^4\ M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500\times10^4\ M^{-1}S^{-1}$.

For specific cleavage by an enzyme, contact between the enzyme and CM1-CM2 substrate is made. When the activatable antibody comprising an AB coupled to a MM and a CM1-CM2 substrate is in the presence of target and sufficient enzyme activity, the CM1-CM2 substrate can be cleaved. Sufficient enzyme activity can refer to the ability of the enzyme to make contact with the CM1-CM2 substrate and effect cleavage. It can readily be envisioned that an enzyme may be in the vicinity of the CM1-CM2 substrate but unable to cleave because of other cellular factors or protein modification of the enzyme.

Linkers suitable for use in compositions described herein are generally ones that provide flexibility of the modified AB or the activatable antibodies to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, or 20 amino acids in length.

Exemplary flexible linkers include glycine polymers (G)n, glycine-serine polymers (including, for example, (GS) n, (GSGGS)n (SEQ ID NO: 381) and (GGGS)n (SEQ ID NO: 382), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 202), Gly-Gly-Ser-Gly-Gly (SEQ ID NO: 203), Gly-Ser-Gly-Ser-Gly (SEQ ID NO: 204), Gly-Ser-Gly-Gly-Gly (SEQ ID NO: 205), Gly-Gly-Gly-Ser-Gly (SEQ ID NO: 206), Gly-Ser-Ser-Ser-Gly (SEQ ID NO: 207), and the like. The ordinarily skilled artisan will recognize that design of an activatable antibodies can include linkers that are all or partially flexible, such that the linker can include a flexible linker as well as one or more portions that confer less flexible structure to provide for a desired activatable antibodies structure.

In some embodiments, the activatable antibodies described herein also include an agent conjugated to the activatable antibody. In some embodiments, the conjugated agent is a therapeutic agent, such as an anti-inflammatory and/or an antineoplastic agent. In such embodiments, the agent is conjugated to a carbohydrate moiety of the activatable antibody, for example, in some embodiments, where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate).

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

The disclosure also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, dolastatins and derivatives thereof (e.g. auristatin E, AFP, MMAF, MMAE, MMAD, DMAF, DMAE). For example, the agent is monomethyl auristatin E (MMAE) or monomethyl auristatin D (MMAD). In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is linked to the AB using a maleimide caproyl-valine-citrulline linker or a maleimide PEG-valine-citrulline linker. In some embodiments, the agent is linked to the AB using a maleimide caproyl-valine-citrulline linker. In some embodiments, the agent is linked to the AB using a maleimide PEG-valine-citrulline linker In some embodiments, the agent is monomethyl auristatin D (MMAD) linked to the AB using a maleimide PEG-valine-citrulline-para-aminobenzyloxycarbonyl linker, and this linker payload construct is referred to herein as "vc-MMAD." In some embodiments, the agent is monomethyl auristatin E (MMAE) linked to the AB using a maleimide PEG-valine-citrulline-para-aminobenzyloxycarbonyl linker, and this linker payload construct is referred to herein as "vc-MMAE." The structures of vc-MMAD and vc-MMAE are shown below:

vc-MMAD

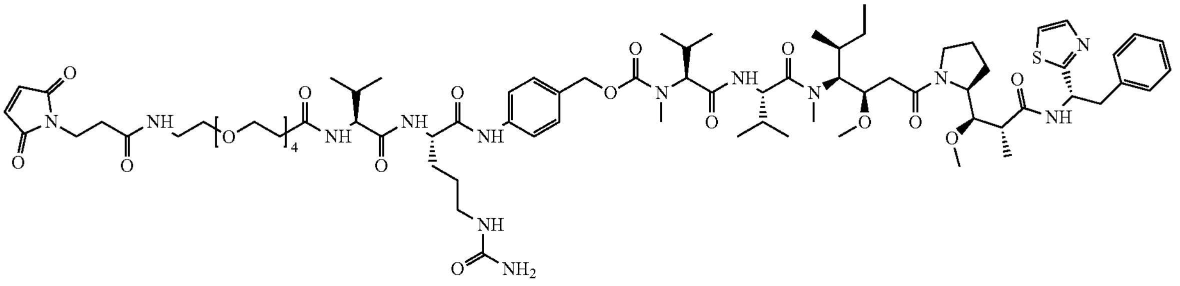

vc-MMAE

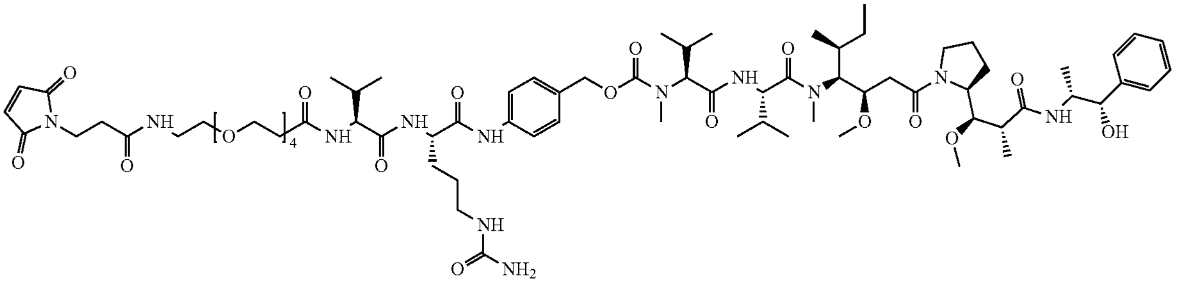

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutarelde-hyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Table 3 lists some of the exemplary pharmaceutical agents that may be employed in the herein described disclosure but in no way is meant to be an exhaustive list.

TABLE 3

| Exemplary Pharmaceutical Agents for Conjugation |
|---|
| CYTOTOXIC AGENTS |
| Auristatins |
| Auristatin E |
| Monomethyl auristatin D (MMAD) |
| Monomethyl auristatin E (MMAE) |
| Desmethyl auristatin E (DMAE) |
| Auristatin F |
| Monomethyl auristatin F (MMAF) |
| Desmethyl auristatin F (DMAF) |
| Auristatin derivatives, e.g., amides thereof |
| Auristatin tyramine |
| Auristatin quinoline |
| Dolastatins |
| Dolastatin derivatives |
| Dolastatin 16 DmJ |
| Dolastatin 16 Dpv |
| Maytansinoids, e.g. DM-1; DM-4 |
| Maytansinoid derivatives |
| Duocarmycin |
| Duocarmycin derivatives |
| Alpha-amanitin |
| Anthracyclines |
| Doxorubicin |
| Daunorubicin |
| Bryostatins |
| Camptothecin |
| Camptothecin derivatives |
| 7-substituted Camptothecin |
| 10, 11-Difluoromethylenedioxycamptothecin |
| Combretastatins |
| Debromoaplysiatoxin |
| Kahalalide-F |
| Discodermolide |
| Ecteinascidins |
| ANTIVIRALS |
| Acyclovir |
| Vira A |
| Symmetrel |

TABLE 3-continued

| Exemplary Pharmaceutical Agents for Conjugation |
| --- |
| ANTIFUNGALS |
| Nystatin |
| ADDITIONAL ANTI-NEOPLASTICS |
| Adriamycin |
| Cerubidine |
| Bleomycin |
| Alkeran |
| Velban |
| Oncovin |
| Fluorouracil |
| Methotrexate |
| Thiotepa |
| Bisantrene |
| Novantrone |
| Thioguanine |
| Procarabizine |
| Cytarabine |
| ANTI-BACTERIALS |
| Aminoglycosides |
| Streptomycin |
| Neomycin |
| Kanamycin |
| Amikacin |
| Gentamicin |
| Tobramycin |
| Streptomycin B |
| Spectinomycin |
| Ampicillin |
| Sulfanilamide |
| Polymyxin |
| Chloramphenicol |
| Turbostatin |
| Phenstatins |
| Hydroxyphenstatin |
| Spongistatin 5 |
| Spongistatin 7 |
| Halistatin 1 |
| Halistatin 2 |
| Halistatin 3 |
| Modified Bryostatins |
| Halocomstatins |
| Pyrrolobenzimidazoles (PBI) |
| Cibrostatin6 |
| Doxaliform |
| Anthracycline analogues |
| Cemadotin analogue (CemCH2-SH) |
| Pseudomonas toxin A (PE38) variant |
| Pseudomonas toxin A (ZZ-PE38) variant |
| ZJ-101 |
| OSW-1 |
| 4-Nitrobenzyloxycarbonyl Derivatives of O6-Benzylguanine |
| Topoisomerase inhibitors |
| Hemiasterlin |
| Cephalotaxine |
| Homoharringtonine |
| Pyrrolobenzodiazepine (PBD) |
| Pyrrolobenzodiazepine (PBD) dimers |
| Functionalized pyrrolobenzodiazepines |
| Functionalized pyrrolobenzodiazepine dimers |
| Calicheamicins |
| Podophyllotoxins |
| Taxanes |
| Vinca alkaloids |
| CONJUGATABLE DETECTION REAGENTS |
| Fluorescein and derivatives thereof |
| Fluorescein isothiocyanate (FITC) |
| RADIOPHARMACEUTICALS |
| $^{125}I$ |
| $^{131}I$ |
| $^{89}Zr$ |
| $^{111}In$ |
| $^{123}I$ |
| $^{131}In$ |
| $^{99}mTc$ |
| $^{201}Tl$ |
| $^{133}Xe$ |
| $^{11}C$ |
| $^{62}Cu$ |
| $^{18}F$ |
| $^{68}Ga$ |
| $^{13}N$ |
| $^{15}O$ |
| $^{38}K$ |
| $^{82}Rb$ |
| $^{99}mTc$ (Technetium) |
| HEAVY METALS |
| Barium |
| Gold |
| Platinum |
| ANTI-MYCOPLASMALS |
| Tylosine |
| Spectinomycin |

Those of ordinary skill in the art will recognize that a large variety of possible moieties can be coupled to the resultant antibodies of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments, the binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present disclosure, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

In some embodiments, in addition to the compositions and methods provided herein, the conjugated activatable antibody can also be modified for site-specific conjugation through modified amino acid sequences inserted or otherwise included in the activatable antibody sequence. These modified amino acid sequences are designed to allow for controlled placement and/or dosage of the conjugated agent within a conjugated activatable antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. In some embodiments, suitable linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC. Additional linkers include, but are not limited to, SMCC, sulfo-SMCC, SPDB, or sulfo-SPDB.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In some embodiments, the linkers are cleavable. In some embodiments, the linkers are non-cleavable. In some embodiments, two or more linkers are present. The two or more linkers are all the same, i.e., cleavable or non-cleavable, or the two or more linkers are different, i.e., at least one cleavable and at least one non-cleavable.

The present disclosure utilizes several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. According to the disclosure, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present disclosure, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

According to the present disclosure, suitable linkers for attachment to neither oxidized nor reduced Abs include those having certain functional groups capable of reaction with the primary amino groups present in unmodified lysine residues in the Ab. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present disclosure, suitable linkers for attachment to neither oxidized nor reduced Abs include those having certain functional groups capable of reaction with the carboxylic acid groups present in aspartate or glutamate residues in the Ab, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In some embodiments, the AB is first attached to the MM, CM1-CM2 substrate and associated linkers and then attached to the linker for conjugation purposes.

Branched Linkers:

In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

In some embodiments, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers:

Peptide linkers that are susceptible to cleavage by enzymes of the complement system, such as but not limited to urokinase, tissue plasminogen activator, trypsin, plasmin, or another enzyme having proteolytic activity may be used in one embodiment of the present disclosure. According to one method of the present disclosure, an agent is attached via a linker susceptible to cleavage by complement. The antibody is selected from a class that can activate complement. The antibody-agent conjugate, thus, activates the complement cascade and releases the agent at the target site. According to another method of the present disclosure, an agent is attached via a linker susceptible to cleavage by enzymes having a proteolytic activity such as a urokinase, a tissue plasminogen activator, plasmin, or trypsin. These cleavable linkers are useful in conjugated activatable antibodies that include an extracellular toxin, e.g., by way of non-limiting example, any of the extracellular toxins shown in Table 3.

Non-limiting examples of cleavable linker sequences are provided in Table 4.

TABLE 4

Exemplary Linker Sequences for Conjugation

| Types of Cleavable Sequences | Amino Acid Sequence |
|---|---|
| **Plasmin cleavable sequences** | |
| Pro-urokinase | PRFKIIGG (SEQ ID NO: 319) PRFRIIGG (SEQ ID NO: 320) |
| TGFβ | SSRHRRALD (SEQ ID NO: 321) |
| Plasminogen | RKSSIIIRMRDVVL (SEQ ID NO: 322) |
| Staphylokinase | SSSFDKGKYKKGDDA (SEQ ID NO: 323) SSSFDKGKYKRGDDA (SEQ ID NO: 324) |
| **Factor Xa cleavable sequences** | |
| | IEGR (SEQ ID NO: 325) IDGR (SEQ ID NO: 326) GGSIDGR (SEQ ID NO: 327) |
| **MMP cleavable sequences** | |
| Gelatinase A | PLGLWA (SEQ ID NO: 328) |
| **Collagenase cleavable sequences** | |
| Calf skin collagen (α1(I) chain) | GPQGIAGQ (SEQ ID NO: 329) |
| Calf skin collagen (α2(I) chain) | GPQGLLGA (SEQ ID NO: 330) |
| Bovine cartilage collagen (α1(II) chain) | GIAGQ (SEQ ID NO: 331) |
| Human liver collagen (α1(III) chain) | GPLGIAGI (SEQ ID NO: 332) |
| Human $\alpha_2$M | GPEGLRVG (SEQ ID NO: 333) |
| Human PZP | YGAGLGVV (SEQ ID NO: 334) AGLGVVER |

TABLE 4-continued

Exemplary Linker Sequences for Conjugation

| Types of Cleavable Sequences | Amino Acid Sequence |
|---|---|
| | (SEQ ID NO: 335) AGLGISST (SEQ ID NO: 336) |
| Rat $\alpha_1$M | EPQALAMS (SEQ ID NO: 337) QALAMSAI (SEQ ID NO: 338) |
| Rat $\alpha_2$M | AAYHLVSQ (SEQ ID NO: 339) MDAFLESS (SEQ ID NO: 340) |
| Rat $\alpha_1I_3$(2J) | ESLPVVAV (SEQ ID NO: 341) |
| Rat $\alpha_1I_3$(27J) | SAPAVESE (SEQ ID NO: 342) |
| Human fibroblast collagenase (autolytic cleavages) | DVAQFVLT (SEQ ID NO: 343) VAQFVLTE (SEQ ID NO: 344) AQFVLTEG (SEQ ID NO: 345) PVQPIGPQ (SEQ ID NO: 346) |

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In certain specific embodiments, the reducing agent that would modify a CM1-CM2 substrate would also modify the linker of the conjugated activatable antibody.

Spacers and Cleavable Elements:

In some embodiments, it may be necessary to construct the linker in such a way as to optimize the spacing between the agent and the AB of the activatable antibody. This may be accomplished by use of a linker of the general structure:

$$W—(CH_2)n\text{-}Q$$

wherein

W is either $—NH—CH_2—$ or $—CH_2—$;

Q is an amino acid, peptide; and n is an integer from 0 to 20.

In some embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

Serum Complement and Selection of Linkers:

According to one method of the present disclosure, when release of an agent is desired, an AB that is an antibody of a class that can activate complement is used. The resulting conjugate retains both the ability to bind antigen and activate the complement cascade. Thus, according to this embodiment of the present disclosure, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 3.

Linkers for Release without Complement Activation:

In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers:

In some embodiments, the activatable antibody may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bis-sialyl ether. Other suitable linkers include cathepsin-labile substrates, particularly those that show optimal function at an acidic pH.

Exemplary hetero-bifunctional cross-linkers are referenced in Table 5.

TABLE 5

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extender spacer arm Water-soluble | 15.6 Å |
| SMCC | Primary amines Sulfhydryls | Stable maleimide reactive group Enzyme-antibody conjugation Hapten-carrier protein conjugation | 11.6 Å |
| Sulfo-SMCC | Primary amines Sulfhydryls | Stable maleimide reactive group Water-soluble Enzyme-antibody conjugation | 11.6 Å |
| MBS | Primary amines Sulfhydryls | Enzyme-antibody conjugation Hapten-carrier protein conjugation | 9.9 Å |
| Sulfo-MBS | Primary amines Sulfhydryls | Water-soluble | 9.9 Å |
| SIAB | Primary amines Sulfhydryls | Enzyme-antibody conjugation | 10.6 Å |
| Sulfo-SIAB | Primary amines Sulfhydryls | Water-soluble | 10.6 Å |
| SMPB | Primary amines Sulfhydryls | Extended spacer arm Enzyme-antibody conjugation | 14.5 Å |
| Sulfo-SMPB | Primary amines Sulfhydryls | Extended spacer arm Water-soluble | 14.5 Å |
| EDE/Sulfo-NHS | Primary amines Carboxyl groups | Hapten-Carrier conjugation | 0 |
| ABH | Carbohydrates Nonselective | Reacts with sugar groups | 11.9 Å |

Non-Cleavable Linkers or Direct Attachment:

In some embodiments of the disclosure, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds that may be modified to include functional groups that can subsequently be utilized in attachment to ABs by the methods described herein. A-general formula for such an organic linker could be $$W—(CH_2)n\text{-}Q$$

wherein

W is either —NH—$CH_2$— or —$CH_2$—;

Q is an amino acid, peptide; and n is an integer from 0 to 20.

Non-Cleavable Conjugates:

In some embodiments, a compound may be attached to ABs that do not activate complement. When using ABs that are incapable of complement activation, this attachment may be accomplished using linkers that are susceptible to cleavage by activated complement or using linkers that are not susceptible to cleavage by activated complement.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al., J. Biol. Chem., 257: 286-288 (1982) via a disulfide-interchange reaction.

Definitions

Unless otherwise defined, scientific and technical terms used in connection with the present disclosure shall have the meanings that are commonly understood by those of ordinary skill in the art. The term “a” entity or “an” entity refers to one or more of that entity. For example, a compound refers to one or more compounds. As such, the terms “a”, “an”, “one or more” and “at least one” can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term “antibody” refers to immunoglobulin molecules and immunologically active portions of immunoglobulin (Ig) molecules, i.e., molecules that contain an antigen binding site that specifically binds (immunoreacts with) an antigen. By “specifically bind” or “immunoreacts with” or “immunospecifically bind” is meant that the antibody reacts with one or more antigenic determinants of the desired antigen and does not react with other polypeptides or binds at much lower affinity ($K_d>10^{-6}$). Antibodies include, but are not limited to, polyclonal, monoclonal, chimeric, domain antibody, single chain, Fab, and $F(ab')_2$ fragments, scFvs, and an Fab expression library.

The basic antibody structural unit is known to comprise a tetramer. Each tetramer is composed of two identical pairs of polypeptide chains, each pair having one “light” (about 25 kDa) and one “heavy” chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term “monoclonal antibody” (mAb) or “monoclonal antibody composition”, as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term “antigen-binding site” or “binding portion” refers to the part of the immunoglobulin molecule that participates in antigen binding. The antigen binding site is formed by amino acid residues of the N-terminal variable (“V”) regions of the heavy (“H”) and light (“L”) chains. Three highly divergent stretches within the V regions of the heavy and light chains, referred to as “hypervariable regions,” are interposed between more conserved flanking stretches known as “framework regions,” or “FRs”. Thus, the term “FR” refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as “complementarity-determining regions,” or “CDRs.” The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term “epitope” includes any protein determinant capable of specific binding to an immunoglobulin, a scFv, or a T-cell receptor. The term “epitope” includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 μM; in some embodiments, ≤100 nM and in some embodiments, ≤10 nM.

As used herein, the terms "specific binding," "immunological binding," and "immunological binding properties" refer to the non-covalent interactions of the type that occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to the target, when the binding constant ($K_d$) is ≤1 μM, in some embodiments ≤100 nM, in some embodiments ≤10 nM, and in some embodiments ≤100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide that it is not linked to in nature, or (3) does not occur in nature as part of a larger sequence. Polynucleotides in accordance with the disclosure include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length and in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, in some embodiments, at least 90 percent sequence identity, in some embodiments, at least 95 percent sequence identity, and in some embodiments, at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present disclosure, providing that the variations in the amino acid sequence maintain at least 75%, in some embodiments, at least 80%, 90%, 95%, and in some embodiments, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Suitable amino acid substitutions are those that: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N. Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, in some embodiments, at least 14 amino acids long, in some embodiments, at least 20 amino acids long, usually at least 50 amino acids long, and in some embodiments, at least 70 amino acids long. The term "analog" as used herein refers to polypeptides that are comprised of a segment of at least 25 amino acids that has substantial identity to a portion of a deduced amino acid sequence and that has specific binding to the target, under suitable binding conditions. Typically, polypeptide analogs comprise a conservative amino acid substitution (or addition or deletion) with respect to the naturally-occurring sequence. Analogs typically are at least 20 amino acids long, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms “label” or “labeled” refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, S, $^{90}Y$ $^{99}Tc$, $^{111}In$, $^{125}I$, $^{131}I$) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term “pharmaceutical agent or drug” as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, “substantially pure” means an object species is the predominant species present (i.e., on a molar basis it is more abundant than any other individual species in the composition), and in some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Activatable antibodies of the disclosure specifically bind a given target, e.g., a human target protein. Also included in the disclosure are activatable antibodies that bind to the same epitope as the activatable antibodies described herein.

Those skilled in the art will recognize that it is possible to determine, without undue experimentation, if a monoclonal antibody (e.g., a murine monoclonal or humanized antibody) has the same specificity as a monoclonal antibody used in the methods described herein by ascertaining whether the former prevents the latter from binding to the target. If the monoclonal antibody being tested competes with the monoclonal antibody of the disclosure, as shown by a decrease in binding by the monoclonal antibody of the disclosure, then the two monoclonal antibodies bind to the same, or a closely related, epitope. A method for determining whether a monoclonal antibody has the specificity of a monoclonal antibody of the disclosure is to pre-incubate the monoclonal antibody of the disclosure with the target and then add the monoclonal antibody being tested to determine if the monoclonal antibody being tested is inhibited in its ability to bind the target. If the monoclonal antibody being tested is inhibited then, in all likelihood, it has the same, or functionally equivalent, epitopic specificity as the monoclonal antibody of the disclosure.

Multispecific Activatable Antibodies

The disclosure also provides multispecific activatable antibodies. The multispecific activatable antibodies provided herein are multispecific antibodies that recognize two or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a CM1-CM2 substrate that functions as a substrate for at least one MMP protease and at least one SP. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the multispecific activatable antibodies are designed to engage immune effector cells, also referred to herein as immune-effector cell engaging multispecific activatable antibodies. In some embodiments, the multispecific activatable antibodies are designed to engage leukocytes, also referred to herein as leukocyte engaging multispecific activatable antibodies. In some embodiments, the multispecific activatable antibodies are designed to engage T cells, also referred to herein as T-cell engaging multispecific activatable antibodies. In some embodiments, the multispecific activatable antibodies engage a surface antigen on a leukocyte, such as on a T cell, on a natural killer (NK) cell, on a myeloid mononuclear cell, on a macrophage, and/or on another immune effector cell. In some embodiments, the immune effector cell is a leukocyte. In some embodiments, the immune effector cell is a T cell. In some embodiments, the immune effector cell is a NK cell. In some embodiments, the immune effector cell is a mononuclear cell, such as a myeloid mononuclear cell. In some embodiments, the multispecific activatable antibodies are designed to bind or otherwise interact with more than one target and/or more than one epitope, also referred to herein as multi-antigen targeting activatable antibodies. As used herein, the terms “target” and “antigen” are used interchangeably.

In some embodiments, immune effector cell engaging multispecific activatable antibodies of the disclosure include a targeting antibody or antigen-binding fragment thereof and an immune effector cell engaging antibody or antigen-binding portion thereof, where at least one of the targeting antibody or antigen-binding fragment thereof and/or the immune effector cell engaging antibody or antigen-binding portion thereof is masked. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the non-immune effector cell engaging antibody is a cancer targeting antibody. In some embodiments the non-immune cell effector antibody is an IgG. In some embodiments the immune effector cell engaging antibody is a scFv. In some embodiments the targeting antibody (e.g., non-immune cell effector antibody) is an IgG and the immune effector cell engaging antibody is a scFv. In some embodiments, the immune effector cell is a leukocyte. In some embodiments, the immune effector cell is a T cell. In some embodiments, the immune effector cell is a NK cell. In some embodiments, the immune effector cell is a myeloid mononuclear cell.

In some embodiments, T-cell engaging multispecific activatable antibodies of the disclosure include a targeting antibody or antigen-binding fragment thereof and a T-cell engaging antibody or antigen-binding portion thereof, where at least one of the targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibodies include a cancer targeting antibody or antigen-binding fragment thereof and a T-cell engaging antibody or antigen-binding portion thereof, where at least one of the cancer targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibodies include a cancer targeting IgG antibody or antigen-binding fragment thereof and a T-cell engaging scFv, where at least one of the cancer targeting IgG antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments of an immune effector cell engaging multispecific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA. In some embodiments, the antigen is a stimulatory receptor present on the surface of a T cell or NK cell; examples of such stimulatory receptors include, but are not limited to, CD3, CD27, CD28, CD137 (also referred to as 4-1BB), GITR, HVEM, ICOS, NKG2D, and OX40. In some embodiments, the antigen is an inhibitory receptor present on the surface of a T-cell; examples of such inhibitory receptors include, but are not limited to, BTLA, CTLA-4, LAG3, PD-1, TIGIT, TIM3, and NK-expressed KIRs. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9.

One embodiment of the disclosure is a multispecific activatable antibody that is activatable in a cancer microenvironment and that includes an antibody, for example a IgG or scFv, directed to a tumor target and an agonist antibody, for example an IgG or scFv, directed to a co-stimulatory receptor expressed on the surface of an activated T cell or NK cell, wherein at least one of the cancer target antibody and/or agonist antibody is masked. Examples of co-stimulatory receptors include, but are not limited to, CD27, CD137, GITR, HVEM, NKG2D, and OX40. In this embodiment, the multispecific activatable antibody, once activated by tumor-associated proteases, would effectively crosslink and activate the T cell or NK cell expressed co-stimulatory receptors in a tumor-dependent manner to enhance the activity of T cells that are responding to any tumor antigen via their endogenous T cell antigen or NK-activating receptors. The activation-dependent nature of these T cell or NK cell costimulatory receptors would focus the activity of the activated multispecific activatable antibody to tumor-specific T cells, without activating all T cells independent of their antigen specificity. In one embodiment, at least the co-stimulatory receptor antibody of the multispecific activatable antibody is masked to prevent activation of autoreactive T cells that may be present in tissues that also express the antigen recognized by the tumor target-directed antibody in the multispecific activatable antibody, but whose activity is restricted by lack of co-receptor engagement.

One embodiment of the disclosure is a multispecific activatable antibody that is activatable in a disease characterized by T cell overstimulation, such as, but not limited to, an autoimmune disease or inflammatory disease microenvironment. Such a multispecific activatable antibody includes an antibody, for example a IgG or scFv, directed to a target comprising a surface antigen expressed in a tissue targeted by a T cell in autoimmune or inflammatory disease and an antibody, for example a IgG or scFv, directed to an inhibitory receptor expressed on the surface of a T cell or NK cell, wherein at least one of the disease tissue target antibody and/or T cell inhibitory receptor antibody is masked. Examples of inhibitory receptors include, but are not limited to, BTLA, CTLA-4, LAG3, PD-1, TIGIT, TIM3, and NK-expressed KIRs. Examples of a tissue antigen targeted by T cells in autoimmune disease include, but are not limited to, a surface antigen expressed on myelin or nerve cells in multiple sclerosis or a surface antigen expressed on pancreatic islet cells in Type 1 diabetes. In this embodiment, the multispecific activatable antibody when localized in the tissue under autoimmune attack or inflammation is activated and co-engages the T cell or NK cell inhibitory receptor to suppress the activity of autoreactive T cells responding to any disease tissue-targeted antigens via their endogenous TCR or activating receptors. In one embodiment, at least one or multiple antibodies are masked to prevent suppression of T cell responses in non-disease tissues where the target antigen may also be expressed.

In some embodiments, the T-cell engaging multispecific activatable antibody includes an anti-CD3 epsilon (CD3ε, also referred to herein as CD3e and CD3) scFv and a targeting antibody or antigen-binding fragment thereof, where at least one of the anti-CD3ε scFv and/or the targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an anti-CD3ε scFv and a cancer targeting antibody or antigen-binding fragment thereof, where at least one of the anti-CD3ε scFv and/or the cancer targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CD3ε scFv and a cancer targeting IgG antibody or antigen-binding fragment thereof, where at least one of the anti-CD3ε scFv and/or the cancer targeting IgG antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody IgG or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CD3 epsilon (CD3ε) scFv that is derived from OKT3, where at least one of the targeting antibody or antigen-binding fragment thereof and/or the OKT3 scFv or OKT3-derived scFv is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an OKT3 scFv or OKT3-derived scFv and a cancer targeting antibody or antigen-binding fragment thereof, where at least one of the OKT3 scFv or OKT3-derived scFv and/or the cancer targeting antibody or antigen-binding portion thereof is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an OKT3 scFv or OKT3-derived scFv and a cancer targeting IgG antibody or antigen-binding fragment thereof, where at least one of the OKT3 scFv or OKT3-derived scFv and/or the cancer targeting IgG antibody or antigen-binding portion thereof is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody IgG or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CTLA-4 scFv, where at least one of the targeting antibody or antigen-binding fragment thereof and/or the anti-CTLA-4 scFv is masked. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an anti-CTLA-4 scFv and a targeting IgG antibody or antigen-binding fragment thereof, where at least one of the anti-CTLA-4 scFv and/or the targeting IgG antibody or antigen-binding portion thereof is masked. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4. In some embodiments, the targeting IgG antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4, and the targeting antibody IgG or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the multi-antigen targeting antibodies and/or multi-antigen targeting activatable antibodies include at least a first antibody or antigen-binding fragment thereof that binds a first target and/or first epitope and a second antibody or antigen-binding fragment thereof that binds a second target and/or a second epitope. In some embodiments, the multi-antigen targeting antibodies and/or multi-antigen targeting activatable antibodies bind two or more different targets. In some embodiments, the multi-antigen targeting antibodies and/or multi-antigen targeting activatable antibodies bind two or more different epitopes on the same target. In some embodiments, the multi-antigen targeting antibodies and/or multi-antigen targeting activatable antibodies bind a combination of two or more different targets and two or more different epitopes on the same target.

In some embodiments, a multispecific activatable antibody comprising an IgG has the IgG variable domains masked. In some embodiments, a multispecific activatable antibody comprising a scFv has the scFv domains masked. In some embodiments, a multispecific activatable antibody has both IgG variable domains and scFv domains, where at least one of the IgG variable domains is coupled to a masking moiety. In some embodiments, a multispecific activatable antibody has both IgG variable domains and scFv domains, where at least one of the scFv domains is coupled to a masking moiety. In some embodiments, a multispecific activatable antibody has both IgG variable domains and scFv domains, where at least one of the IgG variable domains is coupled to a masking moiety and at least one of the scFv domains is coupled to a masking moiety. In some embodiments, a multispecific activatable antibody has both IgG variable domains and scFv domains, where each of the IgG variable domains and the scFv domains is coupled to its own masking moiety. In some embodiments, one antibody domain of a multispecific activatable antibody has specificity for a target antigen and another antibody domain has specificity for a T-cell surface antigen. In some embodiments, one antibody domain of a multispecific activatable antibody has specificity for a target antigen and another antibody domain has specificity for another target antigen. In some embodiments, one antibody domain of a multispecific activatable antibody has specificity for an epitope of a target antigen and another antibody domain has specificity for another epitope of the target antigen.

In a multispecific activatable antibody, a scFv can be fused to the carboxyl terminus of the heavy chain of an IgG activatable antibody, to the carboxyl terminus of the light chain of an IgG activatable antibody, or to the carboxyl termini of both the heavy and light chains of an IgG activatable antibody. In a multispecific activatable antibody, a scFv can be fused to the amino terminus of the heavy chain of an IgG activatable antibody, to the amino terminus of the light chain of an IgG activatable antibody, or to the amino termini of both the heavy and light chains of an IgG activatable antibody. In a multispecific activatable antibody, a scFv can be fused to any combination of one or more carboxyl termini and one or more amino termini of an IgG activatable antibody. In some embodiments, a masking moiety (MM) linked to a CM1-CM2 substrate is attached to and masks an antigen binding domain of the IgG. In some embodiments, a masking moiety (MM) linked to a CM1-CM2 substrate is attached to and masks an antigen binding domain of at least one scFv. In some embodiments, a masking moiety (MM) linked to a CM1-CM2 substrate is attached to and masks an antigen binding domain of an IgG and a masking moiety (MM) linked to a CM1-CM2 substrate is attached to and masks an antigen binding domain of at least one scFv.

The disclosure provides examples of multispecific activatable antibody structures that include, but are not limited to, the following: $(VL-CL)_2$:(VH-CH1-CH2-CH3-L4-VH*-L3-VL*-LP2-CM1-CM2 substrate-LP1-$MM)_2$; $(VL-CL)_2$:(VH-CH1-CH2-CH3-L4-VL*-L3-VH*-LP2-CM1-CM2 substrate-LP1-$MM)_2$; (MM-LP1-CM1-CM2 substrate-LP2-$VL-CL)_2$:(VH-CH1-CH2-CH3-L4-VH*-L3-$VL*)_2$; (MM-LP1-CM1-CM2 substrate-LP2-$VL-CL)_2$:(VH-CH1-CH2-CH3-L4-VL*-L3-$VH*)_2$; $(VL-CL)_2$:(MM-LP1-CM1-CM2 substrate-LP2-VL*-L3-VH*-L4-VH-CH1-CH2-$CH3)_2$; $(VL-CL)_2$:(MM-LP1-CM1-CM2 substrate-LP2-VH*-L3-VL*-L4-VH-CH1-CH2-$CH3)_2$; (MM-LP1-CM1-CM2 substrate-LP2-$VL-CL)_2$:(VL*-L3-VH*-L4-VH-CH1-CH2-$CH3)_2$; (MM-LP1-CM1-CM2 substrate-LP2-$VL-CL)_2$:(VH*-L3-VL*-L4-VH-CH1-CH2-$CH3)_2$; (VL-CL-L4-VH*-L3-VL*-LP2-CM1-CM2 substrate-LP1-$MM)_2$:(VH-CH1-CH2-$CH3)_2$; (VL-CL-L4-VL*-L3-VH*-LP2-CM1-CM2 substrate-LP1-$MM)_2$:(VH-CH1-CH2-$CH3)_2$; (MM-LP1-CM1-CM2 substrate-LP2-VL*-L3-VH*-L4-$VL-CL)_2$:(VH-CH1-CH2-$CH3)_2$; (MM-LP1-CM1-CM2 substrate-LP2-VH*-L3-VL*-L4-$VL-CL)_2$:(VH-CH1-CH2-$CH3)_2$; (VL-CL-L4-VH*-L3-VL*-LP2-CM1-CM2 substrate-LP1-$MM)_2$: (MM-LP1-CM1-CM2 substrate-LP2-VL*-L3-VH*-L4-VH-CH1-CH2-$CH3)_2$; (VL-CL-L4-VH*-L3-VL*-LP2-CM1-CM2 substrate-LP1-$MM)_2$: (MM-LP1-CM1-CM2 substrate-LP2-VH*-L3-VL*-L4-VH-CH1-CH2-$CH3)_2$; (VL-CL-L4-VL*-L3-VH*-LP2-CM1-CM2 substrate-LP1-$MM)_2$: (MM-LP1-CM1-CM2 substrate-LP2-VL*-L3-VH*-L4-VH-CH1-CH2-$CH3)_2$; (VL-CL-L4-VL*-L3-VH*-LP2-CM1-CM2 substrate-LP1-$MM)_2$: (MM-LP1-CM1-CM2 substrate-LP2-VH*-L3-VL*-L4-VH-CH1-CH2-$CH3)_2$; (VL-CL-L4-VH*-L3-$VL*)_2$: (MM-LP1-CM1-CM2 substrate-LP2-VL*-L3-VH*-L4-VH-CH1-CH2-$CH3)_2$; (VL-CL-L4-VH*-L3-$VL*)_2$: (MM-LP1-CM1-CM2 substrate-LP2-VH*-L3-VL*-L4-VH-CH1-CH2-$CH3)_2$; (VL-CL-L4-VL*-L3-$VH*)_2$: (MM-LP1-CM1-CM2 substrate-LP2-VL*-L3-VH*-L4-VH-CH1-CH2-$CH3)_2$; (VL-CL-L4-VL*-L3-$VH*)_2$: (MM-LP1-CM1-CM2 substrate-LP2-VH*-L3-

$VL^*$-L4-VH-CH1-CH2-CH3$)_2$; (VL-CL-L4-$VH^*$-L3-$VL^*$-LP2-CM1-CM2 substrate-LP1-MM$)_2$: ($VL^*$-L3-$VH^*$-L4-VH-CH1-CH2-CH3$)_2$; (VL-CL-L4-$VH^*$-L3-$VL^*$-LP2-CM1-CM2 substrate-LP1-MM$)_2$: ($VH^*$-L3-$VL^*$-L4-VH-CH1-CH2-CH3$)_2$; (VL-CL-L4-$VL^*$-L3-$VH^*$-LP2-CM1-CM2 substrate-LP1-MM$)_2$: ($VL^*$-L3-$VH^*$-L4-VH-CH1-CH2-CH3$)_2$; or (VL-CL-L4-$VL^*$-L3-$VH^*$-LP2-CM1-CM2 substrate-LP1-MM$)_2$: ($VH^*$-L3-$VL^*$-L4-VH-CH1-CH2-CH3$)_2$, wherein: VL and VH represent the light and heavy variable domains of the first specificity, contained in the IgG; VL* and VH* represent the variable domains of the second specificity, contained in the scFv; LP1 is a linker peptide connecting the masking moiety (MM) and the CM1-CM2 substrate; LP2 is a linker peptide connecting the CM1-CM2 substrate, and the antibody; L3 is a linker peptide connecting the variable domains of the scFv; L4 is a linker peptide connecting the antibody of the first specificity to the antibody of the second specificity; CL is the light-chain constant domain; and CH1, CH2, CH3 are the heavy chain constant domains. The first and second specificities may be toward any antigen or epitope.

In some embodiments of a T-cell engaging multispecific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory (also referred to herein as activating) or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137 (also referred to as TNFRSF9), CTLA-4, GITR, HVEM, ICOS, LAG3, NKG2D, OX40, PD-1, TIGIT, TIM3, or VISTA. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9. In some embodiments of a multi-antigen targeting activatable antibody, one antigen is selected from the group of targets listed in Table 1, and another antigen is selected from the group of targets listed in Table 1.

In some embodiments, the targeting antibody is an anti-EGFR antibody. In some embodiments, the targeting antibody is C225v5, which is specific for binding to EGFR. In some embodiments, the targeting antibody is C225, which is specific for binding to EGFR. In some embodiments, the targeting antibody is C225v4, which is specific for binding to EGFR. In some embodiments, the targeting antibody is C225v6, which is specific for binding to EGFR. In some embodiments, the targeting antibody is an anti-Jagged antibody. In some embodiments, the targeting antibody is 4D11, which is specific for binding to human and mouse Jagged 1 and Jagged 2. In some embodiments, the targeting antibody is 4D11v2, which is specific for binding to human and mouse Jagged 1 and Jagged 2.

In some embodiments, the targeting antibody can be in the form an activatable antibody. In some embodiments, the scFv(s) can be in the form of a Pro-scFv (see, e.g., WO 2009/025846, WO 2010/081173).

In some embodiments, the scFv is specific for binding CD3ε, and is or is derived from an antibody or fragment thereof that binds CD3ε, e.g., CH2527, FN18, H2C, OKT3, 2C11, UCHT1, or V9. In some embodiments, the scFv is specific for binding CTLA-4 (also referred to herein as CTLA and CTLA4).

In some embodiments, the anti-CTLA-4 scFv includes the amino acid sequence:

(SEQ ID NO: 347)

```
GGGSGGGGSGSGGGSGGGGSGGGEIVLTQSPGTLSLSPGERATLSCRASQ
SVSSSYLAWYQQKPGQAPRLLIYGASSRATGIPDRFSGSGSGTDFTLTIS
RLEPEDFAVYYCQQYGSSPLTFGGGTKVEIKRSGGSTITSYNVYYTKLSS
SGTQVQLVQTGGGVVQPGRSLRLSCAASGSTFSSYAMSWVRQAPGKGLEW
VSAISGSGGSTYYADSVKGRFTISRDNSKNTLYLQMNSLRAEDTAVYYCA
TNSLYWYFDLWGRGTLVTVSSAS
```

In some embodiments, the anti-CTLA-4 scFv includes the amino acid sequence that is at least 90%, 91%, 92%, 93%, 94%, 95%, 96%, 97%, 98%, 99% or more identical to the amino acid sequence of SEQ ID NO: 347.

In some embodiments, the anti-CD3ε scFv includes the amino acid sequence:

(SEQ ID NO: 349)

```
GGGSGGGGSGSGGGSGGGGSGGGQVQLQQSGAELARPGASVKMSCKASGY
TFTRYTMHWVKQRPGQGLEWIGYINPSRGYTNYNQKFKDKATLTTDKSSS
TAYMQLSSLTSEDSAVYYCARYYDDHYCLDYWGQGTTLTVSSGGGGSGGG
GSGGGGSQIVLTQSPAIMSASPGEKVTMTCSASSSVSYMNWYQQKSGTSP
KRWIYDTSKLASGVPAHFRGSGSGTSYSLTISGMEAEDAATYYCQQWSSN
PFTFGSGTKLEINR
```

In some embodiments, the anti-CD3ε scFv includes the amino acid sequence that is at least 90%, 91%, 92%, 93%, 94%, 95%, 96%, 97%, 98%, 99% or more identical to the amino acid sequence of SEQ ID NO: 349.

In some embodiments, the scFv is specific for binding one or more T-cells, one or more NK-cells and/or one or more macrophages. In some embodiments, the scFv is specific for binding a target selected from the group consisting of B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA.

In some embodiments, the multispecific activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the multispecific activatable antibody via a linker. In some embodiments, the agent is conjugated to the AB via a cleavable linker. In some embodiments, the agent is conjugated to the AB via a linker that includes at least one CM1-CM2 substrate sequence. In some embodiments, the linker is a non-cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is an agent selected from the group listed in Table 4. In some embodiments, the agent is a dolastatin. In some embodiments, the agent is an auristatin or derivative thereof.

In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the multispecific activatable antibody also includes a detectable moiety. In some embodiments, the detectable moiety is a diagnostic agent.

In some embodiments, the multispecific activatable antibody naturally contains one or more disulfide bonds. In some embodiments, the multispecific activatable antibody can be engineered to include one or more disulfide bonds.

The disclosure also provides an isolated nucleic acid molecule encoding a multispecific activatable antibody described herein, as well as vectors that include these isolated nucleic acid sequences. The disclosure provides methods of producing a multispecific activatable antibody by culturing a cell under conditions that lead to expression of the activatable antibody, wherein the cell comprises such a nucleic acid molecule. In some embodiments, the cell comprises such a vector.

The disclosure also provides a method of manufacturing multispecific activatable antibodies of the disclosure by (a) culturing a cell comprising a nucleic acid construct that encodes the multispecific activatable antibody under conditions that lead to expression of the multispecific activatable, and (b) recovering the multispecific activatable antibody.

The disclosure also provides multispecific activatable antibodies and/or multispecific activatable antibody compositions that include at least a first antibody or antigen-binding fragment thereof (AB1) that specifically binds a first target or first epitope and a second antibody or antigen-biding fragment thereof (AB2) that binds a second target or a second epitope, where at least AB1 is coupled or otherwise attached to a masking moiety (MM1), such that coupling of the MM1 reduces the ability of AB1 to bind its target. In some embodiments, the MM1 is coupled to AB1 via a CM1-CM2 substrate for an MMP and a SP, where at least one of the MMP and the SP is co-localized with the target of AB1 at a treatment site or a diagnostic site in a subject. The multispecific activatable antibodies provided herein are stable in circulation, activated at intended sites of therapy and/or diagnosis but not in normal, i.e., healthy tissue, and, when activated, exhibit binding to the target of AB1 that is at least comparable to the corresponding, unmodified multispecific antibody.

In some embodiments, the multispecific activatable antibody comprises a linking peptide between the MM1 and the CM1-CM2 substrate.

In some embodiments, the multispecific activatable antibody comprises a linking peptide between the CM1-CM2 substrate and the AB1.

In some embodiments, the activatable antibody comprises a first linking peptide (LP1) and a second linking peptide (LP2), and at least a portion of the multispecific activatable antibody has the structural arrangement from N-terminus to C-terminus as follows in the uncleaved state: MM1-LP1-CM1-CM2 substrate-LP2-AB1 or AB1-LP2-CM1-CM2 substrate-LP1-MM1. In some embodiments, the two linking peptides need not be identical to each other.

In some embodiments, at least one of LP1 or LP2 includes an amino acid sequence selected from the group consisting of $(GS)_n$, $(GGS)_n$, $(GSGGS)_n$ (SEQ ID NO: 381) and $(GGGS)_n$ (SEQ ID NO: 382), where n is an integer of at least one. In some embodiments, at least one of LP1 or LP2 includes an amino acid sequence selected from the group consisting of GGSG (SEQ ID NO: 383), GGSGG (SEQ ID NO: 384), GSGSG (SEQ ID NO: 385), GSGGG (SEQ ID NO: 386), GGGSG (SEQ ID NO: 387), and GSSSG (SEQ ID NO: 388).

In some embodiments, the activatable antibody includes a linking peptide (LP') between CM1 and CM2.

In some embodiments, the activatable antibody comprises a first linking peptide (LP1), a second linking peptide (LP2), and a linking peptide (LP') between CM1 and CM2, and at least a portion of the multispecific activatable antibody has the structural arrangement from N-terminus to C-terminus as follows in the uncleaved state: MM1-LP1-CM1-CM2 substrate-LP2-AB1 or AB1-LP2-CM1-CM2 substrate-LP1-MM1. In some embodiments, linking peptides need not be identical to each other.

In some embodiments, LP' is GG. In some embodiments, LP' is GGSGGS (SEQ ID NO: 218).

In some embodiments, the multispecific activatable antibody includes at least a first antibody or antigen-binding fragment thereof (AB1) that specifically binds a first target or first epitope and a second antibody or antigen-binding fragment thereof (AB2) that specifically binds a second target or second epitope. In some embodiments, each of the AB in the multispecific activatable antibody is independently selected from the group consisting of a monoclonal antibody, domain antibody, single chain, Fab fragment, a $F(ab')_2$ fragment, a scFv, a scAb, a dAb, a single domain heavy chain antibody, and a single domain light chain antibody. In some embodiments, each of the AB in the multispecific activatable antibody is a rodent (e.g., mouse or rat), chimeric, humanized or fully human monoclonal antibody.

In some embodiments, each of the AB in the multispecific activatable antibody has a dissociation constant of about 100 nM or less for binding to its corresponding target or epitope.

In some embodiments, MM1 has a dissociation constant for binding to its corresponding AB that is greater than the dissociation constant of the AB to its corresponding target or epitope.

In some embodiments, MM1 has a dissociation constant for binding to its corresponding AB that is no more than the dissociation constant of the AB to its corresponding target or epitope.

In some embodiments, MM1 does not interfere or compete with its corresponding AB for binding to the corresponding target or epitope when the multispecific activatable antibody is in a cleaved state.

In some embodiments, MM1 is a polypeptide of about 2 to 40 amino acids in length. In some embodiments, each of the MM in the multispecific activatable antibody is a polypeptide of no more than 40 amino acids in length.

In some embodiments, MM1 has a polypeptide sequence that is different from that of target of the corresponding AB.

In some embodiments, MM1 has a polypeptide sequence that is no more than 50% identical to any natural binding partner of the corresponding AB. In some embodiments, MM1 has a polypeptide sequence that is no more than 25% identical to any natural binding partner of the corresponding AB. In some embodiments, MM1 has a polypeptide sequence that is no more than 10% identical to any natural binding partner of the corresponding AB.

In some embodiments, the coupling of MM1 reduces the ability of the corresponding AB to bind its target or epitope such that the dissociation constant ($K_d$) of the AB when coupled to the MM1 towards its corresponding target or epitope is at least 20 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 40 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 100 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 1000 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 10,000 times greater than the $K_d$ of the AB when not coupled to the MM1 towards its corresponding target or epitope.

In some embodiments, MM1 is an amino acid sequence selected from a MM disclosed herein.

In some embodiments, the multispecific activatable antibody includes at least a second masking moiety (MM2) that inhibits the binding of the AB2 to its target when the multispecific activatable antibody is in an uncleaved state, and an additional cleavable moiety (CM') coupled to the AB2, wherein the CM' is either a CM1-CM2 substrate or a polypeptide that functions as a substrate for a second protease. In some embodiments, CM' is a polypeptide of no more than 15 amino acids long. In some embodiments, CM' is a CM1-CM2 substrate, wherein each of CM1 and CM2 in the CM1-CM2 substrate is independently no more than 15 amino acids long.

In some embodiments, the MMP protease, the SP protease, and/or the second protease is co-localized with the second target or epitope in a tissue, and wherein the MMP protease, the SP protease, and/or the second protease cleaves the CM' in the multispecific activatable antibody when the multispecific activatable antibody is exposed to the MMP protease, the SP protease, and/or the second protease. In some embodiments, the MMP protease, the SP protease, and/or the second protease are co-localized with the first target or epitope and the second target or epitope in a tissue. In some embodiments, the MMP protease, the SP protease, and/or the second protease are the same MMP protease and the same SP protease. In some embodiments, the MMP protease, the SP protease, and/or the second protease are not the same MMP protease and not the same SP protease. In some embodiments, the CM1-CM2 substrate and CM' are different substrates for the same MMP protease and same SP protease. In some embodiments, the protease that cleaves CM' is selected from the group consisting of those shown in Table 6.

In some embodiments, each of the MM in the multispecific activatable antibody, e.g., MM1 and at least MM2, has a dissociation constant for binding to its corresponding AB that is greater than the dissociation constant of the AB to its corresponding target or epitope.

In some embodiments, each of the MM in the multispecific activatable antibody has a dissociation constant for binding to its corresponding AB that is no more than the dissociation constant of the AB to its corresponding target or epitope.

In some embodiments, each of the MM in the multispecific activatable antibody does not interfere or compete with its corresponding AB for binding to the corresponding target or epitope when the multispecific activatable antibody is in a cleaved state.

In some embodiments, each of the MM in the multispecific activatable antibody is a polypeptide of about 2 to 40 amino acids in length. In some embodiments, each of the MM in the multispecific activatable antibody is a polypeptide of no more than 40 amino acids in length.

In some embodiments, each of the MM in the multispecific activatable antibody has a polypeptide sequence that is different from that of target of the corresponding AB.

In some embodiments, each of the MM in the multispecific activatable antibody has a polypeptide sequence that is no more than 50% identical to any natural binding partner of the corresponding AB. In some embodiments, each of the MM in the multispecific activatable antibody has a polypeptide sequence that is no more than 25% identical to any natural binding partner of the corresponding AB. In some embodiments, each of the MM in the multispecific activatable antibody has a polypeptide sequence that is no more than 10% identical to any natural binding partner of the corresponding AB.

In some embodiments, the coupling of each of the MM reduces the ability of the corresponding AB to bind its target or epitope such that the dissociation constant ($K_d$) of the AB when coupled to the MM towards its corresponding target or epitope is at least 20 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 40 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 100 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 1000 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 10,000 times greater than the $K_d$ of the AB when not coupled to the MM towards its corresponding target or epitope.

In some embodiments, each of the MM is an amino acid sequence selected from a MM disclosed herein.

In some embodiments, the protease that cleaves the CM1-CM2 substrate sequence is co-localized with the target of the AB1 in the multispecific activatable antibody in a tissue, and the MMP protease and/or SP protease, i.e., at least one of the MMP protease and the SP protease, cleave the CM1-CM2 substrate in the multispecific activatable antibody when the multispecific activatable antibody is exposed to the proteases.

In some embodiments, the multispecific activatable antibody includes more than one CM1-CM2 substrate sequence, and the MMP protease and/or the SP protease that cleaves at least one CM1-CM2 substrate sequence is co-localized with the target of at least one of the AB regions in the multispecific activatable antibody in a tissue, and the MMP protease and/or SP protease cleaves the CM1-CM2 substrate in the multispecific activatable antibody when the multispecific activatable antibody is exposed to the proteases.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least twofold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least threefold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least fourfold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least fivefold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least tenfold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least 20-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 40-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 50-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 100-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 200-fold greater than the dissociation constant of an unmodified AB binding to its target, and whereas in the cleaved state, the AB binds its target.

The disclosure also provides compositions and methods that include a multispecific activatable antibody that includes at least a first antibody or antibody fragment (AB1) that specifically binds a target and a second antibody or antibody fragment (AB2), where at least the first AB in the multispecific activatable antibody is coupled to a masking moiety (MM1) that decreases the ability of AB1 to bind its target. In some embodiments, each AB is coupled to a MM that decreases the ability of its corresponding AB to each target. For example, in bispecific activatable antibody embodiments, AB1 is coupled to a first masking moiety (MM1) that decreases the ability of AB1 to bind its target, and AB2 is coupled to a second masking moiety (MM2) that decreases the ability of AB2 to bind its target. In some embodiments, the multispecific activatable antibody comprises more than two AB regions; in such embodiments, AB1 is coupled to a first masking moiety (MM1) that decreases the ability of AB1 to bind its target, AB2 is coupled to a second masking moiety (MM2) that decreases the ability of AB2 to bind its target, AB3 is coupled to a third masking moiety (MM3) that decreases the ability of AB3 to bind its target, and so on for each AB in the multispecific activatable antibody.

In some embodiments, the multispecific activatable antibody further includes at least one CM1-CM2 substrate that is a substrate for a MMP protease and a SP protease, where the CM1-CM2 substrate links a MM to an AB. For example, in some embodiments, the multispecific activatable antibody includes at least a first antibody or antibody fragment (AB1) that specifically binds a target and a second antibody or antibody fragment (AB2), where at least the first AB in the multispecific activatable antibody is coupled via a first CM1-CM2 substrate to a masking moiety (MM1) that decreases the ability of AB1 to bind its target. In some bispecific activatable antibody embodiments, AB1 is coupled via the first CM1-CM2 substrate to MM1, and AB2 is coupled via a second CM1-CM2 substrate to a second masking moiety (MM2) that decreases the ability of AB2 to bind its target. In some embodiments, the multispecific activatable antibody comprises more than two AB regions; in some of these embodiments, AB1 is coupled via the first CM1-CM2 substrate to MM1, AB2 is coupled via the second CM1-CM2 substrate to MM2, and AB3 is coupled via a third CM1-CM2 substrate to a third masking moiety (MM3) that decreases the ability of AB3 to bind its target, and so on for each AB in the multispecific activatable antibody.

Activatable Antibodies Having Non-Binding Steric Moieties or Binding Partners for Non-Binding Steric Moieties The disclosure also provides activatable antibodies that include non-binding steric moieties (NB) or binding partners (BP) for non-binding steric moieties, where the BP recruits or otherwise attracts the NB to the activatable antibody. The activatable antibodies provided herein include, for example, an activatable antibody that includes a non-binding steric moiety (NB), a CM1-CM2 substrate and antibody or antibody fragment (AB) that binds a target; an activatable antibody that includes a binding partner for a non-binding steric moiety (BP), a CM1-CM2 substrate and an AB; and an activatable antibody that includes a BP to which an NB has been recruited, a CM1-CM2 substrate and an AB that binds the target. Activatable antibodies in which the NB is covalently linked to the CM1-CM2 substrate and AB of the activatable antibody or is associated by interaction with a BP that is covalently linked to the CM1-CM2 substrate and AB of the activatable antibody are referred to herein as "NB-containing activatable antibodies." By activatable or switchable is meant that the activatable antibody exhibits a first level of binding to a target when the activatable antibody is in an inhibited, masked or uncleaved state (i.e., a first conformation), and a second level of binding to the target when the activatable antibody is in an uninhibited, unmasked and/or cleaved state (i.e., a second conformation, i.e., activated antibody), where the second level of target binding is greater than the first level of target binding. The activatable antibody compositions can exhibit increased bioavailability and more favorable biodistribution compared to conventional antibody therapeutics.

In some embodiments, activatable antibodies provide for reduced toxicity and/or adverse side effects that could otherwise result from binding of the at non-treatment sites and/or non-diagnostic sites if the AB were not masked or otherwise inhibited from binding to such a site.

In one embodiment, the activatable antibody includes a non-binding steric moiety (NB); a CM1-CM2 substrate; and an antibody or antibody fragment (AB) that binds specifically to the target, wherein the NB is a polypeptide that does not bind specifically to the AB; the CM1-CM2 substrate is a polypeptide that includes a substrate (S) for an enzyme; the CM1-CM2 substrate is positioned such that in an uncleaved state, the NB interferes with binding of the AB to the target and in a cleaved state, the NB does not interfere with binding of the AB to the target; and the NB does not inhibit cleavage of the CM1-CM2 substrate by the enzyme. As used herein and throughout, the term polypeptide refers to any polypeptide that includes at least two amino acid residues, including larger polypeptides, full-length proteins and fragments thereof, and the term polypeptide is not limited to single-chain polypeptides and can include multi-unit, e.g., multi-chain, polypeptides. In cases where the polypeptide is of a shorter length, for example, less than 50 amino acids total, the terms peptide and polypeptide are used interchangeably herein, and in cases where the polypeptide is of a longer length, e.g., 50 amino acids or greater, the terms polypeptide and protein are used interchangeably herein.

In one embodiment, the activatable antibody includes a non-binding steric moiety (NB); a CM1-CM2 substrate; and an antibody or antibody fragment (AB) that binds specifically to the target, wherein (i) the NB includes a polypeptide that does not bind specifically to the AB; (ii) CM1-CM2 substrate is a polypeptide of up to 50 amino acids in length that includes a substrate (S) for an enzyme; (iii) the CM1-CM2 substrate is positioned such that in an uncleaved state, the NB interferes with binding of the AB to the target and in a cleaved state, the NB does not interfere with binding of the AB to the target; and (iv) the NB does not inhibit cleavage of the CM1-CM2 substrate by the enzyme. For example, each of the CM1 substrate sequence and the CM2 substrate sequence in the CM1-CM2 substrate independent has a length of up to 15 amino acids.

In one embodiment, the activatable antibody includes a non-binding steric moiety (NB); a CM1-CM2 substrate; and an antibody or antibody fragment (AB) that binds specifically to the target, wherein (i) the NB includes a polypeptide that does not bind specifically to the AB; (ii) the CM1-CM2 substrate is a polypeptide that includes a substrate (S) for an enzyme; (iii) the CM1-CM2 substrate is positioned such that in an uncleaved state, the NB interferes with binding of the AB to the target and in a cleaved state, the NB does not interfere with binding of the AB to the target; (iv) the NB does not inhibit cleavage of the CM1-CM2 substrate by the enzyme; and (v) the activatable antibody has the structural arrangement from N-terminus to C-terminus as follows in the uncleaved state: NB-CM1-CM2 substrate-AB or AB-CM1-CM2 substrate-NB.

In one embodiment, the activatable antibody includes a non-binding steric moiety (NB); a CM1-CM2 substrate; and an antibody or antibody fragment (AB) that binds specifically to the target, wherein (i) the NB includes a polypeptide that does not bind specifically to the AB; (ii) the CM1-CM2 substrate is a polypeptide that includes a substrate (S) for an enzyme; (iii) the CM1-CM2 substrate is positioned such that in an uncleaved state, the NB interferes with binding of the AB to the target and in a cleaved state, the NB does not interfere with binding of the AB to the target, and wherein the NB in the uncleaved activatable antibody reduces the ability of the AB to bind the target by at least 50%, for example, by at least 60%, by at least 70%, by at least 75%, by at least 80%, by at least 85%, by at least 90%, by at least 95%, by at least 96%, by at least 97%, by at least 98%, by at least 99%, by at least 100% as compared to the ability of the cleaved AB to bind the target; and (iv) the NB does not inhibit cleavage of the CM1-CM2 substrate by the enzyme. The reduction in the ability of the AB to bind the target is determined, e.g., using an assay as described herein or an in vitro target displacement assay such as, for example, the assay described in PCT Publication Nos. WO 2009/025846 and WO 2010/081173.

In one embodiment, the activatable antibody includes a binding partner (BP) for a non-binding steric moiety (NB); a CM1-CM2 substrate; and an antibody or antibody fragment (AB) that binds specifically to the target, wherein the BP is a polypeptide that binds to the NB when exposed thereto; the NB does not bind specifically to the AB; the CM1-CM2 substrate is a polypeptide that includes a substrate (S) for an enzyme; the CM1-CM2 substrate is positioned such that in an uncleaved state in the presence of the NB, the NB interferes with binding of the AB to the target and in a cleaved state, the NB does not interfere with binding of the AB to the target and the BP does not interfere with binding of the AB to the target; and the NB and the BP do not inhibit cleavage of the CM1-CM2 substrate by the enzyme. In some examples of this embodiment, the BP of the activatable antibody is optionally bound to the NB. In one embodiment, the NB is recruited by the BP of the activatable antibody in vivo.

In some examples of any of these activatable antibody embodiments, the activatable antibody is formulated as a composition. In some of these embodiments, the composition also includes the NB, where the NB is co-formulated with the activatable antibody that includes the BP, the CM1-CM2 substrate, and the AB. In some examples of this embodiment, the BP is selected from the group consisting of an albumin binding peptide, a fibrinogen binding peptide, a fibronectin binding peptide, a hemoglobin binding peptide, a transferrin binding peptide, an immunoglobulin domain binding peptide, and other serum protein binding peptides.

In some examples of any of these activatable antibody embodiments, the NB is a soluble, globular protein. In some examples of any of these activatable antibody embodiments, the NB is a protein that circulates in the bloodstream. In some examples of any of these activatable antibody embodiments, the NB is selected from the group consisting of albumin, fibrinogen, fibronectin, hemoglobin, transferrin, an immunoglobulin domain, and other serum proteins.

In some examples of any of these activatable antibody embodiments, the CM1-CM2 substrate is a polypeptide that includes a substrate (S) for a protease. In some examples of any of these activatable antibody embodiments, the protease is co-localized with the in a tissue, and the protease cleaves the CM1-CM2 substrate in the activatable antibody when the activatable antibody is exposed to the protease. In some examples of any of these activatable antibody embodiments, the CM1-CM2 substrate is a polypeptide of up to 50 amino acids in length. In some examples of any of these activatable antibody embodiments, the CM1-CM2 substrate is a polypeptide that includes a substrate (S) having a length of up to 15 amino acids, e.g., 3 amino acids long, 4 amino acids long, 5 amino acids long, 6 amino acids long, 7 amino acids long, 8 amino acids long, 9 amino acids long, 10 amino acids long, 11 amino acids long, 12 amino acids long, 13 amino acids long, 14 amino acids long, or 15 amino acids long.

In some examples of any of these activatable antibody embodiments, the activatable antibody has the structural arrangement from N-terminus to C-terminus as follows in the uncleaved state: NB-CM1-CM2 substrate-AB, AB-CM1-CM2 substrate-NB, BP-CM1-CM2 substrate-AB or AB-CM1-CM2 substrate-BP. In embodiments where the activatable antibody includes a BP and the activatable antibody is in the presence of the corresponding NB, the activatable antibody has a structural arrangement from N-terminus to C-terminus as follows in the uncleaved state: NB:BP-CM1-CM2-AB, NB:BP-CM2-CM1-AB, AB-CM1-CM2-BP:NB or AB-CM2-CM1-BP:NB, where ":" represents an interaction, e.g., binding, between the NB and BP.

In some examples of any of these activatable antibody embodiments, the activatable antibody includes an antibody or antigen-binding fragment thereof that specifically binds a given target and is a monoclonal antibody, domain antibody, single chain, Fab fragment, a $F(ab')_2$ fragment, a scFv, a scab, a dAb, a single domain heavy chain antibody, or a single domain light chain antibody. In some embodiments, such an antibody or immunologically active fragment thereof that binds the target a mouse, other rodent, chimeric, humanized or fully human monoclonal antibody.

In some examples of any of these activatable antibody embodiments, the activatable antibody includes a combination of a variable heavy chain region comprising an amino acid sequence presented herein and a variable light chain region comprising an amino acid sequence presented herein. In some embodiments, the activatable antibody includes a combination of a variable heavy chain region comprising an amino acid sequence that is at least 90%, 91%, 92%, 93%, 94%, 95%, 96%, 97%, 98%, 99% or more identical to an amino acid sequence presented herein, and a variable light chain region comprising an amino acid sequence that is at least 90%, 91%, 92%, 93%, 94%, 95%, 96%, 97%, 98%, 99% or more identical to an amino acid sequence presented herein.

In some examples of any of these activatable antibody embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the AB via a linker. In some embodiments, the linker is a cleavable linker. In some embodiments, the agent is conjugated to the AB via a noncleavable linker. In some embodiments, the agent is an agent selected from the group listed in Table 3. In some embodiments, the agent is a microtubule inhibitor. In some embodiments, the agent is a nucleic acid damaging agent, such as a DNA alkylator or DNA intercalator, or other DNA damaging agent. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some examples of any of these activatable antibody embodiments, the activatable antibody also includes a detectable moiety. In some embodiments, the detectable moiety is a diagnostic agent.

In some examples of any of these activatable antibody embodiments, the activatable antibody also includes a spacer. In some examples of any of these activatable antibody embodiments, the activatable antibody also includes a signal peptide. In some embodiments, the signal peptide is conjugated to the activatable antibody via a spacer. In some examples of any of these activatable antibody embodiments, the spacer is joined directly to the MM of the activatable antibody.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is similar to that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism. In some embodiments, the serum half-life of the activatable antibody is at least 9 days when administered to an organism. In some embodiments, the serum half-life of the activatable antibody is at least 8 days when administered to an organism. In some embodiments, the serum half-life of the activatable antibody is at least 7 days when administered to an organism. In some embodiments, the serum half-life of the activatable antibody is at least 6 days when administered to an organism. In some examples of any of these activatable antibody embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

The disclosure also provides an isolated nucleic acid molecule encoding any of these activatable antibodies, as well as vectors that include these isolated nucleic acid sequences. The disclosure provides methods of producing an activatable antibody by culturing a cell under conditions that lead to expression of the activatable antibody, wherein the cell comprises such a nucleic acid sequence. In some embodiments, the cell comprises such a vector.

The dissociation constant ($K_d$) of the NB-containing activatable antibody toward the target is greater than the $K_d$ of the AB towards the target when it is not associated with the NB or NB:BP. The dissociation constant ($K_d$) of the NB-containing activatable antibody toward the target is greater than the $K_d$ of the parental AB towards the target. For example, the $K_d$ of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB when it is not associated with the NB or NB:BP or the $K_d$ of the parental AB towards the target. Conversely, the binding affinity of the NB-containing activatable antibody towards the target is lower than the binding affinity of the AB when it is not associated with the NB or NB:BP or lower than the binding affinity of the parental AB towards the target. For example, the binding affinity of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB when it is not associated with the NB or NB:BP or lower than the binding affinity of the parental AB towards the target.

When the NB-containing activatable antibody is in the presence of the target, specific binding of the AB to the target is reduced or inhibited, as compared to the specific binding of the AB when it is not associated with the NB or NB:BP. When the NB-containing activatable antibody is in the presence of the target, specific binding of the AB to the target is reduced or inhibited, as compared to the specific binding of the parental AB to the target. When compared to the binding of the AB not associated with an NB or NB:BP or the binding of the parental AB to the target, the ability of the NB-containing activatable antibody to bind the target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

When the NB-containing activatable antibody is in the presence of the target but not in the presence of a modifying agent (for example a protease or other enzyme), specific binding of the AB to the target is reduced or inhibited, as compared to the specific binding of the AB when it is not associated with the NB or NB:BP. When the NB-containing activatable antibody is in the presence of the target but not in the presence of a modifying agent (for example a protease, other enzyme, reduction agent, or light), specific binding of the AB to the target is reduced or inhibited, as compared to the specific binding of the parental AB to the target. When compared to the binding of the AB not associated with an NB or NB:BP or the binding of the parental AB to the target, the ability of the NB-containing activatable antibody to bind the target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

In some examples of any of these activatable antibody embodiments, the activatable antibody includes an agent conjugated to the AB to produce an activatable antibody conjugate. In some embodiments of the activatable antibody conjugate, the agent is a therapeutic agent. In some embodiments, the agent is a diagnostic agent. In some embodiments, the agent is a detectable marker. In some embodiments of the activatable antibody conjugate, the agent is an antineoplastic agent. In some embodiments of the activatable antibody conjugate, the agent is a toxin or fragment thereof. In some embodiments of the activatable antibody conjugate, the agent is conjugated to the AB via a linker. In some embodiments of the activatable antibody conjugate, the linker is a cleavable linker. In some embodiments, the agent is conjugated to the AB via a noncleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some examples of any of these activatable antibody embodiments, the activatable antibodies are dual-target binding activatable antibodies. Such dual target binding activatable antibodies contain two Abs that may bind the same or different targets. In specific embodiments, dual-targeting activatable antibodies contain bispecific antibodies or antibody fragments.

Dual target binding activatable antibodies are designed so as to have a CM1-CM2 substrate cleavable by a cleaving agent that is co-localized in a target tissue with one or both of the targets capable of binding to the ABs of the activatable antibodies. Dual target binding activatable antibodies with more than one AB to the same or different targets can be designed so as to have more than one CM1-CM2 substrate, wherein the first CM1-CM2 substrate is cleavable by a cleaving agent in a first target tissue and wherein the second CM1-CM2 substrate is cleavable by a cleaving agent in a second target tissue, with one or more of the targets binding to the ABs of the activatable antibodies. In one embodiment, the first and second target tissues are spatially separated, for example, at different sites in the organism. In one embodiment, the first and second target tissues are the same tissue temporally separated, for example the same tissue at two different points in time, for example the first time point is when the tissue is an early stage tumor, and the second time point is when the tissue is a late stage tumor.

The disclosure also provides nucleic acid molecules encoding the activatable antibodies described herein. The disclosure also provides vectors that include these nucleic acids. The activatable antibodies described herein are produced by culturing a cell under conditions that lead to expression of the activatable antibody, wherein the cell includes these nucleic acid molecules or vectors.

The disclosure also provides methods of manufacturing activatable antibodies. In one embodiment, the method includes the steps of (a) culturing a cell that includes a nucleic acid construct that encodes the activatable antibody under conditions that lead to expression of the activatable antibody, wherein the activatable antibody includes (i) a non-binding steric moiety (NB); (ii) a CM1-CM2 substrate; and (iii) an antibody or an antigen binding fragment thereof (AB) that specifically binds a target, wherein (1) the NB does not bind specifically to the AB; (2) the CM1-CM2 substrate is a polypeptide that includes a substrate (S) for an enzyme; (3) the CM1-CM2 substrate is positioned such that in an uncleaved state, the NB interferes with binding of the AB to the target and in a cleaved state, the NB does not interfere with binding of the AB to the target; and (4) the NB does not inhibit cleavage of the CM1-CM2 substrate by the enzyme; and (b) recovering the activatable antibody.

In some embodiments, the method includes the steps of (a) culturing a cell that includes a nucleic acid construct that encodes the activatable antibody under conditions that lead to expression of the activatable antibody, wherein the activatable antibody includes (i) a binding partner (BP) for a non-binding steric moiety (NB); (ii) a CM1-CM2 substrate; and (iii) an antibody or an antigen binding fragment thereof (AB) that specifically binds a target, wherein (1) the NB does not bind specifically to the AB; (2) the CM1-CM2 substrate is a polypeptide that includes a substrate (S) for an enzyme; (3) the CM1-CM2 substrate is positioned such that in an uncleaved state in the presence of the NB, the NB interferes with binding of the AB to the target and in a cleaved state, the NB does not interfere with binding of the AB to the target and the BP does not interfere with binding of the AB to the target; and (4) the NB and the BP do not inhibit cleavage of the CM1-CM2 substrate by the enzyme; and (b) recovering the activatable antibody. In some examples of this embodiment, the BP of the activatable antibody is bound to the NB.

Use of Activatable Antibodies and Conjugated Activatable Antibodies

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the disclosure, which include a conjugated antibody, an activatable antibody and/or a conjugated activatable antibody, are used to prevent, treat or otherwise ameliorate a disease or disorder associated with aberrant target expression and/or activity. For example, therapeutic formulations of the disclosure, which include a conjugated antibody, an activatable antibody and/or a conjugated activatable antibody, are used to treat or otherwise ameliorate inflammation, an inflammatory disorder, an autoimmune disease and/or a cancer or other neoplastic condition. In some embodiments, the cancer is a solid tumor or a hematologic malignancy where the target is expressed. In some embodiments, the cancer is a solid tumor where the target is expressed. In some embodiments, the cancer is a hematologic malignancy where the target is expressed. In some embodiments, the target is expressed on parenchyma (e.g., in cancer, the portion of an organ or tissue that often carries out function(s) of the organ or tissue). In some embodiments, the target is expressed on a cell, tissue, or organ. In some embodiments, the target is expressed on stroma (i.e., the connective supportive framework of a cell, tissue, or organ). In some embodiments, the target is expressed on an osteoblast. In some embodiments, the target is expressed on the endothelium (vasculature). In some embodiments, the target is expressed on a cancer stem cell. In some embodiments, the agent to which the activatable antibody is conjugated is a microtubule inhibitor. In some embodiments, the agent to which the activatable antibody is conjugated is a nucleic acid damaging agent.

Efficaciousness of prevention, amelioration or treatment is determined in association with any known method for diagnosing or treating the disease or disorder associated with target expression and/or activity, such as, for example, aberrant target expression and/or activity. Prolonging the survival of a subject or otherwise delaying the progression of the disease or disorder associated with target expression and/or activity, e.g., aberrant target expression and/or activity, in a subject indicates that the conjugated antibody, activatable antibody and/or conjugated activatable antibody confers a clinical benefit.

A conjugated antibody, an activatable antibody and/or a conjugated activatable antibody can be administered in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

In some embodiments where antibody fragments are used, the smallest fragment that specifically binds to the binding domain of the target protein is selected. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compounds as necessary for the particular indication being treated, for example, in some embodiments, those with complementary activities that do not adversely affect each other. In some embodiments, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

In some embodiments, the conjugated antibody, activatable antibody and/or conjugated activatable antibody contains a detectable label. An intact antibody, or a fragment thereof (e.g., Fab, scFv, or $F(ab)_2$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the disclosure can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, immunochemical staining, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N J, 1995; "Immunoassay", E. Diamandis and T. Christopoulus, Academic Press, Inc., San Diego, C A, 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The conjugated antibodies, activatable antibodies and/or conjugated activatable antibodies of the disclosure are also useful in a variety of diagnostic and prophylactic formulations. In one embodiment, a conjugated antibody, an activatable antibody and/or a conjugated activatable antibody is administered to patients that are at risk of developing one or more of the aforementioned disorders. A patient's or organ's predisposition to one or more of the aforementioned disorders can be determined using genotypic, serological or biochemical markers.

In some embodiments, a conjugated antibody, an activatable antibody and/or a conjugated activatable antibody is administered to human individuals diagnosed with a clinical indication associated with one or more of the aforementioned disorders. Upon diagnosis, a conjugated antibody, an activatable antibody and/or a conjugated activatable antibody is administered to mitigate or reverse the effects of the clinical indication.

A conjugated antibody, an activatable antibody and/or a conjugated activatable antibody of the disclosure is also useful in the detection of a target in patient samples and accordingly are useful as diagnostics. For example, the antibodies and/or activatable antibodies, and conjugated versions thereof, of the disclosure are used in in vitro assays, e.g., ELISA, to detect target levels in a patient sample.

In one embodiment, a conjugated antibody, an activatable antibody and/or a conjugated activatable antibody of the disclosure is immobilized on a solid support (e.g., the well(s) of a microtiter plate). The immobilized conjugated antibody, activatable antibody and/or conjugated activatable antibody serves as a capture antibody for any target that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies of the disclosure, and conjugated versions thereof, in an in vitro diagnostic assay, it is possible to stage a disease in a subject based on expression levels of the target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

A conjugated antibody, an activatable antibody and/or a conjugated activatable antibody can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM1-CM2 substrate can be used to detect the presence or absence of an enzyme that is capable of cleaving the CM1-CM2 substrate. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM1-CM2 substrate) but also that the tissue expresses target to which the activated antibody binds.

For example, the CM1-CM2 substrate can be selected to be substrate for a matrix metalloprotease (MMP) and a serine protease (SP) found at the site of a tumor, at the site of a viral or bacterial infection at a biologically confined site (e.g., such as in an abscess, in an organ, and the like), and the like. The AB can be one that binds a target antigen. Using methods as disclosed herein, or when appropriate, methods familiar to one skilled in the art, a detectable label (e.g., a fluorescent label or radioactive label or radiotracer) can be conjugated to an AB or other region of an antibody and/or activatable antibody. Suitable detectable labels are discussed in the context of the above screening methods and additional specific examples are provided below. Using an AB specific to a protein or peptide of the disease state, along with an MMP whose activity is elevated in the disease tissue of interest, activatable antibodies will exhibit an increased rate of binding to disease tissue relative to tissues where the CM1-CM2 substrate specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM1-CM2 substrate is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM1-CM2 substrate susceptible to cleavage by an enzyme, the activatable antibodies can be used to detect (either qualitatively or quantitatively) the presence of an enzyme in the sample. In another example, where the activatable antibodies contain a CM1-CM2 substrate susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. a fluorophore, Fluorescein Isothiocyanate (FITC), Rhodamine Isothiocyanate (TRITC), an Alexa Fluor® label), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a matrix metalloprotease (MMP) and one serine protease (SP) that are specific for the CM1-CM2 substrate of the activatable antibody. In some embodiments, the presence of the MMP can be confirmed using broad spectrum protease inhibitors such as those described herein, and/or by using an agent that is specific for the protease, for example, an antibody such as All, which is specific for the protease matriptase (MT-SP1) and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a MMP and a SP specific for the CM1-CM2 substrate of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a MMP and a SP that is specific for the CM1-CM2 substrate of the activatable antibody.

These techniques are also useful in kits and/or as reagents for the detection, identification or characterization of protease activity in a variety of cells, tissues, and organisms based on the protease-specific CM1-CM2 substrate in the activatable antibody.

The disclosure provides methods of using the antibodies and/or activatable antibodies in a variety of diagnostic and/or prophylactic indications. For example, the disclosure provides methods of detecting presence or absence of a cleaving agent and a target of interest in a subject or a sample by (i) contacting a subject or sample with an activatable antibody, wherein the activatable antibody comprises a masking moiety (MM), a CM1-CM2 substrate that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent and the target are present in the subject or sample and wherein no detectable level of activated activatable antibody in the subject or sample indicates that the cleaving agent, the target or both the cleaving agent and the target are absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody in the presence of a target of interest, e.g., the target, wherein the activatable antibody comprises a masking moiety (MM), a CM1-CM2 substrate that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody comprises a masking moiety (MM), a CM1-CM2 substrate that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody, wherein the activatable antibody comprises a masking moiety (MM), a CM1-CM2 substrate that is cleaved by the cleaving agent, an antigen binding domain (AB) that specifically binds the target, and a detectable label, wherein the activatable antibody in an uncleaved, non-activated state comprises a structural arrangement from N-terminus to C-terminus as follows: MM-CM1-CM2 substrate-AB or AB-CM1-CM2 substrate-MM; wherein the MM is a peptide that inhibits binding of the AB to the target, and wherein the MM does not have an amino acid sequence of a naturally occurring binding partner of the AB and is not a modified form of a natural binding partner of the AB; wherein, in an uncleaved, non-activated state, the MM interferes with specific binding of the AB to the target, and in a cleaved, activated state the MM does not interfere or compete with specific binding of the AB to the target; and wherein the detectable label is positioned on a portion of the activatable antibody that is released following cleavage of the CM1-CM2 substrate; and (ii) measuring a level of detectable label in the subject or sample, wherein a detectable level of the detectable label in the subject or sample indicates that the cleaving agent is absent and/or not sufficiently present in the subject or sample and wherein no detectable level of the detectable label in the subject or sample indicates that the cleaving agent is present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody (e.g., an activatable antibody to which a therapeutic agent is conjugated) described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent and the target are present in the subject or biological sample and wherein no detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample.

The disclosure also provides methods of detecting presence or absence of a cleaving agent in a subject or a sample by (i) contacting a subject or biological sample with an activatable antibody in the presence of the target, and (ii) measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments, all antigen binding sites are masked. In some embodiments, the measuring step includes use of a secondary reagent comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample with an activatable antibody in the presence of the target, and measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments, all antigen binding sites are masked. In some embodiments, the measuring step includes use of a secondary reagent comprising a detectable label.

The disclosure also provides kits for use in methods of detecting presence or absence of a cleaving agent in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM1-CM2 substrate, wherein a detectable level of activated activatable antibody in the subject or biological sample indicates that the cleaving agent is absent and/or not sufficiently present in the subject or biological sample such that the target binding and/or protease cleavage of the activatable antibody cannot be detected in the subject or biological sample, and wherein no detectable level of activated activatable antibody in the subject or biological sample indicates that the cleaving agent is present in the subject or biological sample at a detectable level.

The disclosure provides methods of detecting presence or absence of a cleaving agent and the target in a subject or a sample by (i) contacting a subject or biological sample with an activatable antibody, wherein the activatable antibody includes a detectable label that is positioned on a portion of the activatable antibody that is released following cleavage of the CM1-CM2 substrate and (ii) measuring a level of activated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

The disclosure also provides methods of detecting presence or absence of a cleaving agent in a subject or a sample by (i) contacting a subject or biological sample with an activatable antibody, wherein the activatable antibody includes a detectable label that is positioned on a portion of the activatable antibody that is released following cleavage of the CM1-CM2 substrate; and (ii) measuring a level of detectable label in the subject or biological sample, wherein a detectable level of the detectable label in the subject or biological sample indicates that the cleaving agent is absent and/or not sufficiently present in the subject or biological sample at a detectable level, such that protease cleavage of the activatable antibody cannot be detected in the subject or biological sample, and wherein a reduced detectable level of the detectable label in the subject or biological sample indicates that the cleaving agent is present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent of interest in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM1-CM2 substrate, wherein a detectable level of the detectable label in the subject or biological sample indicates that the cleaving agent, the target, or both the cleaving agent and the target are absent and/or not sufficiently present in the subject or biological sample, such that the target binding and/or protease cleavage of the activatable antibody cannot be detected in the subject or biological sample, and wherein a reduced detectable level of the detectable label in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

In some embodiments of these methods and kits, the activatable antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods and kits, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments, in situ imaging is used to identify or otherwise refine a patient population suitable for treatment with an activatable antibody of the disclosure. For example, patients that test positive for both the target (e.g., the target) and a protease that cleaves the substrate in the CM1-CM2 substrate of the activatable antibody being tested (e.g., accumulate activated antibodies at the disease site) are identified as suitable candidates for treatment with such an activatable antibody comprising such a CM1-CM2 substrate. Likewise, patients that test negative for either or both of the target (e.g., the target) and the protease that cleaves the substrate in the CM1-CM2 substrate in the activatable antibody being tested using these methods might be identified as suitable candidates for another form of therapy. In some embodiments, such patients that test negative with respect to a first activatable antibody can be tested with other activatable antibodies comprising different CM1-CM2 substrates until a suitable activatable antibody for treatment is identified (e.g., an activatable antibody comprising a CM1-CM2 substrate that is cleaved by the patient at the site of disease). In some embodiments, the patient is then administered a therapeutically effective amount of the conjugated activatable antibody for which the patient tested positive.

In some embodiments, in vivo imaging is used to identify or otherwise refine a patient population suitable for treatment with an activatable antibody of the disclosure. For example, patients that test positive for both the target (e.g., the target) and a protease that cleaves the substrate in the CM1-CM2 substrate of the activatable antibody being tested (e.g., accumulate activated antibodies at the disease site) are identified as suitable candidates for treatment with such an activatable antibody comprising such a CM1-CM2 substrate. Likewise, patients that test negative might be identified as suitable candidates for another form of therapy. In some embodiments, such patients that test negative with respect to a first activatable antibody can be tested with other activatable antibodies comprising different CM1-CM2 substrates until a suitable activatable antibody for treatment is identified (e.g., an activatable antibody comprising a CM1-CM2 substrate that is cleaved by the patient at the site of disease). In some embodiments, the patient is then administered a therapeutically effective amount of the conjugated activatable antibody for which the patient tested positive.

In some embodiments of the methods and kits, the method or kit is used to identify or otherwise refine a patient population suitable for treatment with an activatable antibody of the disclosure. For example, patients that test positive for both the target (e.g., the target) and a protease that cleaves the substrate in the CM1-CM2 substrate of the activatable antibody being tested in these methods are identified as suitable candidates for treatment with such an activatable antibody comprising such a CM1-CM2 substrate. Likewise, patients that test negative for both of the targets (e.g., the target) and the protease that cleaves the substrate in the CM1-CM2 substrate in the activatable antibody being tested using these methods might be identified as suitable candidates for another form of therapy. In some embodiments, such patients can be tested with other activatable antibodies until a suitable activatable antibody for treatment is identified (e.g., an activatable antibody comprising a CM1-CM2 substrate that is cleaved by the patient at the site of disease). In some embodiments, patients that test negative for either of the target (e.g., the target) are identified as suitable candidates for treatment with such an activatable antibody comprising such a CM1-CM2 substrate. In some embodiments, patients that test negative for either of the target (e.g., the target) are identified as not being suitable candidates for treatment with such an activatable antibody comprising such a CM1-CM2 substrate. In some embodiments, such patients can be tested with other activatable antibodies until a suitable activatable antibody for treatment is identified (e.g., an activatable antibody comprising a CM1-CM2 substrate that is cleaved by the patient at the site of disease). In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

In some embodiments, a method or kit is used to identify or otherwise refine a patient population suitable for treatment with an anti-the target activatable antibody and/or conjugated activatable antibody (e.g., activatable antibody to which a therapeutic agent is conjugated) of the disclosure, followed by treatment by administering that activatable antibody and/or conjugated activatable antibody to a subject in need thereof. For example, patients that test positive for both the targets (e.g., the target) and a protease that cleaves the CM1-CM2 substrate of the activatable antibody and/or conjugated activatable antibody being tested in these methods are identified as suitable candidates for treatment with such antibody and/or such a conjugated activatable antibody comprising such a CM1-CM2 substrate, and the patient is then administered a therapeutically effective amount of the activatable antibody and/or conjugated activatable antibody that was tested. Likewise, patients that test negative for either or both of the target (e.g., the target) and the protease that cleaves the substrate in the CM1-CM2 substrate in the activatable antibody being tested using these methods might be identified as suitable candidates for another form of therapy. In some embodiments, such patients can be tested with other antibody and/or conjugated activatable antibody until a suitable antibody and/or conjugated activatable antibody for treatment is identified (e.g., an activatable antibody and/or conjugated activatable antibody comprising a CM1-CM2 substrate that is cleaved by the patient at the site of disease). In some embodiments, the patient is then administered a therapeutically effective amount of the activatable antibody and/or conjugated for which the patient tested positive.

In some embodiments of these methods and kits, the MM is a peptide having a length from about 4 to 40 amino acids. In some embodiments of these methods and kits, the activatable antibody comprises a linker peptide, wherein the linker peptide is positioned between the MM and the CM1-CM2 substrate. In some embodiments of these methods and kits, the activatable antibody comprises a linker peptide, where the linker peptide is positioned between the AB and the CM1-CM2 substrate. In some embodiments of these methods and kits, the activatable antibody comprises a first linker peptide (LP1) and a second linker peptide (LP2), wherein the first linker peptide is positioned between the MM and the CM1-CM2 substrate and the second linker peptide is positioned between the AB and the CM1-CM2 substrate. In some embodiments of these methods and kits, each of LP1 and LP2 is a peptide of about 1 to 20 amino acids in length, and wherein each of LP1 and LP2 need not be the same linker. In some embodiments of these methods and kits, one or both of LP1 and LP2 comprises a glycine-serine polymer. In some embodiments of these methods and kits, at least one of LP1 and LP2 comprises an amino acid sequence selected from the group consisting of (GS)n, (GSGGS)n (SEQ ID NO: 381) and (GGGS)n (SEQ ID NO: 382), where n is an integer of at least one. In some embodiments of these methods and kits, at least one of LP1 and LP2 comprises an amino acid sequence having the formula (GGS)n, where n is an integer of at least one. In some embodiments of these methods and kits, at least one of LP1 and LP2 comprises an amino acid sequence selected from the group consisting of Gly-Gly-Ser-Gly (SEQ ID NO: 383), Gly-Gly-Ser-Gly-Gly (SEQ ID NO: 384), Gly-Ser-Gly-Ser-Gly (SEQ ID NO: 385), Gly-Ser-Gly-Gly-Gly (SEQ ID NO: 386), Gly-Gly-Gly-Ser-Gly (SEQ ID NO: 387), and Gly-Ser-Ser-Ser-Gly (SEQ ID NO: 388).

In some embodiments of these methods and kits, the AB comprises an antibody or antibody fragment sequence selected from the cross-reactive antibody sequences presented herein. In some embodiments of these methods and kits, the AB comprises a Fab fragment, a scFv or a single chain antibody (scAb).

In some embodiments of these methods and kits, the cleaving agent is a protease that is co-localized in the subject or sample with the target and the CM1-CM2 substrate is a polypeptide that functions as a substrate for the protease, wherein the protease cleaves the CM1-CM2 substrate in the activatable antibody when the activatable antibody is exposed to the protease. In some embodiments of these methods and kits, each of the CM1 substrate sequence and the CM2 substrate sequence in the CM1-CM2 substrate is independently a polypeptide of up to 15 amino acids in length. In some embodiments of these methods and kits, the CM1-CM2 substrate is coupled to the N-terminus of the AB. In some embodiments of these methods and kits, the CM1-CM2 substrate is coupled to the C-terminus of the AB. In some embodiments of these methods and kits, the CM1-CM2 substrate is coupled to the N-terminus of a VL chain of the AB.

The activatable antibodies and/or conjugated activatable antibodies of the disclosure are used in diagnostic and prophylactic formulations. In one embodiment, an activatable antibody is administered to patients that are at risk of developing one or more of the aforementioned inflammation, inflammatory disorders, cancer or other disorders.

A patient's or organ's predisposition to one or more of the aforementioned disorders can be determined using genotypic, serological or biochemical markers.

In some embodiments, an activatable antibody and/or conjugated activatable antibodies is administered to human individuals diagnosed with a clinical indication associated with one or more of the aforementioned disorders. Upon diagnosis, an activatable antibody and/or conjugated activatable antibodies is administered to mitigate or reverse the effects of the clinical indication.

Activatable antibodies and/or conjugated activatable antibodies of the disclosure are also useful in the detection of the target in patient samples and accordingly are useful as diagnostics. For example, the activatable antibodies and/or conjugated activatable antibodies of the disclosure are used in in vitro assays, e.g., ELISA, to detect target levels in a patient sample.

In one embodiment, an activatable antibody of the disclosure is immobilized on a solid support (e.g., the well(s) of a microtiter plate). The immobilized activatable antibody serves as a capture antibody for any target that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies of the disclosure in an in vitro diagnostic assay, it is possible to stage a disease in a subject based on expression levels of the Target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Activatable antibodies and/or conjugated activatable antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods.

For example, activatable antibodies having an enzymatically cleavable CM1-CM2 substrate can be used to detect the presence or absence of an enzyme that is capable of cleaving the CM1-CM2 substrate. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM1-CM2 substrate) but also that the tissue expresses target to which the activated antibody binds.

For example, the CM1-CM2 substrate can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label or radioactive label or radiotracer) can be conjugated to an AB or other region of an activatable antibody. Suitable detectable labels are discussed in the context of the above screening methods and additional specific examples are provided below. Using an AB specific to a protein or peptide of the disease state, along with a protease whose activity is elevated in the disease tissue of interest, activatable antibodies will exhibit an increased rate of binding to disease tissue relative to tissues where the CM1-CM2 substrate specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM1-CM2 substrate is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM1-CM2 substrate susceptible to cleavage by an enzyme, the activatable antibodies can be used to detect (either qualitatively or quantitatively) the presence of an enzyme in the sample. In another example, where the activatable antibodies contain a CM1-CM2 substrate susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. Fluorescein Isothiocyanate (FITC), Rhodamine Isothiocyanate (TRITC), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a protease that is specific for the CM1-CM2 substrate of the activatable antibody. In some embodiments, the presence of the protease can be confirmed using broad spectrum protease inhibitors such as those described herein, and/or by using an agent that is specific for the protease, for example, an antibody such as All, which is specific for the protease matriptase (MT-SP1) and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM1-CM2 substrate of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease that is specific for the CM1-CM2 substrate of the activatable antibody.

These techniques are also useful in kits and/or as reagents for the detection, identification or characterization of protease activity in a variety of cells, tissues, and organisms based on the protease-specific CM1-CM2 substrate in the activatable antibody.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments, in situ imaging is used to identify or otherwise refine a patient population suitable for treatment with an activatable antibody of the disclosure. For example, patients that test positive for both the target and a protease that cleaves the substrate in the cleavable moiety (CM1-CM2 substrate) of the activatable antibody being tested (e.g., accumulate activated antibodies at the disease site) are identified as suitable candidates for treatment with such an activatable antibody comprising such a CM1-CM2 substrate.

Likewise, patients that test negative for either or both of the target and the protease that cleaves the substrate in the CM1-CM2 substrate in the activatable antibody being tested using these methods are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM1-CM2 substrate that is cleaved by the patient at the site of disease).

In some embodiments, in vivo imaging is used to identify or otherwise refine a patient population suitable for treatment with an activatable antibody of the disclosure. For example, patients that test positive for both the target and a protease that cleaves the substrate in the cleavable moiety (CM1-CM2 substrate) of the activatable antibody being tested (e.g., accumulate activated antibodies at the disease site) are identified as suitable candidates for treatment with such an activatable antibody comprising such a CM1-CM2 substrate. Likewise, patients that test negative are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM1-CM2 substrate that is cleaved by the patient at the site of disease).

Pharmaceutical Compositions

The conjugated antibodies, activatable antibodies and/or conjugated activatable antibodies of the disclosure (also referred to herein as “active compounds”), and derivatives, fragments, analogs and homologs thereof, can be incorporated into pharmaceutical compositions suitable for administration. Such compositions typically comprise the conjugated antibody, activatable antibody and/or conjugated activatable antibody and a pharmaceutically acceptable carrier. As used herein, the term “pharmaceutically acceptable carrier” is intended to include any and all solvents, dispersion media, coatings, antibacterial and antifungal agents, isotonic and absorption delaying agents, and the like, compatible with pharmaceutical administration. Suitable carriers are described in the most recent edition of Remington’s Pharmaceutical Sciences, a standard reference text in the field, which is incorporated herein by reference. Suitable examples of such carriers or diluents include, but are not limited to, water, saline, ringer’s solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1: Activatable Antibodies and Matrix Metalloprotease (MMP) Cleavable Substrates The studies provided herein describe exemplary matrix metalloprotease (MMP) substrates of the present disclosure and exemplary activatable antibodies that include MMP substrates of the present disclosure.

Exemplary activatable antibodies were constructed such that each one includes one of the MMP substrates listed in Table 1. The exemplary activatable antibodies of the present disclosure, the sequences of which are listed in Table 2, include an antibody or antigen binding fragment thereof (AB) that is based on a mouse/human chimeric monoclonal antibody that specifically binds to epidermal growth factor receptor (EGFR). The exemplary activatable antibodies also include a prodomain coupled to the N-terminus of the light chain of the AB. Each prodomain includes a masking moiety (MM) and a cleavable moiety (CM), and the CM includes at least one MMP substrate sequence of Table 1.

TABLE 1

Matrix Metalloprotease (MMP) Substrates

| Name | Sequence | SEQ ID NO: |
|---|---|---|
| 4001 | ALAHGLF | 1 |
| 4002 | DLAHPLL | 2 |
| 4003 | AFRHLR | 3 |
| 4004 | PHGFFQ | 4 |
| 4005 | SVHHLI | 5 |
| 4006 | RGPKLYW | 6 |
| 4007 | RFPYGVW | 7 |
| 4008 | HVPRQV | 8 |
| 4009 | SNPFKY | 9 |
| 4010 | RFPLKV | 10 |
| 4011 | PFHLSR | 11 |
| 4012 | STVFHM | 12 |
| 4013 | MGPWFM | 13 |
| 4014 | RHLAKL | 14 |
| 4015 | PLGVRGK | 15 |
| 4016 | QNQALRIA | 16 |

TABLE 2

| Activatable Antibody Sequences |
|---|
| Anti-EGFR Activatable Antibody (c225v5) Heavy Chain (amino acid sequence) (SEQ ID NO: 400)<br>QVQLKQSGPGLVQPSQSLSITCTVSGFSLTNYGVHWVRQSPGKGLEWLGVIWSGGNTDYNTPFT<br>SRLSINKDNSKSQVFFKMNSLQSQDTAIYYCARALTYYDYEFAYWGQGTLVTVSAASTKGPSVF |

TABLE 2-continued

| Activatable Antibody Sequences |
|---|
| PLAPSSKSTSGGTAALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYTQKSLSLSPG K |
| Anti-EGFR Activatable Antibody Light Chain (amino acid sequence) (SEQ ID NO: 399) DILLTQSPVILSVSPGERVSFSCRASQSIGTNIHWYQQRTNGSPRLLIKYASESISGIPSRFSG SGSGTDFTLSINSVESEDIADYYCQQNNNWPTTFGAGTKLELKRTVAAPSVFIFPPSDEQLKSG TASVVCLLNNFYPREAKVQWKVDNALQSGNSQESVTEQDSKDSTYSLSSTLTLSKADYEKHKVY ACEVTHQGLSSPVTKSFNRGEC |
| Anti-EGFR Activatable Antibody Light Chain (amino acid sequence) (SEQ ID NO: 401) QILLTQSPVILSVSPGERVSFSCRASQSIGTNIHWYQQRTNGSPRLLIKYASESISGIPSRFSG SGSGTDFTLSINSVESEDIADYYCQQNNNWPTTFGAGTKLELKRTVAAPSVFIFPPSDEQLKSG TASVVCLLNNFYPREAKVQWKVDNALQSGNSQESVTEQDSKDSTYSLSSTLTLSKADYEKHKVY ACEVTHQGLSSPVTKSFNRGEC |
| Anti-EGFR Activatable Antibody (c225v5-3954-NSUB) Light Chain (amino acid sequence) (SEQ ID NO: 402) QGQSGQCISPRGCPDGPYVMYGSSGGSGGSGGSGGGSGGGSGGSDILLTQSPVILSVSPGERVS FSCRASQSIGTNIHWYQQRTNGSPRLLIKYASESISGIPSRFSGSGSGTDFTLSINSVESEDIA DYYCQQNNNWPTTFGAGTKLELKRTVAAPSVFIFPPSDEQLKSGTASVVCLLNNFYPREAKVQW KVDNALQSGNSQESVTEQDSKDSTYSLSSTLTLSKADYEKHKVYACEVTHQGLSSPVTKSFNRG EC |
| Anti-EGFR Activatable Antibody (c225v5-3954-4001SL) Light Chain (amino acid sequence) (SEQ ID NO: 403) QGQSGQCISPRGCPDGPYVMYGGGSSGGSALAHGLFGGGSQILLTQSPVILSVSPGERVSFSCR ASQSIGTNIHWYQQRTNGSPRLLIKYASESISGIPSRFSGSGSGTDFTLSINSVESEDIADYYC QQNNNWPTTFGAGTKLELKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSPVTKSFNRGEC |
| Anti-EGFR Activatable Antibody (c225v5-3954-4001LL) Light Chain (amino acid sequence) (SEQ ID NO: 404) QGQSGQCISPRGCPDGPYVMYGSSGGSGGSGGSGALAHGLFGGGSQILLTQSPVILSVSPGERV SFSCRASQSIGTNIHWYQQRTNGSPRLLIKYASESISGIPSRFSGSGSGTDFTLSINSVESEDI ADYYCQQNNNWPTTFGAGTKLELKRTVAAPSVFIFPPSDEQLKSGTASVVCLLNNFYPREAKVQ WKVDNALQSGNSQESVTEQDSKDSTYSLSSTLTLSKADYEKHKVYACEVTHQGLSSPVTKSFNR GEC |
| Anti-EGFR Activatable Antibody (c225v5-3954-4002SL) Light Chain (amino acid sequence) (SEQ ID NO: 405) QGQSGQCISPRGCPDGPYVMYGGGSSGGSDLAHPLLGGGSQILLTQSPVILSVSPGERVSFSCR ASQSIGTNIHWYQQRTNGSPRLLIKYASESISGIPSRFSGSGSGTDFTLSINSVESEDIADYYC QQNNNWPTTFGAGTKLELKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSPVTKSFNRGEC |
| Anti-EGFR Activatable Antibody (c225v5-3954-4003SL) Light Chain (amino acid sequence) (SEQ ID NO: 406) QGQSGQCISPRGCPDGPYVMYGGGSSGGSAFRHLRGGGSQILLTQSPVILSVSPGERVSFSCRA SQSIGTNIHWYQQRTNGSPRLLIKYASESISGIPSRFSGSGSGTDFTLSINSVESEDIADYYCQ QNNNWPTTFGAGTKLELKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPVTKSFNRGEC |
| Anti-EGFR Activatable Antibody (c225v5-3954-4004LL) Light Chain (amino acid sequence) (SEQ ID NO: 407) QGQSGQCISPRGCPDGPYVMYGSSGGSGGSGGSGPHGFFQGGGSQILLTQSPVILSVSPGERVS FSCRASQSIGTNIHWYQQRTNGSPRLLIKYASESISGIPSRFSGSGSGTDFTLSINSVESEDIA DYYCQQNNNWPTTFGAGTKLELKRTVAAPSVFIFPPSDEQLKSGTASVVCLLNNFYPREAKVQW KVDNALQSGNSQESVTEQDSKDSTYSLSSTLTLSKADYEKHKVYACEVTHQGLSSPVTKSFNRG EC |
| Anti-EGFR Activatable Antibody (c225v5-3954-4005SL) Light Chain (amino acid sequence) (SEQ ID NO: 408) QGQSGQCISPRGCPDGPYVMYGGGSSGGSSVHHLIGGGSQILLTQSPVILSVSPGERVSFSCRA SQSIGTNIHWYQQRTNGSPRLLIKYASESISGIPSRFSGSGSGTDFTLSINSVESEDIADYYCQ QNNNWPTTFGAGTKLELKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPVTKSFNRGEC |
| Anti-EGFR Activatable Antibody (c225v5-3954-4006SL) Light Chain (amino acid sequence) (SEQ ID NO: 409) QGQSGQCISPRGCPDGPYVMYGGGSSGGSRGPKLYWGGGSQILLTQSPVILSVSPGERVSFSCR ASQSIGTNIHWYQQRTNGSPRLLIKYASESISGIPSRFSGSGSGTDFTLSINSVESEDIADYYC |

TABLE 2-continued

| Activatable Antibody Sequences |
|---|
| QQNNNWPTTFGAGTKLELKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSPVTKSFNRGEC |
| Anti-EGFR Activatable Antibody (c225v5-3954-4006LL) Light Chain (amino acid sequence) (SEQ ID NO: 410) QGQSGQCISPRGCPDGPYVMYGSSGGSGGSGGSGRGPKLYWGGGSQILLTQSPVILSVSPGERV SFSCRASQSIGTNIHWYQQRTNGSPRLLIKYASESISGIPSRFSGSGSGTDFTLSINSVESEDI ADYYCQQNNNWPTTFGAGTKLELKRTVAAPSVFIFPPSDEQLKSGTASVVCLLNNFYPREAKVQ WKVDNALQSGNSQESVTEQDSKDSTYSLSSTLTLSKADYEKHKVYACEVTHQGLSSPVTKSFNR GEC |
| Anti-EGFR Activatable Antibody (c225v5-3954-4007SL) Light Chain (amino acid sequence) (SEQ ID NO: 411) QGQSGQCISPRGCPDGPYVMYGGGSSGGSRFPYGVWGGGSQILLTQSPVILSVSPGERVSFSCR ASQSIGTNIHWYQQRTNGSPRLLIKYASESISGIPSRFSGSGSGTDFTLSINSVESEDIADYYC QQNNNWPTTFGAGTKLELKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSPVTKSFNRGEC |
| Anti-EGFR Activatable Antibody (c225v5-3954-4008SL) Light Chain (amino acid sequence) (SEQ ID NO: 412) QGQSGQCISPRGCPDGPYVMYGGGSSGGSHVPRQVGGGSQILLTQSPVILSVSPGERVSFSCRA SQSIGTNIHWYQQRTNGSPRLLIKYASESISGIPSRFSGSGSGTDFTLSINSVESEDIADYYCQ QNNNWPTTFGAGTKLELKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPVTKSFNRGEC |
| Anti-EGFR Activatable Antibody (c225v5-3954-4008LL) Light Chain (amino acid sequence) (SEQ ID NO: 413) QGQSGQCISPRGCPDGPYVMYGSSGGSGGSGGSGHVPRQVGGGSQILLTQSPVILSVSPGERVS FSCRASQSIGTNIHWYQQRTNGSPRLLIKYASESISGIPSRFSGSGSGTDFTLSINSVESEDIA DYYCQQNNNWPTTFGAGTKLELKRTVAAPSVFIFPPSDEQLKSGTASVVCLLNNFYPREAKVQW KVDNALQSGNSQESVTEQDSKDSTYSLSSTLTLSKADYEKHKVYACEVTHQGLSSPVTKSFNRG EC |
| Anti-EGFR Activatable Antibody (c225v5-3954-4009SL) Light Chain (amino acid sequence) (SEQ ID NO: 414) QGQSGQCISPRGCPDGPYVMYGGGSSGGSSNPFKYGGGSQILLTQSPVILSVSPGERVSFSCRA SQSIGTNIHWYQQRTNGSPRLLIKYASESISGIPSRFSGSGSGTDFTLSINSVESEDIADYYCQ QNNNWPTTFGAGTKLELKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPVTKSFNRGEC |
| Anti-EGFR Activatable Antibody (c225v5-3954-4010SL) Light Chain (amino acid sequence) (SEQ ID NO: 415) QGQSGQCISPRGCPDGPYVMYGGGSSGGSRFPLKVGGGSQILLTQSPVILSVSPGERVSFSCRA SQSIGTNIHWYQQRTNGSPRLLIKYASESISGIPSRFSGSGSGTDFTLSINSVESEDIADYYCQ QNNNWPTTFGAGTKLELKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPVTKSFNRGEC |
| Anti-EGFR Activatable Antibody (c225v5-3954-4011SL) Light Chain (amino acid sequence) (SEQ ID NO: 416) QGQSGQCISPRGCPDGPYVMYGGGSSGGSPFHLSRGGGSQILLTQSPVILSVSPGERVSFSCRA SQSIGTNIHWYQQRTNGSPRLLIKYASESISGIPSRFSGSGSGTDFTLSINSVESEDIADYYCQ QNNNWPTTFGAGTKLELKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPVTKSFNRGEC |
| Anti-EGFR Activatable Antibody (c225v5-3954-4012SL) Light Chain (amino acid sequence) (SEQ ID NO: 417) QGQSGQCISPRGCPDGPYVMYGGGSSGGSSTVFHMGGGSQILLTQSPVILSVSPGERVSFSCRA SQSIGTNIHWYQQRTNGSPRLLIKYASESISGIPSRFSGSGSGTDFTLSINSVESEDIADYYCQ QNNNWPTTFGAGTKLELKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPVTKSFNRGEC |
| Anti-EGFR Activatable Antibody (c225v5-3954-4013SL) Light Chain (amino acid sequence) (SEQ ID NO: 418) QGQSGQCISPRGCPDGPYVMYGGGSSGGSMGPWFMGGGSQILLTQSPVILSVSPGERVSFSCRA SQSIGTNIHWYQQRTNGSPRLLIKYASESISGIPSRFSGSGSGTDFTLSINSVESEDIADYYCQ QNNNWPTTFGAGTKLELKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPVTKSFNRGEC |
| Anti-EGFR Activatable Antibody (c225v5-3954-4013LL) Light Chain (amino acid sequence) (SEQ ID NO: 419) QGQSGQCISPRGCPDGPYVMYGSSGGSGGSGGSGMGPWFMGGGSQILLTQSPVILSVSPGERVS FSCRASQSIGTNIHWYQQRTNGSPRLLIKYASESISGIPSRFSGSGSGTDFTLSINSVESEDIA DYYCQQNNNWPTTFGAGTKLELKRTVAAPSVFIFPPSDEQLKSGTASVVCLLNNFYPREAKVQW KVDNALQSGNSQESVTEQDSKDSTYSLSSTLTLSKADYEKHKVYACEVTHQGLSSPVTKSFNRG EC |

TABLE 2-continued

| Activatable Antibody Sequences |
|---|
| Anti-EGFR Activatable Antibody (c225v5-3954-4014SL) Light Chain (amino acid sequence) (SEQ ID NO: 420) QGQSGQCISPRGCPDGPYVMYGGGSSGGSRHLAKLGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| Anti-EGFR Activatable Antibody (c225v5-3954-4015SL) Light Chain (amino acid sequence) (SEQ ID NO: 421) QGQSGQCISPRGCPDGPYVMYGGGSSGGSPLGVRGKGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| Anti-EGFR Activatable Antibody (c225v5-3954-4015LL) Light Chain (amino acid sequence) (SEQ ID NO: 422) QGQSGQCISPRGCPDGPYVMYGSSGGSGGSGGSGPLGVRGKGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| Anti-EGFR Activatable Antibody (c225v5-3954-4016) Light Chain (amino acid sequence) (SEQ ID NO: 423) QGQSGQCISPRGCPDGPYVMYGSSGGSGGSGGSGQNQALRIAGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| Anti-EGFR Activatable Antibody (c225v5-3954-2011LL) Light Chain (amino acid sequence) (SEQ ID NO: 480) QGQSGQCISPRGCPDGPYVMYGSSGGSGGSGGSGISSGLLSGRSDNPGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| Anti-EGFR Activatable Antibody (c225v5-3954-3011LL) Light Chain (amino acid sequence) (SEQ ID NO: 481) QGQSGQCISPRGCPDGPYVMYGSSGGSGGSGGSGAVGLLAPPGGLSGRSDNPGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| Anti-EGFR Activatable Antibody (c225v5-3954-1001SL) Light Chain (amino acid sequence) (SEQ ID NO: 482) QGQSGQCISPRGCPDGPYVMYGGGSSGGSISSGLLSSGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| Anti-EGFR Activatable Antibody (c225v5-3954-1001LL) Light Chain (amino acid sequence) (SEQ ID NO: 483) QGQSGQCISPRGCPDGPYVMYGSSGGSGGSGGSGISSGLLSSGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| Anti-EGFR Activatable Antibody (c225v5-3954-1004SL) Light Chain (amino acid sequence) (SEQ ID NO: 484) QGQSGQCISPRGCPDGPYVMYGGGSSGGSAVGLLAPPGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| Anti-EGFR Activatable Antibody (c225v5-3954-1004LL) Light Chain (amino acid sequence) (SEQ ID NO: 485) QGQSGQCISPRGCPDGPYVMYGSSGGSGGSGGSGPAVGLLAPPGGGSQILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 2-continued

| Activatable Antibody Sequences |
|---|
| Anti-EGFR Activatable Antibody (c225v5-3954-1005SL) Light Chain (amino acid sequence) (SEQ ID NO: 486)<br>QGQSGQCISPRGCPDGPYVMYGGGSSGGSGPSHLVLTGGGSQILLTQSPVILSVSPGERVSFSC<br>RASQSIGTNIHWYQQRTNGSPRLLIKYASESISGIPSRFSGSGSGTDFTLSINSVESEDIADYY<br>CQQNNNWPTTFGAGTKLELKRTVAAPSVFIFPPSDEQLKSGTASVVCLLNNFYPREAKVQWKVD<br>NALQSGNSQESVTEQDSKDSTYSLSSTLTLSKADYEKHKVYACEVTHQGLSSPVTKSFNRGEC |
| Anti-EGFR Activatable Antibody (c225v5-3954-1005LL) Light Chain (amino acid sequence) (SEQ ID NO: 487)<br>QGQSGQCISPRGCPDGPYVMYGSSGGSGGSGGSGGPSHLVLTGGGSQILLTQSPVILSVSPGER<br>VSFSCRASQSIGTNIHWYQQRTNGSPRLLIKYASESISGIPSRFSGSGSGTDFTLSINSVESED<br>IADYYCQQNNNWPTTFGAGTKLELKRTVAAPSVFIFPPSDEQLKSGTASVVCLLNNFYPREAKV<br>QWKVDNALQSGNSQESVTEQDSKDSTYSLSSTLTLSKADYEKHKVYACEVTHQGLSSPVTKSFN<br>RGEC |

Example 2: In Vitro Stability of Activatable Antibodies with MMP-Cleavable Substrates The studies provided herein evaluate the in vitro stability of activatable antibodies containing matrix metalloprotease (MMP) substrates of the present disclosure.

The stability of the activatable antibodies of the present disclosure were measured by in the presence of either recombinant MMP9 or recombinant MMP14 matrix metalloproteases. Each activatable antibody (100 μg/mL) was incubated with 50 mM of the indicated recombinant protease for 24 hours at 37° C., and the fraction of the activatable antibody that was cleaved was measured by capillary electrophoresis for each protease enzyme. The exemplary results of this in vitro study are summarized in Table 3.

These exemplary results show that the substrates of the present disclosure showed a range of cleavability by MMP9 or MMP14 enzymes. These exemplary results also show a group of substrates in which the MMP9 and MMP14 cleavability are both at least 85%. In some embodiments, such substrates may include isolated polypeptide that include the amino acid sequence of ALAHGLF (SEQ ID NO: 1), DLAHPLL (SEQ ID NO: 2), or RGPKLYW (SEQ ID NO: 6).

These exemplary results also show a group of substrates in which the MMP9 and MMP14 cleavability are both at least 90%. In some embodiments, such substrates may include isolated polypeptide that include the amino acid sequence of ALAHGLF (SEQ ID NO: 1).

TABLE 3

In Vitro Activation of MMP-Cleavable Activatable Antibodies

| Substrate in Activatable Antibody (%) | Substrate | Substrate SEQ ID NO. | MMP14 Cleavability (%) | MMP9 Cleavability |
|---|---|---|---|---|
| c225v5-3954-4001-SL | ALAHGLF | 1 | 96.5 | 94.5 |
| c225v5-3954-4001-LL | ALAHGLF | 1 | 100 | 100.0 |
| c225v5-3954-4002-SL | DLAHPLL | 2 | 85.9 | 87.5 |
| c225v5-3954-4003-SL | AFRHLR | 3 | 53.1 | 6.0 |
| c225v5-3954-4004-LL | PHGFFQ | 4 | 46.2 | 29.8 |
| c225v5-3954-4005-SL | SVHHLI | 5 | 24.4 | 70.5 |
| c225v5-3954-4006-LL | RGPKLYW | 6 | 84.2 | 90.8 |
| c225v5-3954-4006-SL | RGPKLYW | 6 | 85.7 | 92.9 |
| c225v5-3954-4007-SL | RFPYGVW | 7 | 0.0 | 69.5 |
| c225v5-3954-4008-LL | HVPRQV | 8 | 0.0 | 55.2 |
| c225v5-3954-4009-SL | SNPFKY | 9 | 0.0 | 22.1 |
| c225v5-3954-4010-SL | RFPLKV | 10 | 0.0 | 18.0 |
| c225v5-3954-4011-SL | PFHLSR | 11 | 9.9 | 78.8 |
| c225v5-3954-4012-SL | STVFHM | 12 | 0.0 | 56.5 |
| c225v5-3954-4014-SL | RHLAKL | 14 | 30.5 | 0.0 |
| c225v5-3954-4015-LL | PLGVRGK | 15 | 0.0 | 90.0 |

Example 3: In Vivo Stability of Activatable Antibodies with MMP-Cleavable Substrates The studies provided herein evaluate the in vivo stability of activatable antibodies containing matrix metalloprotease (MMP) substrates of the present disclosure.

These exemplary studies measured the stability of activatable antibodies containing MMP substrates of the present disclosure by administering a dose of the activatable antibodies to mice, and then measuring by Western blot the fraction of the activatable antibody in plasma that was observed to be cleaved. The stability was compared to other known activatable antibodies that have substrates e.g. 2011 (ISSGLLSGRSDNP, SEQ ID NO: 21), and 3011 (AVGLLAPPGGLSGRSDNP, SEQ ID NO: 22) that include at least one MMP substrate and at least serine protease substrate or a substrate 1001 (ISSGLLSS, SEQ ID NO: 17) that includes at least one MMP substrate.

Figure 1:
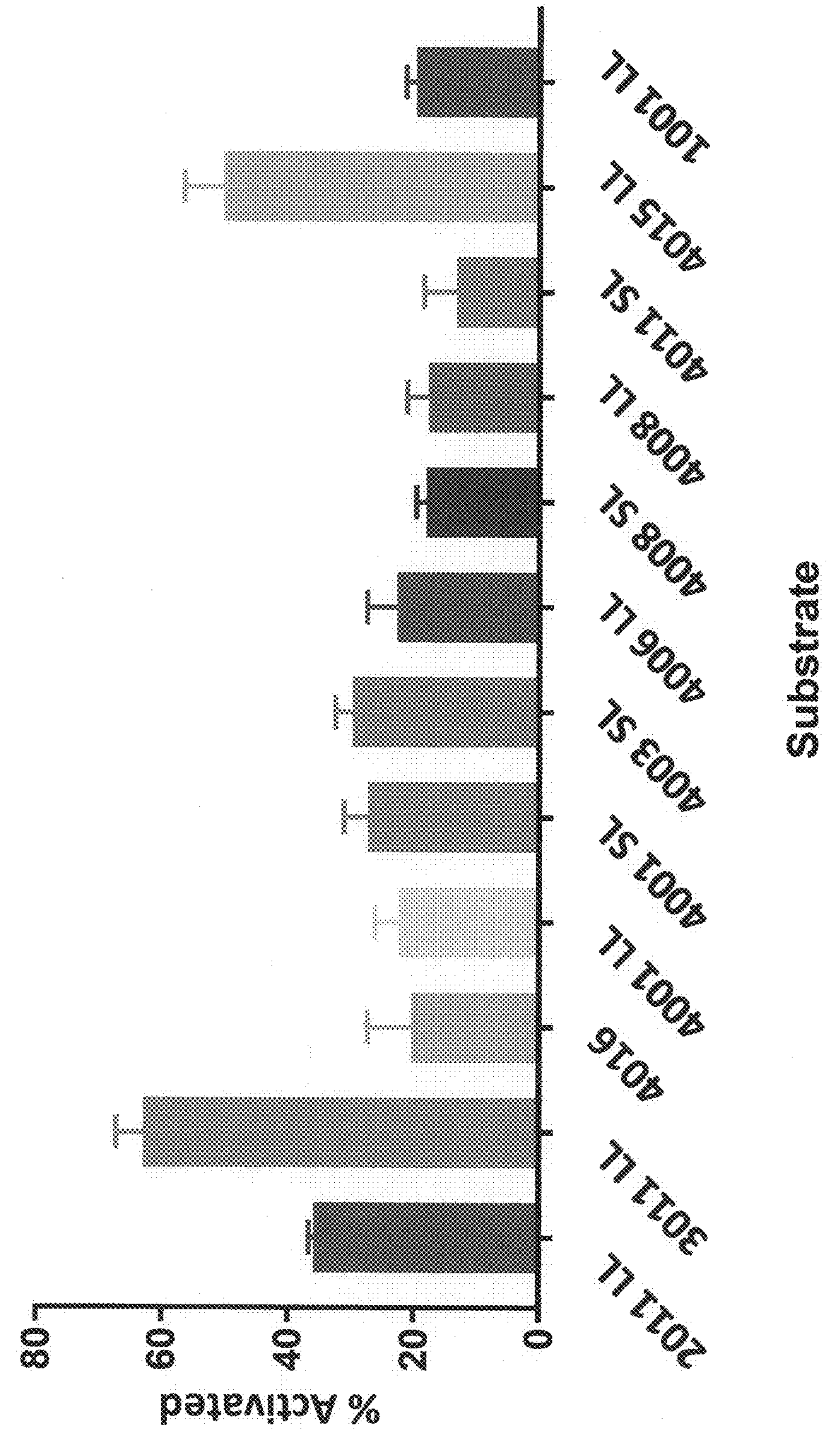
FIG. 1 is a graph showing exemplary results of the percent of the indicated activatable anti-EGFR antibodies of the present disclosure that were observed to be cleaved in vivo following their administration to nu/nu mice. These exemplary results showed that several of the tested activatable antibodies showed a higher degree of stability than other substrates that are cleavable by multiple enzymes.

In this study, nu/nu mice of about 7-8 weeks of age were administered intraperitoneally with the indicated test article at a dosage of 12.5 mg/kg. After 7 days following the administration, terminal blood was collected by cardiac puncture and processed to plasma within 1 hour of collection. The collected sample was diluted 1:100 in phosphate-buffered saline solution and denatured and analyzed using the WES Western Blot protocol (Protein Simple) using A110UK goat anti-human IgG antibodies (American Qualex) and anti-goat secondary antibodies (Jackson ImmunoResearch). The fraction of cleaved activatable antibody was determined by quantifying the fraction of the higher mobility polypeptide corresponding to the cleaved activatable antibody. The results of these exemplary assays are summarized in Table 4 and FIG. 1.

TABLE 4

In Vivo Stability of Activatable Antibodies

| Test Article | % Activated after 7 days |
|---|---|
| C225v5-3954-2011 LL | 35.80 |
| C225v5-3954-3011 LL | 62.85 |
| C225v5-3954-4016 | 20.30 |
| C225v5-3954-4001 LL | 22.37 |
| C225v5-3954-4001 SL | 27.23 |
| C225v5-3954-4003 SL | 29.70 |
| C225v5-3954-4006 LL | 22.70 |
| C225v5-3954-4008 SL | 17.93 |
| C225v5-3954-4008 LL | 17.77 |
| C225v5-3954-4012 SL | 13.20 |
| C225v5-3954-4015 LL | 50.43 |
| C225v5-3954-1001 LL | 19.77 |

These exemplary results showed that certain activatable antibodies that include MMP substrates of the present disclosure demonstrated a higher in vivo stability than activatable antibodies with both serine protease and MMP substrates.

These exemplary results also show a group of substrates in which the in vivo stability is less than 30% activation. In some embodiments, such substrates may include isolated polypeptide that include the amino acid sequence of ALAHGLF (SEQ ID NO: 1) or RGPKLYW (SEQ ID NO: 6).

These exemplary results also show a group of substrates in which the in vivo stability is less than 25% activation. In some embodiments, such substrates may include isolated polypeptide that include the amino acid sequence of ALAHGLF (SEQ ID NO: 1) or RGPKLYW (SEQ ID NO: 6).

Example 4: Masking Efficiency of Activatable Antibodies with MMP-Cleavable Substrates The studies provided herein evaluate the in vitro masking efficiency of activatable antibodies that include matrix metalloprotease (MMP) substrates of the present disclosure.

Figure 2A:
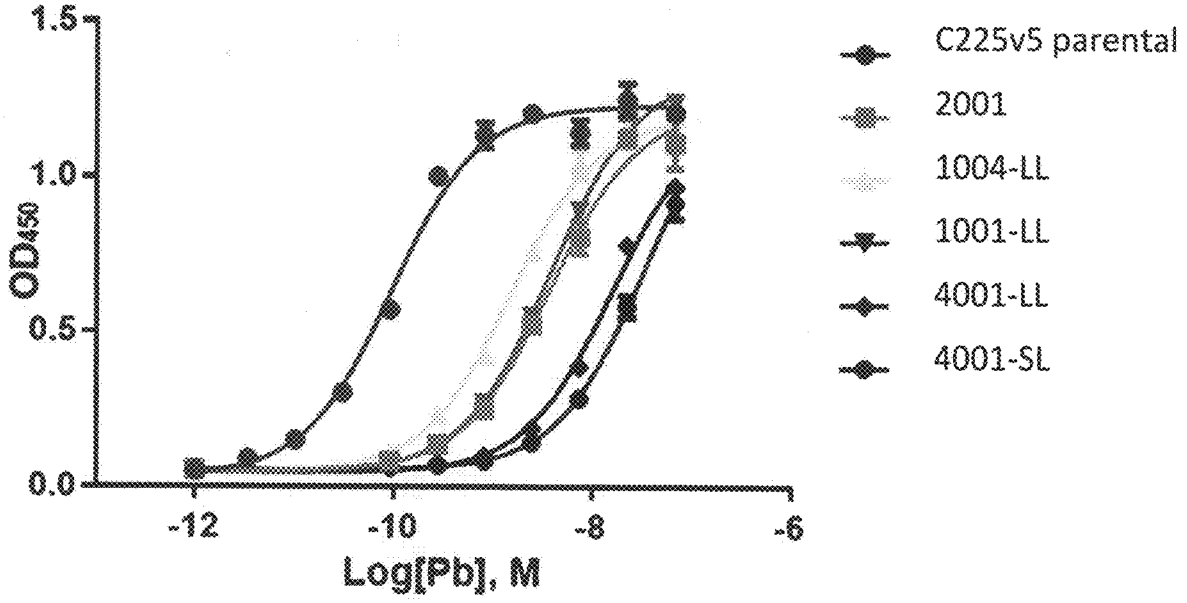
Figure 2A:
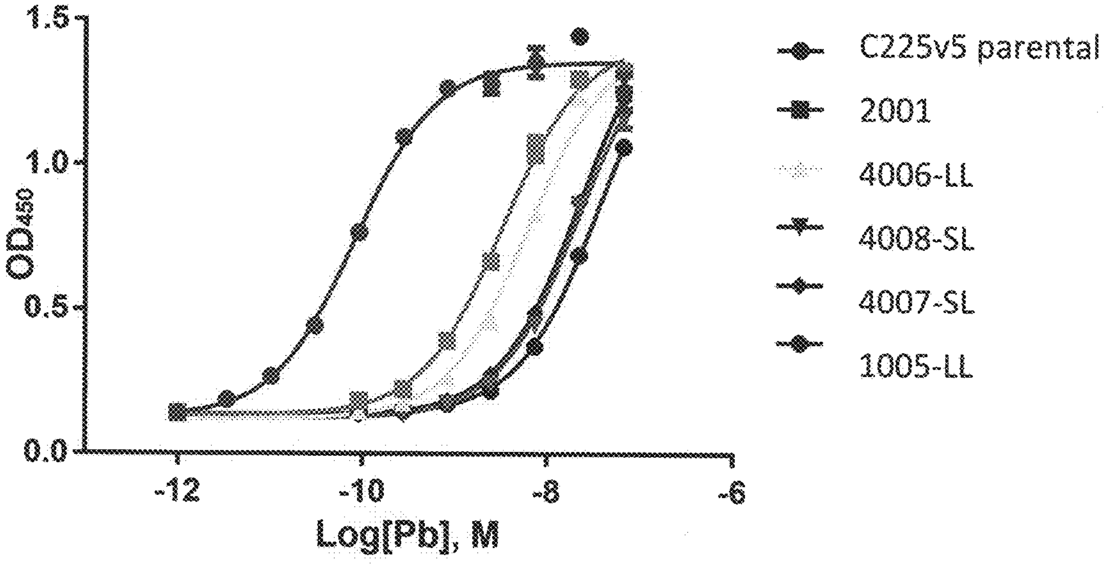

In these studies, a solid-phase binding assay (ELISA) was used to demonstrate the binding affinity of anti-EGFR activatable antibodies that include MMP substrates of the present disclosure to recombinant EGFR. As shown in FIGS. 2A and 2B, the binding affinity to EGFR of the activatable antibodies with the indicated substrate of the present disclosure was measured and compared to the c225v5 parental antibody. The masking efficiency was compared to other activatable antibodies that having known substrates e.g. 2001 (ISSGLLSGRSDNH, SEQ ID NO: 23) that includes at least one MMP substrate and at least serine protease substrate or a substrate 1001 (ISSGLLSS, SEQ ID NO: 17), 1004 (AVGLLAPP, SEQ ID NO: 18), and 1005 (GPSHLVLT, SEQ ID NO: 19) that includes at least one MMP substrate. A summary of these exemplary results is shown in Table 5 and FIGS. 2A and 2B.

These exemplary results showed that the MMP substrate had an effect on the masking efficiency of the masking moiety in the activatable antibody, in some cases increasing the apparent masking efficiency of the masking moiety in the prodomain of the activatable antibody.

These exemplary results also show a group of substrates in which the masking efficiency is greater than 70. In some embodiments, such substrates may include isolated polypeptide that include the amino acid sequence of ALAHGLF (SEQ ID NO: 1), RGPKLYW (SEQ ID NO: 6), or RFPYGVW (SEQ ID NO: 7).

These exemplary results also show a group of substrates in which the masking efficiency is greater than 160. These exemplary results also show a group of substrates in which the masking efficiency is from 160 to 350. In some embodiments, such substrates may include isolated polypeptide that include the amino acid sequence of ALAHGLF (SEQ ID NO: 1) or RFPYGVW (SEQ ID NO: 7).

TABLE 5

In Vitro Binding Activity and Masking Efficiency of Activatable Antibodies

| Test Article | $K_{Da}$ (nM) | Masking Efficiency |
|---|---|---|
| C225v5 parental antibody (FIG. 2A) | 0.094 | 1 |
| C225v5-3954-2001 (FIG. 2A) | 3.71 | 39.5 |
| C225v5-3954-1004-LL | 1.51 | 16.1 |
| C225v5-3954-1001-LL | 3.83 | 40.7 |
| C225v5-3954-4001-LL | 15.8 | 168 |
| C225v5-3954-4001-SL | 32.9 | 350 |
| C225v5 parental antibody (FIG. 2B) | 0.082 | 1 |
| C225v5-3954-2001 (FIG. 2B) | 3.23 | 39.4 |
| C225v5-3954-4006-LL | 6.12 | 74.6 |
| C225v5-3954-4008-SL | 22.2 | 271 |
| C225v5-3954-4007-SL | 22.6 | 276 |
| C225v5-3954-1005-LL | 36.6 | 446 |

Example 5: In Vivo Efficacy of Anti-EGFR Activatable Antibodies

The studies provided herein evaluate the in vivo efficacy of activatable antibodies that include matrix metalloprotease (MMP) substrates of the present disclosure using a mouse H292 (human lung cancer cell line) xenograft model.

Figure 3A:
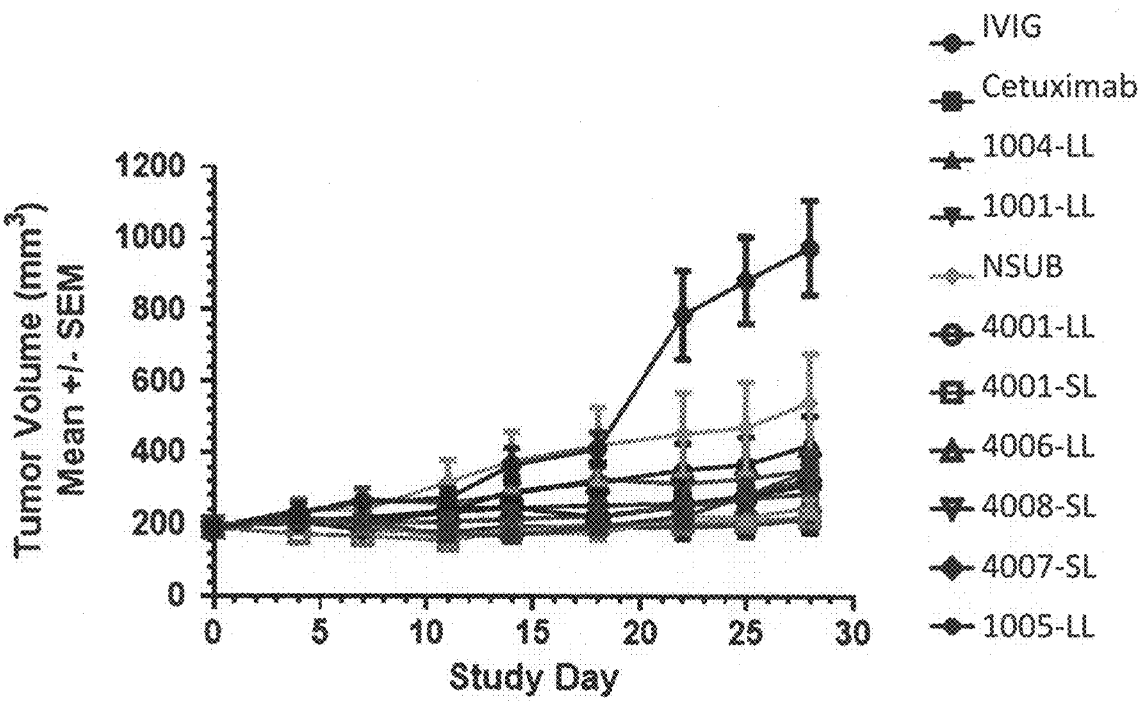
FIGS. 3A and 3B are graphs showing exemplary results of the in vivo efficacy of the indicated activatable anti-EGFR antibodies of the present disclosure using a mouse H292 xenograft model. These exemplary results showed that activatable antibodies with certain MMP substrates of the present disclosure showed efficacy in this xenograft model that was comparable to unmasked anti-EGFR cetuximab.
Figure 3B:
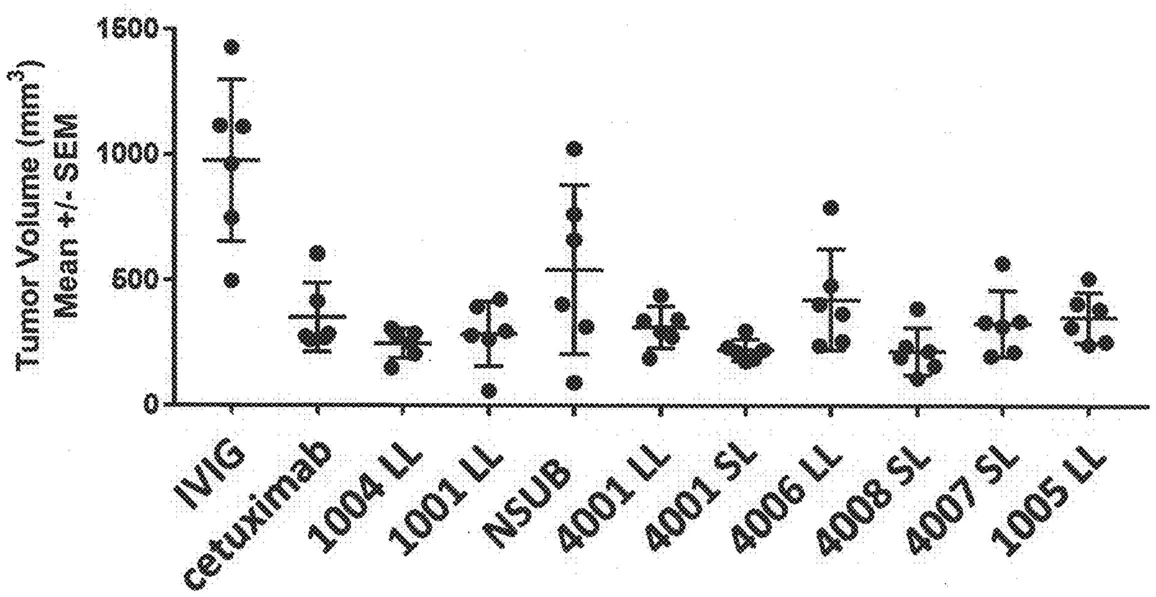

In these studies, H292 (human lung cancer-derived cell line) subcutaneous xenograft tumors in female nu/nu mice of 6-8 weeks of age were grown to an average volume of 180-260 mm$^3$. The H292 cell line is responsive to the anti-EGFR antibody cetuximab. The mice were then randomized into groups of 7 mice each and each group was dosed intraperitoneally on day 1 with 10 mg/kg of the indicated test article. The mean tumor volume±SEM was plotted for each time point following administration of the test article, as shown in FIG. 3A. FIG. 3B shows the distribution of absolute tumor volumes at day 28 for each mouse treated with activated antibodies with the indicated substrates, or with cetuximab or immunoglobulin (IVIG) control. The efficacy was determined with activatable antibodies that having known substrates e.g. 1001 (ISSGLLSS), 1004 (AVGLLAPP), and 1005 (GPSHLVLT) that includes at least one MMP substrate, or with an uncleavable glycine-serine linker (NSUB).

As shown in FIGS. 3A and 3B, certain of the activatable antibodies with MMP substrates of the present disclosure demonstrated an in vivo efficacy that was comparable with cetuximab, which lacks a prodomain.

Example 6: In Vivo Intra-Tumoral Activation of Anti-EGFR Activatable Antibodies The studies provided herein evaluate the in vivo intratumoral activation of activatable antibodies that include matrix metalloprotease (MMP) substrates of the present disclosure following administration to a mouse H292 (human lung cancer cell line) xenograft model.

In these studies, H292 (human lung cancer-derived cell line) subcutaneous xenograft tumors in female nu/nu mice of 6-8 weeks of age were grown to an average volume of 180-260 mm$^3$. The H292 cell line is responsive to the anti-EGFR antibody cetuximab. The mice were then randomized into groups of 7 mice each and each group was dosed intraperitoneally on day 1 with 10 mg/kg of the indicated test article. Each mouse was treated with activated antibodies with the indicated substrates, or with cetuximab or immunoglobulin (IVIG) control. The efficacy was determined with activatable antibodies that having known substrates e.g. 1001 (ISSGLLSS, SEQ ID NO: 17), 1004 (AVGLLAPP, SEQ ID NO: 18), and 1005 (GPSHLVLT, SEQ ID NO: 19) that includes at least one MMP substrate, or with an uncleavable glycine-serine linker (NSUB).

Figure 4:
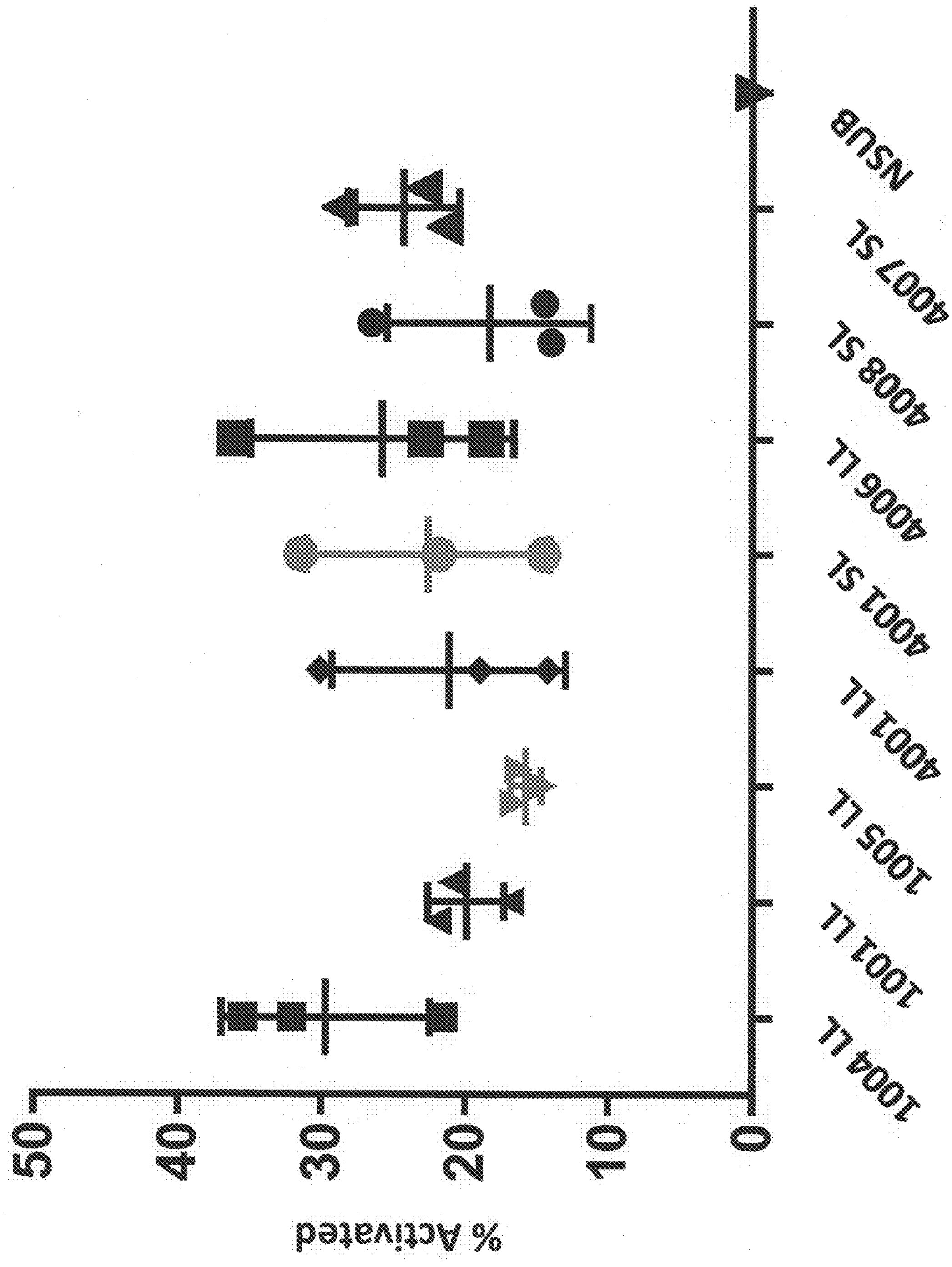
FIG. 4 is a graph showing exemplary results of the percent of the indicated activatable anti-EGFR antibodies of the present disclosure that were activated within intra-tumoral tissue following administration to a mouse H292 xenograft model.
Figure 5:
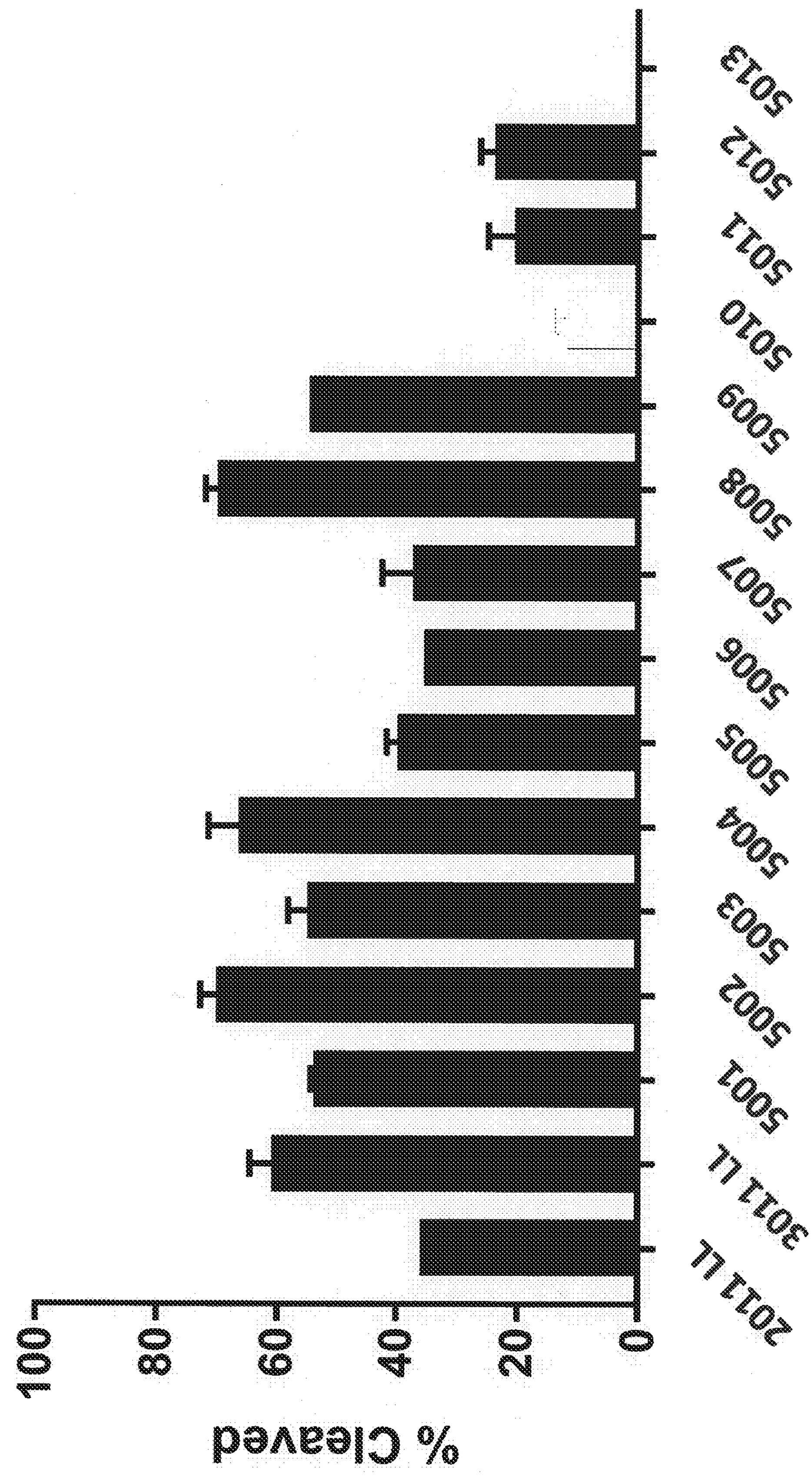
FIG. 5 is a graph showing exemplary results of the percent of the indicated activatable anti-EGFR antibodies with single MMP or tandem substrates of the present disclosure that were observed to be cleaved in vivo following their administration to nu/nu mice. These exemplary results showed that several of the tested activatable antibodies with tandem substrates showed a higher degree of in vivo stability than other substrates that are cleavable by multiple enzymes.

Tumors and plasma were collected from the mice 4 days after dosing. The tumor tissue was lysed with immunoprecipitation buffer (Pierce) containing HALT protease inhibitor cocktail (Thermo Fisher) and EDTA and lysed using the Barocycler (Pressure Bioscience). The sample was analyzed using the WES Western Blot protocol (Protein Simple) using A110UK goat anti-human IgG antibodies (American Qualex) and anti-goat secondary antibodies (Jackson ImmunoResearch). The fraction of cleaved activatable antibody was determined by quantifying the fraction of the higher mobility polypeptide corresponding to the cleaved activatable antibody. The results of these exemplary assays are summarized in Table 6 and FIG. 4.

A summary of the properties of certain activatable antibodies with MMP substrates of the present disclosure is shown in Table 6. The in vivo stability of the indicated test articles from Example 3, Table 4 are presented are comparison. These exemplary results show the MMP substrate 4001 demonstrated desirable properties, including cleavability by both MMP9 and MMP14. Some substrates also showed a higher relative stability than other reference MMP substrates (1001 and 1004).

These exemplary results also show a group of substrates in which the in vivo non-tumor and/or intra-tumor stability is less than 30% activation. These exemplary results also show a group of substrates in which the in vivo non-tumor and/or intra-tumor stability is between 20% and 30% activation. These exemplary results also show a group of substrates in which the in vivo non-tumor and/or intra-tumor stability is between 22% and 27% activation. In some embodiments, such substrates may include isolated polypeptide that include the amino acid sequence of ALAHGLF (SEQ ID NO: 1), RGPKLYW (SEQ ID NO: 6), or RFPYGVW (SEQ ID NO: 7).

TABLE 6

Summary of MMP Substrate Characteristics

| Substrate | Substrate Sequence | Substrate SEQ ID NO | In Vivo Stability (Non-Tumor) | In Vivo Stability (Intra-Tumor) |
|---|---|---|---|---|
| 2001 | ISSGLLSGRSDNH | 23 | 30% | Not Tested |
| 4001-LL | ALAHGLF | 1 | 22% | 27% |
| 4001-SL | ALAHGLF | 1 | 27% | 25% |
| 4007-SL | RFPYGVW | 7 | N/A | 22% |
| 4006-LL | RGPKLYW | 6 | 23% | 26% |
| 4008-SL | HVPRQV | 8 | 18% | 14% |
| 1005-LL | GPSHLVLT | 19 | 11% | 16% |
| 1001-LL | ISSGLLSS | 17 | 20% | 20% |
| 1004-LL | AVGLLAPP | 18 | Not determined | 37% |

Example 7: Activatable Antibodies and Tandem Cleavable Substrates

The studies provided herein describe exemplary tandem substrates of the present disclosure that include at least one substrate cleavable by a matrix metalloprotease (MMP) substrates of the present disclosure and at least one substrate cleavable by a serine protease.

Exemplary activatable antibodies were constructed such that each one includes one of the tandem substrates listed in Table 7. The exemplary activatable antibodies of the present disclosure, the sequences of which are listed in Table 7, include an antibody or antigen binding fragment thereof (AB) that is based on a mouse/human chimeric monoclonal antibody that specifically binds to epidermal growth factor receptor (EGFR). The exemplary activatable antibodies also include a prodomain coupled to the N-terminus of the light chain of the AB. Each prodomain includes a masking moiety (MM) and a cleavable moiety (CM), and the CM includes at least one tandem substrate sequence of Table 7.

TABLE 7

Tandem MMP / Serine Protease Substrates

| Name | Sequence | SEQ ID NO: |
|---|---|---|
| 5001 | LSGRSALAHGLF | 25 |
| 5002 | ALAHGLFSGRSAN | 26 |
| 5003 | HVPRQVLSGRS | 27 |
| 5004 | HVPRQVLSGRSAN | 28 |
| 5005 | TARGPALAHGLF | 29 |
| 5006 | TARGPVPRQV | 30 |
| 5007 | APRSALAHGLF | 31 |
| 5008 | ALAHGLFAPRSF | 32 |
| 5009 | HVPRQVAPRSF | 33 |
| 5010 | ALAHGLPTFVHL | 34 |
| 5011 | GLPTFVHLPRQV | 35 |
| 5012 | AANALAHGLF | 36 |
| 5013 | GPTNALAHGLF | 37 |
| 5014 | ISSGLLSGRSNI | 38 |
| 5015 | AVGLLAPPGGLSGRSNI | 39 |
| 5016 | ISSGLLSGRSNIGS | 40 |
| 5017 | AVGLLAPPGGLSGRSNIGS | 41 |
| 5018 | ISSGLLSGRSNIG | 42 |
| 5019 | AVGLLAPPGGLSGRSNIG | 43 |

TABLE 7

Activatable Antibody Sequences

Anti-EGFR Activatable Antibody (c225v5-3954-5001) Light Chain (amino acid sequence) (SEQ ID NO: 450)
QGQSGQCISPRGCPDGPYVMYGGGSSGGSLSGRSALAHGLFGGGSQILLTQSPVILSVSPGERV
SFSCRASQSIGTNIHWYQQRTNGSPRLLIKYASESISGIPSRFSGSGSGTDFTLSINSVESEDI
ADYYCQQNNNWPTTFGAGTKLELKRTVAAPSVFIFPPSDEQLKSGTASVVCLLNNFYPREAKVQ
WKVDNALQSGNSQESVTEQDSKDSTYSLSSTLTLSKADYEKHKVYACEVTHQGLSSPVTKSFNR
GEC Anti-EGFR Activatable Antibody (c225v5-3954-5002) Light Chain (amino acid sequence) (SEQ ID NO: 451)
QGQSGQCISPRGCPDGPYVMYGGGSSGGSALAHGLFSGRSANGGGSQILLTQSPVILSVSPGER
VSFSCRASQSIGTNIHWYQQRTNGSPRLLIKYASESISGIPSRFSGSGSGTDFTLSINSVESED
IADYYCQQNNNWPTTFGAGTKLELKRTVAAPSVFIFPPSDEQLKSGTASVVCLLNNFYPREAKV
QWKVDNALQSGNSQESVTEQDSKDSTYSLSSTLTLSKADYEKHKVYACEVTHQGLSSPVTKSFN
RGEC Anti-EGFR Activatable Antibody (c225v5-3954-5003) Light Chain (amino acid sequence) (SEQ ID NO: 452)
QGQSGQCISPRGCPDGPYVMYGGGSSGGSHVPRQVLSGRSGGGSQILLTQSPVILSVSPGERVS
FSCRASQSIGTNIHWYQQRTNGSPRLLIKYASESISGIPSRFSGSGSGTDFTLSINSVESEDIA
DYYCQQNNNWPTTFGAGTKLELKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC Anti-EGFR Activatable Antibody (c225v5-3954-5004) Light Chain (amino acid sequence) (SEQ ID NO: 453)
QGQSGQCISPRGCPDGPYVMYGGGSSGGSHVPRQVLSGRSANGGGSQILLTQSPVILSVSPGER
VSFSCRASQSIGTNIHWYQQRTNGSPRLLIKYASESISGIPSRFSGSGSGTDFTLSINSVESED
IADYYCQQNNNWPTTFGAGTKLELKRTVAAPSVFIFPPSDEQLKSGTASVVCLLNNFYPREAKV
QWKVDNALQSGNSQESVTEQDSKDSTYSLSSTLTLSKADYEKHKVYACEVTHQGLSSPVTKSFN
RGEC Anti-EGFR Activatable Antibody (c225v5-3954-5005) Light Chain (amino acid sequence) (SEQ ID NO: 454)
QGQSGQCISPRGCPDGPYVMYGGGSSGGSTARGPALAHGLFGGGSQILLTQSPVILSVSPGERV
SFSCRASQSIGTNIHWYQQRTNGSPRLLIKYASESISGIPSRFSGSGSGTDFTLSINSVESEDI TABLE 7-continued

| Activatable Antibody Sequences |
|---|
| ADYYCQQNNNWPTTFGAGTKLELKRTVAAPSVFIFPPSDEQLKSGTASVVCLLNNFYPREAKVQ WKVDNALQSGNSQESVTEQDSKDSTYSLSSTLTLSKADYEKHKVYACEVTHQGLSSPVTKSFNR GEC |
| Anti-EGFR Activatable Antibody (c225v5-3954-5006) Light Chain (amino acid sequence) (SEQ ID NO: 455) QGQSGQCISPRGCPDGPYVMYGGGSSGGSTARGPVPRQVGGGSQILLTQSPVILSVSPGERVSF SCRASQSIGTNIHWYQQRTNGSPRLLIKYASESISGIPSRFSGSGSGTDFTLSINSVESEDIAD YYCQQNNNWPTTFGAGTKLELKRTVAAPSVFIFPPSDEQLKSGTASVVCLLNNFYPREAKVQWK VDNALQSGNSQESVTEQDSKDSTYSLSSTLTLSKADYEKHKVYACEVTHQGLSSPVTKSFNRGE C |
| Anti-EGFR Activatable Antibody (c225v5-3954-5007) Light Chain (amino acid sequence) (SEQ ID NO: 456) QGQSGQCISPRGCPDGPYVMYGGGSSGGSAPRSALAHGLFGGGSQILLTQSPVILSVSPGERVS FSCRASQSIGTNIHWYQQRTNGSPRLLIKYASESISGIPSRFSGSGSGTDFTLSINSVESEDIA DYYCQQNNNWPTTFGAGTKLELKRTVAAPSVFIFPPSDEQLKSGTASVVCLLNNFYPREAKVQW KVDNALQSGNSQESVTEQDSKDSTYSLSSTLTLSKADYEKHKVYACEVTHQGLSSPVTKSFNRG EC |
| Anti-EGFR Activatable Antibody (c225v5-3954-5008) Light Chain (amino acid sequence) (SEQ ID NO: 457) QGQSGQCISPRGCPDGPYVMYGGGSSGGSALAHGLFAPRSFGGGSQILLTQSPVILSVSPGERV SFSCRASQSIGTNIHWYQQRTNGSPRLLIKYASESISGIPSRFSGSGSGTDFTLSINSVESEDI ADYYCQQNNNWPTTFGAGTKLELKRTVAAPSVFIFPPSDEQLKSGTASVVCLLNNFYPREAKVQ WKVDNALQSGNSQESVTEQDSKDSTYSLSSTLTLSKADYEKHKVYACEVTHQGLSSPVTKSFNR GEC |
| Anti-EGFR Activatable Antibody (c225v5-3954-5009) Light Chain (amino acid sequence) (SEQ ID NO: 458) QGQSGQCISPRGCPDGPYVMYGGGSSGGSHVPRQVAPRSFGGGSQILLTQSPVILSVSPGERVS FSCRASQSIGTNIHWYQQRTNGSPRLLIKYASESISGIPSRFSGSGSGTDFTLSINSVESEDIA DYYCQQNNNWPTTFGAGTKLELKRTVAAPSVFIFPPSDEQLKSGTASVVCLLNNFYPREAKVQW KVDNALQSGNSQESVTEQDSKDSTYSLSSTLTLSKADYEKHKVYACEVTHQGLSSPVTKSFNRG EC |
| Anti-EGFR Activatable Antibody (c225v5-3954-5010) Light Chain (amino acid sequence) (SEQ ID NO: 459) QGQSGQCISPRGCPDGPYVMYGGGSSGGSALAHGLPTFVHLGGGSQILLTQSPVILSVSPGERV SFSCRASQSIGTNIHWYQQRTNGSPRLLIKYASESISGIPSRFSGSGSGTDFTLSINSVESEDI ADYYCQQNNNWPTTFGAGTKLELKRTVAAPSVFIFPPSDEQLKSGTASVVCLLNNFYPREAKVQ WKVDNALQSGNSQESVTEQDSKDSTYSLSSTLTLSKADYEKHKVYACEVTHQGLSSPVTKSFNR GEC |
| Anti-EGFR Activatable Antibody (c225v5-3954-5011) Light Chain (amino acid sequence) (SEQ ID NO: 460) QGQSGQCISPRGCPDGPYVMYGGGSSGGSGLPTFVHLPRQVGGGSQILLTQSPVILSVSPGERV SFSCRASQSIGTNIHWYQQRTNGSPRLLIKYASESISGIPSRFSGSGSGTDFTLSINSVESEDI ADYYCQQNNNWPTTFGAGTKLELKRTVAAPSVFIFPPSDEQLKSGTASVVCLLNNFYPREAKVQ WKVDNALQSGNSQESVTEQDSKDSTYSLSSTLTLSKADYEKHKVYACEVTHQGLSSPVTKSFNR GEC |
| Anti-EGFR Activatable Antibody (c225v5-3954-5012) Light Chain (amino acid sequence) (SEQ ID NO: 461) QGQSGQCISPRGCPDGPYVMYGGGSSGGSAANALAHGLFGGGSQILLTQSPVILSVSPGERVSF SCRASQSIGTNIHWYQQRTNGSPRLLIKYASESISGIPSRFSGSGSGTDFTLSINSVESEDIAD YYCQQNNNWPTTFGAGTKLELKRTVAAPSVFIFPPSDEQLKSGTASVVCLLNNFYPREAKVQWK VDNALQSGNSQESVTEQDSKDSTYSLSSTLTLSKADYEKHKVYACEVTHQGLSSPVTKSFNRGE C |
| Anti-EGFR Activatable Antibody (c225v5-3954-5013) Light Chain (amino acid sequence) (SEQ ID NO: 462) QGQSGQCISPRGCPDGPYVMYGGGSSGGSGPTNALAHGLFGGGSQILLTQSPVILSVSPGERVS FSCRASQSIGTNIHWYQQRTNGSPRLLIKYASESISGIPSRFSGSGSGTDFTLSINSVESEDIA DYYCQQNNNWPTTFGAGTKLELKRTVAAPSVFIFPPSDEQLKSGTASVVCLLNNFYPREAKVQW KVDNALQSGNSQESVTEQDSKDSTYSLSSTLTLSKADYEKHKVYACEVTHQGLSSPVTKSFNRG EC |
| Anti-EGFR Activatable Antibody (c225v5-3954-2001) Light Chain (amino acid sequence) (SEQ ID NO: 488) QGQSGQCISPRGCPDGPYVMYGGGSSGGSISSGLLSGRSDNHGSSGTQILLTQSPVILSVSPGE RVSFSCRASQSIGTNIHWYQQRTNGSPRLLIKYASESISGIPSRFSGSGSGTDFTLSINSVESE DIADYYCQQNNNWPTTFGAGTKLELKRTVAAPSVFIFPPSDEQLKSGTASVVCLLNNFYPREAK VQWKVDNALQSGNSQESVTEQDSKDSTYSLSSTLTLSKADYEKHKVYACEVTHQGLSSPVTKSF NRGEC |

TABLE 7-continued

| Activatable Antibody Sequences |
|---|
| Anti-EGFR Activatable Antibody (c225v5-3954-2001TT) Light Chain (amino acid sequence) (SEQ ID NO: 489)<br>QGQSGQCISPRGCPDGPYVMYGGGSSGGSISSGLLSGRSDNHGGGSQILLTQSPVILSVSPGER VSFSCRASQSIGTNIHWYQQRTNGSPRLLIKYASESISGIPSRFSGSGSGTDFTLSINSVESED IADYYCQQNNNWPTTFGAGTKLELKRTVAAPSVFIFPPSDEQLKSGTASVVCLLNNFYPREAKV QWKVDNALQSGNSQESVTEQDSKDSTYSLSSTLTLSKADYEKHKVYACEVTHQGLSSPVTKSFN RGEC |
| Anti-EGFR Activatable Antibody (c225v5-3954-3001) Light Chain (amino acid sequence) (SEQ ID NO: 490)<br>QGQSGQCISPRGCPDGPYVMYGGGSSGGSAVGLLAPPGGLSGRSDNHGGGSQILLTQSPVILSV SPGERVSFSCRASQSIGTNIHWYQQRTNGSPRLLIKYASESISGIPSRFSGSGSGTDFTLSINS VESEDIADYYCQQNNNWPTTFGAGTKLELKRTVAAPSVFIFPPSDEQLKSGTASVVCLLNNFYP REAKVQWKVDNALQSGNSQESVTEQDSKDSTYSLSSTLTLSKADYEKHKVYACEVTHQGLSSPV TKSFNRGEC |

Example 8: In Vitro Stability of Activatable Antibodies with Tandem Substrates The studies provided herein evaluate the in vitro stability of activatable antibodies containing exemplary tandem substrates of the present disclosure that include at least one substrate cleavable by a matrix metalloprotease (MMP) substrates and at least one substrate cleavable by a serine protease.

The stability of the activatable antibodies of the present disclosure were measured by in the presence of the indicated recombinant proteases (matriptase, legumain, neutrophil elastase, MMP2, MMP9, and MMP14). Each activatable antibody (250 nM/38.5 μg/mL) was incubated with 10 mM of the indicated protease for 24 hours at 37° C., and the fraction of the activatable antibody that was cleaved was measured by capillary electrophoresis for each protease enzyme. The sample was analyzed using the WES Western Blot protocol (Protein Simple) using A110UK goat anti-human IgG antibodies (American Qualex) and anti-goat secondary antibodies (Jackson ImmunoResearch). The fraction of cleaved activatable antibody was determined by quantifying the fraction of the higher mobility polypeptide corresponding to the cleaved activatable antibody. The exemplary results of this in vitro study are summarized in Table 8A.

In addition, an exemplary study to determine the cleavability kinetics (i.e., Kcat/Km ($M^{-1}$ $s^{-1}$)) of the indicated substrates of the present disclosure with the indicated protease enzymes. The exemplary results of this in vitro study are summarized in Table 8A.

These exemplary results show that the substrates of the present disclosure showed a range of cleavability by the indicated proteases.

These exemplary results show that the tandem substrates of the present disclosure showed a range of cleavability by matriptase, MMP9, MMP14, legumain, and/or neutrophil elastase enzymes. These exemplary results also show a group of substrates in which the MMP9 and MMP14 cleavability are both at least 30%. In some embodiments, such substrates may include isolated polypeptide that include the amino acid sequence of LSGRSALAHGLF (SEQ ID NO: 25), ALAHGLFSGRSAN (SEQ ID NO: 26), TARGPALAHGLF (SEQ ID NO: 29), APRSALAHGLF (SEQ ID NO: 31), ALAHGLFAPRSF (SEQ ID NO: 32), AANALAHGLF (SEQ ID NO: 36), or GPTNALAHGLF (SEQ ID NO: 37).

These exemplary results also show a group of substrates in which the MMP9 and MMP14 cleavability are both at least 50%. In some embodiments, such substrates may include isolated polypeptide that include the amino acid sequence of LSGRSALAHGLF (SEQ ID NO: 25), APRSALAHGLF (SEQ ID NO: 31), ALAHGLFAPRSF (SEQ ID NO: 32), AANALAHGLF (SEQ ID NO: 36), or GPTNALAHGLF (SEQ ID NO: 37).

These exemplary results also show a group of substrates in which the MMP9 and MMP14 cleavability are both at least 70%. In some embodiments, such substrates may include isolated polypeptide that include the amino acid sequence of LSGRSALAHGLF (SEQ ID NO: 25) or APRSALAHGLF (SEQ ID NO: 31).

These exemplary results also show a group of substrates in which the MMP9 and MMP14 cleavability are both at least 15% and the matriptase cleavability is at least 50%. In some embodiments, such substrates may include isolated polypeptide that include the amino acid sequence of LSGRSALAHGLF (SEQ ID NO: 25), ALAHGLFSGRSAN (SEQ ID NO: 26), HVPRQVLSGRS (SEQ ID NO: 27), HVPRQVLSGRSAN (SEQ ID NO: 28), APRSALAHGLF (SEQ ID NO: 31), or ALAHGLFAPRSF (SEQ ID NO: 32).

These exemplary results also show a group of substrates in which the MMP9 and MMP14 cleavability are both at least 15% and the neutrophil elastase cleavability is at least 30%. In some embodiments, such substrates may include isolated polypeptide that include the amino acid sequence of LSGRSALAHGLF (SEQ ID NO: 25), ALAHGLFSGRSAN (SEQ ID NO: 26), HVPRQVLSGRS (SEQ ID NO: 27), HVPRQVLSGRSAN (SEQ ID NO: 28), TARGPALAHGLF (SEQ ID NO: 29), APRSALAHGLF (SEQ ID NO: 31), ALAHGLFAPRSF (SEQ ID NO: 32), AANALAHGLF (SEQ ID NO: 36), or GPTNALAHGLF (SEQ ID NO: 37).

These exemplary results also show a group of substrates in which the MMP9 and MMP14 cleavability are both at least 30% and the neutrophil elastase cleavability is at least 30%. In some embodiments, such substrates may include isolated polypeptide that include the amino acid sequence of LSGRSALAHGLF (SEQ ID NO: 25), ALAHGLFSGRSAN (SEQ ID NO: 26), TARGPALAHGLF (SEQ ID NO: 29), APRSALAHGLF (SEQ ID NO: 31), ALAHGLFAPRSF (SEQ ID NO: 32), AANALAHGLF (SEQ ID NO: 36), or GPTNALAHGLF (SEQ ID NO: 37).

These exemplary results also show a group of substrates in which the MMP9 and MMP14 cleavability are both at least 50% and the neutrophil elastase cleavability is at least 50%. In some embodiments, such substrates may include isolated polypeptide that include the amino acid sequence of LSGRSALAHGLF (SEQ ID NO: 25), APRSALAHGLF (SEQ ID NO: 31), ALAHGLFAPRSF (SEQ ID NO: 32), AANALAHGLF (SEQ ID NO: 36), or GPTNALAHGLF (SEQ ID NO: 37).

These exemplary results also show a group of substrates in which the MMP9 and MMP14 cleavability are both at least 70% and the neutrophil elastase cleavability is at least 70%. In some embodiments, such substrates may include isolated polypeptide that include the amino acid sequence of LSGRSALAHGLF (SEQ ID NO: 25) or APRSALAHGLF (SEQ ID NO: 31).

TABLE 8A

In Vitro Activation of Activatable Antibodies with Tandem Substrates

| Substrate of Activatable Antibody | Substrate (SEQ ID NO) | Cleavability (%) Matriptase | MMP14 | MMP9 | Legumain | Neutrophil Elastase |
|---|---|---|---|---|---|---|
| 2001 | ISSGLLSGRSDNH (23) | 53 | 58 | 22 | 5 | 18 |
| 3001 | AVGLLAPPGGLSGRSDNH (24) | NT | NT | NT | 0 | 52 |
| 4001 | ALAHGLF (1) | 0 | 77 | 100 | 0 | 37 |
| 4008 | HVPRQV (8) | 40 | 6 | 100 | 0 | 28 |
| 5001 | LSGRSALAHGLF (25) | 100 | 76 | 76 | 0 | 88 |
| 5002 | ALAHGLFSGRSAN (26) | 100 | 58 | 37 | 21 | 67 |
| 5003 | HVPRQVLSGRS (27) | 99 | 20 | 100 | 0 | 77 |
| 5004 | HVPRQVLSGRSAN (28) | 75 | 19 | 86 | 27 | 84 |
| 5005 | TARGPALAHGLF (29) | 6 | 34 | 72 | 0 | 81 |
| 5006 | TARGPVPRQV (30) | 100 | 6 | 81 | 0 | 30 |
| 5007 | APRSALAHGLF (31) | 100 | 90 | 77 | 0 | 74 |
| 5008 | ALAHGLFAPRSF (32) | 98 | 55 | 100 | 0 | 66 |
| 5009 | HVPRQVAPRSF (33) | 100 | 9 | 78 | 0 | 31 |
| 5010 | ALAHGLPTFVHL (34) | 0 | 11 | 0 | 0 | 100 |
| 5011 | GLPTFVHLPRQV (35) | 80 | 7 | 55 | 0 | 100 |
| 5012 | AANALAHGLF (36) | 0 | 72 | 52 | 7 | 55 |
| 5013 | GPTNALAHGLF (37) | 0 | 78 | 62 | 9 | 56 |

NT = not tested

TABLE 8B

In Vitro Activation of Activatable Antibodies with Tandem Substrates

| Activatable Antibody | Substrate of Substrate (SEQ ID NO) | Kcat / Km ($M^{-1}$ $s^{-1}$) Matriptase | MMP14 | MMP9 | MMP2 | Neutrophil Elastase |
|---|---|---|---|---|---|---|
| 2001 | ISSGLLSGRSDNH (23) | 2.55 E+03 | 6.33 E+03 | 3.94 E+02 | 1.32 E+04 | 3.17 E+03 |
| 3001 | AVGLLAPPGGLSGRSDNH (24) | 5.35 E+03 | 1.70 E+04 | 5.05 E+04 | 3.10 E+05 | 1.91 E+04 |
| 4001 | ALAHGLF (1) | 0.00 E+00 | 6.01 E+03 | 8.84 E+03 | 5.76 E+04 | N/D |
| 5007 | APRSALAHGLF (31) | 2.72 E+04 | 9.25 E+03 | 2.53 E+04 | 9.83 E+04 | 2.42 E+04 |
| 5013 | GPTNALAHGLF (37) | 0.00 | 7.77 E+03 | 1.04 E+04 | 7.65 E+04 | N/D |
| 4008 | HVPRQV (8) | 4.76 E+02 | 2.30 E+02 | 1.87 E+04 | 1.30 E+04 | N/D |
| 5006 | TARGPVPRQV (30) | 5.37 E+03 | 5.64 E+02 | 3.39 E+04 | 3.69 E+04 | N/D |
| 5011 | GLPTFVHLPRQV (35) | 1.43 E+03 | 4.44 E+02 | 4.18 E+03 | 3.38 E+03 | 6.65 E+05 |

N/D = not determined

Example 9: In Vivo Efficacy of Anti-EGFR Activatable Antibodies with Tandem Substrates The studies provided herein evaluate the in vivo efficacy of activatable antibodies of the present disclosure that include matrix metalloprotease (MMP) substrates and at least one serine protease substrate using a mouse H292 (human lung cancer cell line) xenograft model.

Figure 6:
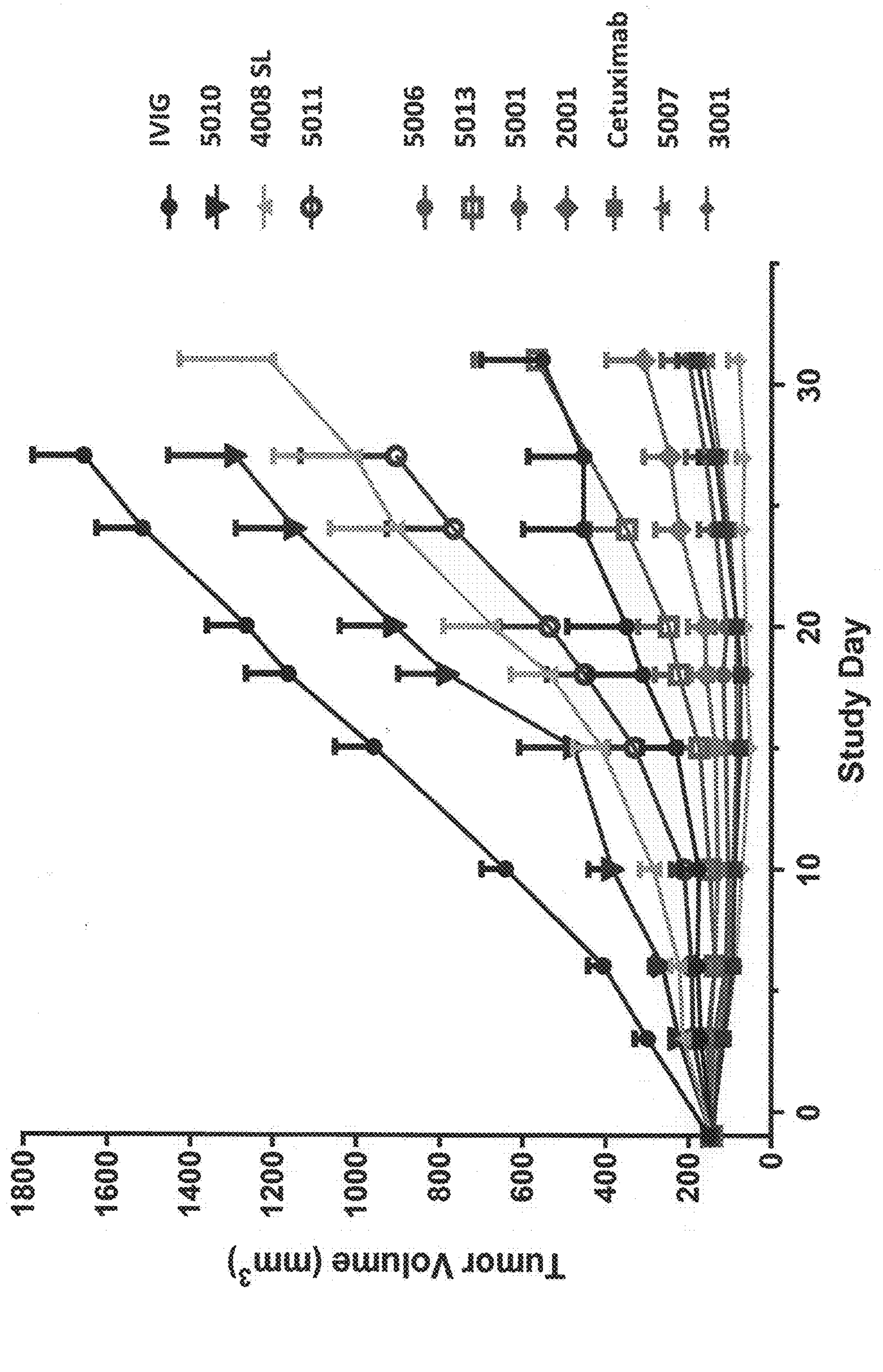
FIG. 6 is a graph showing exemplary results of the in vivo efficacy of the indicated activatable anti-EGFR antibodies of the present disclosure using a mouse H292 xenograft model.

In these studies, H292 (human lung cancer-derived cell line) subcutaneous xenograft tumors in female nu/nu mice of 6-8 weeks of age were grown to an average volume of 180-260 $mm^3$. The H292 cell line is responsive to the anti-EGFR antibody cetuximab. The mice were then randomized into groups of 7 mice each and each group was dosed intraperitoneally on day 1 with 12.5 mg/kg of the indicated test article. The mean tumor volume±SEM was plotted for each time point following administration of the test article, as shown in FIG. 6. Each mouse was treated with activated antibodies with the indicated substrates, or with cetuximab or immunoglobulin (IVIG) control. The efficacy was determined with activatable antibodies that having known substrates e.g. 2001 (ISSGLLSGRSDNH) and 3001 (AVGLLAPPGGLSGRSDNH).

In addition to the in vivo stability assay, and intra-tumoral assay was performed using the indicated activatable antibodies as shown in FIG. 7. Tumors and plasma were collected from the mice 4 days after dosing. The tumor tissue was lysed with immunoprecipitation buffer (Pierce) containing HALT protease inhibitor cocktail (Thermo Fisher) and EDTA and lysed using the Barocycler (Pressure Bioscience). The sample was analyzed using the WES Western Blot protocol (Protein Simple) using A110UK goat anti-human IgG antibodies (American Qualex) and anti-goat secondary antibodies (Jackson ImmunoResearch). The fraction of cleaved activatable antibody was determined by quantifying the fraction of the higher mobility polypeptide corresponding to the cleaved activatable antibody. The results of these exemplary assays are summarized in FIG. 7.

As shown in FIGS. 6, certain of the activatable antibodies with tandem MMP and serine protease substrates of the present disclosure demonstrated an in vivo efficacy that was comparable with cetuximab, which lacks a prodomain.

Example 10: Masking Efficiency of Activatable Antibodies with Tandem Substrates The studies provided herein evaluate the in vitro masking efficiency of activatable antibodies of the present disclose that include tandem matrix metalloprotease (MMP) and serine protease substrates.

In these studies, a solid-phase binding assay (ELISA) was used to demonstrate the binding affinity of anti-EGFR activatable antibodies that include MMP substrates of the present disclosure to recombinant EGFR. The binding affinity to EGFR of the activatable antibodies with the indicated substrate of the present disclosure was measured and compared to the c225v5 parental antibody. A summary of these exemplary results is shown in Table 9 and FIG. 8.

These exemplary results showed that the tandem substrates had an effect by increasing the apparent masking efficiency of the masking moiety in the activatable antibody.

TABLE 9

In Vitro Binding Activity and Masking Efficiency of Activatable Antibodies

| Test Article | $K_{Da}$ in nM (Std. Err) | Masking Efficiency |
|---|---|---|
| C225v5 parental antibody | 0.1585 (0.01978) | 1 |
| C225v5-3954-2001 | 5.062 (0.8141) | 32 |
| C225v5-3954-3001 | 9.095 (1.598) | 57 |
| C225v5-3954-4008 | 32.11 (6.39) | 203 |
| C225v5-3954-5007 | 26.61 (3.946) | 168 |
| C225v5-3954-5006 | 19.08 (3.15) | 120 |
| C225v5-3954-5013 | 29.85 (4.287) | 188 |
| C225v5-3954-5010 | 34.26 (4.212) | 216 |

TABLE 9-continued

In Vitro Binding Activity and Masking Efficiency of Activatable Antibodies

| Test Article | $K_{Da}$ in nM (Std. Err) | Masking Efficiency |
|---|---|---|
| C225v5-3954-5011 | 29.03 (2.524) | 183 |
| C225v5-3954-5001 | 17.13 (2.538) | 108 |

Example 11: In Vivo Stability of Activatable Antibodies with Tandem Substrates The studies provided herein evaluate the in vivo stability of activatable antibodies containing exemplary tandem substrates of the present disclosure that include at least one substrate cleavable by a matrix metalloprotease (MMP) and at least one substrate cleavable by a serine and/or cysteine protease.

These exemplary studies measured the stability of activatable antibodies containing MMP substrates of the present disclosure by administering a dose of the activatable antibodies to mice, and then measuring by Western blot the fraction of the activatable antibody in plasma that was observed to be cleaved. The stability was compared to other known activatable antibodies that have substrates e.g. 2001 (ISSGLLSGRSDNH), and 3001 (AVGLLAPPGGLSGRSDNH) that include at least one MMP substrate and at least serine protease substrate.

In this study, nu/nu mice of about 7-8 weeks of age were administered intraperitoneally with the indicated test article at a dosage I'm of 12.5 mg/kg. After 7 days following the administration, terminal blood was collected by cardiac puncture and processed to plasma within 1 hour of collection. The collected sample was diluted 1:100 in phosphate-buffered saline solution and denatured and analyzed using the WES Western Blot protocol (Protein Simple) using A110UK goat anti-human IgG antibodies (American Qualex) and anti-goat secondary antibodies (Jackson ImmunoResearch). The fraction of cleaved activatable antibody was determined by quantifying the fraction of the higher mobility polypeptide corresponding to the cleaved activatable antibody. The results of these exemplary assays are summarized in Table 10.

These exemplary results showed that certain activatable antibodies that include tandem substrates of the present disclosure demonstrated a higher in vivo stability than activatable antibodies with both serine protease and MMP substrates.

TABLE 10

In Vivo Stability of Activatable Antibodies with Tandem Substrates

| Activatable Antibody | Substrate | Substrate SEQ ID NO | % cleaved |
|---|---|---|---|
| c225v5-3954-2001 | ISSGLLSGRSDNH | 23 | 36% (DNP) |
| c225v5-3954-4001 | ALAHGLF | 1 | 27% |
| c225v5-3954-4008 | HVPRQV | 8 | 18% |
| c225v5-3954-5001 | LSGRSALAHGLF | 25 | 54% |
| c225v5-3954-5002 | ALAHGLFSGRSAN | 26 | 70% |
| c225v5-3954-5003 | HVPRQVLSGRS | 27 | 55% |
| c225v5-3954-5004 | HVPRQVLSGRSAN | 28 | 65% |
| c225v5-3954-5005 | TARGPALAHGLF | 29 | 40% |
| c225v5-3954-5006 | TARGPVPRQV | 30 | 36% |
| c225v5-3954-5007 | APRSALAHGLF | 31 | 37% |
| c225v5-3954-5008 | ALAHGLFAPRSF | 32 | 70% |
| c225v5-3954-5009 | HVPRQVAPRSF | 33 | 55% |
| c225v5-3954-5010 | ALAHGLPTFVHL | 34 | 12% |
| c225v5-3954-5011 | GLPTFVHLPRQV | 35 | 21% |
| c225v5-3954-5012 | AANALAHGLF | 36 | 24% |
| c225v5-3954-5013 | GPTNALAHGLF | 37 | 21% |

Example 12: In Vivo Tumor Tissue Activation of Anti-EGFR Activatable Antibodies The studies provided herein evaluate the in vitro activation of activatable antibodies that include tandem substrates of the present disclosure by human tumor lysates.

In these studies, human tumor tissues (head & neck cancer or pancreatic cancer) were incubated with anti-EGFR activatable antibodies with the substrates indicated in FIG. 9. The exemplary results showed that activatable antibodies with the 5007 substrate (APRSALAHGLF; SEQ ID NO: 31) showed a higher level of activation compared to activatable antibodies having the tandem substrate 2001 (ISSGLLSGRSDNH; SEQ ID NO: 23) or 3001 (AVGLLAPPGGLSGRSDNH; SEQ ID NO: 24).

In a further study, a similar activation study of activatable antibodies with the 5007 tandem substrate of the present invention (APRSALAHGLF; SEQ ID NO: 31) with head and neck tumor tissue or pancreatic tumor tissue were performed with a class-specific protease inhibitor selected from galardin, EDTA, aprotinin, or sivelestat. The studies showed that aprotinin, which is a broad-spectrum serine protease inhibitor, reduced the amount of activation to ≤5%. In comparison, treatment with the other three inhibitors showed activation at a level comparable to the non-inhibitor control study. These exemplary results showed that this activation was not inhibited by MMP (galardin, EDTA) or neutrophil elastase (sivelestat) inhibitors.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed:

1. An isolated polypeptide comprising a tandem substrate, wherein the tandem substrate comprises at least a first cleavable moiety (CM1) that is a substrate for at least one matrix metalloprotease (MMP) and at least a second cleavable moiety (CM2) that is a substrate for at least one serine protease (SP) or cysteine protease (CP), wherein CM1 comprises the amino acid sequence AHGL (SEQ ID NO: 54) or PRQV (SEQ ID NO: 61), wherein CM2 comprises an amino acid sequence selected from the group consisting of SGR, LSGR (SEQ ID NO: 73), ARG, PRS, TFVH (SEQ ID NO: 141), AAN, SAN, LPTFV (SEQ ID NO: 140), and GPTN (SEQ ID NO: 152), and wherein the N-terminal to C-terminal arrangement of the tandem substrate is CM1-CM2 or CM2-CM1.

2. The isolated polypeptide of claim 1, wherein CM2 comprises an amino acid sequence selected from the group consisting of SGR, LSGR (SEQ ID NO: 73), LSGRS (SEQ ID NO: 72), LSGRSD (SEQ ID NO: 71), LSGRSA(SEQ ID NO: 110), LSGRSDN (SEQ ID NO: 70), LSGRSAN (SEQ ID NO: 109), LSGRSDNH (SEQ ID NO: 20), LSGRSGNH (SEQ ID NO: 78), LSGRSDNP (SEQ ID NO: 90), LSGRSDNI (SEQ ID NO: 84), LSGRSANI (SEQ ID NO: 108), LSGRSANP (SEQ ID NO: 114), LSGRSDYH (SEQ ID NO: 86), LSGRSDTH (SEQ ID NO: 92), LSGRSDQH (SEQ ID NO: 96), LSGRSDIH (SEQ ID NO: 100), and LSGRSDDH (SEQ ID NO: 104).

3. The isolated polypeptide of claim 1, wherein CM2 comprises an amino acid sequence selected from the group consisting of ARGP (SEQ ID NO: 128), TARG (SEQ ID NO: 125), and TARGP (SEQ ID NO: 124).

4. The isolated polypeptide of claim 1, wherein CM2 comprises an amino acid sequence selected from the group consisting of APRSF (SEQ ID NO: 130), APRS (SEQ ID NO: 131), and PRSF (SEQ ID NO: 132).

5. The isolated polypeptide of claim 1, wherein CM2 comprises an amino acid sequence selected from the group consisting of AAN, SAN, and GPTN (SEQ ID NO: 150).

6. The isolated polypeptide of claim 1, wherein CM2 comprises an amino acid sequence selected from the group consisting of GLPTFVHL (SEQ ID NO: 135), GLPTFVH (SEQ ID NO: 136), GLPTFV (SEQ ID NO: 137), LPTFVHL (SEQ ID NO: 138), LPTFVH (SEQ ID NO: 139), and LPTFV (SEQ ID NO: 140).

7. The isolated polypeptide of claim 1, wherein CM2 comprises an amino acid sequence selected from the group consisting of AAN, SAN, and GPTN (SEQ ID NO: 150); and
an amino acid sequence selected from the group consisting of SGR, LSGR (SEQ ID NO: 73), LSGRS (SEQ ID NO: 72), LSGRSD (SEQ ID NO: 71), LSGRSA (SEQ ID NO: 110), LSGRSDN (SEQ ID NO: 70), LSGRSAN (SEQ ID NO: 109), LSGRSDNH (SEQ ID NO: 20), LSGRSGNH (SEQ ID NO: 78), LSGRSDNP (SEQ ID NO: 90), LSGRSDNI (SEQ ID NO: 84), LSGRSANI (SEQ ID NO: 108), LSGRSANP (SEQ ID NO: 114), LSGRSDYH (SEQ ID NO: 86), LSGRSDTH (SEQ ID NO: 92), LSGRSDQH (SEQ ID NO: 96), LSGRSDIH (SEQ ID NO: 100), and LSGRSDDH (SEQ ID NO: 104).

8. The isolated polypeptide of claim 1, wherein the N-terminal to C-terminal arrangement of the tandem substrate is CM1-CM2.

9. The isolated polypeptide of claim 1, wherein the N-terminal to C-terminal arrangement of the tandem substrate is CM2-CM1.

10. An isolated polypeptide comprising a tandem substrate, wherein the tandem substrate comprises at least a first cleavable moiety (CM1) that is a substrate for at least one matrix metalloprotease (MMP) and at least a second cleavable moiety (CM2) that is a substrate for at least one serine protease (SP) or cysteine protease (CP),
wherein the tandem substrate comprises an amino acid sequence selected from the group consisting of SEQ ID NOs: 25-43.

11. The isolated polypeptide of claim 1, wherein the CM1 comprises the amino acid sequence of ALAHGLF (SEQ ID NO: 1).

12. The isolated polypeptide of claim 1, wherein the isolated polypeptide comprises the amino acid sequence of LSGRSALAHGLF (SEQ ID NO: 25), ALAHGLFSGRSAN (SEQ ID NO: 26), TARGPALAHGLF (SEQ ID NO: 29), APRSALAHGLF (SEQ ID NO: 31), ALAHGLFAPRSF (SEQ ID NO: 32), AANALAHGLF (SEQ ID NO: 36), or GPTNALAHGLF (SEQ ID NO: 37).

13. The isolated polypeptide of claim 1, wherein the isolated polypeptide comprises the amino acid sequence of LSGRSALAHGLF (SEQ ID NO: 25), ALAHGLFSGRSAN (SEQ ID NO: 26), HVPRQVLSGRS (SEQ ID NO: 27), HVPRQVLSGRSAN (SEQ ID NO: 28), TARGPALAHGLF (SEQ ID NO: 29), APRSALAHGLF (SEQ ID NO: 31), ALAHGLFAPRSF (SEQ ID NO: 32), AANALAHGLF (SEQ ID NO: 36), or GPTNALAHGLF (SEQ ID NO: 37).

14. A conjugated polypeptide comprising the isolated polypeptide of claim 1 conjugated to an agent.

15. The isolated polypeptide of claim 1, wherein CM1 comprises an amino acid sequence that is selected from the group consisting of ALAHGLF (SEQ ID NO: 1), ALAHGL (SEQ ID NO: 52), LAHGLF (SEQ ID NO: 50), LAHGL (SEQ ID NO: 53), and AHGLF (SEQ ID NO: 51).

16. The isolated polypeptide of claim 1, wherein CM1 comprises an amino acid sequence that is selected from the group consisting of HVPRQV (SEQ ID NO: 8) and VPRQV (SEQ ID NO: 60).

17. The isolated polypeptide of claim 1, wherein CM1 and CM2 are linked via a linking peptide.

18. The isolated polypeptide of claim 1, wherein CM1 and CM2 are directly linked to each other.

19. The isolated polypeptide of claim 1, wherein the MMP is MMP2, MMP9, or MMP14.

20. The isolated polypeptide of claim 1, wherein the CM2 comprises a substrate for a CP enzyme, and wherein the CP enzyme is a legumain.

21. The isolated polypeptide of claim 1, wherein the CM2 comprises a substrate for a SP enzyme selected from the group consisting of a urokinase, a matriptase, and a neutrophil elastase.

22. The isolated polypeptide of claim 1, wherein the CM2 comprises a substrate for a SP enzyme selected from the group consisting of a urokinase, a matriptase, and a neutrophil elastase, and a substrate for a CP enzyme, and wherein the CP enzyme is a legumain.

23. The isolated polypeptide of claim 1, wherein the tandem substrate comprises an amino acid sequence selected from the group consisting of SEQ ID NOs: 25-43.

* * * * *

UNITED STATES PATENT AND TRADEMARK OFFICE

CERTIFICATE OF CORRECTION

PATENT NO. : 12,049,505 B2
APPLICATION NO. : 16/705124
DATED : July 30, 2024
INVENTOR(S) : Vasiljeva et al.

It is certified that error appears in the above-identified patent and that said Letters Patent is hereby corrected as shown below:

In the Drawings

On page 2 of 9 of the Drawings, delete the second occurrence of “Figure 2A” and insert --Figure 2B--.

In the Claims

In Column 332, Claim 2, Lines 59-60, delete “LSGRSA(SEQ ID NO: 110)” and insert --LSGRSA (SEQ ID NO: 110)--.

Column 333, Claim 5, Line 11, delete “(SEQ ID NO: 150)” and insert --(SEQ ID NO: 152).--;

Column 333, Claim 7, Line 20, delete “(SEQ ID NO: 150)” and insert --(SEQ ID NO: 152)--; and Column 333, Claim 7, Lines 24-25, delete “LSGRSA(SEQ ID NO: 110)” and insert --LSGRSA (SEQ ID NO: 110)--.

Signed and Sealed this
Eighth Day of July, 2025

Coke Morgan Stewart
*Acting Director of the United States Patent and Trademark Office*

SEQUENCE LISTING

<160> NUMBER OF SEQ ID NOS: 490

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Ala Leu Ala His Gly Leu Phe
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Asp Leu Ala His Pro Leu Leu
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Ala Phe Arg His Leu Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Pro His Gly Phe Phe Gln
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Ser Val His His Leu Ile
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Arg Gly Pro Lys Leu Tyr Trp
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Arg Phe Pro Tyr Gly Val Trp
1 5

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

His Val Pro Arg Gln Val
1 5

<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Ser Asn Pro Phe Lys Tyr
1 5

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Arg Phe Pro Leu Lys Val
1 5

<210> SEQ ID NO 11
<211> LENGTH: 6
<212> TYPE: PRT
<213> ORGANISM: Artificial Sequence
<220> FEATURE:
<223> OTHER INFORMATION: Synthetic

<400> SEQUENCE: 11

Pro Phe His Leu Ser Arg
1 5

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Ser Thr Val Phe His Met
1 5

```
<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

Met Gly Pro Trp Phe Met
1               5


<210> SEQ ID NO 14
<211> LENGTH: 6
<212> TYPE: PRT
<213> ORGANISM: Artificial Sequence
<220> FEATURE:
<223> OTHER INFORMATION: Synthetic

<400> SEQUENCE: 14

Arg His Leu Ala Lys Leu
1               5


<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

Pro Leu Gly Val Arg Gly Lys
1               5


<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Gln Asn Gln Ala Leu Arg Ile Ala
1               5


<210> SEQ ID NO 17
<211> LENGTH: 8
<212> TYPE: PRT
<213> ORGANISM: Artificial Sequence
<220> FEATURE:
<223> OTHER INFORMATION: Synthetic

<400> SEQUENCE: 17

Ile Ser Ser Gly Leu Leu Ser Ser
1               5


<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Ala Val Gly Leu Leu Ala Pro Pro
1               5
```

-continued

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Gly Pro Ser His Leu Val Leu Thr
1 5

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Leu Ser Gly Arg Ser Asp Asn His
1 5

<210> SEQ ID NO 21
<211> LENGTH: 13
<212> TYPE: PRT
<213> ORGANISM: Artificial Sequence
<220> FEATURE:
<223> OTHER INFORMATION: Synthetic

<400> SEQUENCE: 21

Ile Ser Ser Gly Leu Leu Ser Gly Arg Ser Asp Asn Pro
1 5 10

<210> SEQ ID NO 22
<211> LENGTH: 18
<212> TYPE: PRT
<213> ORGANISM: Artificial Sequence
<220> FEATURE:
<223> OTHER INFORMATION: Synthetic

<400> SEQUENCE: 22

Ala Val Gly Leu Leu Ala Pro Pro Gly Gly Leu Ser Gly Arg Ser Asp
1 5 10 15

Asn Pro

<210> SEQ ID NO 23
<211> LENGTH: 13
<212> TYPE: PRT
<213> ORGANISM: Artificial Sequence
<220> FEATURE:
<223> OTHER INFORMATION: Synthetic

<400> SEQUENCE: 23

Ile Ser Ser Gly Leu Leu Ser Gly Arg Ser Asp Asn His
1 5 10

<210> SEQ ID NO 24
<211> LENGTH: 18
<212> TYPE: PRT
<213> ORGANISM: Artificial Sequence
<220> FEATURE:
<223> OTHER INFORMATION: Synthetic

<400> SEQUENCE: 24

Ala Val Gly Leu Leu Ala Pro Pro Gly Gly Leu Ser Gly Arg Ser Asp
1 5 10 15

-continued

Asn His

<210> SEQ ID NO 25
<211> LENGTH: 12
<212> TYPE: PRT
<213> ORGANISM: Artificial Sequence
<220> FEATURE:
<223> OTHER INFORMATION: Synthetic

<400> SEQUENCE: 25

Leu Ser Gly Arg Ser Ala Leu Ala His Gly Leu Phe
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic

<400> SEQUENCE: 26

Ala Leu Ala His Gly Leu Phe Ser Gly Arg Ser Ala Asn
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic

<400> SEQUENCE: 27

His Val Pro Arg Gln Val Leu Ser Gly Arg Ser
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic

<400> SEQUENCE: 28

His Val Pro Arg Gln Val Leu Ser Gly Arg Ser Ala Asn
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic

<400> SEQUENCE: 29

Thr Ala Arg Gly Pro Ala Leu Ala His Gly Leu Phe
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic

<400> SEQUENCE: 30

Thr Ala Arg Gly Pro Val Pro Arg Gln Val
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic

<400> SEQUENCE: 31

Ala Pro Arg Ser Ala Leu Ala His Gly Leu Phe
1 5 10

<210> SEQ ID NO 32
<211> LENGTH: 12
<212> TYPE: PRT
<213> ORGANISM: Artificial Sequence
<220> FEATURE:
<223> OTHER INFORMATION: Synthetic

<400> SEQUENCE: 32

Ala Leu Ala His Gly Leu Phe Ala Pro Arg Ser Phe
1 5 10

<210> SEQ ID NO 33
<211> LENGTH: 11
<212> TYPE: PRT
<213> ORGANISM: Artificial Sequence
<220> FEATURE:
<223> OTHER INFORMATION: Synthetic

<400> SEQUENCE: 33

His Val Pro Arg Gln Val Ala Pro Arg Ser Phe
1 5 10

<210> SEQ ID NO 34
<211> LENGTH: 12
<212> TYPE: PRT
<213> ORGANISM: Artificial Sequence
<220> FEATURE:
<223> OTHER INFORMATION: Synthetic

<400> SEQUENCE: 34

Ala Leu Ala His Gly Leu Pro Thr Phe Val His Leu
1 5 10

<210> SEQ ID NO 35
<211> LENGTH: 12
<212> TYPE: PRT
<213> ORGANISM: Artificial Sequence
<220> FEATURE:
<223> OTHER INFORMATION: Synthetic

<400> SEQUENCE: 35

Gly Leu Pro Thr Phe Val His Leu Pro Arg Gln Val
1 5 10

<210> SEQ ID NO 36
<211> LENGTH: 10
<212> TYPE: PRT
<213> ORGANISM: Artificial Sequence
<220> FEATURE:
<223> OTHER INFORMATION: Synthetic

<400> SEQUENCE: 36

Ala Ala Asn Ala Leu Ala His Gly Leu Phe
1 5 10

-continued

<210> SEQ ID NO 37
<211> LENGTH: 11
<212> TYPE: PRT
<213> ORGANISM: Artificial Sequence
<220> FEATURE:
<223> OTHER INFORMATION: Synthetic

<400> SEQUENCE: 37

Gly Pro Thr Asn Ala Leu Ala His Gly Leu Phe
1 5 10

<210> SEQ ID NO 38
<211> LENGTH: 12
<212> TYPE: PRT
<213> ORGANISM: Artificial Sequence
<220> FEATURE:
<223> OTHER INFORMATION: Synthetic

<400> SEQUENCE: 38

Ile Ser Ser Gly Leu Leu Ser Gly Arg Ser Asn Ile
1 5 10

<210> SEQ ID NO 39
<211> LENGTH: 17
<212> TYPE: PRT
<213> ORGANISM: Artificial Sequence
<220> FEATURE:
<223> OTHER INFORMATION: Synthetic

<400> SEQUENCE: 39

Ala Val Gly Leu Leu Ala Pro Pro Gly Gly Leu Ser Gly Arg Ser Asn
1 5 10 15

Ile

<210> SEQ ID NO 40
<211> LENGTH: 14
<212> TYPE: PRT
<213> ORGANISM: Artificial Sequence
<220> FEATURE:
<223> OTHER INFORMATION: Synthetic

<400> SEQUENCE: 40

Ile Ser Ser Gly Leu Leu Ser Gly Arg Ser Asn Ile Gly Ser
1 5 10

<210> SEQ ID NO 41
<211> LENGTH: 19
<212> TYPE: PRT
<213> ORGANISM: Artificial Sequence
<220> FEATURE:
<223> OTHER INFORMATION: Synthetic

<400> SEQUENCE: 41

Ala Val Gly Leu Leu Ala Pro Pro Gly Gly Leu Ser Gly Arg Ser Asn
1 5 10 15

Ile Gly Ser

<210> SEQ ID NO 42
<211> LENGTH: 13
<212> TYPE: PRT
<213> ORGANISM: Artificial Sequence
<220> FEATURE:
<223> OTHER INFORMATION: Synthetic

<400> SEQUENCE: 42

Ile Ser Ser Gly Leu Leu Ser Gly Arg Ser Asn Ile Gly
1 5 10

<210> SEQ ID NO 43
<211> LENGTH: 18
<212> TYPE: PRT
<213> ORGANISM: Artificial Sequence
<220> FEATURE:
<223> OTHER INFORMATION: Synthetic

<400> SEQUENCE: 43

Ala Val Gly Leu Leu Ala Pro Pro Gly Gly Leu Ser Gly Arg Ser Asn
1 5 10 15

Ile Gly

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 6
<212> TYPE: PRT
<213> ORGANISM: Artificial Sequence
<220> FEATURE:
<223> OTHER INFORMATION: Synthetic

<400> SEQUENCE: 50

Leu Ala His Gly Leu Phe
1 5

<210> SEQ ID NO 51
<211> LENGTH: 5
<212> TYPE: PRT
<213> ORGANISM: Artificial Sequence
<220> FEATURE:

<223> OTHER INFORMATION: Synthetic

<400> SEQUENCE: 51

Ala His Gly Leu Phe
1 5

<210> SEQ ID NO 52
<211> LENGTH: 6
<212> TYPE: PRT
<213> ORGANISM: Artificial Sequence
<220> FEATURE:
<223> OTHER INFORMATION: Synthetic

<400> SEQUENCE: 52

Ala Leu Ala His Gly Leu
1 5

<210> SEQ ID NO 53
<211> LENGTH: 5
<212> TYPE: PRT
<213> ORGANISM: Artificial Sequence
<220> FEATURE:
<223> OTHER INFORMATION: Synthetic

<400> SEQUENCE: 53

Leu Ala His Gly Leu
1 5

<210> SEQ ID NO 54
<211> LENGTH: 4
<212> TYPE: PRT
<213> ORGANISM: Artificial Sequence
<220> FEATURE:
<223> OTHER INFORMATION: Synthetic

<400> SEQUENCE: 54

Ala His Gly Leu
1

<210> SEQ ID NO 55
<211> LENGTH: 5
<212> TYPE: PRT
<213> ORGANISM: Artificial Sequence
<220> FEATURE:
<223> OTHER INFORMATION: Synthetic

<400> SEQUENCE: 55

Ala Leu Ala His Gly
1 5

<210> SEQ ID NO 56
<211> LENGTH: 4
<212> TYPE: PRT
<213> ORGANISM: Artificial Sequence
<220> FEATURE:
<223> OTHER INFORMATION: Synthetic

<400> SEQUENCE: 56

Leu Ala His Gly
1

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60
<211> LENGTH: 5
<212> TYPE: PRT
<213> ORGANISM: Artificial Sequence
<220> FEATURE:
<223> OTHER INFORMATION: Synthetic

<400> SEQUENCE: 60

Val Pro Arg Gln Val
1               5

<210> SEQ ID NO 61
<211> LENGTH: 4
<212> TYPE: PRT
<213> ORGANISM: Artificial Sequence
<220> FEATURE:
<223> OTHER INFORMATION: Synthetic

<400> SEQUENCE: 61

Pro Arg Gln Val
1

<210> SEQ ID NO 62
<211> LENGTH: 5
<212> TYPE: PRT
<213> ORGANISM: Artificial Sequence
<220> FEATURE:
<223> OTHER INFORMATION: Synthetic

<400> SEQUENCE: 62

His Val Pro Arg Gln
1               5

<210> SEQ ID NO 63
<211> LENGTH: 4
<212> TYPE: PRT
<213> ORGANISM: Artificial Sequence
<220> FEATURE:
<223> OTHER INFORMATION: Synthetic

<400> SEQUENCE: 63

Val Pro Arg Gln
1

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70
<211> LENGTH: 7
<212> TYPE: PRT
<213> ORGANISM: Artificial Sequence
<220> FEATURE:
<223> OTHER INFORMATION: Synthetic

<400> SEQUENCE: 70

Leu Ser Gly Arg Ser Asp Asn
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic

<400> SEQUENCE: 71

Leu Ser Gly Arg Ser Asp
1               5

<210> SEQ ID NO 72
<211> LENGTH: 5
<212> TYPE: PRT
<213> ORGANISM: Artificial Sequence
<220> FEATURE:
<223> OTHER INFORMATION: Synthetic

<400> SEQUENCE: 72

Leu Ser Gly Arg Ser
1               5

<210> SEQ ID NO 73
<211> LENGTH: 4
<212> TYPE: PRT
<213> ORGANISM: Artificial Sequence
<220> FEATURE:
<223> OTHER INFORMATION: Synthetic

<400> SEQUENCE: 73

Leu Ser Gly Arg

-continued

1

<210> SEQ ID NO 74
<211> LENGTH: 6
<212> TYPE: PRT
<213> ORGANISM: Artificial Sequence
<220> FEATURE:
<223> OTHER INFORMATION: Synthetic

<400> SEQUENCE: 74

Ser Gly Arg Ser Asp Asn
1 5

<210> SEQ ID NO 75
<211> LENGTH: 5
<212> TYPE: PRT
<213> ORGANISM: Artificial Sequence
<220> FEATURE:
<223> OTHER INFORMATION: Synthetic

<400> SEQUENCE: 75

Ser Gly Arg Ser Asp
1 5

<210> SEQ ID NO 76
<211> LENGTH: 4
<212> TYPE: PRT
<213> ORGANISM: Artificial Sequence
<220> FEATURE:
<223> OTHER INFORMATION: Synthetic

<400> SEQUENCE: 76

Ser Gly Arg Ser
1

<210> SEQ ID NO 77

<400> SEQUENCE: 77

000

<210> SEQ ID NO 78
<211> LENGTH: 8
<212> TYPE: PRT
<213> ORGANISM: Artificial Sequence
<220> FEATURE:
<223> OTHER INFORMATION: Synthetic

<400> SEQUENCE: 78

Leu Ser Gly Arg Ser Gly Asn His
1 5

<210> SEQ ID NO 79
<211> LENGTH: 7
<212> TYPE: PRT
<213> ORGANISM: Artificial Sequence
<220> FEATURE:
<223> OTHER INFORMATION: Synthetic

<400> SEQUENCE: 79

Leu Ser Gly Arg Ser Gly Asn
1 5

<210> SEQ ID NO 80
<211> LENGTH: 6
<212> TYPE: PRT
<213> ORGANISM: Artificial Sequence
<220> FEATURE:
<223> OTHER INFORMATION: Synthetic

<400> SEQUENCE: 80

Leu Ser Gly Arg Ser Gly
1 5

<210> SEQ ID NO 81
<211> LENGTH: 7
<212> TYPE: PRT
<213> ORGANISM: Artificial Sequence
<220> FEATURE:
<223> OTHER INFORMATION: Synthetic

<400> SEQUENCE: 81

Ser Gly Arg Ser Gly Asn His
1 5

<210> SEQ ID NO 82
<211> LENGTH: 6
<212> TYPE: PRT
<213> ORGANISM: Artificial Sequence
<220> FEATURE:
<223> OTHER INFORMATION: Synthetic

<400> SEQUENCE: 82

Ser Gly Arg Ser Gly Asn
1 5

<210> SEQ ID NO 83
<211> LENGTH: 5
<212> TYPE: PRT
<213> ORGANISM: Artificial Sequence
<220> FEATURE:
<223> OTHER INFORMATION: Synthetic

<400> SEQUENCE: 83

Ser Gly Arg Ser Gly
1 5

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Leu Ser Gly Arg Ser Asp Asn Ile
1 5

<210> SEQ ID NO 85
<211> LENGTH: 7
<212> TYPE: PRT
<213> ORGANISM: Artificial Sequence
<220> FEATURE:
<223> OTHER INFORMATION: Synthetic

<400> SEQUENCE: 85

Ser Gly Arg Ser Asp Asn Ile
1 5

<210> SEQ ID NO 86
<211> LENGTH: 8
<212> TYPE: PRT
<213> ORGANISM: Artificial Sequence
<220> FEATURE:

<223> OTHER INFORMATION: Synthetic

<400> SEQUENCE: 86

Leu Ser Gly Arg Ser Asp Tyr His
1 5

<210> SEQ ID NO 87
<211> LENGTH: 7
<212> TYPE: PRT
<213> ORGANISM: Artificial Sequence
<220> FEATURE:
<223> OTHER INFORMATION: Synthetic

<400> SEQUENCE: 87

Leu Ser Gly Arg Ser Asp Tyr
1 5

<210> SEQ ID NO 88
<211> LENGTH: 7
<212> TYPE: PRT
<213> ORGANISM: Artificial Sequence
<220> FEATURE:
<223> OTHER INFORMATION: Synthetic

<400> SEQUENCE: 88

Ser Gly Arg Ser Asp Tyr His
1 5

<210> SEQ ID NO 89
<211> LENGTH: 6
<212> TYPE: PRT
<213> ORGANISM: Artificial Sequence
<220> FEATURE:
<223> OTHER INFORMATION: Synthetic

<400> SEQUENCE: 89

Ser Gly Arg Ser Asp Tyr
1 5

<210> SEQ ID NO 90
<211> LENGTH: 8
<212> TYPE: PRT
<213> ORGANISM: Artificial Sequence
<220> FEATURE:
<223> OTHER INFORMATION: Synthetic

<400> SEQUENCE: 90

Leu Ser Gly Arg Ser Asp Asn Pro
1 5

<210> SEQ ID NO 91
<211> LENGTH: 7
<212> TYPE: PRT
<213> ORGANISM: Artificial Sequence
<220> FEATURE:
<223> OTHER INFORMATION: Synthetic

<400> SEQUENCE: 91

Ser Gly Arg Ser Asp Asn Pro
1 5

<210> SEQ ID NO 92
<211> LENGTH: 8
<212> TYPE: PRT
<213> ORGANISM: Artificial Sequence
<220> FEATURE:
<223> OTHER INFORMATION: Synthetic

<400> SEQUENCE: 92

Leu Ser Gly Arg Ser Asp Thr His
1 5

<210> SEQ ID NO 93
<211> LENGTH: 7
<212> TYPE: PRT
<213> ORGANISM: Artificial Sequence
<220> FEATURE:
<223> OTHER INFORMATION: Synthetic

<400> SEQUENCE: 93

Leu Ser Gly Arg Ser Asp Thr
1 5

<210> SEQ ID NO 94
<211> LENGTH: 7
<212> TYPE: PRT
<213> ORGANISM: Artificial Sequence
<220> FEATURE:
<223> OTHER INFORMATION: Synthetic

<400> SEQUENCE: 94

Ser Gly Arg Ser Asp Thr His
1 5

<210> SEQ ID NO 95
<211> LENGTH: 6
<212> TYPE: PRT
<213> ORGANISM: Artificial Sequence
<220> FEATURE:
<223> OTHER INFORMATION: Synthetic

<400> SEQUENCE: 95

Ser Gly Arg Ser Asp Thr
1 5

<210> SEQ ID NO 96
<211> LENGTH: 8
<212> TYPE: PRT
<213> ORGANISM: Artificial Sequence
<220> FEATURE:
<223> OTHER INFORMATION: Synthetic

<400> SEQUENCE: 96

Leu Ser Gly Arg Ser Asp Gln His
1 5

<210> SEQ ID NO 97
<211> LENGTH: 7
<212> TYPE: PRT
<213> ORGANISM: Artificial Sequence
<220> FEATURE:
<223> OTHER INFORMATION: Synthetic

<400> SEQUENCE: 97

Leu Ser Gly Arg Ser Asp Gln
1 5

<210> SEQ ID NO 98
<211> LENGTH: 7
<212> TYPE: PRT
<213> ORGANISM: Artificial Sequence
<220> FEATURE:
<223> OTHER INFORMATION: Synthetic -continued

<400> SEQUENCE: 98

Ser Gly Arg Ser Asp Gln His
1               5

<210> SEQ ID NO 99
<211> LENGTH: 6
<212> TYPE: PRT
<213> ORGANISM: Artificial Sequence
<220> FEATURE:
<223> OTHER INFORMATION: Synthetic

<400> SEQUENCE: 99

Ser Gly Arg Ser Asp Gln
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Leu Ser Gly Arg Ser Asp Ile His
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic

<400> SEQUENCE: 101

Leu Ser Gly Arg Ser Asp Ile
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ser Gly Arg Ser Asp Ile His
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic

<400> SEQUENCE: 103

Ser Gly Arg Ser Asp Ile
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic

<400> SEQUENCE: 104

Leu Ser Gly Arg Ser Asp Asp His
1 5

<210> SEQ ID NO 105
<211> LENGTH: 7
<212> TYPE: PRT
<213> ORGANISM: Artificial Sequence
<220> FEATURE:
<223> OTHER INFORMATION: Synthetic

<400> SEQUENCE: 105

Leu Ser Gly Arg Ser Asp Asp
1 5

<210> SEQ ID NO 106
<211> LENGTH: 7
<212> TYPE: PRT
<213> ORGANISM: Artificial Sequence
<220> FEATURE:
<223> OTHER INFORMATION: Synthetic

<400> SEQUENCE: 106

Ser Gly Arg Ser Asp Asp His
1 5

<210> SEQ ID NO 107
<211> LENGTH: 6
<212> TYPE: PRT
<213> ORGANISM: Artificial Sequence
<220> FEATURE:
<223> OTHER INFORMATION: Synthetic

<400> SEQUENCE: 107

Ser Gly Arg Ser Asp Asp
1 5

<210> SEQ ID NO 108
<211> LENGTH: 8
<212> TYPE: PRT
<213> ORGANISM: Artificial Sequence
<220> FEATURE:
<223> OTHER INFORMATION: Synthetic

<400> SEQUENCE: 108

Leu Ser Gly Arg Ser Ala Asn Ile
1 5

<210> SEQ ID NO 109
<211> LENGTH: 7
<212> TYPE: PRT
<213> ORGANISM: Artificial Sequence
<220> FEATURE:
<223> OTHER INFORMATION: Synthetic

<400> SEQUENCE: 109

Leu Ser Gly Arg Ser Ala Asn
1 5

<210> SEQ ID NO 110
<211> LENGTH: 6
<212> TYPE: PRT
<213> ORGANISM: Artificial Sequence
<220> FEATURE:
<223> OTHER INFORMATION: Synthetic

<400> SEQUENCE: 110

Leu Ser Gly Arg Ser Ala
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic

<400> SEQUENCE: 111

Ser Gly Arg Ser Ala Asn Ile
1               5

<210> SEQ ID NO 112
<211> LENGTH: 6
<212> TYPE: PRT
<213> ORGANISM: Artificial Sequence
<220> FEATURE:
<223> OTHER INFORMATION: Synthetic

<400> SEQUENCE: 112

Ser Gly Arg Ser Ala Asn
1               5

<210> SEQ ID NO 113
<211> LENGTH: 5
<212> TYPE: PRT
<213> ORGANISM: Artificial Sequence
<220> FEATURE:
<223> OTHER INFORMATION: Synthetic

<400> SEQUENCE: 113

Ser Gly Arg Ser Ala
1               5

<210> SEQ ID NO 114
<211> LENGTH: 8
<212> TYPE: PRT
<213> ORGANISM: Artificial Sequence
<220> FEATURE:
<223> OTHER INFORMATION: Synthetic

<400> SEQUENCE: 114

Leu Ser Gly Arg Ser Ala Asn Pro
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic

<400> SEQUENCE: 115

Ser Gly Arg Ser Ala Asn Pro
1               5

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120
<211> LENGTH: 8
<212> TYPE: PRT
<213> ORGANISM: Artificial Sequence
<220> FEATURE:
<223> OTHER INFORMATION: Synthetic

<400> SEQUENCE: 120

Thr Ala Arg Gly Pro Ser Phe Lys
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic

<400> SEQUENCE: 121

Ala Arg Gly Pro Ser Phe Lys
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic

<400> SEQUENCE: 122

Thr Ala Arg Gly Pro Ser Phe
1               5

<210> SEQ ID NO 123
<211> LENGTH: 6
<212> TYPE: PRT
<213> ORGANISM: Artificial Sequence
<220> FEATURE:
<223> OTHER INFORMATION: Synthetic

<400> SEQUENCE: 123

Thr Ala Arg Gly Pro Ser
1               5

<210> SEQ ID NO 124
<211> LENGTH: 5
<212> TYPE: PRT
<213> ORGANISM: Artificial Sequence
<220> FEATURE:
<223> OTHER INFORMATION: Synthetic

<400> SEQUENCE: 124

-continued

Thr Ala Arg Gly Pro
1 5

<210> SEQ ID NO 125
<211> LENGTH: 4
<212> TYPE: PRT
<213> ORGANISM: Artificial Sequence
<220> FEATURE:
<223> OTHER INFORMATION: Synthetic

<400> SEQUENCE: 125

Thr Ala Arg Gly
1

<210> SEQ ID NO 126
<211> LENGTH: 6
<212> TYPE: PRT
<213> ORGANISM: Artificial Sequence
<220> FEATURE:
<223> OTHER INFORMATION: Synthetic

<400> SEQUENCE: 126

Ala Arg Gly Pro Ser Phe
1 5

<210> SEQ ID NO 127
<211> LENGTH: 5
<212> TYPE: PRT
<213> ORGANISM: Artificial Sequence
<220> FEATURE:
<223> OTHER INFORMATION: Synthetic

<400> SEQUENCE: 127

Ala Arg Gly Pro Ser
1 5

<210> SEQ ID NO 128
<211> LENGTH: 4
<212> TYPE: PRT
<213> ORGANISM: Artificial Sequence
<220> FEATURE:
<223> OTHER INFORMATION: Synthetic

<400> SEQUENCE: 128

Ala Arg Gly Pro
1

<210> SEQ ID NO 129

<400> SEQUENCE: 129

000

<210> SEQ ID NO 130
<211> LENGTH: 5
<212> TYPE: PRT
<213> ORGANISM: Artificial Sequence
<220> FEATURE:
<223> OTHER INFORMATION: Synthetic

<400> SEQUENCE: 130

Ala Pro Arg Ser Phe
1 5

<210> SEQ ID NO 131
<211> LENGTH: 4
<212> TYPE: PRT

<213> ORGANISM: Artificial Sequence
<220> FEATURE:
<223> OTHER INFORMATION: Synthetic

<400> SEQUENCE: 131

Ala Pro Arg Ser
1

<210> SEQ ID NO 132
<211> LENGTH: 4
<212> TYPE: PRT
<213> ORGANISM: Artificial Sequence
<220> FEATURE:
<223> OTHER INFORMATION: Synthetic

<400> SEQUENCE: 132

Pro Arg Ser Phe
1

<210> SEQ ID NO 133

<400> SEQUENCE: 133

000

<210> SEQ ID NO 134

<400> SEQUENCE: 134

000

<210> SEQ ID NO 135
<211> LENGTH: 8
<212> TYPE: PRT
<213> ORGANISM: Artificial Sequence
<220> FEATURE:
<223> OTHER INFORMATION: Synthetic

<400> SEQUENCE: 135

Gly Leu Pro Thr Phe Val His Leu
1 5

<210> SEQ ID NO 136
<211> LENGTH: 7
<212> TYPE: PRT
<213> ORGANISM: Artificial Sequence
<220> FEATURE:
<223> OTHER INFORMATION: Synthetic

<400> SEQUENCE: 136

Gly Leu Pro Thr Phe Val His
1 5

<210> SEQ ID NO 137
<211> LENGTH: 6
<212> TYPE: PRT
<213> ORGANISM: Artificial Sequence
<220> FEATURE:
<223> OTHER INFORMATION: Synthetic

<400> SEQUENCE: 137

Gly Leu Pro Thr Phe Val
1 5

<210> SEQ ID NO 138
<211> LENGTH: 7
<212> TYPE: PRT

<213> ORGANISM: Artificial Sequence
<220> FEATURE:
<223> OTHER INFORMATION: Synthetic

<400> SEQUENCE: 138

Leu Pro Thr Phe Val His Leu
1 5

<210> SEQ ID NO 139
<211> LENGTH: 6
<212> TYPE: PRT
<213> ORGANISM: Artificial Sequence
<220> FEATURE:
<223> OTHER INFORMATION: Synthetic

<400> SEQUENCE: 139

Leu Pro Thr Phe Val His
1 5

<210> SEQ ID NO 140
<211> LENGTH: 5
<212> TYPE: PRT
<213> ORGANISM: Artificial Sequence
<220> FEATURE:
<223> OTHER INFORMATION: Synthetic

<400> SEQUENCE: 140

Leu Pro Thr Phe Val
1 5

<210> SEQ ID NO 141
<211> LENGTH: 4
<212> TYPE: PRT
<213> ORGANISM: Artificial Sequence
<220> FEATURE:
<223> OTHER INFORMATION: Synthetic

<400> SEQUENCE: 141

Thr Phe Val His
1

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152
<211> LENGTH: 4
<212> TYPE: PRT
<213> ORGANISM: Artificial Sequence
<220> FEATURE:
<223> OTHER INFORMATION: Synthetic

<400> SEQUENCE: 152

Gly Pro Thr Asn
1

<210> SEQ ID NO 153
<211> LENGTH: 6
<212> TYPE: PRT
<213> ORGANISM: Artificial Sequence
<220> FEATURE:
<223> OTHER INFORMATION: Synthetic

<400> SEQUENCE: 153

Gln Gly Gln Ser Gly Gln
1 5

<210> SEQ ID NO 154
<211> LENGTH: 5
<212> TYPE: PRT
<213> ORGANISM: Artificial Sequence
<220> FEATURE:
<223> OTHER INFORMATION: Synthetic

<400> SEQUENCE: 154

Gly Gln Ser Gly Gln
1 5

<210> SEQ ID NO 155
<211> LENGTH: 4
<212> TYPE: PRT
<213> ORGANISM: Artificial Sequence
<220> FEATURE:
<223> OTHER INFORMATION: Synthetic

<400> SEQUENCE: 155

Gln Ser Gly Gln
1

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164
<211> LENGTH: 15
<212> TYPE: PRT
<213> ORGANISM: Artificial Sequence
<220> FEATURE:
<223> OTHER INFORMATION: Synthetic

<400> SEQUENCE: 164

Cys Ile Ser Pro Arg Gly Cys Asn Ala Val Ser Gly Leu Gly Ser 1 5 10 15

<210> SEQ ID NO 165
<211> LENGTH: 6
<212> TYPE: PRT
<213> ORGANISM: Artificial Sequence
<220> FEATURE:
<223> OTHER INFORMATION: Synthetic

<400> SEQUENCE: 165

Cys Ile Ser Pro Arg Gly
1 5

<210> SEQ ID NO 166
<211> LENGTH: 7
<212> TYPE: PRT
<213> ORGANISM: Artificial Sequence
<220> FEATURE:
<223> OTHER INFORMATION: Synthetic

<400> SEQUENCE: 166

Cys Ile Ser Pro Arg Gly Cys
1 5

<210> SEQ ID NO 167
<211> LENGTH: 8
<212> TYPE: PRT
<213> ORGANISM: Artificial Sequence
<220> FEATURE:
<223> OTHER INFORMATION: Synthetic

<400> SEQUENCE: 167

Cys Ile Ser Pro Arg Gly Cys Gly
1 5

<210> SEQ ID NO 168
<211> LENGTH: 15
<212> TYPE: PRT
<213> ORGANISM: Artificial Sequence
<220> FEATURE:
<223> OTHER INFORMATION: Synthetic

<400> SEQUENCE: 168

Cys Ile Ser Pro Arg Gly Cys Pro Asp Gly Pro Tyr Val Met Tyr
1 5 10 15

<210> SEQ ID NO 169
<211> LENGTH: 14
<212> TYPE: PRT
<213> ORGANISM: Artificial Sequence
<220> FEATURE:
<223> OTHER INFORMATION: Synthetic

<400> SEQUENCE: 169

Cys Ile Ser Pro Arg Gly Cys Pro Asp Gly Pro Tyr Val Met
1 5 10

<210> SEQ ID NO 170
<211> LENGTH: 15
<212> TYPE: PRT
<213> ORGANISM: Artificial Sequence
<220> FEATURE:
<223> OTHER INFORMATION: Synthetic

<400> SEQUENCE: 170

Cys Ile Ser Pro Arg Gly Cys Glu Pro Gly Thr Tyr Val Pro Thr
1 5 10 15

<210> SEQ ID NO 171
<211> LENGTH: 15
<212> TYPE: PRT
<213> ORGANISM: Artificial Sequence
<220> FEATURE:
<223> OTHER INFORMATION: Synthetic

<400> SEQUENCE: 171

Cys Ile Ser Pro Arg Gly Cys Pro Gly Gln Ile Trp His Pro Pro
1 5 10 15

<210> SEQ ID NO 172
<211> LENGTH: 15
<212> TYPE: PRT
<213> ORGANISM: Artificial Sequence
<220> FEATURE:
<223> OTHER INFORMATION: Synthetic

<400> SEQUENCE: 172

Gly Ser His Cys Leu Ile Pro Ile Asn Met Gly Ala Pro Ser Cys
1 5 10 15

<210> SEQ ID NO 173
<211> LENGTH: 32
<212> TYPE: PRT
<213> ORGANISM: Artificial Sequence
<220> FEATURE:
<223> OTHER INFORMATION: Synthetic

<400> SEQUENCE: 173

Cys Ile Ser Pro Arg Gly Cys Gly Gly Ser Ser Ala Ser Gln Ser Gly
1 5 10 15

Gln Gly Ser His Cys Leu Ile Pro Ile Asn Met Gly Ala Pro Ser Cys
20 25 30

<210> SEQ ID NO 174
<211> LENGTH: 19
<212> TYPE: PRT
<213> ORGANISM: Artificial Sequence
<220> FEATURE:
<223> OTHER INFORMATION: Synthetic

<400> SEQUENCE: 174

Cys Asn His His Tyr Phe Tyr Thr Cys Gly Cys Ile Ser Pro Arg Gly
1 5 10 15

Cys Pro Gly

<210> SEQ ID NO 175
<211> LENGTH: 19
<212> TYPE: PRT
<213> ORGANISM: Artificial Sequence
<220> FEATURE:
<223> OTHER INFORMATION: Synthetic

<400> SEQUENCE: 175

Ala Asp His Val Phe Trp Gly Ser Tyr Gly Cys Ile Ser Pro Arg Gly
1 5 10 15

Cys Pro Gly

<210> SEQ ID NO 176
<211> LENGTH: 19
<212> TYPE: PRT
<213> ORGANISM: Artificial Sequence
<220> FEATURE:

-continued

<223> OTHER INFORMATION: Synthetic

<400> SEQUENCE: 176

Cys His His Val Tyr Trp Gly His Cys Gly Cys Ile Ser Pro Arg Gly
1 5 10 15

Cys Pro Gly

<210> SEQ ID NO 177
<211> LENGTH: 19
<212> TYPE: PRT
<213> ORGANISM: Artificial Sequence
<220> FEATURE:
<223> OTHER INFORMATION: Synthetic

<400> SEQUENCE: 177

Cys Pro His Phe Thr Thr Thr Ser Cys Gly Cys Ile Ser Pro Arg Gly
1 5 10 15

Cys Pro Gly

<210> SEQ ID NO 178
<211> LENGTH: 19
<212> TYPE: PRT
<213> ORGANISM: Artificial Sequence
<220> FEATURE:
<223> OTHER INFORMATION: Synthetic

<400> SEQUENCE: 178

Cys Asn His His Tyr His Tyr Tyr Cys Gly Cys Ile Ser Pro Arg Gly
1 5 10 15

Cys Pro Gly

<210> SEQ ID NO 179
<211> LENGTH: 19
<212> TYPE: PRT
<213> ORGANISM: Artificial Sequence
<220> FEATURE:
<223> OTHER INFORMATION: Synthetic

<400> SEQUENCE: 179

Cys Pro His Val Ser Phe Gly Ser Cys Gly Cys Ile Ser Pro Arg Gly
1 5 10 15

Cys Pro Gly

<210> SEQ ID NO 180
<211> LENGTH: 19
<212> TYPE: PRT
<213> ORGANISM: Artificial Sequence
<220> FEATURE:
<223> OTHER INFORMATION: Synthetic

<400> SEQUENCE: 180

Cys Pro Tyr Tyr Thr Leu Ser Tyr Cys Gly Cys Ile Ser Pro Arg Gly
1 5 10 15

Cys Pro Gly

<210> SEQ ID NO 181
<211> LENGTH: 19
<212> TYPE: PRT
<213> ORGANISM: Artificial Sequence
<220> FEATURE:
<223> OTHER INFORMATION: Synthetic

<400> SEQUENCE: 181

-continued

Cys Asn His Val Tyr Phe Gly Thr Cys Gly Cys Ile Ser Pro Arg Gly
1 5 10 15

Cys Pro Gly

<210> SEQ ID NO 182
<211> LENGTH: 19
<212> TYPE: PRT
<213> ORGANISM: Artificial Sequence
<220> FEATURE:
<223> OTHER INFORMATION: Synthetic

<400> SEQUENCE: 182

Cys Asn His Phe Thr Leu Thr Thr Cys Gly Cys Ile Ser Pro Arg Gly
1 5 10 15

Cys Pro Gly

<210> SEQ ID NO 183
<211> LENGTH: 19
<212> TYPE: PRT
<213> ORGANISM: Artificial Sequence
<220> FEATURE:
<223> OTHER INFORMATION: Synthetic

<400> SEQUENCE: 183

Cys His His Phe Thr Leu Thr Thr Cys Gly Cys Ile Ser Pro Arg Gly
1 5 10 15

Cys Pro Gly

<210> SEQ ID NO 184
<211> LENGTH: 18
<212> TYPE: PRT
<213> ORGANISM: Artificial Sequence
<220> FEATURE:
<223> OTHER INFORMATION: Synthetic

<400> SEQUENCE: 184

Tyr Asn Pro Cys Ala Thr Pro Met Cys Cys Ile Ser Pro Arg Gly Cys
1 5 10 15

Pro Gly

<210> SEQ ID NO 185
<211> LENGTH: 18
<212> TYPE: PRT
<213> ORGANISM: Artificial Sequence
<220> FEATURE:
<223> OTHER INFORMATION: Synthetic

<400> SEQUENCE: 185

Cys Asn His His Tyr Phe Tyr Thr Cys Gly Cys Ile Ser Pro Arg Gly
1 5 10 15

Cys Gly

<210> SEQ ID NO 186
<211> LENGTH: 18
<212> TYPE: PRT
<213> ORGANISM: Artificial Sequence
<220> FEATURE:
<223> OTHER INFORMATION: Synthetic

<400> SEQUENCE: 186

Cys Asn His His Tyr His Tyr Tyr Cys Gly Cys Ile Ser Pro Arg Gly
1 5 10 15

Cys Gly

<210> SEQ ID NO 187
<211> LENGTH: 18
<212> TYPE: PRT
<213> ORGANISM: Artificial Sequence
<220> FEATURE:
<223> OTHER INFORMATION: Synthetic

<400> SEQUENCE: 187

Cys Asn His Val Tyr Phe Gly Thr Cys Gly Cys Ile Ser Pro Arg Gly
1 5 10 15

Cys Gly

<210> SEQ ID NO 188
<211> LENGTH: 18
<212> TYPE: PRT
<213> ORGANISM: Artificial Sequence
<220> FEATURE:
<223> OTHER INFORMATION: Synthetic

<400> SEQUENCE: 188

Cys His His Val Tyr Trp Gly His Cys Gly Cys Ile Ser Pro Arg Gly
1 5 10 15

Cys Gly

<210> SEQ ID NO 189
<211> LENGTH: 18
<212> TYPE: PRT
<213> ORGANISM: Artificial Sequence
<220> FEATURE:
<223> OTHER INFORMATION: Synthetic

<400> SEQUENCE: 189

Cys Pro His Phe Thr Thr Thr Ser Cys Gly Cys Ile Ser Pro Arg Gly
1 5 10 15

Cys Gly

<210> SEQ ID NO 190
<211> LENGTH: 18
<212> TYPE: PRT
<213> ORGANISM: Artificial Sequence
<220> FEATURE:
<223> OTHER INFORMATION: Synthetic

<400> SEQUENCE: 190

Cys Asn His Phe Thr Leu Thr Thr Cys Gly Cys Ile Ser Pro Arg Gly
1 5 10 15

Cys Gly

<210> SEQ ID NO 191
<211> LENGTH: 18
<212> TYPE: PRT
<213> ORGANISM: Artificial Sequence
<220> FEATURE:
<223> OTHER INFORMATION: Synthetic

<400> SEQUENCE: 191

Cys His His Phe Thr Leu Thr Thr Cys Gly Cys Ile Ser Pro Arg Gly
1 5 10 15

Cys Gly

<210> SEQ ID NO 192
<211> LENGTH: 18

<212> TYPE: PRT
<213> ORGANISM: Artificial Sequence
<220> FEATURE:
<223> OTHER INFORMATION: Synthetic

<400> SEQUENCE: 192

Cys Pro Tyr Tyr Thr Leu Ser Tyr Cys Gly Cys Ile Ser Pro Arg Gly
1 5 10 15

Cys Gly

<210> SEQ ID NO 193
<211> LENGTH: 18
<212> TYPE: PRT
<213> ORGANISM: Artificial Sequence
<220> FEATURE:
<223> OTHER INFORMATION: Synthetic

<400> SEQUENCE: 193

Cys Pro His Val Ser Phe Gly Ser Cys Gly Cys Ile Ser Pro Arg Gly
1 5 10 15

Cys Gly

<210> SEQ ID NO 194
<211> LENGTH: 18
<212> TYPE: PRT
<213> ORGANISM: Artificial Sequence
<220> FEATURE:
<223> OTHER INFORMATION: Synthetic

<400> SEQUENCE: 194

Ala Asp His Val Phe Trp Gly Ser Tyr Gly Cys Ile Ser Pro Arg Gly
1 5 10 15

Cys Gly

<210> SEQ ID NO 195
<211> LENGTH: 17
<212> TYPE: PRT
<213> ORGANISM: Artificial Sequence
<220> FEATURE:
<223> OTHER INFORMATION: Synthetic

<400> SEQUENCE: 195

Tyr Asn Pro Cys Ala Thr Pro Met Cys Cys Ile Ser Pro Arg Gly Cys
1 5 10 15

Gly

<210> SEQ ID NO 196
<211> LENGTH: 18
<212> TYPE: PRT
<213> ORGANISM: Artificial Sequence
<220> FEATURE:
<223> OTHER INFORMATION: Synthetic

<400> SEQUENCE: 196

Cys His His Val Tyr Trp Gly His Cys Gly Cys Ile Ser Pro Arg Gly
1 5 10 15

Cys Gly

<210> SEQ ID NO 197
<211> LENGTH: 18
<212> TYPE: PRT
<213> ORGANISM: Artificial Sequence
<220> FEATURE:
<223> OTHER INFORMATION: Synthetic

```
<220> FEATURE:
<221> NAME/KEY: MISC_FEATURE
<222> LOCATION: (2)..(2)
<223> OTHER INFORMATION: Xaa=Asn or Pro
<220> FEATURE:
<221> NAME/KEY: MISC_FEATURE
<222> LOCATION: (4)..(4)
<223> OTHER INFORMATION: Xaa=His or Val or Phe
<220> FEATURE:
<221> NAME/KEY: MISC_FEATURE
<222> LOCATION: (5)..(5)
<223> OTHER INFORMATION: Xaa=Tyr or Thr
<220> FEATURE:
<221> NAME/KEY: MISC_FEATURE
<222> LOCATION: (6)..(6)
<223> OTHER INFORMATION: Xaa=Phe or Trp or Thr or Leu
<220> FEATURE:
<221> NAME/KEY: MISC_FEATURE
<222> LOCATION: (7)..(7)
<223> OTHER INFORMATION: Xaa=Tyr or Gly or Thr or Ser
<220> FEATURE:
<221> NAME/KEY: MISC_FEATURE
<222> LOCATION: (8)..(8)
<223> OTHER INFORMATION: Xaa=Thr or Ser or Tyr or His

<400> SEQUENCE: 197

Cys Xaa His Xaa Xaa Xaa Xaa Xaa Cys Gly Cys Ile Ser Pro Arg Gly
1               5                   10                  15

Cys Gly


<210> SEQ ID NO 198
<211> LENGTH: 15
<212> TYPE: PRT
<213> ORGANISM: Artificial Sequence
<220> FEATURE:
<223> OTHER INFORMATION: Synthetic

<400> SEQUENCE: 198

Cys Ile Ser Pro Arg Gly Cys Gly Gln Pro Ile Pro Ser Val Lys
1               5                   10                  15


<210> SEQ ID NO 199
<211> LENGTH: 15
<212> TYPE: PRT
<213> ORGANISM: Artificial Sequence
<220> FEATURE:
<223> OTHER INFORMATION: Synthetic

<400> SEQUENCE: 199

Cys Ile Ser Pro Arg Gly Cys Thr Gln Pro Tyr His Val Ser Arg
1               5                   10                  15


<210> SEQ ID NO 200
<211> LENGTH: 5
<212> TYPE: PRT
<213> ORGANISM: Artificial Sequence
<220> FEATURE:
<223> OTHER INFORMATION: Synthetic

<400> SEQUENCE: 200

Gly Ser Gly Gly Ser
1               5


<210> SEQ ID NO 201
<211> LENGTH: 4
<212> TYPE: PRT
<213> ORGANISM: Artificial Sequence
<220> FEATURE:
<223> OTHER INFORMATION: Synthetic
```

<400> SEQUENCE: 201

Gly Gly Gly Ser
1

<210> SEQ ID NO 202
<211> LENGTH: 4
<212> TYPE: PRT
<213> ORGANISM: Artificial Sequence
<220> FEATURE:
<223> OTHER INFORMATION: Synthetic

<400> SEQUENCE: 202

Gly Gly Ser Gly
1

<210> SEQ ID NO 203
<211> LENGTH: 5
<212> TYPE: PRT
<213> ORGANISM: Artificial Sequence
<220> FEATURE:
<223> OTHER INFORMATION: Synthetic

<400> SEQUENCE: 203

Gly Gly Ser Gly Gly
1 5

<210> SEQ ID NO 204
<211> LENGTH: 5
<212> TYPE: PRT
<213> ORGANISM: Artificial Sequence
<220> FEATURE:
<223> OTHER INFORMATION: Synthetic

<400> SEQUENCE: 204

Gly Ser Gly Ser Gly
1 5

<210> SEQ ID NO 205
<211> LENGTH: 5
<212> TYPE: PRT
<213> ORGANISM: Artificial Sequence
<220> FEATURE:
<223> OTHER INFORMATION: Synthetic

<400> SEQUENCE: 205

Gly Ser Gly Gly Gly
1 5

<210> SEQ ID NO 206
<211> LENGTH: 5
<212> TYPE: PRT
<213> ORGANISM: Artificial Sequence
<220> FEATURE:
<223> OTHER INFORMATION: Synthetic

<400> SEQUENCE: 206

Gly Gly Gly Ser Gly
1 5

<210> SEQ ID NO 207
<211> LENGTH: 5
<212> TYPE: PRT
<213> ORGANISM: Artificial Sequence
<220> FEATURE:
<223> OTHER INFORMATION: Synthetic

<400> SEQUENCE: 207

Gly Ser Ser Ser Gly
1 5

<210> SEQ ID NO 208
<211> LENGTH: 13
<212> TYPE: PRT
<213> ORGANISM: Artificial Sequence
<220> FEATURE:
<223> OTHER INFORMATION: Synthetic

<400> SEQUENCE: 208

Gly Ser Ser Gly Gly Ser Gly Gly Ser Gly Gly Ser Gly
1 5 10

<210> SEQ ID NO 209
<211> LENGTH: 11
<212> TYPE: PRT
<213> ORGANISM: Artificial Sequence
<220> FEATURE:
<223> OTHER INFORMATION: Synthetic

<400> SEQUENCE: 209

Gly Ser Ser Gly Gly Ser Gly Gly Ser Gly Gly
1 5 10

<210> SEQ ID NO 210
<211> LENGTH: 12
<212> TYPE: PRT
<213> ORGANISM: Artificial Sequence
<220> FEATURE:
<223> OTHER INFORMATION: Synthetic

<400> SEQUENCE: 210

Gly Ser Ser Gly Gly Ser Gly Gly Ser Gly Gly Ser
1 5 10

<210> SEQ ID NO 211
<211> LENGTH: 16
<212> TYPE: PRT
<213> ORGANISM: Artificial Sequence
<220> FEATURE:
<223> OTHER INFORMATION: Synthetic

<400> SEQUENCE: 211

Gly Ser Ser Gly Gly Ser Gly Gly Ser Gly Gly Ser Gly Gly Gly Ser
1 5 10 15

<210> SEQ ID NO 212
<211> LENGTH: 10
<212> TYPE: PRT
<213> ORGANISM: Artificial Sequence
<220> FEATURE:
<223> OTHER INFORMATION: Synthetic

<400> SEQUENCE: 212

Gly Ser Ser Gly Gly Ser Gly Gly Ser Gly
1 5 10

<210> SEQ ID NO 213
<211> LENGTH: 11
<212> TYPE: PRT
<213> ORGANISM: Artificial Sequence
<220> FEATURE:
<223> OTHER INFORMATION: Synthetic

<400> SEQUENCE: 213

-continued

Gly Ser Ser Gly Gly Ser Gly Gly Ser Gly Ser
1 5 10

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Gly Gly Gly Ser Ser Gly Gly Ser
1 5

<210> SEQ ID NO 215
<211> LENGTH: 4
<212> TYPE: PRT
<213> ORGANISM: Artificial Sequence
<220> FEATURE:
<223> OTHER INFORMATION: Synthetic

<400> SEQUENCE: 215

Gly Gly Gly Ser
1

<210> SEQ ID NO 216
<211> LENGTH: 5
<212> TYPE: PRT
<213> ORGANISM: Artificial Sequence
<220> FEATURE:
<223> OTHER INFORMATION: Synthetic

<400> SEQUENCE: 216

Gly Ser Ser Gly Thr
1 5

<210> SEQ ID NO 217
<211> LENGTH: 4
<212> TYPE: PRT
<213> ORGANISM: Artificial Sequence
<220> FEATURE:
<223> OTHER INFORMATION: Synthetic

<400> SEQUENCE: 217

Gly Ser Ser Gly
1

<210> SEQ ID NO 218
<211> LENGTH: 6
<212> TYPE: PRT
<213> ORGANISM: Artificial Sequence
<220> FEATURE:
<223> OTHER INFORMATION: Synthetic

<400> SEQUENCE: 218

Gly Gly Ser Gly Gly Ser
1 5

<210> SEQ ID NO 219

<400> SEQUENCE: 219

000

<210> SEQ ID NO 220
<211> LENGTH: 5
<212> TYPE: PRT

<213> ORGANISM: Artificial Sequence
<220> FEATURE:
<223> OTHER INFORMATION: Synthetic

<400> SEQUENCE: 220

Asn Tyr Gly Val His
1 5

<210> SEQ ID NO 221
<211> LENGTH: 16
<212> TYPE: PRT
<213> ORGANISM: Artificial Sequence
<220> FEATURE:
<223> OTHER INFORMATION: Synthetic

<400> SEQUENCE: 221

Val Ile Trp Ser Gly Gly Asn Thr Asp Tyr Asn Thr Pro Phe Thr Ser
1 5 10 15

<210> SEQ ID NO 222
<211> LENGTH: 11
<212> TYPE: PRT
<213> ORGANISM: Artificial Sequence
<220> FEATURE:
<223> OTHER INFORMATION: Synthetic

<400> SEQUENCE: 222

Ala Leu Thr Tyr Tyr Asp Tyr Glu Phe Ala Tyr
1 5 10

<210> SEQ ID NO 223
<211> LENGTH: 11
<212> TYPE: PRT
<213> ORGANISM: Artificial Sequence
<220> FEATURE:
<223> OTHER INFORMATION: Synthetic

<400> SEQUENCE: 223

Arg Ala Ser Gln Ser Ile Gly Thr Asn Ile His
1 5 10

<210> SEQ ID NO 224
<211> LENGTH: 8
<212> TYPE: PRT
<213> ORGANISM: Artificial Sequence
<220> FEATURE:
<223> OTHER INFORMATION: Synthetic

<400> SEQUENCE: 224

Lys Tyr Ala Ser Glu Ser Ile Ser
1 5

<210> SEQ ID NO 225
<211> LENGTH: 9
<212> TYPE: PRT
<213> ORGANISM: Artificial Sequence
<220> FEATURE:
<223> OTHER INFORMATION: Synthetic

<400> SEQUENCE: 225

Gln Gln Asn Asn Asn Trp Pro Thr Thr
1 5

<210> SEQ ID NO 226
<211> LENGTH: 16
<212> TYPE: PRT
<213> ORGANISM: Artificial Sequence
<220> FEATURE:
<223> OTHER INFORMATION: Synthetic

<400> SEQUENCE: 226

Leu Ser Gly Arg Ser Ala Leu Ala His Gly Leu Phe Gly Gly Gly Ser
1 5 10 15

<210> SEQ ID NO 227
<211> LENGTH: 17
<212> TYPE: PRT
<213> ORGANISM: Artificial Sequence
<220> FEATURE:
<223> OTHER INFORMATION: Synthetic

<400> SEQUENCE: 227

Ala Leu Ala His Gly Leu Phe Ser Gly Arg Ser Ala Asn Gly Gly Gly
1 5 10 15

Ser

<210> SEQ ID NO 228
<211> LENGTH: 15
<212> TYPE: PRT
<213> ORGANISM: Artificial Sequence
<220> FEATURE:
<223> OTHER INFORMATION: Synthetic

<400> SEQUENCE: 228

His Val Pro Arg Gln Val Leu Ser Gly Arg Ser Gly Gly Gly Ser
1 5 10 15

<210> SEQ ID NO 229
<211> LENGTH: 17
<212> TYPE: PRT
<213> ORGANISM: Artificial Sequence
<220> FEATURE:
<223> OTHER INFORMATION: Synthetic

<400> SEQUENCE: 229

His Val Pro Arg Gln Val Leu Ser Gly Arg Ser Ala Asn Gly Gly Gly
1 5 10 15

Ser

<210> SEQ ID NO 230
<211> LENGTH: 16
<212> TYPE: PRT
<213> ORGANISM: Artificial Sequence
<220> FEATURE:
<223> OTHER INFORMATION: Synthetic

<400> SEQUENCE: 230

Thr Ala Arg Gly Pro Ala Leu Ala His Gly Leu Phe Gly Gly Gly Ser
1 5 10 15

<210> SEQ ID NO 231
<211> LENGTH: 14
<212> TYPE: PRT
<213> ORGANISM: Artificial Sequence
<220> FEATURE:
<223> OTHER INFORMATION: Synthetic

<400> SEQUENCE: 231

Thr Ala Arg Gly Pro Val Pro Arg Gln Val Gly Gly Gly Ser
1 5 10

<210> SEQ ID NO 232

<211> LENGTH: 15
<212> TYPE: PRT
<213> ORGANISM: Artificial Sequence
<220> FEATURE:
<223> OTHER INFORMATION: Synthetic

<400> SEQUENCE: 232

Ala Pro Arg Ser Ala Leu Ala His Gly Leu Phe Gly Gly Gly Ser
1 5 10 15

<210> SEQ ID NO 233
<211> LENGTH: 16
<212> TYPE: PRT
<213> ORGANISM: Artificial Sequence
<220> FEATURE:
<223> OTHER INFORMATION: Synthetic

<400> SEQUENCE: 233

Ala Leu Ala His Gly Leu Phe Ala Pro Arg Ser Phe Gly Gly Gly Ser
1 5 10 15

<210> SEQ ID NO 234
<211> LENGTH: 15
<212> TYPE: PRT
<213> ORGANISM: Artificial Sequence
<220> FEATURE:
<223> OTHER INFORMATION: Synthetic

<400> SEQUENCE: 234

His Val Pro Arg Gln Val Ala Pro Arg Ser Phe Gly Gly Gly Ser
1 5 10 15

<210> SEQ ID NO 235
<211> LENGTH: 16
<212> TYPE: PRT
<213> ORGANISM: Artificial Sequence
<220> FEATURE:
<223> OTHER INFORMATION: Synthetic

<400> SEQUENCE: 235

Ala Leu Ala His Gly Leu Pro Thr Phe Val His Leu Gly Gly Gly Ser
1 5 10 15

<210> SEQ ID NO 236
<211> LENGTH: 16
<212> TYPE: PRT
<213> ORGANISM: Artificial Sequence
<220> FEATURE:
<223> OTHER INFORMATION: Synthetic

<400> SEQUENCE: 236

Gly Leu Pro Thr Phe Val His Leu Pro Arg Gln Val Gly Gly Gly Ser
1 5 10 15

<210> SEQ ID NO 237
<211> LENGTH: 14
<212> TYPE: PRT
<213> ORGANISM: Artificial Sequence
<220> FEATURE:
<223> OTHER INFORMATION: Synthetic

<400> SEQUENCE: 237

Ala Ala Asn Ala Leu Ala His Gly Leu Phe Gly Gly Gly Ser
1 5 10

<210> SEQ ID NO 238
<211> LENGTH: 15

<212> TYPE: PRT
<213> ORGANISM: Artificial Sequence
<220> FEATURE:
<223> OTHER INFORMATION: Synthetic

<400> SEQUENCE: 238

```
Gly Pro Thr Asn Ala Leu Ala His Gly Leu Phe Gly Gly Gly Ser
1               5                   10                  15
```

<210> SEQ ID NO 239
<211> LENGTH: 16
<212> TYPE: PRT
<213> ORGANISM: Artificial Sequence
<220> FEATURE:
<223> OTHER INFORMATION: Synthetic

<400> SEQUENCE: 239

```
Ile Ser Ser Gly Leu Leu Ser Gly Arg Ser Asn Ile Gly Gly Gly Ser
1               5                   10                  15
```

<210> SEQ ID NO 240
<211> LENGTH: 21
<212> TYPE: PRT
<213> ORGANISM: Artificial Sequence
<220> FEATURE:
<223> OTHER INFORMATION: Synthetic

<400> SEQUENCE: 240

```
Ala Val Gly Leu Leu Ala Pro Pro Gly Gly Leu Ser Gly Arg Ser Asn
1               5                   10                  15

Ile Gly Gly Gly Ser
            20
```

<210> SEQ ID NO 241
<211> LENGTH: 15
<212> TYPE: PRT
<213> ORGANISM: Artificial Sequence
<220> FEATURE:
<223> OTHER INFORMATION: Synthetic

<400> SEQUENCE: 241

```
Leu Ser Gly Arg Ser Ala Leu Ala His Gly Leu Phe Gly Gly Ser
1               5                   10                  15
```

<210> SEQ ID NO 242
<211> LENGTH: 16
<212> TYPE: PRT
<213> ORGANISM: Artificial Sequence
<220> FEATURE:
<223> OTHER INFORMATION: Synthetic

<400> SEQUENCE: 242

```
Ala Leu Ala His Gly Leu Phe Ser Gly Arg Ser Ala Asn Gly Gly Ser
1               5                   10                  15
```

<210> SEQ ID NO 243
<211> LENGTH: 14
<212> TYPE: PRT
<213> ORGANISM: Artificial Sequence
<220> FEATURE:
<223> OTHER INFORMATION: Synthetic

<400> SEQUENCE: 243

```
His Val Pro Arg Gln Val Leu Ser Gly Arg Ser Gly Gly Ser
1               5                   10
```

<210> SEQ ID NO 244
<211> LENGTH: 16
<212> TYPE: PRT
<213> ORGANISM: Artificial Sequence
<220> FEATURE:
<223> OTHER INFORMATION: Synthetic

<400> SEQUENCE: 244

His Val Pro Arg Gln Val Leu Ser Gly Arg Ser Ala Asn Gly Gly Ser
1 5 10 15

<210> SEQ ID NO 245
<211> LENGTH: 15
<212> TYPE: PRT
<213> ORGANISM: Artificial Sequence
<220> FEATURE:
<223> OTHER INFORMATION: Synthetic

<400> SEQUENCE: 245

Thr Ala Arg Gly Pro Ala Leu Ala His Gly Leu Phe Gly Gly Ser
1 5 10 15

<210> SEQ ID NO 246
<211> LENGTH: 13
<212> TYPE: PRT
<213> ORGANISM: Artificial Sequence
<220> FEATURE:
<223> OTHER INFORMATION: Synthetic

<400> SEQUENCE: 246

Thr Ala Arg Gly Pro Val Pro Arg Gln Val Gly Gly Ser
1 5 10

<210> SEQ ID NO 247
<211> LENGTH: 14
<212> TYPE: PRT
<213> ORGANISM: Artificial Sequence
<220> FEATURE:
<223> OTHER INFORMATION: Synthetic

<400> SEQUENCE: 247

Ala Pro Arg Ser Ala Leu Ala His Gly Leu Phe Gly Gly Ser
1 5 10

<210> SEQ ID NO 248
<211> LENGTH: 15
<212> TYPE: PRT
<213> ORGANISM: Artificial Sequence
<220> FEATURE:
<223> OTHER INFORMATION: Synthetic

<400> SEQUENCE: 248

Ala Leu Ala His Gly Leu Phe Ala Pro Arg Ser Phe Gly Gly Ser
1 5 10 15

<210> SEQ ID NO 249
<211> LENGTH: 14
<212> TYPE: PRT
<213> ORGANISM: Artificial Sequence
<220> FEATURE:
<223> OTHER INFORMATION: Synthetic

<400> SEQUENCE: 249

His Val Pro Arg Gln Val Ala Pro Arg Ser Phe Gly Gly Ser
1 5 10

<210> SEQ ID NO 250

<211> LENGTH: 15
<212> TYPE: PRT
<213> ORGANISM: Artificial Sequence
<220> FEATURE:
<223> OTHER INFORMATION: Synthetic

<400> SEQUENCE: 250

Ala Leu Ala His Gly Leu Pro Thr Phe Val His Leu Gly Gly Ser
1 5 10 15

<210> SEQ ID NO 251
<211> LENGTH: 15
<212> TYPE: PRT
<213> ORGANISM: Artificial Sequence
<220> FEATURE:
<223> OTHER INFORMATION: Synthetic

<400> SEQUENCE: 251

Gly Leu Pro Thr Phe Val His Leu Pro Arg Gln Val Gly Gly Ser
1 5 10 15

<210> SEQ ID NO 252
<211> LENGTH: 13
<212> TYPE: PRT
<213> ORGANISM: Artificial Sequence
<220> FEATURE:
<223> OTHER INFORMATION: Synthetic

<400> SEQUENCE: 252

Ala Ala Asn Ala Leu Ala His Gly Leu Phe Gly Gly Ser
1 5 10

<210> SEQ ID NO 253
<211> LENGTH: 14
<212> TYPE: PRT
<213> ORGANISM: Artificial Sequence
<220> FEATURE:
<223> OTHER INFORMATION: Synthetic

<400> SEQUENCE: 253

Gly Pro Thr Asn Ala Leu Ala His Gly Leu Phe Gly Gly Ser
1 5 10

<210> SEQ ID NO 254
<211> LENGTH: 15
<212> TYPE: PRT
<213> ORGANISM: Artificial Sequence
<220> FEATURE:
<223> OTHER INFORMATION: Synthetic

<400> SEQUENCE: 254

Ile Ser Ser Gly Leu Leu Ser Gly Arg Ser Asn Ile Gly Gly Ser
1 5 10 15

<210> SEQ ID NO 255
<211> LENGTH: 20
<212> TYPE: PRT
<213> ORGANISM: Artificial Sequence
<220> FEATURE:
<223> OTHER INFORMATION: Synthetic

<400> SEQUENCE: 255

Ala Val Gly Leu Leu Ala Pro Pro Gly Gly Leu Ser Gly Arg Ser Asn
1 5 10 15

Ile Gly Gly Ser
20

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279
<400> SEQUENCE: 279
000

<210> SEQ ID NO 280
<400> SEQUENCE: 280
000

<210> SEQ ID NO 281
<400> SEQUENCE: 281
000

<210> SEQ ID NO 282
<400> SEQUENCE: 282
000

<210> SEQ ID NO 283
<400> SEQUENCE: 283
000

<210> SEQ ID NO 284
<400> SEQUENCE: 284
000

<210> SEQ ID NO 285
<400> SEQUENCE: 285
000

<210> SEQ ID NO 286
<400> SEQUENCE: 286
000

<210> SEQ ID NO 287
<400> SEQUENCE: 287
000

<210> SEQ ID NO 288
<400> SEQUENCE: 288
000

<210> SEQ ID NO 289
<400> SEQUENCE: 289
000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319
<211> LENGTH: 8
<212> TYPE: PRT
<213> ORGANISM: Artificial Sequence
<220> FEATURE:
<223> OTHER INFORMATION: Synthetic

<400> SEQUENCE: 319

Pro Arg Phe Lys Ile Ile Gly Gly
1               5

<210> SEQ ID NO 320
<211> LENGTH: 8
<212> TYPE: PRT
<213> ORGANISM: Artificial Sequence
<220> FEATURE:
<223> OTHER INFORMATION: Synthetic

<400> SEQUENCE: 320

Pro Arg Phe Arg Ile Ile Gly Gly
1               5

<210> SEQ ID NO 321
<211> LENGTH: 9
<212> TYPE: PRT
<213> ORGANISM: Artificial Sequence
<220> FEATURE:
<223> OTHER INFORMATION: Synthetic

<400> SEQUENCE: 321

Ser Ser Arg His Arg Arg Ala Leu Asp
1 5

<210> SEQ ID NO 322
<211> LENGTH: 14
<212> TYPE: PRT
<213> ORGANISM: Artificial Sequence
<220> FEATURE:
<223> OTHER INFORMATION: Synthetic

<400> SEQUENCE: 322

Arg Lys Ser Ser Ile Ile Ile Arg Met Arg Asp Val Val Leu
1 5 10

<210> SEQ ID NO 323
<211> LENGTH: 15
<212> TYPE: PRT
<213> ORGANISM: Artificial Sequence
<220> FEATURE:
<223> OTHER INFORMATION: Synthetic

<400> SEQUENCE: 323

Ser Ser Ser Phe Asp Lys Gly Lys Tyr Lys Lys Gly Asp Asp Ala
1 5 10 15

<210> SEQ ID NO 324
<211> LENGTH: 15
<212> TYPE: PRT
<213> ORGANISM: Artificial Sequence
<220> FEATURE:
<223> OTHER INFORMATION: Synthetic

<400> SEQUENCE: 324

Ser Ser Ser Phe Asp Lys Gly Lys Tyr Lys Arg Gly Asp Asp Ala
1 5 10 15

<210> SEQ ID NO 325
<211> LENGTH: 4
<212> TYPE: PRT
<213> ORGANISM: Artificial Sequence
<220> FEATURE:
<223> OTHER INFORMATION: Synthetic

<400> SEQUENCE: 325

Ile Glu Gly Arg
1

<210> SEQ ID NO 326
<211> LENGTH: 4
<212> TYPE: PRT
<213> ORGANISM: Artificial Sequence
<220> FEATURE:
<223> OTHER INFORMATION: Synthetic

<400> SEQUENCE: 326

Ile Asp Gly Arg
1

<210> SEQ ID NO 327
<211> LENGTH: 7
<212> TYPE: PRT
<213> ORGANISM: Artificial Sequence
<220> FEATURE:
<223> OTHER INFORMATION: Synthetic

<400> SEQUENCE: 327

Gly Gly Ser Ile Asp Gly Arg
1 5

<210> SEQ ID NO 328
<211> LENGTH: 6
<212> TYPE: PRT
<213> ORGANISM: Artificial Sequence
<220> FEATURE:
<223> OTHER INFORMATION: Synthetic

<400> SEQUENCE: 328

Pro Leu Gly Leu Trp Ala
1 5

<210> SEQ ID NO 329
<211> LENGTH: 8
<212> TYPE: PRT
<213> ORGANISM: Artificial Sequence
<220> FEATURE:
<223> OTHER INFORMATION: Synthetic

<400> SEQUENCE: 329

Gly Pro Gln Gly Ile Ala Gly Gln
1 5

<210> SEQ ID NO 330
<211> LENGTH: 8
<212> TYPE: PRT
<213> ORGANISM: Artificial Sequence
<220> FEATURE:
<223> OTHER INFORMATION: Synthetic

<400> SEQUENCE: 330

Gly Pro Gln Gly Leu Leu Gly Ala
1 5

<210> SEQ ID NO 331
<211> LENGTH: 5
<212> TYPE: PRT
<213> ORGANISM: Artificial Sequence
<220> FEATURE:
<223> OTHER INFORMATION: Synthetic

<400> SEQUENCE: 331

Gly Ile Ala Gly Gln
1 5

<210> SEQ ID NO 332
<211> LENGTH: 8
<212> TYPE: PRT
<213> ORGANISM: Artificial Sequence
<220> FEATURE:
<223> OTHER INFORMATION: Synthetic

<400> SEQUENCE: 332

Gly Pro Leu Gly Ile Ala Gly Ile
1 5

<210> SEQ ID NO 333
<211> LENGTH: 8
<212> TYPE: PRT
<213> ORGANISM: Artificial Sequence
<220> FEATURE:
<223> OTHER INFORMATION: Synthetic

<400> SEQUENCE: 333

Gly Pro Glu Gly Leu Arg Val Gly
1               5

<210> SEQ ID NO 334
<211> LENGTH: 8
<212> TYPE: PRT
<213> ORGANISM: Artificial Sequence
<220> FEATURE:
<223> OTHER INFORMATION: Synthetic

<400> SEQUENCE: 334

Tyr Gly Ala Gly Leu Gly Val Val
1               5

<210> SEQ ID NO 335
<211> LENGTH: 8
<212> TYPE: PRT
<213> ORGANISM: Artificial Sequence
<220> FEATURE:
<223> OTHER INFORMATION: Synthetic

<400> SEQUENCE: 335

Ala Gly Leu Gly Val Val Glu Arg
1               5

<210> SEQ ID NO 336
<211> LENGTH: 8
<212> TYPE: PRT
<213> ORGANISM: Artificial Sequence
<220> FEATURE:
<223> OTHER INFORMATION: Synthetic

<400> SEQUENCE: 336

Ala Gly Leu Gly Ile Ser Ser Thr
1               5

<210> SEQ ID NO 337
<211> LENGTH: 8
<212> TYPE: PRT
<213> ORGANISM: Artificial Sequence
<220> FEATURE:
<223> OTHER INFORMATION: Synthetic

<400> SEQUENCE: 337

Glu Pro Gln Ala Leu Ala Met Ser
1               5

<210> SEQ ID NO 338
<211> LENGTH: 8
<212> TYPE: PRT
<213> ORGANISM: Artificial Sequence
<220> FEATURE:
<223> OTHER INFORMATION: Synthetic

<400> SEQUENCE: 338

Gln Ala Leu Ala Met Ser Ala Ile
1               5

<210> SEQ ID NO 339
<211> LENGTH: 8
<212> TYPE: PRT
<213> ORGANISM: Artificial Sequence
<220> FEATURE:
<223> OTHER INFORMATION: Synthetic

<400> SEQUENCE: 339

Ala Ala Tyr His Leu Val Ser Gln
1 5

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Met Asp Ala Phe Leu Glu Ser Ser
1 5

<210> SEQ ID NO 341
<211> LENGTH: 8
<212> TYPE: PRT
<213> ORGANISM: Artificial Sequence
<220> FEATURE:
<223> OTHER INFORMATION: Synthetic

<400> SEQUENCE: 341

Glu Ser Leu Pro Val Val Ala Val
1 5

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Ser Ala Pro Ala Val Glu Ser Glu
1 5

<210> SEQ ID NO 343
<211> LENGTH: 8
<212> TYPE: PRT
<213> ORGANISM: Artificial Sequence
<220> FEATURE:
<223> OTHER INFORMATION: Synthetic

<400> SEQUENCE: 343

Asp Val Ala Gln Phe Val Leu Thr
1 5

<210> SEQ ID NO 344
<211> LENGTH: 8
<212> TYPE: PRT
<213> ORGANISM: Artificial Sequence
<220> FEATURE:
<223> OTHER INFORMATION: Synthetic

<400> SEQUENCE: 344

Val Ala Gln Phe Val Leu Thr Glu
1 5

<210> SEQ ID NO 345
<211> LENGTH: 8
<212> TYPE: PRT
<213> ORGANISM: Artificial Sequence
<220> FEATURE:
<223> OTHER INFORMATION: Synthetic

<400> SEQUENCE: 345

Ala Gln Phe Val Leu Thr Glu Gly 1 5

<210> SEQ ID NO 346
<211> LENGTH: 8
<212> TYPE: PRT
<213> ORGANISM: Artificial Sequence
<220> FEATURE:
<223> OTHER INFORMATION: Synthetic

<400> SEQUENCE: 346

Pro Val Gln Pro Ile Gly Pro Gln
1 5

<210> SEQ ID NO 347
<211> LENGTH: 273
<212> TYPE: PRT
<213> ORGANISM: Artificial Sequence
<220> FEATURE:
<223> OTHER INFORMATION: Synthetic

<400> SEQUENCE: 347

Gly Gly Gly Ser Gly Gly Gly Gly Ser Gly Ser Gly Gly Gly Ser Gly
1 5 10 15

Gly Gly Gly Ser Gly Gly Gly Glu Ile Val Leu Thr Gln Ser Pro Gly
20 25 30

Thr Leu Ser Leu Ser Pro Gly Glu Arg Ala Thr Leu Ser Cys Arg Ala
35 40 45

Ser Gln Ser Val Ser Ser Ser Tyr Leu Ala Trp Tyr Gln Gln Lys Pro
50 55 60

Gly Gln Ala Pro Arg Leu Leu Ile Tyr Gly Ala Ser Ser Arg Ala Thr
65 70 75 80

Gly Ile Pro Asp Arg Phe Ser Gly Ser Gly Ser Gly Thr Asp Phe Thr
85 90 95

Leu Thr Ile Ser Arg Leu Glu Pro Glu Asp Phe Ala Val Tyr Tyr Cys
100 105 110

Gln Gln Tyr Gly Ser Ser Pro Leu Thr Phe Gly Gly Gly Thr Lys Val
115 120 125

Glu Ile Lys Arg Ser Gly Gly Ser Thr Ile Thr Ser Tyr Asn Val Tyr
130 135 140

Tyr Thr Lys Leu Ser Ser Ser Gly Thr Gln Val Gln Leu Val Gln Thr
145 150 155 160

Gly Gly Gly Val Val Gln Pro Gly Arg Ser Leu Arg Leu Ser Cys Ala
165 170 175

Ala Ser Gly Ser Thr Phe Ser Ser Tyr Ala Met Ser Trp Val Arg Gln
180 185 190

Ala Pro Gly Lys Gly Leu Glu Trp Val Ser Ala Ile Ser Gly Ser Gly
195 200 205

Gly Ser Thr Tyr Tyr Ala Asp Ser Val Lys Gly Arg Phe Thr Ile Ser
210 215 220

Arg Asp Asn Ser Lys Asn Thr Leu Tyr Leu Gln Met Asn Ser Leu Arg
225 230 235 240

Ala Glu Asp Thr Ala Val Tyr Tyr Cys Ala Thr Asn Ser Leu Tyr Trp
245 250 255

Tyr Phe Asp Leu Trp Gly Arg Gly Thr Leu Val Thr Val Ser Ser Ala
260 265 270

Ser

<210> SEQ ID NO 348

<400> SEQUENCE: 348

000

<210> SEQ ID NO 349
<211> LENGTH: 264
<212> TYPE: PRT
<213> ORGANISM: Artificial Sequence
<220> FEATURE:
<223> OTHER INFORMATION: Synthetic

<400> SEQUENCE: 349

```
Gly Gly Gly Ser Gly Gly Gly Gly Ser Gly Ser Gly Gly Gly Ser Gly
1               5                   10                  15

Gly Gly Gly Ser Gly Gly Gly Gln Val Gln Leu Gln Gln Ser Gly Ala
            20                  25                  30

Glu Leu Ala Arg Pro Gly Ala Ser Val Lys Met Ser Cys Lys Ala Ser
        35                  40                  45

Gly Tyr Thr Phe Thr Arg Tyr Thr Met His Trp Val Lys Gln Arg Pro
    50                  55                  60

Gly Gln Gly Leu Glu Trp Ile Gly Tyr Ile Asn Pro Ser Arg Gly Tyr
65                  70                  75                  80

Thr Asn Tyr Asn Gln Lys Phe Lys Asp Lys Ala Thr Leu Thr Thr Asp
                85                  90                  95

Lys Ser Ser Ser Thr Ala Tyr Met Gln Leu Ser Ser Leu Thr Ser Glu
            100                 105                 110

Asp Ser Ala Val Tyr Tyr Cys Ala Arg Tyr Tyr Asp Asp His Tyr Cys
        115                 120                 125

Leu Asp Tyr Trp Gly Gln Gly Thr Thr Leu Thr Val Ser Ser Gly Gly
    130                 135                 140

Gly Gly Ser Gly Gly Gly Gly Ser Gly Gly Gly Gly Ser Gln Ile Val
145                 150                 155                 160

Leu Thr Gln Ser Pro Ala Ile Met Ser Ala Ser Pro Gly Glu Lys Val
                165                 170                 175

Thr Met Thr Cys Ser Ala Ser Ser Ser Val Ser Tyr Met Asn Trp Tyr
            180                 185                 190

Gln Gln Lys Ser Gly Thr Ser Pro Lys Arg Trp Ile Tyr Asp Thr Ser
        195                 200                 205

Lys Leu Ala Ser Gly Val Pro Ala His Phe Arg Gly Ser Gly Ser Gly
    210                 215                 220

Thr Ser Tyr Ser Leu Thr Ile Ser Gly Met Glu Ala Glu Asp Ala Ala
225                 230                 235                 240

Thr Tyr Tyr Cys Gln Gln Trp Ser Ser Asn Pro Phe Thr Phe Gly Ser
                245                 250                 255

Gly Thr Lys Leu Glu Ile Asn Arg
            260
```

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381
<211> LENGTH: 5
<212> TYPE: PRT
<213> ORGANISM: Artificial Sequence
<220> FEATURE:
<223> OTHER INFORMATION: Synthetic

<400> SEQUENCE: 381

Gly Ser Gly Gly Ser
1               5

<210> SEQ ID NO 382
<211> LENGTH: 4
<212> TYPE: PRT
<213> ORGANISM: Artificial Sequence
<220> FEATURE:
<223> OTHER INFORMATION: Synthetic

<400> SEQUENCE: 382

Gly Gly Gly Ser
1

<210> SEQ ID NO 383
<211> LENGTH: 4
<212> TYPE: PRT
<213> ORGANISM: Artificial Sequence
<220> FEATURE:

<223> OTHER INFORMATION: Synthetic

<400> SEQUENCE: 383

Gly Gly Ser Gly
1

<210> SEQ ID NO 384
<211> LENGTH: 5
<212> TYPE: PRT
<213> ORGANISM: Artificial Sequence
<220> FEATURE:
<223> OTHER INFORMATION: Synthetic

<400> SEQUENCE: 384

Gly Gly Ser Gly Gly
1               5

<210> SEQ ID NO 385
<211> LENGTH: 5
<212> TYPE: PRT
<213> ORGANISM: Artificial Sequence
<220> FEATURE:
<223> OTHER INFORMATION: Synthetic

<400> SEQUENCE: 385

Gly Ser Gly Ser Gly
1               5

<210> SEQ ID NO 386
<211> LENGTH: 5
<212> TYPE: PRT
<213> ORGANISM: Artificial Sequence
<220> FEATURE:
<223> OTHER INFORMATION: Synthetic

<400> SEQUENCE: 386

Gly Ser Gly Gly Gly
1               5

<210> SEQ ID NO 387
<211> LENGTH: 5
<212> TYPE: PRT
<213> ORGANISM: Artificial Sequence
<220> FEATURE:
<223> OTHER INFORMATION: Synthetic

<400> SEQUENCE: 387

Gly Gly Gly Ser Gly
1               5

<210> SEQ ID NO 388
<211> LENGTH: 5
<212> TYPE: PRT
<213> ORGANISM: Artificial Sequence
<220> FEATURE:
<223> OTHER INFORMATION: Synthetic

<400> SEQUENCE: 388

Gly Ser Ser Ser Gly
1               5

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399
<211> LENGTH: 214
<212> TYPE: PRT
<213> ORGANISM: Artificial Sequence
<220> FEATURE:
<223> OTHER INFORMATION: Synthetic

<400> SEQUENCE: 399

Asp Ile Leu Leu Thr Gln Ser Pro Val Ile Leu Ser Val Ser Pro Gly
1 5 10 15

Glu Arg Val Ser Phe Ser Cys Arg Ala Ser Gln Ser Ile Gly Thr Asn
20 25 30

-continued

```
Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 400
<211> LENGTH: 449
<212> TYPE: PRT
<213> ORGANISM: Artificial Sequence
<220> FEATURE:
<223> OTHER INFORMATION: Synthetic

<400> SEQUENCE: 400

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 401
<211> LENGTH: 214
<212> TYPE: PRT
<213> ORGANISM: Artificial Sequence
<220> FEATURE:
<223> OTHER INFORMATION: Synthetic

<400> SEQUENCE: 401

Gln Ile Leu Leu Thr Gln Ser Pro Val Ile Leu Ser Val Ser Pro Gly
1 5 10 15

Glu Arg Val Ser Phe Ser Cys Arg Ala Ser Gln Ser Ile Gly Thr Asn
20 25 30

Ile His Trp Tyr Gln Gln Arg Thr Asn Gly Ser Pro Arg Leu Leu Ile
35 40 45

Lys Tyr Ala Ser Glu Ser Ile Ser Gly Ile Pro Ser Arg Phe Ser Gly
50 55 60

Ser Gly Ser Gly Thr Asp Phe Thr Leu Ser Ile Asn Ser Val Glu Ser
65 70 75 80

Glu Asp Ile Ala Asp Tyr Tyr Cys Gln Gln Asn Asn Asn Trp Pro Thr 85 90 95

Thr Phe Gly Ala Gly Thr Lys Leu Glu Leu Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 402
<211> LENGTH: 258
<212> TYPE: PRT
<213> ORGANISM: Artificial Sequence
<220> FEATURE:
<223> OTHER INFORMATION: Synthetic

<400> SEQUENCE: 402

Gln Gly Gln Ser Gly Gln Cys Ile Ser Pro Arg Gly Cys Pro Asp Gly
1 5 10 15

Pro Tyr Val Met Tyr Gly Ser Ser Gly Gly Ser Gly Gly Ser Gly Gly
20 25 30

Ser Gly Gly Gly Ser Gly Gly Gly Ser Gly Gly Ser Asp Ile Leu Leu
35 40 45

Thr Gln Ser Pro Val Ile Leu Ser Val Ser Pro Gly Glu Arg Val Ser
50 55 60

Phe Ser Cys Arg Ala Ser Gln Ser Ile Gly Thr Asn Ile His Trp Tyr
65 70 75 80

Gln Gln Arg Thr Asn Gly Ser Pro Arg Leu Leu Ile Lys Tyr Ala Ser
85 90 95

Glu Ser Ile Ser Gly Ile Pro Ser Arg Phe Ser Gly Ser Gly Ser Gly
100 105 110

Thr Asp Phe Thr Leu Ser Ile Asn Ser Val Glu Ser Glu Asp Ile Ala
115 120 125

Asp Tyr Tyr Cys Gln Gln Asn Asn Asn Trp Pro Thr Thr Phe Gly Ala
130 135 140

Gly Thr Lys Leu Glu Leu Lys Arg Thr Val Ala Ala Pro Ser Val Phe
145 150 155 160

Ile Phe Pro Pro Ser Asp Glu Gln Leu Lys Ser Gly Thr Ala Ser Val
165 170 175

Val Cys Leu Leu Asn Asn Phe Tyr Pro Arg Glu Ala Lys Val Gln Trp
180 185 190

Lys Val Asp Asn Ala Leu Gln Ser Gly Asn Ser Gln Glu Ser Val Thr
195 200 205

Glu Gln Asp Ser Lys Asp Ser Thr Tyr Ser Leu Ser Ser Thr Leu Thr
210 215 220

Leu Ser Lys Ala Asp Tyr Glu Lys His Lys Val Tyr Ala Cys Glu Val

```
225                 230                 235                 240

Thr His Gln Gly Leu Ser Ser Pro Val Thr Lys Ser Phe Asn Arg Gly
                245                 250                 255

Glu Cys
```

<210> SEQ ID NO 403
<211> LENGTH: 254
<212> TYPE: PRT
<213> ORGANISM: Artificial Sequence
<220> FEATURE:
<223> OTHER INFORMATION: Synthetic

<400> SEQUENCE: 403

```
Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Ala Leu Ala
            20                  25                  30

His Gly Leu Phe Gly Gly Gly Ser Gln Ile Leu Leu Thr Gln Ser Pro
        35                  40                  45

Val Ile Leu Ser Val Ser Pro Gly Glu Arg Val Ser Phe Ser Cys Arg
    50                  55                  60

Ala Ser Gln Ser Ile Gly Thr Asn Ile His Trp Tyr Gln Gln Arg Thr
65                  70                  75                  80

Asn Gly Ser Pro Arg Leu Leu Ile Lys Tyr Ala Ser Glu Ser Ile Ser
                85                  90                  95

Gly Ile Pro Ser Arg Phe Ser Gly Ser Gly Ser Gly Thr Asp Phe Thr
            100                 105                 110

Leu Ser Ile Asn Ser Val Glu Ser Glu Asp Ile Ala Asp Tyr Tyr Cys
        115                 120                 125

Gln Gln Asn Asn Asn Trp Pro Thr Thr Phe Gly Ala Gly Thr Lys Leu
    130                 135                 140

Glu Leu Lys Arg Thr Val Ala Ala Pro Ser Val Phe Ile Phe Pro Pro
145                 150                 155                 160

Ser Asp Glu Gln Leu Lys Ser Gly Thr Ala Ser Val Val Cys Leu Leu
                165                 170                 175

Asn Asn Phe Tyr Pro Arg Glu Ala Lys Val Gln Trp Lys Val Asp Asn
            180                 185                 190

Ala Leu Gln Ser Gly Asn Ser Gln Glu Ser Val Thr Glu Gln Asp Ser
        195                 200                 205

Lys Asp Ser Thr Tyr Ser Leu Ser Ser Thr Leu Thr Leu Ser Lys Ala
    210                 215                 220

Asp Tyr Glu Lys His Lys Val Tyr Ala Cys Glu Val Thr His Gln Gly
225                 230                 235                 240

Leu Ser Ser Pro Val Thr Lys Ser Phe Asn Arg Gly Glu Cys
                245                 250
```

<210> SEQ ID NO 404
<211> LENGTH: 259
<212> TYPE: PRT
<213> ORGANISM: Artificial Sequence
<220> FEATURE:
<223> OTHER INFORMATION: Synthetic

<400> SEQUENCE: 404

```
Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
```

20 25 30

Ser Gly Ala Leu Ala His Gly Leu Phe Gly Gly Gly Ser Gln Ile Leu
35 40 45

Leu Thr Gln Ser Pro Val Ile Leu Ser Val Ser Pro Gly Glu Arg Val
50 55 60

Ser Phe Ser Cys Arg Ala Ser Gln Ser Ile Gly Thr Asn Ile His Trp
65 70 75 80

Tyr Gln Gln Arg Thr Asn Gly Ser Pro Arg Leu Leu Ile Lys Tyr Ala
85 90 95

Ser Glu Ser Ile Ser Gly Ile Pro Ser Arg Phe Ser Gly Ser Gly Ser
100 105 110

Gly Thr Asp Phe Thr Leu Ser Ile Asn Ser Val Glu Ser Glu Asp Ile
115 120 125

Ala Asp Tyr Tyr Cys Gln Gln Asn Asn Asn Trp Pro Thr Thr Phe Gly
130 135 140

Ala Gly Thr Lys Leu Glu Leu Lys Arg Thr Val Ala Ala Pro Ser Val
145 150 155 160

Phe Ile Phe Pro Pro Ser Asp Glu Gln Leu Lys Ser Gly Thr Ala Ser
165 170 175

Val Val Cys Leu Leu Asn Asn Phe Tyr Pro Arg Glu Ala Lys Val Gln
180 185 190

Trp Lys Val Asp Asn Ala Leu Gln Ser Gly Asn Ser Gln Glu Ser Val
195 200 205

Thr Glu Gln Asp Ser Lys Asp Ser Thr Tyr Ser Leu Ser Ser Thr Leu
210 215 220

Thr Leu Ser Lys Ala Asp Tyr Glu Lys His Lys Val Tyr Ala Cys Glu
225 230 235 240

Val Thr His Gln Gly Leu Ser Ser Pro Val Thr Lys Ser Phe Asn Arg
245 250 255

Gly Glu Cys

<210> SEQ ID NO 405
<211> LENGTH: 254
<212> TYPE: PRT
<213> ORGANISM: Artificial Sequence
<220> FEATURE:
<223> OTHER INFORMATION: Synthetic

<400> SEQUENCE: 405

Gln Gly Gln Ser Gly Gln Cys Ile Ser Pro Arg Gly Cys Pro Asp Gly
1 5 10 15

Pro Tyr Val Met Tyr Gly Gly Gly Ser Ser Gly Gly Ser Asp Leu Ala
20 25 30

His Pro Leu Leu Gly Gly Gly Ser Gln Ile Leu Leu Thr Gln Ser Pro
35 40 45

Val Ile Leu Ser Val Ser Pro Gly Glu Arg Val Ser Phe Ser Cys Arg
50 55 60

Ala Ser Gln Ser Ile Gly Thr Asn Ile His Trp Tyr Gln Gln Arg Thr
65 70 75 80

Asn Gly Ser Pro Arg Leu Leu Ile Lys Tyr Ala Ser Glu Ser Ile Ser
85 90 95

Gly Ile Pro Ser Arg Phe Ser Gly Ser Gly Ser Gly Thr Asp Phe Thr
100 105 110

Leu Ser Ile Asn Ser Val Glu Ser Glu Asp Ile Ala Asp Tyr Tyr Cys
115 120 125

```
Gln Gln Asn Asn Asn Trp Pro Thr Thr Phe Gly Ala Gly Thr Lys Leu
    130                 135                 140

Glu Leu Lys Arg Thr Val Ala Ala Pro Ser Val Phe Ile Phe Pro Pro
145                 150                 155                 160

Ser Asp Glu Gln Leu Lys Ser Gly Thr Ala Ser Val Val Cys Leu Leu
                165                 170                 175

Asn Asn Phe Tyr Pro Arg Glu Ala Lys Val Gln Trp Lys Val Asp Asn
            180                 185                 190

Ala Leu Gln Ser Gly Asn Ser Gln Glu Ser Val Thr Glu Gln Asp Ser
        195                 200                 205

Lys Asp Ser Thr Tyr Ser Leu Ser Ser Thr Leu Thr Leu Ser Lys Ala
    210                 215                 220

Asp Tyr Glu Lys His Lys Val Tyr Ala Cys Glu Val Thr His Gln Gly
225                 230                 235                 240

Leu Ser Ser Pro Val Thr Lys Ser Phe Asn Arg Gly Glu Cys
                245                 250


<210> SEQ ID NO 406
<211> LENGTH: 253
<212> TYPE: PRT
<213> ORGANISM: Artificial Sequence
<220> FEATURE:
<223> OTHER INFORMATION: Synthetic

<400> SEQUENCE: 406

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Ala Phe Arg
            20                  25                  30

His Leu Arg Gly Gly Gly Ser Gln Ile Leu Leu Thr Gln Ser Pro Val
        35                  40                  45

Ile Leu Ser Val Ser Pro Gly Glu Arg Val Ser Phe Ser Cys Arg Ala
    50                  55                  60

Ser Gln Ser Ile Gly Thr Asn Ile His Trp Tyr Gln Gln Arg Thr Asn
65                  70                  75                  80

Gly Ser Pro Arg Leu Leu Ile Lys Tyr Ala Ser Glu Ser Ile Ser Gly
                85                  90                  95

Ile Pro Ser Arg Phe Ser Gly Ser Gly Ser Gly Thr Asp Phe Thr Leu
            100                 105                 110

Ser Ile Asn Ser Val Glu Ser Glu Asp Ile Ala Asp Tyr Tyr Cys Gln
        115                 120                 125

Gln Asn Asn Asn Trp Pro Thr Thr Phe Gly Ala Gly Thr Lys Leu Glu
    130                 135                 140

Leu Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240
```

```
Ser Ser Pro Val Thr Lys Ser Phe Asn Arg Gly Glu Cys
                245                 250


<210> SEQ ID NO 407
<211> LENGTH: 258
<212> TYPE: PRT
<213> ORGANISM: Artificial Sequence
<220> FEATURE:
<223> OTHER INFORMATION: Synthetic

<400> SEQUENCE: 407

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Pro His Gly Phe Phe Gln Gly Gly Gly Ser Gln Ile Leu Leu
        35                  40                  45

Thr Gln Ser Pro Val Ile Leu Ser Val Ser Pro Gly Glu Arg Val Ser
    50                  55                  60

Phe Ser Cys Arg Ala Ser Gln Ser Ile Gly Thr Asn Ile His Trp Tyr
65                  70                  75                  80

Gln Gln Arg Thr Asn Gly Ser Pro Arg Leu Leu Ile Lys Tyr Ala Ser
                85                  90                  95

Glu Ser Ile Ser Gly Ile Pro Ser Arg Phe Ser Gly Ser Gly Ser Gly
            100                 105                 110

Thr Asp Phe Thr Leu Ser Ile Asn Ser Val Glu Ser Glu Asp Ile Ala
        115                 120                 125

Asp Tyr Tyr Cys Gln Gln Asn Asn Asn Trp Pro Thr Thr Phe Gly Ala
    130                 135                 140

Gly Thr Lys Leu Glu Leu Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys


<210> SEQ ID NO 408
<211> LENGTH: 253
<212> TYPE: PRT
<213> ORGANISM: Artificial Sequence
<220> FEATURE:
<223> OTHER INFORMATION: Synthetic

<400> SEQUENCE: 408

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Ser Val His
            20                  25                  30
```

```
His Leu Ile Gly Gly Gly Ser Gln Ile Leu Leu Thr Gln Ser Pro Val
        35                  40                  45

Ile Leu Ser Val Ser Pro Gly Glu Arg Val Ser Phe Ser Cys Arg Ala
    50                  55                  60

Ser Gln Ser Ile Gly Thr Asn Ile His Trp Tyr Gln Gln Arg Thr Asn
65                  70                  75                  80

Gly Ser Pro Arg Leu Leu Ile Lys Tyr Ala Ser Glu Ser Ile Ser Gly
                85                  90                  95

Ile Pro Ser Arg Phe Ser Gly Ser Gly Ser Gly Thr Asp Phe Thr Leu
            100                 105                 110

Ser Ile Asn Ser Val Glu Ser Glu Asp Ile Ala Asp Tyr Tyr Cys Gln
        115                 120                 125

Gln Asn Asn Asn Trp Pro Thr Thr Phe Gly Ala Gly Thr Lys Leu Glu
    130                 135                 140

Leu Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250


<210> SEQ ID NO 409
<211> LENGTH: 254
<212> TYPE: PRT
<213> ORGANISM: Artificial Sequence
<220> FEATURE:
<223> OTHER INFORMATION: Synthetic

<400> SEQUENCE: 409

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Arg Gly Pro
            20                  25                  30

Lys Leu Tyr Trp Gly Gly Gly Ser Gln Ile Leu Leu Thr Gln Ser Pro
        35                  40                  45

Val Ile Leu Ser Val Ser Pro Gly Glu Arg Val Ser Phe Ser Cys Arg
    50                  55                  60

Ala Ser Gln Ser Ile Gly Thr Asn Ile His Trp Tyr Gln Gln Arg Thr
65                  70                  75                  80

Asn Gly Ser Pro Arg Leu Leu Ile Lys Tyr Ala Ser Glu Ser Ile Ser
                85                  90                  95

Gly Ile Pro Ser Arg Phe Ser Gly Ser Gly Ser Gly Thr Asp Phe Thr
            100                 105                 110

Leu Ser Ile Asn Ser Val Glu Ser Glu Asp Ile Ala Asp Tyr Tyr Cys
        115                 120                 125

Gln Gln Asn Asn Asn Trp Pro Thr Thr Phe Gly Ala Gly Thr Lys Leu
    130                 135                 140
```

```
Glu Leu Lys Arg Thr Val Ala Ala Pro Ser Val Phe Ile Phe Pro Pro
145                 150                 155                 160

Ser Asp Glu Gln Leu Lys Ser Gly Thr Ala Ser Val Val Cys Leu Leu
                165                 170                 175

Asn Asn Phe Tyr Pro Arg Glu Ala Lys Val Gln Trp Lys Val Asp Asn
            180                 185                 190

Ala Leu Gln Ser Gly Asn Ser Gln Glu Ser Val Thr Glu Gln Asp Ser
        195                 200                 205

Lys Asp Ser Thr Tyr Ser Leu Ser Ser Thr Leu Thr Leu Ser Lys Ala
    210                 215                 220

Asp Tyr Glu Lys His Lys Val Tyr Ala Cys Glu Val Thr His Gln Gly
225                 230                 235                 240

Leu Ser Ser Pro Val Thr Lys Ser Phe Asn Arg Gly Glu Cys
                245                 250


<210> SEQ ID NO 410
<211> LENGTH: 259
<212> TYPE: PRT
<213> ORGANISM: Artificial Sequence
<220> FEATURE:
<223> OTHER INFORMATION: Synthetic

<400> SEQUENCE: 410

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Arg Gly Pro Lys Leu Tyr Trp Gly Gly Gly Ser Gln Ile Leu
        35                  40                  45

Leu Thr Gln Ser Pro Val Ile Leu Ser Val Ser Pro Gly Glu Arg Val
    50                  55                  60

Ser Phe Ser Cys Arg Ala Ser Gln Ser Ile Gly Thr Asn Ile His Trp
65                  70                  75                  80

Tyr Gln Gln Arg Thr Asn Gly Ser Pro Arg Leu Leu Ile Lys Tyr Ala
                85                  90                  95

Ser Glu Ser Ile Ser Gly Ile Pro Ser Arg Phe Ser Gly Ser Gly Ser
            100                 105                 110

Gly Thr Asp Phe Thr Leu Ser Ile Asn Ser Val Glu Ser Glu Asp Ile
        115                 120                 125

Ala Asp Tyr Tyr Cys Gln Gln Asn Asn Asn Trp Pro Thr Thr Phe Gly
    130                 135                 140

Ala Gly Thr Lys Leu Glu Leu Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255
```

Gly Glu Cys

<210> SEQ ID NO 411
<211> LENGTH: 254
<212> TYPE: PRT
<213> ORGANISM: Artificial Sequence
<220> FEATURE:
<223> OTHER INFORMATION: Synthetic

<400> SEQUENCE: 411

```
Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Arg Phe Pro
            20                  25                  30

Tyr Gly Val Trp Gly Gly Gly Ser Gln Ile Leu Leu Thr Gln Ser Pro
        35                  40                  45

Val Ile Leu Ser Val Ser Pro Gly Glu Arg Val Ser Phe Ser Cys Arg
    50                  55                  60

Ala Ser Gln Ser Ile Gly Thr Asn Ile His Trp Tyr Gln Gln Arg Thr
65                  70                  75                  80

Asn Gly Ser Pro Arg Leu Leu Ile Lys Tyr Ala Ser Glu Ser Ile Ser
                85                  90                  95

Gly Ile Pro Ser Arg Phe Ser Gly Ser Gly Ser Gly Thr Asp Phe Thr
            100                 105                 110

Leu Ser Ile Asn Ser Val Glu Ser Glu Asp Ile Ala Asp Tyr Tyr Cys
        115                 120                 125

Gln Gln Asn Asn Asn Trp Pro Thr Thr Phe Gly Ala Gly Thr Lys Leu
    130                 135                 140

Glu Leu Lys Arg Thr Val Ala Ala Pro Ser Val Phe Ile Phe Pro Pro
145                 150                 155                 160

Ser Asp Glu Gln Leu Lys Ser Gly Thr Ala Ser Val Val Cys Leu Leu
                165                 170                 175

Asn Asn Phe Tyr Pro Arg Glu Ala Lys Val Gln Trp Lys Val Asp Asn
            180                 185                 190

Ala Leu Gln Ser Gly Asn Ser Gln Glu Ser Val Thr Glu Gln Asp Ser
        195                 200                 205

Lys Asp Ser Thr Tyr Ser Leu Ser Ser Thr Leu Thr Leu Ser Lys Ala
    210                 215                 220

Asp Tyr Glu Lys His Lys Val Tyr Ala Cys Glu Val Thr His Gln Gly
225                 230                 235                 240

Leu Ser Ser Pro Val Thr Lys Ser Phe Asn Arg Gly Glu Cys
                245                 250
```

<210> SEQ ID NO 412
<211> LENGTH: 253
<212> TYPE: PRT
<213> ORGANISM: Artificial Sequence
<220> FEATURE:
<223> OTHER INFORMATION: Synthetic

<400> SEQUENCE: 412

```
Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser His Val Pro
            20                  25                  30

Arg Gln Val Gly Gly Gly Ser Gln Ile Leu Leu Thr Gln Ser Pro Val
        35                  40                  45
```

```
Ile Leu Ser Val Ser Pro Gly Glu Arg Val Ser Phe Ser Cys Arg Ala
    50                  55                  60

Ser Gln Ser Ile Gly Thr Asn Ile His Trp Tyr Gln Gln Arg Thr Asn
65                  70                  75                  80

Gly Ser Pro Arg Leu Leu Ile Lys Tyr Ala Ser Glu Ser Ile Ser Gly
                85                  90                  95

Ile Pro Ser Arg Phe Ser Gly Ser Gly Ser Gly Thr Asp Phe Thr Leu
            100                 105                 110

Ser Ile Asn Ser Val Glu Ser Glu Asp Ile Ala Asp Tyr Tyr Cys Gln
        115                 120                 125

Gln Asn Asn Asn Trp Pro Thr Thr Phe Gly Ala Gly Thr Lys Leu Glu
    130                 135                 140

Leu Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250


<210> SEQ ID NO 413
<211> LENGTH: 258
<212> TYPE: PRT
<213> ORGANISM: Artificial Sequence
<220> FEATURE:
<223> OTHER INFORMATION: Synthetic

<400> SEQUENCE: 413

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly His Val Pro Arg Gln Val Gly Gly Gly Ser Gln Ile Leu Leu
        35                  40                  45

Thr Gln Ser Pro Val Ile Leu Ser Val Ser Pro Gly Glu Arg Val Ser
    50                  55                  60

Phe Ser Cys Arg Ala Ser Gln Ser Ile Gly Thr Asn Ile His Trp Tyr
65                  70                  75                  80

Gln Gln Arg Thr Asn Gly Ser Pro Arg Leu Leu Ile Lys Tyr Ala Ser
                85                  90                  95

Glu Ser Ile Ser Gly Ile Pro Ser Arg Phe Ser Gly Ser Gly Ser Gly
            100                 105                 110

Thr Asp Phe Thr Leu Ser Ile Asn Ser Val Glu Ser Glu Asp Ile Ala
        115                 120                 125

Asp Tyr Tyr Cys Gln Gln Asn Asn Asn Trp Pro Thr Thr Phe Gly Ala
    130                 135                 140

Gly Thr Lys Leu Glu Leu Lys Arg Thr Val Ala Ala Pro Ser Val Phe
145                 150                 155                 160
```

```
Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys


<210> SEQ ID NO 414
<211> LENGTH: 253
<212> TYPE: PRT
<213> ORGANISM: Artificial Sequence
<220> FEATURE:
<223> OTHER INFORMATION: Synthetic

<400> SEQUENCE: 414

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Ser Asn Pro
            20                  25                  30

Phe Lys Tyr Gly Gly Gly Ser Gln Ile Leu Leu Thr Gln Ser Pro Val
        35                  40                  45

Ile Leu Ser Val Ser Pro Gly Glu Arg Val Ser Phe Ser Cys Arg Ala
    50                  55                  60

Ser Gln Ser Ile Gly Thr Asn Ile His Trp Tyr Gln Gln Arg Thr Asn
65                  70                  75                  80

Gly Ser Pro Arg Leu Leu Ile Lys Tyr Ala Ser Glu Ser Ile Ser Gly
                85                  90                  95

Ile Pro Ser Arg Phe Ser Gly Ser Gly Ser Gly Thr Asp Phe Thr Leu
            100                 105                 110

Ser Ile Asn Ser Val Glu Ser Glu Asp Ile Ala Asp Tyr Tyr Cys Gln
        115                 120                 125

Gln Asn Asn Asn Trp Pro Thr Thr Phe Gly Ala Gly Thr Lys Leu Glu
    130                 135                 140

Leu Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250
```

<210> SEQ ID NO 415
<211> LENGTH: 253
<212> TYPE: PRT
<213> ORGANISM: Artificial Sequence
<220> FEATURE:
<223> OTHER INFORMATION: Synthetic

<400> SEQUENCE: 415

```
Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Arg Phe Pro
            20                  25                  30

Leu Lys Val Gly Gly Gly Ser Gln Ile Leu Leu Thr Gln Ser Pro Val
        35                  40                  45

Ile Leu Ser Val Ser Pro Gly Glu Arg Val Ser Phe Ser Cys Arg Ala
    50                  55                  60

Ser Gln Ser Ile Gly Thr Asn Ile His Trp Tyr Gln Gln Arg Thr Asn
65                  70                  75                  80

Gly Ser Pro Arg Leu Leu Ile Lys Tyr Ala Ser Glu Ser Ile Ser Gly
                85                  90                  95

Ile Pro Ser Arg Phe Ser Gly Ser Gly Ser Gly Thr Asp Phe Thr Leu
            100                 105                 110

Ser Ile Asn Ser Val Glu Ser Glu Asp Ile Ala Asp Tyr Tyr Cys Gln
        115                 120                 125

Gln Asn Asn Asn Trp Pro Thr Thr Phe Gly Ala Gly Thr Lys Leu Glu
    130                 135                 140

Leu Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250
```

<210> SEQ ID NO 416
<211> LENGTH: 253
<212> TYPE: PRT
<213> ORGANISM: Artificial Sequence
<220> FEATURE:
<223> OTHER INFORMATION: Synthetic

<400> SEQUENCE: 416

```
Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Pro Phe His
            20                  25                  30

Leu Ser Arg Gly Gly Gly Ser Gln Ile Leu Leu Thr Gln Ser Pro Val
        35                  40                  45

Ile Leu Ser Val Ser Pro Gly Glu Arg Val Ser Phe Ser Cys Arg Ala
    50                  55                  60
```

Ser Gln Ser Ile Gly Thr Asn Ile His Trp Tyr Gln Gln Arg Thr Asn
65 70 75 80

Gly Ser Pro Arg Leu Leu Ile Lys Tyr Ala Ser Glu Ser Ile Ser Gly
85 90 95

Ile Pro Ser Arg Phe Ser Gly Ser Gly Ser Gly Thr Asp Phe Thr Leu
100 105 110

Ser Ile Asn Ser Val Glu Ser Glu Asp Ile Ala Asp Tyr Tyr Cys Gln
115 120 125

Gln Asn Asn Asn Trp Pro Thr Thr Phe Gly Ala Gly Thr Lys Leu Glu
130 135 140

Leu Lys Arg Thr Val Ala Ala Pro Ser Val Phe Ile Phe Pro Pro Ser
145 150 155 160

Asp Glu Gln Leu Lys Ser Gly Thr Ala Ser Val Val Cys Leu Leu Asn
165 170 175

Asn Phe Tyr Pro Arg Glu Ala Lys Val Gln Trp Lys Val Asp Asn Ala
180 185 190

Leu Gln Ser Gly Asn Ser Gln Glu Ser Val Thr Glu Gln Asp Ser Lys
195 200 205

Asp Ser Thr Tyr Ser Leu Ser Ser Thr Leu Thr Leu Ser Lys Ala Asp
210 215 220

Tyr Glu Lys His Lys Val Tyr Ala Cys Glu Val Thr His Gln Gly Leu
225 230 235 240

Ser Ser Pro Val Thr Lys Ser Phe Asn Arg Gly Glu Cys
245 250

<210> SEQ ID NO 417
<211> LENGTH: 253
<212> TYPE: PRT
<213> ORGANISM: Artificial Sequence
<220> FEATURE:
<223> OTHER INFORMATION: Synthetic

<400> SEQUENCE: 417

Gln Gly Gln Ser Gly Gln Cys Ile Ser Pro Arg Gly Cys Pro Asp Gly
1 5 10 15

Pro Tyr Val Met Tyr Gly Gly Gly Ser Ser Gly Gly Ser Ser Thr Val
20 25 30

Phe His Met Gly Gly Gly Ser Gln Ile Leu Leu Thr Gln Ser Pro Val
35 40 45

Ile Leu Ser Val Ser Pro Gly Glu Arg Val Ser Phe Ser Cys Arg Ala
50 55 60

Ser Gln Ser Ile Gly Thr Asn Ile His Trp Tyr Gln Gln Arg Thr Asn
65 70 75 80

Gly Ser Pro Arg Leu Leu Ile Lys Tyr Ala Ser Glu Ser Ile Ser Gly
85 90 95

Ile Pro Ser Arg Phe Ser Gly Ser Gly Ser Gly Thr Asp Phe Thr Leu
100 105 110

Ser Ile Asn Ser Val Glu Ser Glu Asp Ile Ala Asp Tyr Tyr Cys Gln
115 120 125

Gln Asn Asn Asn Trp Pro Thr Thr Phe Gly Ala Gly Thr Lys Leu Glu
130 135 140

Leu Lys Arg Thr Val Ala Ala Pro Ser Val Phe Ile Phe Pro Pro Ser
145 150 155 160

Asp Glu Gln Leu Lys Ser Gly Thr Ala Ser Val Val Cys Leu Leu Asn
165 170 175

```
Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250


<210> SEQ ID NO 418
<211> LENGTH: 253
<212> TYPE: PRT
<213> ORGANISM: Artificial Sequence
<220> FEATURE:
<223> OTHER INFORMATION: Synthetic

<400> SEQUENCE: 418

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Met Gly Pro
            20                  25                  30

Trp Phe Met Gly Gly Gly Ser Gln Ile Leu Leu Thr Gln Ser Pro Val
        35                  40                  45

Ile Leu Ser Val Ser Pro Gly Glu Arg Val Ser Phe Ser Cys Arg Ala
    50                  55                  60

Ser Gln Ser Ile Gly Thr Asn Ile His Trp Tyr Gln Gln Arg Thr Asn
65                  70                  75                  80

Gly Ser Pro Arg Leu Leu Ile Lys Tyr Ala Ser Glu Ser Ile Ser Gly
                85                  90                  95

Ile Pro Ser Arg Phe Ser Gly Ser Gly Ser Gly Thr Asp Phe Thr Leu
            100                 105                 110

Ser Ile Asn Ser Val Glu Ser Glu Asp Ile Ala Asp Tyr Tyr Cys Gln
        115                 120                 125

Gln Asn Asn Asn Trp Pro Thr Thr Phe Gly Ala Gly Thr Lys Leu Glu
    130                 135                 140

Leu Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250


<210> SEQ ID NO 419
<211> LENGTH: 258
<212> TYPE: PRT
<213> ORGANISM: Artificial Sequence
```

<220> FEATURE:
<223> OTHER INFORMATION: Synthetic

<400> SEQUENCE: 419

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Met Gly Pro Trp Phe Met Gly Gly Gly Ser Gln Ile Leu Leu
        35                  40                  45

Thr Gln Ser Pro Val Ile Leu Ser Val Ser Pro Gly Glu Arg Val Ser
    50                  55                  60

Phe Ser Cys Arg Ala Ser Gln Ser Ile Gly Thr Asn Ile His Trp Tyr
65                  70                  75                  80

Gln Gln Arg Thr Asn Gly Ser Pro Arg Leu Leu Ile Lys Tyr Ala Ser
                85                  90                  95

Glu Ser Ile Ser Gly Ile Pro Ser Arg Phe Ser Gly Ser Gly Ser Gly
            100                 105                 110

Thr Asp Phe Thr Leu Ser Ile Asn Ser Val Glu Ser Glu Asp Ile Ala
        115                 120                 125

Asp Tyr Tyr Cys Gln Gln Asn Asn Asn Trp Pro Thr Thr Phe Gly Ala
    130                 135                 140

Gly Thr Lys Leu Glu Leu Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 420
<211> LENGTH: 253
<212> TYPE: PRT
<213> ORGANISM: Artificial Sequence
<220> FEATURE:
<223> OTHER INFORMATION: Synthetic

<400> SEQUENCE: 420

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Arg His Leu
            20                  25                  30

Ala Lys Leu Gly Gly Gly Ser Gln Ile Leu Leu Thr Gln Ser Pro Val
        35                  40                  45

Ile Leu Ser Val Ser Pro Gly Glu Arg Val Ser Phe Ser Cys Arg Ala
    50                  55                  60

Ser Gln Ser Ile Gly Thr Asn Ile His Trp Tyr Gln Gln Arg Thr Asn
65                  70                  75                  80

```
Gly Ser Pro Arg Leu Leu Ile Lys Tyr Ala Ser Glu Ser Ile Ser Gly
                85                  90                  95

Ile Pro Ser Arg Phe Ser Gly Ser Gly Ser Gly Thr Asp Phe Thr Leu
            100                 105                 110

Ser Ile Asn Ser Val Glu Ser Glu Asp Ile Ala Asp Tyr Tyr Cys Gln
        115                 120                 125

Gln Asn Asn Asn Trp Pro Thr Thr Phe Gly Ala Gly Thr Lys Leu Glu
    130                 135                 140

Leu Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250


<210> SEQ ID NO 421
<211> LENGTH: 254
<212> TYPE: PRT
<213> ORGANISM: Artificial Sequence
<220> FEATURE:
<223> OTHER INFORMATION: Synthetic

<400> SEQUENCE: 421

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Pro Leu Gly
            20                  25                  30

Val Arg Gly Lys Gly Gly Gly Ser Gln Ile Leu Leu Thr Gln Ser Pro
        35                  40                  45

Val Ile Leu Ser Val Ser Pro Gly Glu Arg Val Ser Phe Ser Cys Arg
    50                  55                  60

Ala Ser Gln Ser Ile Gly Thr Asn Ile His Trp Tyr Gln Gln Arg Thr
65                  70                  75                  80

Asn Gly Ser Pro Arg Leu Leu Ile Lys Tyr Ala Ser Glu Ser Ile Ser
                85                  90                  95

Gly Ile Pro Ser Arg Phe Ser Gly Ser Gly Ser Gly Thr Asp Phe Thr
            100                 105                 110

Leu Ser Ile Asn Ser Val Glu Ser Glu Asp Ile Ala Asp Tyr Tyr Cys
        115                 120                 125

Gln Gln Asn Asn Asn Trp Pro Thr Thr Phe Gly Ala Gly Thr Lys Leu
    130                 135                 140

Glu Leu Lys Arg Thr Val Ala Ala Pro Ser Val Phe Ile Phe Pro Pro
145                 150                 155                 160

Ser Asp Glu Gln Leu Lys Ser Gly Thr Ala Ser Val Val Cys Leu Leu
                165                 170                 175

Asn Asn Phe Tyr Pro Arg Glu Ala Lys Val Gln Trp Lys Val Asp Asn
            180                 185                 190
```

```
Ala Leu Gln Ser Gly Asn Ser Gln Glu Ser Val Thr Glu Gln Asp Ser
        195                 200                 205

Lys Asp Ser Thr Tyr Ser Leu Ser Ser Thr Leu Thr Leu Ser Lys Ala
    210                 215                 220

Asp Tyr Glu Lys His Lys Val Tyr Ala Cys Glu Val Thr His Gln Gly
225                 230                 235                 240

Leu Ser Ser Pro Val Thr Lys Ser Phe Asn Arg Gly Glu Cys
                245                 250


<210> SEQ ID NO 422
<211> LENGTH: 259
<212> TYPE: PRT
<213> ORGANISM: Artificial Sequence
<220> FEATURE:
<223> OTHER INFORMATION: Synthetic

<400> SEQUENCE: 422

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Pro Leu Gly Val Arg Gly Lys Gly Gly Gly Ser Gln Ile Leu
        35                  40                  45

Leu Thr Gln Ser Pro Val Ile Leu Ser Val Ser Pro Gly Glu Arg Val
    50                  55                  60

Ser Phe Ser Cys Arg Ala Ser Gln Ser Ile Gly Thr Asn Ile His Trp
65                  70                  75                  80

Tyr Gln Gln Arg Thr Asn Gly Ser Pro Arg Leu Leu Ile Lys Tyr Ala
                85                  90                  95

Ser Glu Ser Ile Ser Gly Ile Pro Ser Arg Phe Ser Gly Ser Gly Ser
            100                 105                 110

Gly Thr Asp Phe Thr Leu Ser Ile Asn Ser Val Glu Ser Glu Asp Ile
        115                 120                 125

Ala Asp Tyr Tyr Cys Gln Gln Asn Asn Asn Trp Pro Thr Thr Phe Gly
    130                 135                 140

Ala Gly Thr Lys Leu Glu Leu Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 423
<211> LENGTH: 260
<212> TYPE: PRT
<213> ORGANISM: Artificial Sequence
<220> FEATURE:
```

-continued

<223> OTHER INFORMATION: Synthetic

<400> SEQUENCE: 423

```
Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Gln Asn Gln Ala Leu Arg Ile Ala Gly Gly Gly Ser Gln Ile
        35                  40                  45

Leu Leu Thr Gln Ser Pro Val Ile Leu Ser Val Ser Pro Gly Glu Arg
    50                  55                  60

Val Ser Phe Ser Cys Arg Ala Ser Gln Ser Ile Gly Thr Asn Ile His
65                  70                  75                  80

Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260
```

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450
<211> LENGTH: 259
<212> TYPE: PRT
<213> ORGANISM: Artificial Sequence
<220> FEATURE:
<223> OTHER INFORMATION: Synthetic

<400> SEQUENCE: 450

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Leu Ser Gly
            20                  25                  30

Arg Ser Ala Leu Ala His Gly Leu Phe Gly Gly Gly Ser Gln Ile Leu
        35                  40                  45

Leu Thr Gln Ser Pro Val Ile Leu Ser Val Ser Pro Gly Glu Arg Val
    50                  55                  60

Ser Phe Ser Cys Arg Ala Ser Gln Ser Ile Gly Thr Asn Ile His Trp
65                  70                  75                  80

Tyr Gln Gln Arg Thr Asn Gly Ser Pro Arg Leu Leu Ile Lys Tyr Ala
                85                  90                  95

Ser Glu Ser Ile Ser Gly Ile Pro Ser Arg Phe Ser Gly Ser Gly Ser
            100                 105                 110

Gly Thr Asp Phe Thr Leu Ser Ile Asn Ser Val Glu Ser Glu Asp Ile
        115                 120                 125

Ala Asp Tyr Tyr Cys Gln Gln Asn Asn Asn Trp Pro Thr Thr Phe Gly
    130                 135                 140

Ala Gly Thr Lys Leu Glu Leu Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 451
<211> LENGTH: 260
<212> TYPE: PRT
<213> ORGANISM: Artificial Sequence
<220> FEATURE:
<223> OTHER INFORMATION: Synthetic

<400> SEQUENCE: 451

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Ala Leu Ala
            20                  25                  30

His Gly Leu Phe Ser Gly Arg Ser Ala Asn Gly Gly Gly Ser Gln Ile
        35                  40                  45

```
Leu Leu Thr Gln Ser Pro Val Ile Leu Ser Val Ser Pro Gly Glu Arg
    50                  55                  60

Val Ser Phe Ser Cys Arg Ala Ser Gln Ser Ile Gly Thr Asn Ile His
65                  70                  75                  80

Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260


<210> SEQ ID NO 452
<211> LENGTH: 258
<212> TYPE: PRT
<213> ORGANISM: Artificial Sequence
<220> FEATURE:
<223> OTHER INFORMATION: Synthetic

<400> SEQUENCE: 452

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser His Val Pro
            20                  25                  30

Arg Gln Val Leu Ser Gly Arg Ser Gly Gly Gly Ser Gln Ile Leu Leu
        35                  40                  45

Thr Gln Ser Pro Val Ile Leu Ser Val Ser Pro Gly Glu Arg Val Ser
    50                  55                  60

Phe Ser Cys Arg Ala Ser Gln Ser Ile Gly Thr Asn Ile His Trp Tyr
65                  70                  75                  80

Gln Gln Arg Thr Asn Gly Ser Pro Arg Leu Leu Ile Lys Tyr Ala Ser
                85                  90                  95

Glu Ser Ile Ser Gly Ile Pro Ser Arg Phe Ser Gly Ser Gly Ser Gly
            100                 105                 110

Thr Asp Phe Thr Leu Ser Ile Asn Ser Val Glu Ser Glu Asp Ile Ala
        115                 120                 125

Asp Tyr Tyr Cys Gln Gln Asn Asn Asn Trp Pro Thr Thr Phe Gly Ala
    130                 135                 140
```

```
Gly Thr Lys Leu Glu Leu Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys


<210> SEQ ID NO 453
<211> LENGTH: 260
<212> TYPE: PRT
<213> ORGANISM: Artificial Sequence
<220> FEATURE:
<223> OTHER INFORMATION: Synthetic

<400> SEQUENCE: 453

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser His Val Pro
            20                  25                  30

Arg Gln Val Leu Ser Gly Arg Ser Ala Asn Gly Gly Gly Ser Gln Ile
        35                  40                  45

Leu Leu Thr Gln Ser Pro Val Ile Leu Ser Val Ser Pro Gly Glu Arg
    50                  55                  60

Val Ser Phe Ser Cys Arg Ala Ser Gln Ser Ile Gly Thr Asn Ile His
65                  70                  75                  80

Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
```

```
                245                 250                 255

Arg Gly Glu Cys
            260


<210> SEQ ID NO 454
<211> LENGTH: 259
<212> TYPE: PRT
<213> ORGANISM: Artificial Sequence
<220> FEATURE:
<223> OTHER INFORMATION: Synthetic

<400> SEQUENCE: 454

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Thr Ala Arg
            20                  25                  30

Gly Pro Ala Leu Ala His Gly Leu Phe Gly Gly Gly Ser Gln Ile Leu
        35                  40                  45

Leu Thr Gln Ser Pro Val Ile Leu Ser Val Ser Pro Gly Glu Arg Val
    50                  55                  60

Ser Phe Ser Cys Arg Ala Ser Gln Ser Ile Gly Thr Asn Ile His Trp
65                  70                  75                  80

Tyr Gln Gln Arg Thr Asn Gly Ser Pro Arg Leu Leu Ile Lys Tyr Ala
                85                  90                  95

Ser Glu Ser Ile Ser Gly Ile Pro Ser Arg Phe Ser Gly Ser Gly Ser
            100                 105                 110

Gly Thr Asp Phe Thr Leu Ser Ile Asn Ser Val Glu Ser Glu Asp Ile
        115                 120                 125

Ala Asp Tyr Tyr Cys Gln Gln Asn Asn Asn Trp Pro Thr Thr Phe Gly
    130                 135                 140

Ala Gly Thr Lys Leu Glu Leu Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 455
<211> LENGTH: 257
<212> TYPE: PRT
<213> ORGANISM: Artificial Sequence
<220> FEATURE:
<223> OTHER INFORMATION: Synthetic

<400> SEQUENCE: 455

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Thr Ala Arg
```

```
            20                  25                  30

Gly Pro Val Pro Arg Gln Val Gly Gly Gly Ser Gln Ile Leu Leu Thr
        35                  40                  45

Gln Ser Pro Val Ile Leu Ser Val Ser Pro Gly Glu Arg Val Ser Phe
    50                  55                  60

Ser Cys Arg Ala Ser Gln Ser Ile Gly Thr Asn Ile His Trp Tyr Gln
65                  70                  75                  80

Gln Arg Thr Asn Gly Ser Pro Arg Leu Leu Ile Lys Tyr Ala Ser Glu
                85                  90                  95

Ser Ile Ser Gly Ile Pro Ser Arg Phe Ser Gly Ser Gly Ser Gly Thr
            100                 105                 110

Asp Phe Thr Leu Ser Ile Asn Ser Val Glu Ser Glu Asp Ile Ala Asp
        115                 120                 125

Tyr Tyr Cys Gln Gln Asn Asn Asn Trp Pro Thr Thr Phe Gly Ala Gly
    130                 135                 140

Thr Lys Leu Glu Leu Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys


<210> SEQ ID NO 456
<211> LENGTH: 258
<212> TYPE: PRT
<213> ORGANISM: Artificial Sequence
<220> FEATURE:
<223> OTHER INFORMATION: Synthetic

<400> SEQUENCE: 456

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Ala Pro Arg
            20                  25                  30

Ser Ala Leu Ala His Gly Leu Phe Gly Gly Gly Ser Gln Ile Leu Leu
        35                  40                  45

Thr Gln Ser Pro Val Ile Leu Ser Val Ser Pro Gly Glu Arg Val Ser
    50                  55                  60

Phe Ser Cys Arg Ala Ser Gln Ser Ile Gly Thr Asn Ile His Trp Tyr
65                  70                  75                  80

Gln Gln Arg Thr Asn Gly Ser Pro Arg Leu Leu Ile Lys Tyr Ala Ser
                85                  90                  95

Glu Ser Ile Ser Gly Ile Pro Ser Arg Phe Ser Gly Ser Gly Ser Gly
            100                 105                 110

Thr Asp Phe Thr Leu Ser Ile Asn Ser Val Glu Ser Glu Asp Ile Ala
        115                 120                 125
```

```
Asp Tyr Tyr Cys Gln Gln Asn Asn Asn Trp Pro Thr Thr Phe Gly Ala
    130                 135                 140

Gly Thr Lys Leu Glu Leu Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys


<210> SEQ ID NO 457
<211> LENGTH: 259
<212> TYPE: PRT
<213> ORGANISM: Artificial Sequence
<220> FEATURE:
<223> OTHER INFORMATION: Synthetic

<400> SEQUENCE: 457

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Ala Leu Ala
            20                  25                  30

His Gly Leu Phe Ala Pro Arg Ser Phe Gly Gly Gly Ser Gln Ile Leu
        35                  40                  45

Leu Thr Gln Ser Pro Val Ile Leu Ser Val Ser Pro Gly Glu Arg Val
    50                  55                  60

Ser Phe Ser Cys Arg Ala Ser Gln Ser Ile Gly Thr Asn Ile His Trp
65                  70                  75                  80

Tyr Gln Gln Arg Thr Asn Gly Ser Pro Arg Leu Leu Ile Lys Tyr Ala
                85                  90                  95

Ser Glu Ser Ile Ser Gly Ile Pro Ser Arg Phe Ser Gly Ser Gly Ser
            100                 105                 110

Gly Thr Asp Phe Thr Leu Ser Ile Asn Ser Val Glu Ser Glu Asp Ile
        115                 120                 125

Ala Asp Tyr Tyr Cys Gln Gln Asn Asn Asn Trp Pro Thr Thr Phe Gly
    130                 135                 140

Ala Gly Thr Lys Leu Glu Leu Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220
```

```
Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 458
<211> LENGTH: 258
<212> TYPE: PRT
<213> ORGANISM: Artificial Sequence
<220> FEATURE:
<223> OTHER INFORMATION: Synthetic

<400> SEQUENCE: 458

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser His Val Pro
            20                  25                  30

Arg Gln Val Ala Pro Arg Ser Phe Gly Gly Gly Ser Gln Ile Leu Leu
        35                  40                  45

Thr Gln Ser Pro Val Ile Leu Ser Val Ser Pro Gly Glu Arg Val Ser
    50                  55                  60

Phe Ser Cys Arg Ala Ser Gln Ser Ile Gly Thr Asn Ile His Trp Tyr
65                  70                  75                  80

Gln Gln Arg Thr Asn Gly Ser Pro Arg Leu Leu Ile Lys Tyr Ala Ser
                85                  90                  95

Glu Ser Ile Ser Gly Ile Pro Ser Arg Phe Ser Gly Ser Gly Ser Gly
            100                 105                 110

Thr Asp Phe Thr Leu Ser Ile Asn Ser Val Glu Ser Glu Asp Ile Ala
        115                 120                 125

Asp Tyr Tyr Cys Gln Gln Asn Asn Asn Trp Pro Thr Thr Phe Gly Ala
    130                 135                 140

Gly Thr Lys Leu Glu Leu Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys


<210> SEQ ID NO 459
<211> LENGTH: 259
<212> TYPE: PRT
<213> ORGANISM: Artificial Sequence
<220> FEATURE:
<223> OTHER INFORMATION: Synthetic

<400> SEQUENCE: 459

Gln Gly Gln Ser Gly Gln Cys Ile Ser Pro Arg Gly Cys Pro Asp Gly
```

-continued 1 5 10 15

Pro Tyr Val Met Tyr Gly Gly Gly Ser Ser Gly Gly Ser Ala Leu Ala
20 25 30

His Gly Leu Pro Thr Phe Val His Leu Gly Gly Gly Ser Gln Ile Leu
35 40 45

Leu Thr Gln Ser Pro Val Ile Leu Ser Val Ser Pro Gly Glu Arg Val
50 55 60

Ser Phe Ser Cys Arg Ala Ser Gln Ser Ile Gly Thr Asn Ile His Trp
65 70 75 80

Tyr Gln Gln Arg Thr Asn Gly Ser Pro Arg Leu Leu Ile Lys Tyr Ala
85 90 95

Ser Glu Ser Ile Ser Gly Ile Pro Ser Arg Phe Ser Gly Ser Gly Ser
100 105 110

Gly Thr Asp Phe Thr Leu Ser Ile Asn Ser Val Glu Ser Glu Asp Ile
115 120 125

Ala Asp Tyr Tyr Cys Gln Gln Asn Asn Asn Trp Pro Thr Thr Phe Gly
130 135 140

Ala Gly Thr Lys Leu Glu Leu Lys Arg Thr Val Ala Ala Pro Ser Val
145 150 155 160

Phe Ile Phe Pro Pro Ser Asp Glu Gln Leu Lys Ser Gly Thr Ala Ser
165 170 175

Val Val Cys Leu Leu Asn Asn Phe Tyr Pro Arg Glu Ala Lys Val Gln
180 185 190

Trp Lys Val Asp Asn Ala Leu Gln Ser Gly Asn Ser Gln Glu Ser Val
195 200 205

Thr Glu Gln Asp Ser Lys Asp Ser Thr Tyr Ser Leu Ser Ser Thr Leu
210 215 220

Thr Leu Ser Lys Ala Asp Tyr Glu Lys His Lys Val Tyr Ala Cys Glu
225 230 235 240

Val Thr His Gln Gly Leu Ser Ser Pro Val Thr Lys Ser Phe Asn Arg
245 250 255

Gly Glu Cys

<210> SEQ ID NO 460
<211> LENGTH: 259
<212> TYPE: PRT
<213> ORGANISM: Artificial Sequence
<220> FEATURE:
<223> OTHER INFORMATION: Synthetic

<400> SEQUENCE: 460

Gln Gly Gln Ser Gly Gln Cys Ile Ser Pro Arg Gly Cys Pro Asp Gly
1 5 10 15

Pro Tyr Val Met Tyr Gly Gly Gly Ser Ser Gly Gly Ser Gly Leu Pro
20 25 30

Thr Phe Val His Leu Pro Arg Gln Val Gly Gly Gly Ser Gln Ile Leu
35 40 45

Leu Thr Gln Ser Pro Val Ile Leu Ser Val Ser Pro Gly Glu Arg Val
50 55 60

Ser Phe Ser Cys Arg Ala Ser Gln Ser Ile Gly Thr Asn Ile His Trp
65 70 75 80

Tyr Gln Gln Arg Thr Asn Gly Ser Pro Arg Leu Leu Ile Lys Tyr Ala
85 90 95

Ser Glu Ser Ile Ser Gly Ile Pro Ser Arg Phe Ser Gly Ser Gly Ser
100 105 110

```
Gly Thr Asp Phe Thr Leu Ser Ile Asn Ser Val Glu Ser Glu Asp Ile
        115                 120                 125

Ala Asp Tyr Tyr Cys Gln Gln Asn Asn Asn Trp Pro Thr Thr Phe Gly
    130                 135                 140

Ala Gly Thr Lys Leu Glu Leu Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 461
<211> LENGTH: 257
<212> TYPE: PRT
<213> ORGANISM: Artificial Sequence
<220> FEATURE:
<223> OTHER INFORMATION: Synthetic

<400> SEQUENCE: 461

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Ala Ala Asn
            20                  25                  30

Ala Leu Ala His Gly Leu Phe Gly Gly Gly Ser Gln Ile Leu Leu Thr
        35                  40                  45

Gln Ser Pro Val Ile Leu Ser Val Ser Pro Gly Glu Arg Val Ser Phe
    50                  55                  60

Ser Cys Arg Ala Ser Gln Ser Ile Gly Thr Asn Ile His Trp Tyr Gln
65                  70                  75                  80

Gln Arg Thr Asn Gly Ser Pro Arg Leu Leu Ile Lys Tyr Ala Ser Glu
                85                  90                  95

Ser Ile Ser Gly Ile Pro Ser Arg Phe Ser Gly Ser Gly Ser Gly Thr
            100                 105                 110

Asp Phe Thr Leu Ser Ile Asn Ser Val Glu Ser Glu Asp Ile Ala Asp
        115                 120                 125

Tyr Tyr Cys Gln Gln Asn Asn Asn Trp Pro Thr Thr Phe Gly Ala Gly
    130                 135                 140

Thr Lys Leu Glu Leu Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205
```

Gln Asp Ser Lys Asp Ser Thr Tyr Ser Leu Ser Ser Thr Leu Thr Leu
210 215 220

Ser Lys Ala Asp Tyr Glu Lys His Lys Val Tyr Ala Cys Glu Val Thr
225 230 235 240

His Gln Gly Leu Ser Ser Pro Val Thr Lys Ser Phe Asn Arg Gly Glu
245 250 255

Cys

<210> SEQ ID NO 462
<211> LENGTH: 258
<212> TYPE: PRT
<213> ORGANISM: Artificial Sequence
<220> FEATURE:
<223> OTHER INFORMATION: Synthetic

<400> SEQUENCE: 462

Gln Gly Gln Ser Gly Gln Cys Ile Ser Pro Arg Gly Cys Pro Asp Gly
1 5 10 15

Pro Tyr Val Met Tyr Gly Gly Gly Ser Ser Gly Gly Ser Gly Pro Thr
20 25 30

Asn Ala Leu Ala His Gly Leu Phe Gly Gly Gly Ser Gln Ile Leu Leu
35 40 45

Thr Gln Ser Pro Val Ile Leu Ser Val Ser Pro Gly Glu Arg Val Ser
50 55 60

Phe Ser Cys Arg Ala Ser Gln Ser Ile Gly Thr Asn Ile His Trp Tyr
65 70 75 80

Gln Gln Arg Thr Asn Gly Ser Pro Arg Leu Leu Ile Lys Tyr Ala Ser
85 90 95

Glu Ser Ile Ser Gly Ile Pro Ser Arg Phe Ser Gly Ser Gly Ser Gly
100 105 110

Thr Asp Phe Thr Leu Ser Ile Asn Ser Val Glu Ser Glu Asp Ile Ala
115 120 125

Asp Tyr Tyr Cys Gln Gln Asn Asn Asn Trp Pro Thr Thr Phe Gly Ala
130 135 140

Gly Thr Lys Leu Glu Leu Lys Arg Thr Val Ala Ala Pro Ser Val Phe
145 150 155 160

Ile Phe Pro Pro Ser Asp Glu Gln Leu Lys Ser Gly Thr Ala Ser Val
165 170 175

Val Cys Leu Leu Asn Asn Phe Tyr Pro Arg Glu Ala Lys Val Gln Trp
180 185 190

Lys Val Asp Asn Ala Leu Gln Ser Gly Asn Ser Gln Glu Ser Val Thr
195 200 205

Glu Gln Asp Ser Lys Asp Ser Thr Tyr Ser Leu Ser Ser Thr Leu Thr
210 215 220

Leu Ser Lys Ala Asp Tyr Glu Lys His Lys Val Tyr Ala Cys Glu Val
225 230 235 240

Thr His Gln Gly Leu Ser Ser Pro Val Thr Lys Ser Phe Asn Arg Gly
245 250 255

Glu Cys

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480
<211> LENGTH: 265
<212> TYPE: PRT
<213> ORGANISM: Artificial Sequence
<220> FEATURE:
<223> OTHER INFORMATION: Synthetic

<400> SEQUENCE: 480

```
Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Ile Ser Ser Gly Leu Leu Ser Gly Arg Ser Asp Asn Pro Gly
        35                  40                  45

Gly Gly Ser Gln Ile Leu Leu Thr Gln Ser Pro Val Ile Leu Ser Val
    50                  55                  60

Ser Pro Gly Glu Arg Val Ser Phe Ser Cys Arg Ala Ser Gln Ser Ile
65                  70                  75                  80

Gly Thr Asn Ile His Trp Tyr Gln Gln Arg Thr Asn Gly Ser Pro Arg
                85                  90                  95

Leu Leu Ile Lys Tyr Ala Ser Glu Ser Ile Ser Gly Ile Pro Ser Arg
            100                 105                 110

Phe Ser Gly Ser Gly Ser Gly Thr Asp Phe Thr Leu Ser Ile Asn Ser
        115                 120                 125

Val Glu Ser Glu Asp Ile Ala Asp Tyr Tyr Cys Gln Gln Asn Asn Asn
    130                 135                 140

Trp Pro Thr Thr Phe Gly Ala Gly Thr Lys Leu Glu Leu Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
```

```
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265


<210> SEQ ID NO 481
<211> LENGTH: 270
<212> TYPE: PRT
<213> ORGANISM: Artificial Sequence
<220> FEATURE:
<223> OTHER INFORMATION: Synthetic

<400> SEQUENCE: 481

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Ala Val Gly Leu Leu Ala Pro Pro Gly Gly Leu Ser Gly Arg
        35                  40                  45

Ser Asp Asn Pro Gly Gly Gly Ser Gln Ile Leu Leu Thr Gln Ser Pro
    50                  55                  60

Val Ile Leu Ser Val Ser Pro Gly Glu Arg Val Ser Phe Ser Cys Arg
65                  70                  75                  80

Ala Ser Gln Ser Ile Gly Thr Asn Ile His Trp Tyr Gln Gln Arg Thr
                85                  90                  95

Asn Gly Ser Pro Arg Leu Leu Ile Lys Tyr Ala Ser Glu Ser Ile Ser
            100                 105                 110

Gly Ile Pro Ser Arg Phe Ser Gly Ser Gly Ser Gly Thr Asp Phe Thr
        115                 120                 125

Leu Ser Ile Asn Ser Val Glu Ser Glu Asp Ile Ala Asp Tyr Tyr Cys
    130                 135                 140

Gln Gln Asn Asn Asn Trp Pro Thr Thr Phe Gly Ala Gly Thr Lys Leu
145                 150                 155                 160

Glu Leu Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
        195                 200                 205

Ala Leu Gln Ser Gly Asn Ser Gln Glu Ser Val Thr Glu Gln Asp Ser
    210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270


<210> SEQ ID NO 482
<211> LENGTH: 255
<212> TYPE: PRT
```

<213> ORGANISM: Artificial Sequence
<220> FEATURE:
<223> OTHER INFORMATION: Synthetic

<400> SEQUENCE: 482

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Ile Ser Ser
            20                  25                  30

Gly Leu Leu Ser Ser Gly Gly Gly Ser Gln Ile Leu Leu Thr Gln Ser
        35                  40                  45

Pro Val Ile Leu Ser Val Ser Pro Gly Glu Arg Val Ser Phe Ser Cys
    50                  55                  60

Arg Ala Ser Gln Ser Ile Gly Thr Asn Ile His Trp Tyr Gln Gln Arg
65                  70                  75                  80

Thr Asn Gly Ser Pro Arg Leu Leu Ile Lys Tyr Ala Ser Glu Ser Ile
                85                  90                  95

Ser Gly Ile Pro Ser Arg Phe Ser Gly Ser Gly Ser Gly Thr Asp Phe
            100                 105                 110

Thr Leu Ser Ile Asn Ser Val Glu Ser Glu Asp Ile Ala Asp Tyr Tyr
        115                 120                 125

Cys Gln Gln Asn Asn Asn Trp Pro Thr Thr Phe Gly Ala Gly Thr Lys
    130                 135                 140

Leu Glu Leu Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255

<210> SEQ ID NO 483
<211> LENGTH: 260
<212> TYPE: PRT
<213> ORGANISM: Artificial Sequence
<220> FEATURE:
<223> OTHER INFORMATION: Synthetic

<400> SEQUENCE: 483

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Ile Ser Ser Gly Leu Leu Ser Ser Gly Gly Gly Ser Gln Ile
        35                  40                  45

Leu Leu Thr Gln Ser Pro Val Ile Leu Ser Val Ser Pro Gly Glu Arg
    50                  55                  60

Val Ser Phe Ser Cys Arg Ala Ser Gln Ser Ile Gly Thr Asn Ile His
65                  70                  75                  80

```
Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260


<210> SEQ ID NO 484
<211> LENGTH: 255
<212> TYPE: PRT
<213> ORGANISM: Artificial Sequence
<220> FEATURE:
<223> OTHER INFORMATION: Synthetic

<400> SEQUENCE: 484

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Ala Val Gly
            20                  25                  30

Leu Leu Ala Pro Pro Gly Gly Gly Ser Gln Ile Leu Leu Thr Gln Ser
        35                  40                  45

Pro Val Ile Leu Ser Val Ser Pro Gly Glu Arg Val Ser Phe Ser Cys
    50                  55                  60

Arg Ala Ser Gln Ser Ile Gly Thr Asn Ile His Trp Tyr Gln Gln Arg
65                  70                  75                  80

Thr Asn Gly Ser Pro Arg Leu Leu Ile Lys Tyr Ala Ser Glu Ser Ile
                85                  90                  95

Ser Gly Ile Pro Ser Arg Phe Ser Gly Ser Gly Ser Gly Thr Asp Phe
            100                 105                 110

Thr Leu Ser Ile Asn Ser Val Glu Ser Glu Asp Ile Ala Asp Tyr Tyr
        115                 120                 125

Cys Gln Gln Asn Asn Asn Trp Pro Thr Thr Phe Gly Ala Gly Thr Lys
    130                 135                 140

Leu Glu Leu Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175
```

```
Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 485
<211> LENGTH: 261
<212> TYPE: PRT
<213> ORGANISM: Artificial Sequence
<220> FEATURE:
<223> OTHER INFORMATION: Synthetic

<400> SEQUENCE: 485

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Pro Ala Val Gly Leu Leu Ala Pro Pro Gly Gly Gly Ser Gln
        35                  40                  45

Ile Leu Leu Thr Gln Ser Pro Val Ile Leu Ser Val Ser Pro Gly Glu
    50                  55                  60

Arg Val Ser Phe Ser Cys Arg Ala Ser Gln Ser Ile Gly Thr Asn Ile
65                  70                  75                  80

His Trp Tyr Gln Gln Arg Thr Asn Gly Ser Pro Arg Leu Leu Ile Lys
                85                  90                  95

Tyr Ala Ser Glu Ser Ile Ser Gly Ile Pro Ser Arg Phe Ser Gly Ser
            100                 105                 110

Gly Ser Gly Thr Asp Phe Thr Leu Ser Ile Asn Ser Val Glu Ser Glu
        115                 120                 125

Asp Ile Ala Asp Tyr Tyr Cys Gln Gln Asn Asn Asn Trp Pro Thr Thr
    130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260


<210> SEQ ID NO 486
<211> LENGTH: 255
```

```
<212> TYPE: PRT
<213> ORGANISM: Artificial Sequence
<220> FEATURE:
<223> OTHER INFORMATION: Synthetic

<400> SEQUENCE: 486

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Gly Pro Ser
            20                  25                  30

His Leu Val Leu Thr Gly Gly Gly Ser Gln Ile Leu Leu Thr Gln Ser
        35                  40                  45

Pro Val Ile Leu Ser Val Ser Pro Gly Glu Arg Val Ser Phe Ser Cys
    50                  55                  60

Arg Ala Ser Gln Ser Ile Gly Thr Asn Ile His Trp Tyr Gln Gln Arg
65                  70                  75                  80

Thr Asn Gly Ser Pro Arg Leu Leu Ile Lys Tyr Ala Ser Glu Ser Ile
                85                  90                  95

Ser Gly Ile Pro Ser Arg Phe Ser Gly Ser Gly Ser Gly Thr Asp Phe
            100                 105                 110

Thr Leu Ser Ile Asn Ser Val Glu Ser Glu Asp Ile Ala Asp Tyr Tyr
        115                 120                 125

Cys Gln Gln Asn Asn Asn Trp Pro Thr Thr Phe Gly Ala Gly Thr Lys
    130                 135                 140

Leu Glu Leu Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 487
<211> LENGTH: 260
<212> TYPE: PRT
<213> ORGANISM: Artificial Sequence
<220> FEATURE:
<223> OTHER INFORMATION: Synthetic

<400> SEQUENCE: 487

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Gly Pro Ser His Leu Val Leu Thr Gly Gly Gly Ser Gln Ile
        35                  40                  45

Leu Leu Thr Gln Ser Pro Val Ile Leu Ser Val Ser Pro Gly Glu Arg
    50                  55                  60

Val Ser Phe Ser Cys Arg Ala Ser Gln Ser Ile Gly Thr Asn Ile His
65                  70                  75                  80
```

```
Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260
```

<210> SEQ ID NO 488
<211> LENGTH: 261
<212> TYPE: PRT
<213> ORGANISM: Artificial Sequence
<220> FEATURE:
<223> OTHER INFORMATION: Synthetic

<400> SEQUENCE: 488

```
Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Ile Ser Ser
            20                  25                  30

Gly Leu Leu Ser Gly Arg Ser Asp Asn His Gly Ser Ser Gly Thr Gln
        35                  40                  45

Ile Leu Leu Thr Gln Ser Pro Val Ile Leu Ser Val Ser Pro Gly Glu
    50                  55                  60

Arg Val Ser Phe Ser Cys Arg Ala Ser Gln Ser Ile Gly Thr Asn Ile
65                  70                  75                  80

His Trp Tyr Gln Gln Arg Thr Asn Gly Ser Pro Arg Leu Leu Ile Lys
                85                  90                  95

Tyr Ala Ser Glu Ser Ile Ser Gly Ile Pro Ser Arg Phe Ser Gly Ser
            100                 105                 110

Gly Ser Gly Thr Asp Phe Thr Leu Ser Ile Asn Ser Val Glu Ser Glu
        115                 120                 125

Asp Ile Ala Asp Tyr Tyr Cys Gln Gln Asn Asn Asn Trp Pro Thr Thr
    130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
                165                 170                 175
```

```
Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260


<210> SEQ ID NO 489
<211> LENGTH: 260
<212> TYPE: PRT
<213> ORGANISM: Artificial Sequence
<220> FEATURE:
<223> OTHER INFORMATION: Synthetic

<400> SEQUENCE: 489

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Ile Ser Ser
            20                  25                  30

Gly Leu Leu Ser Gly Arg Ser Asp Asn His Gly Gly Gly Ser Gln Ile
        35                  40                  45

Leu Leu Thr Gln Ser Pro Val Ile Leu Ser Val Ser Pro Gly Glu Arg
    50                  55                  60

Val Ser Phe Ser Cys Arg Ala Ser Gln Ser Ile Gly Thr Asn Ile His
65                  70                  75                  80

Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260
```

-continued

```
<210> SEQ ID NO 490
<211> LENGTH: 265
<212> TYPE: PRT
<213> ORGANISM: Artificial Sequence
<220> FEATURE:
<223> OTHER INFORMATION: Synthetic

<400> SEQUENCE: 490

Gln Gly Gln Ser Gly Gln Cys Ile Ser Pro Arg Gly Cys Pro Asp Gly
1               5                   10                  15

Pro Tyr Val Met Tyr Gly Gly Gly Ser Ser Gly Gly Ser Ala Val Gly
            20                  25                  30

Leu Leu Ala Pro Pro Gly Gly Leu Ser Gly Arg Ser Asp Asn His Gly
        35                  40                  45

Gly Gly Ser Gln Ile Leu Leu Thr Gln Ser Pro Val Ile Leu Ser Val
    50                  55                  60

Ser Pro Gly Glu Arg Val Ser Phe Ser Cys Arg Ala Ser Gln Ser Ile
65                  70                  75                  80

Gly Thr Asn Ile His Trp Tyr Gln Gln Arg Thr Asn Gly Ser Pro Arg
                85                  90                  95

Leu Leu Ile Lys Tyr Ala Ser Glu Ser Ile Ser Gly Ile Pro Ser Arg
            100                 105                 110

Phe Ser Gly Ser Gly Ser Gly Thr Asp Phe Thr Leu Ser Ile Asn Ser
        115                 120                 125

Val Glu Ser Glu Asp Ile Ala Asp Tyr Tyr Cys Gln Gln Asn Asn Asn
    130                 135                 140

Trp Pro Thr Thr Phe Gly Ala Gly Thr Lys Leu Glu Leu Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265
```